US010471155B2

(12) United States Patent
Hubbell et al.

(10) Patent No.: US 10,471,155 B2
(45) Date of Patent: *Nov. 12, 2019

(54) ANTIGEN-SPECIFIC TOLERANCE AND COMPOSITIONS FOR INDUCTION OF SAME

(71) Applicant: École Polytechnique Fédérale de Lausanne (EPFL), Lausanne (CH)

(72) Inventors: Jeffrey A. Hubbell, Lausanne (CH); Stephan Kontos, Lausanne (CH); Karen Y. Dane, Lausanne (CH)

(73) Assignee: École Polytechnique Fédérale de Lausanne (EPFL) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/904,254

(22) Filed: Feb. 23, 2018

(65) Prior Publication Data

US 2018/0185508 A1 Jul. 5, 2018

Related U.S. Application Data

(63) Continuation of application No. 15/232,724, filed on Aug. 9, 2016, now Pat. No. 9,901,646, which is a continuation of application No. 13/397,202, filed on Feb. 15, 2012, now Pat. No. 9,517,257, which is a continuation-in-part of application No. 13/206,034, filed on Aug. 9, 2011, now Pat. No. 9,518,087.

(60) Provisional application No. 61/372,181, filed on Aug. 10, 2010.

(51) Int. Cl.
| | | |
|---|---|---|
| A61K 47/68 | (2017.01) | |
| A61K 9/107 | (2006.01) | |
| C07K 7/08 | (2006.01) | |
| C07K 16/18 | (2006.01) | |
| C12N 9/82 | (2006.01) | |
| C12N 9/96 | (2006.01) | |
| A61K 9/51 | (2006.01) | |
| A61K 39/00 | (2006.01) | |
| C07K 14/62 | (2006.01) | |
| C07K 14/74 | (2006.01) | |
| C07K 16/28 | (2006.01) | |
| A61K 47/64 | (2017.01) | |
| A61K 38/00 | (2006.01) | |

(52) U.S. Cl.
CPC ........ *A61K 47/6811* (2017.08); *A61K 9/1075* (2013.01); *A61K 9/513* (2013.01); *A61K 39/001* (2013.01); *A61K 39/0008* (2013.01); *A61K 47/64* (2017.08); *A61K 47/6803* (2017.08); *A61K 47/6815* (2017.08); *A61K 47/6843* (2017.08); *A61K 47/6849* (2017.08); *C07K 7/08* (2013.01); *C07K 14/62* (2013.01); *C07K 14/70539* (2013.01); *C07K 16/18* (2013.01); *C07K 16/28* (2013.01); *C12N 9/82* (2013.01); *C12N 9/96* (2013.01); *C12Y 305/01001* (2013.01); *A61K 38/00* (2013.01); *A61K 2039/605* (2013.01); *A61K 2039/6031* (2013.01); *A61K 2039/6056* (2013.01); *C07K 2317/56* (2013.01); *C07K 2317/622* (2013.01); *C07K 2317/92* (2013.01); *C07K 2319/00* (2013.01); *C07K 2319/21* (2013.01); *C07K 2319/22* (2013.01); *C07K 2319/23* (2013.01); *C07K 2319/30* (2013.01); *C07K 2319/33* (2013.01); *C07K 2319/41* (2013.01); *C07K 2319/43* (2013.01); *C07K 2319/74* (2013.01)

(58) Field of Classification Search
CPC combination set(s) only.
See application file for complete search history.

(56) References Cited

U.S. PATENT DOCUMENTS

| | | |
|---|---|---|
| 4,671,958 A | 6/1987 | Rodwell et al. |
| 4,741,900 A | 5/1988 | Alvarez et al. |
| 4,859,449 A | 8/1989 | Mattes |
| 4,867,973 A | 9/1989 | Goers et al. |
| 4,950,738 A | 8/1990 | King et al. |
| 5,086,002 A | 2/1992 | Hillyard et al. |
| 5,140,104 A | 8/1992 | Coughlin et al. |
| 5,156,840 A | 10/1992 | Goers et al. |
| 5,162,512 A | 11/1992 | King et al. |
| 5,227,165 A | 7/1993 | Domb et al. |
| 5,227,293 A | 7/1993 | Stengelin et al. |
| 5,346,696 A | 9/1994 | Kim et al. |
| 5,358,857 A | 10/1994 | Stengelin et al. |
| 5,470,570 A | 11/1995 | Taylor et al. |

(Continued)

FOREIGN PATENT DOCUMENTS

| | | |
|---|---|---|
| EP | 0119650 | 9/1984 |
| EP | 0175617 | 10/1991 |

(Continued)

OTHER PUBLICATIONS

"cMET-HGF Binding Peptide #65,", XP002717161, Retrieved From EBI Accession No. GSP:ADS33412 (Dec. 2, 2004).

(Continued)

*Primary Examiner* — Kagnew H Gebreyesus
(74) *Attorney, Agent, or Firm* — Knobbe, Martens, Olson & Bear LLP

(57) ABSTRACT

Peptides that specifically bind erythrocytes are described. These are provided as peptidic ligands having sequences that specifically bind, or as antibodies or fragments thereof that provide specific binding, to erythrocytes. The peptides may be prepared as molecular fusions with therapeutic agents, tolerizing antigens, or targeting peptides. Immunotolerance may be created by use of the fusions and choice of an antigen on a substance for which tolerance is desired.

14 Claims, 15 Drawing Sheets

Specification includes a Sequence Listing.

(56) References Cited

U.S. PATENT DOCUMENTS

| | | |
|---|---|---|
| 5,487,890 A | 1/1996 | Taylor et al. |
| 5,681,571 A | 10/1997 | Holmgren et al. |
| 5,698,679 A | 12/1997 | Nemazee et al. |
| 5,718,915 A | 2/1998 | Virtanen et al. |
| 5,879,679 A | 3/1999 | Taylor et al. |
| 5,885,808 A | 3/1999 | Spooner et al. |
| 5,886,143 A | 3/1999 | Theodore et al. |
| 5,948,639 A | 9/1999 | Gimeno et al. |
| 5,985,826 A | 11/1999 | Theodore et al. |
| 5,994,104 A | 11/1999 | Anderson et al. |
| 5,997,861 A | 12/1999 | Virtanen et al. |
| 6,022,564 A | 2/2000 | Takechi et al. |
| 6,090,925 A | 7/2000 | Woiszwillo et al. |
| 6,120,770 A | 9/2000 | Adams et al. |
| 6,153,203 A | 11/2000 | Holmgren et al. |
| 6,217,869 B1 | 4/2001 | Meyer et al. |
| 6,224,794 B1 | 5/2001 | Amsden et al. |
| 6,264,950 B1 | 7/2001 | Staerz |
| 6,322,796 B1 | 11/2001 | Holmgren et al. |
| 6,365,163 B1 | 4/2002 | Holmgren et al. |
| 6,379,699 B1 | 4/2002 | Virtanen et al. |
| 6,488,927 B2 | 12/2002 | Muzykantov et al. |
| 6,512,103 B1 | 1/2003 | Dairaghi et al. |
| 6,562,347 B1 | 5/2003 | Kwak et al. |
| 6,703,488 B1 | 3/2004 | Burton et al. |
| 6,737,057 B1 | 5/2004 | Zaghouani et al. |
| 6,814,964 B2 | 11/2004 | Virtanen et al. |
| 6,905,688 B2 | 6/2005 | Rosen et al. |
| 6,953,675 B2 | 10/2005 | Leung et al. |
| 7,041,287 B2 | 5/2006 | Muzykantov et al. |
| 7,132,475 B2 | 11/2006 | Hubbel et al. |
| 7,144,569 B1 | 12/2006 | Anderson et al. |
| 7,148,329 B1 | 12/2006 | Figdor et al. |
| 7,172,760 B2 | 2/2007 | Muzykantov et al. |
| 7,175,988 B2 | 2/2007 | Roschke et al. |
| 7,192,582 B2 | 3/2007 | Hudson et al. |
| 7,285,642 B2 | 10/2007 | Figdor et al. |
| 7,420,040 B2 | 9/2008 | Young et al. |
| 7,420,041 B2 | 9/2008 | Young et al. |
| 7,541,180 B2 | 6/2009 | Valiante et al. |
| 7,585,508 B1 | 9/2009 | Prendergast |
| 7,612,180 B2 | 11/2009 | Goldenberg et al. |
| 7,704,943 B2 | 4/2010 | Griffin et al. |
| 7,704,964 B2 | 4/2010 | Delcayre et al. |
| 7,786,267 B2 | 8/2010 | Zurawski et al. |
| 7,811,809 B2 | 10/2010 | Heyduk et al. |
| 7,837,997 B2 | 11/2010 | Muzykantov et al. |
| 7,884,190 B2 | 2/2011 | Cohen et al. |
| 7,888,460 B2 | 2/2011 | Anderson et al. |
| 7,892,743 B2 | 2/2011 | Owen et al. |
| 7,932,294 B2 | 4/2011 | Satyam |
| 7,994,283 B2 | 8/2011 | Valiante et al. |
| 8,007,805 B2 | 8/2011 | George et al. |
| 8,021,689 B2 | 9/2011 | Reddy et al. |
| 8,057,798 B2 | 11/2011 | Zurawski et al. |
| 8,058,400 B2 | 11/2011 | Figdor et al. |
| 8,058,406 B2 | 11/2011 | Mi et al. |
| 8,105,599 B2 | 1/2012 | Figdor et al. |
| 8,236,934 B2 | 8/2012 | Banchereau et al. |
| 8,252,902 B2 | 8/2012 | Barbas et al. |
| 8,273,357 B2 | 9/2012 | Hacohen et al. |
| 8,277,812 B2 | 10/2012 | Iannacone et al. |
| 8,318,912 B2 | 11/2012 | Simon |
| 8,323,696 B2 | 12/2012 | Hubbel et al. |
| 8,329,144 B2 | 12/2012 | Anderson et al. |
| 8,333,973 B2 | 12/2012 | Muzykantov et al. |
| 8,343,497 B2 | 1/2013 | Shi et al. |
| 8,343,498 B2 | 1/2013 | Alexis et al. |
| 8,425,910 B2 | 4/2013 | Mi et al. |
| 8,449,888 B2 | 5/2013 | Zurawski et al. |
| 8,507,237 B2 | 8/2013 | Hermet et al. |
| 8,518,410 B2 | 8/2013 | Zurawski et al. |
| 8,551,476 B2 | 10/2013 | Mi et al. |
| 8,562,998 B2 | 10/2013 | Shi et al. |
| 8,580,253 B2 | 11/2013 | Rubin-Bejerano et al. |
| 8,586,052 B2 | 11/2013 | Zurawski et al. |
| 8,591,905 B2 | 11/2013 | von Andrian et al. |
| 8,592,364 B2 | 11/2013 | Swartz et al. |
| 8,613,903 B2 | 12/2013 | Goldenberg et al. |
| 8,617,823 B2 | 12/2013 | Rubin-Bejerano et al. |
| 8,637,028 B2 | 1/2014 | Alexis et al. |
| 8,673,293 B2 | 3/2014 | Martin et al. |
| 8,685,408 B2 | 4/2014 | Tartour et al. |
| 8,722,047 B2 | 5/2014 | Goldenberg et al. |
| 8,728,481 B2 | 5/2014 | Banchereau et al. |
| 8,889,140 B2 | 11/2014 | Lee et al. |
| 8,906,381 B2 | 12/2014 | Iannacone et al. |
| 8,932,595 B2 | 1/2015 | Iannacone et al. |
| 8,961,991 B2 | 2/2015 | Zurawski et al. |
| 8,992,917 B2 | 3/2015 | Goldenberg et al. |
| 9,005,903 B2 | 4/2015 | Rubin-Bejerano et al. |
| 9,066,984 B2 | 6/2015 | Mi et al. |
| 9,102,730 B2 | 8/2015 | Zurawski et al. |
| 9,102,734 B2 | 8/2015 | Zurawski et al. |
| 9,187,561 B2 | 11/2015 | Goldenberg et al. |
| 9,216,156 B2 | 12/2015 | Fleury et al. |
| 9,233,072 B2 | 1/2016 | Alexis et al. |
| 9,234,040 B2 | 1/2016 | Zurawski et al. |
| 9,260,692 B2 | 2/2016 | Martin et al. |
| 9,308,280 B2 | 4/2016 | Shi et al. |
| 9,326,939 B2 | 5/2016 | Paulson et al. |
| 9,416,186 B2 | 8/2016 | Zurawski et al. |
| 9,439,859 B2 | 9/2016 | Alexis et al. |
| 9,453,074 B2 | 9/2016 | Oh et al. |
| 9,457,047 B2 | 10/2016 | Rubin-Bejerano et al. |
| 9,474,717 B2 | 10/2016 | von Andrian et al. |
| 9,517,257 B2 | 12/2016 | Hubbell et al. |
| 9,518,087 B2 | 12/2016 | Hubbell et al. |
| 9,522,183 B2 | 12/2016 | Paulson et al. |
| 9,539,210 B2 | 1/2017 | von Andrian et al. |
| 9,561,272 B2 | 2/2017 | Thomas et al. |
| 9,688,991 B2 | 6/2017 | Levy et al. |
| 9,751,945 B2 | 9/2017 | Ploegh et al. |
| 9,814,780 B2 | 11/2017 | Hubbell et al. |
| 9,850,296 B2 | 12/2017 | Hubbell et al. |
| 9,878,048 B2 | 1/2018 | Hubbell et al. |
| 9,901,645 B2 | 2/2018 | Hubbell et al. |
| 9,901,646 B2 | 2/2018 | Hubbell et al. |
| 2002/0004037 A1 | 1/2002 | Koteliansky et al. |
| 2002/0038002 A1 | 3/2002 | Zaghouani |
| 2002/0081298 A1 | 6/2002 | Zaghouani |
| 2002/0103343 A1 | 8/2002 | Taylor et al. |
| 2002/0187131 A1 | 12/2002 | Hawiger et al. |
| 2002/0193572 A1 | 12/2002 | Leung et al. |
| 2003/0022826 A1 | 1/2003 | Haynes |
| 2003/0082643 A1 | 5/2003 | Hudson et al. |
| 2003/0103967 A1 | 5/2003 | Zaghouani |
| 2003/0104045 A1 | 6/2003 | Virtanen et al. |
| 2003/0175921 A1 | 9/2003 | Barbas et al. |
| 2003/0190676 A1 | 10/2003 | Barbas et al. |
| 2003/0211078 A1 | 11/2003 | Heavner |
| 2004/0052815 A1 | 3/2004 | Lycke |
| 2004/0077843 A1 | 4/2004 | Burton et al. |
| 2004/0146948 A1 | 7/2004 | Britton et al. |
| 2004/0147721 A1 | 7/2004 | Valiante |
| 2004/0185057 A1 | 9/2004 | Kirkby et al. |
| 2004/0197314 A1 | 10/2004 | Delcayre et al. |
| 2004/0258688 A1 | 12/2004 | Hawiger et al. |
| 2005/0031628 A1 | 2/2005 | George et al. |
| 2005/0053579 A1 | 3/2005 | Galipeau et al. |
| 2005/0113297 A1 | 5/2005 | Francois et al. |
| 2005/0118168 A1 | 6/2005 | Figdor et al. |
| 2005/0201973 A1 | 9/2005 | Virtanen et al. |
| 2005/0203022 A1 | 9/2005 | Gotwals et al. |
| 2005/0220804 A1 | 10/2005 | Figdor et al. |
| 2005/0250936 A1 | 11/2005 | Oppermann et al. |
| 2006/0034864 A1 | 2/2006 | Zaghouani |
| 2006/0127929 A1 | 6/2006 | Swager et al. |
| 2006/0153881 A1 | 7/2006 | Narum et al. |
| 2006/0173168 A1 | 8/2006 | Carlock et al. |
| 2006/0178299 A1 | 8/2006 | Anderson et al. |
| 2006/0257412 A1 | 11/2006 | Bowdish et al. |
| 2006/0280679 A1 | 12/2006 | Bowdish et al. |
| 2007/0059794 A1 | 3/2007 | Ideno et al. |

(56) References Cited

U.S. PATENT DOCUMENTS

| | | |
|---|---|---|
| 2007/0111222 A1 | 5/2007 | Chasin et al. |
| 2007/0122409 A1 | 5/2007 | Zaghouani |
| 2007/0190615 A1 | 8/2007 | Cohen et al. |
| 2007/0218053 A1 | 9/2007 | Zaghouani |
| 2008/0031899 A1 | 2/2008 | Reddy et al. |
| 2008/0131428 A1 | 6/2008 | Young et al. |
| 2008/0160041 A1 | 7/2008 | Figdor et al. |
| 2008/0175971 A1 | 7/2008 | Anderson et al. |
| 2008/0178299 A1 | 7/2008 | Merkle et al. |
| 2008/0206262 A1 | 8/2008 | Banchereau et al. |
| 2008/0213267 A1 | 9/2008 | Young et al. |
| 2008/0227707 A1 | 9/2008 | Carlock et al. |
| 2008/0233143 A1 | 9/2008 | Jackson et al. |
| 2008/0241170 A1 | 10/2008 | Zurawski et al. |
| 2008/0254044 A1 | 10/2008 | Zurawski |
| 2008/0261262 A1 | 10/2008 | Godfrin |
| 2008/0274092 A1 | 11/2008 | Godfrin et al. |
| 2008/0305104 A1 | 12/2008 | Young et al. |
| 2008/0318852 A1 | 12/2008 | Anderson et al. |
| 2009/0004218 A1 | 1/2009 | Hacohen et al. |
| 2009/0017039 A1 | 1/2009 | Mi et al. |
| 2009/0123467 A1 | 5/2009 | Bedi et al. |
| 2009/0130104 A1 | 5/2009 | Muzykantov et al. |
| 2009/0142263 A1 | 6/2009 | Young et al. |
| 2009/0149656 A1 | 6/2009 | Singaram et al. |
| 2009/0181011 A1 | 7/2009 | Zaghouani |
| 2009/0191118 A1 | 7/2009 | Young et al. |
| 2009/0202622 A1 | 8/2009 | Fleury et al. |
| 2009/0269285 A1 | 10/2009 | Anderson et al. |
| 2009/0280132 A1 | 11/2009 | Zaghouani |
| 2009/0317381 A1 | 12/2009 | Plaut et al. |
| 2009/0324538 A1 | 12/2009 | Wong et al. |
| 2010/0003266 A1 | 1/2010 | Simon |
| 2010/0003338 A1 | 1/2010 | Hubbell et al. |
| 2010/0015131 A1 | 1/2010 | Mi et al. |
| 2010/0055189 A1 | 3/2010 | Hubbell et al. |
| 2010/0092425 A1 | 4/2010 | Von Andrian et al. |
| 2010/0098718 A1 | 4/2010 | Valiante |
| 2010/0129392 A1 | 5/2010 | Shi et al. |
| 2010/0129439 A1 | 5/2010 | Alexis et al. |
| 2010/0129820 A1 | 5/2010 | Kool et al. |
| 2010/0222407 A1 | 9/2010 | Segura et al. |
| 2010/0233251 A1 | 9/2010 | Von Adrian et al. |
| 2010/0239575 A1 | 9/2010 | Banchereau et al. |
| 2010/0285015 A1 | 11/2010 | Muzykantov et al. |
| 2010/0291080 A1 | 11/2010 | Lee et al. |
| 2010/0291082 A1 | 11/2010 | Zurawski |
| 2010/0297114 A1 | 11/2010 | Zurawski |
| 2010/0310612 A1 | 12/2010 | DuFour et al. |
| 2010/0316620 A1 | 12/2010 | Bourgeaux et al. |
| 2010/0322929 A1 | 12/2010 | Zurawski et al. |
| 2010/0330115 A1 | 12/2010 | Zurawski et al. |
| 2011/0014171 A1 | 1/2011 | Bourgeaux et al. |
| 2011/0033426 A1 | 2/2011 | Martin et al. |
| 2011/0044912 A2 | 2/2011 | Anderson et al. |
| 2011/0045049 A1 | 2/2011 | Rubin-Bejerano et al. |
| 2011/0064709 A1 | 3/2011 | Miller et al. |
| 2011/0064754 A1 | 3/2011 | Taylor et al. |
| 2011/0082075 A1 | 4/2011 | Prendergast |
| 2011/0091493 A1 | 4/2011 | Mohamadzadeh et al. |
| 2011/0143994 A1 | 6/2011 | Lycke |
| 2011/0177532 A1 | 7/2011 | Rubin-Bejerano et al. |
| 2011/0200632 A1 | 8/2011 | Jackson et al. |
| 2011/0206759 A1 | 8/2011 | Swartz et al. |
| 2011/0268804 A1 | 11/2011 | Shi et al. |
| 2011/0268805 A1 | 11/2011 | Alexis et al. |
| 2011/0293644 A1 | 12/2011 | Anderson et al. |
| 2011/0311542 A1 | 12/2011 | Mi et al. |
| 2012/0004643 A1 | 1/2012 | Zurawski et al. |
| 2012/0009140 A1 | 1/2012 | Godfrin et al. |
| 2012/0014960 A1 | 1/2012 | Mi et al. |
| 2012/0027808 A1 | 2/2012 | Iannacone |
| 2012/0039989 A1 | 2/2012 | Hubbel et al. |
| 2012/0058180 A1 | 3/2012 | Kren et al. |
| 2012/0076831 A1 | 3/2012 | Miller et al. |
| 2012/0087890 A1 | 4/2012 | Iannacone et al. |
| 2012/0107301 A1 | 5/2012 | Bowdish et al. |
| 2012/0121570 A1 | 5/2012 | Godfrin |
| 2012/0121592 A1 | 5/2012 | Oh et al. |
| 2012/0128635 A1 | 5/2012 | Gregory et al. |
| 2012/0129210 A1 | 5/2012 | Bourgeaux et al. |
| 2012/0178139 A1 | 7/2012 | Hubbel et al. |
| 2012/0207745 A1 | 8/2012 | Godfrin et al. |
| 2012/0237513 A1 | 9/2012 | Zurawski et al. |
| 2012/0276095 A1 | 11/2012 | Langermann et al. |
| 2012/0282281 A1 | 11/2012 | Banchereau et al. |
| 2013/0004427 A1 | 1/2013 | El-Sayed et al. |
| 2013/0022634 A1 | 1/2013 | Lycke |
| 2013/0053543 A1 | 2/2013 | Davis et al. |
| 2013/0071413 A1 | 3/2013 | Simon |
| 2013/0078216 A1 | 3/2013 | Dunlevy et al. |
| 2013/0078267 A1 | 3/2013 | Anderson et al. |
| 2013/0101463 A1 | 4/2013 | Mambrini et al. |
| 2013/0115230 A1 | 5/2013 | Simon |
| 2013/0129790 A1 | 5/2013 | Alexis et al. |
| 2013/0164364 A1 | 6/2013 | Paulson et al. |
| 2013/0171074 A1 | 7/2013 | Barbas et al. |
| 2013/0171233 A1 | 7/2013 | Paulson et al. |
| 2013/0236533 A1 | 9/2013 | Von Adrian et al. |
| 2013/0287810 A1 | 10/2013 | Mohamadzadeh et al. |
| 2013/0287857 A1 | 10/2013 | Von Adrian et al. |
| 2013/0295120 A1 | 11/2013 | Zurawski et al. |
| 2013/0318648 A1 | 11/2013 | Anderson et al. |
| 2013/0323786 A1 | 12/2013 | Mi et al. |
| 2013/0336991 A1 | 12/2013 | Mi et al. |
| 2014/0037736 A1 | 2/2014 | Shi et al. |
| 2014/0079728 A1 | 3/2014 | Jackson et al. |
| 2014/0127198 A1 | 5/2014 | Zurawski et al. |
| 2014/0127301 A1 | 5/2014 | Alexis et al. |
| 2014/0134168 A1 | 5/2014 | Zurawski et al. |
| 2014/0199315 A1 | 7/2014 | Mi et al. |
| 2014/0205630 A1 | 7/2014 | Tartour |
| 2014/0212445 A1 | 7/2014 | Martin et al. |
| 2014/0227268 A1 | 8/2014 | Banchereau et al. |
| 2014/0234344 A1 | 8/2014 | Banchereau et al. |
| 2014/0308238 A1 | 10/2014 | Rubin-Bejerano et al. |
| 2014/0314865 A1 | 10/2014 | Von Adrian et al. |
| 2014/0377291 A1 | 12/2014 | Fischbach et al. |
| 2015/0104478 A1 | 4/2015 | Lee et al. |
| 2015/0166659 A1 | 6/2015 | Goldenberg et al. |
| 2015/0191730 A1 | 7/2015 | Levy et al. |
| 2015/0250862 A1 | 9/2015 | Cantor et al. |
| 2015/0299329 A1 | 10/2015 | Zurawski et al. |
| 2015/0307545 A1 | 10/2015 | Jackson et al. |
| 2016/0015821 A1 | 1/2016 | Hubbell et al. |
| 2016/0022792 A1 | 1/2016 | Zurawski et al. |
| 2016/0024212 A1 | 1/2016 | Goldenberg et al. |
| 2016/0031988 A1 | 2/2016 | Zurawski et al. |
| 2016/0058792 A1 | 3/2016 | Quintana et al. |
| 2016/0060324 A1 | 3/2016 | Paulson et al. |
| 2016/0060358 A1 | 3/2016 | Hay |
| 2016/0083468 A1 | 3/2016 | Mi et al. |
| 2016/0108096 A1 | 4/2016 | Thompson et al. |
| 2016/0243248 A1 | 8/2016 | Hubbell et al. |
| 2016/0346384 A1 | 12/2016 | Porcelli et al. |
| 2016/0375126 A1 | 12/2016 | Oh et al. |
| 2017/0007708 A1 | 1/2017 | Hubbell et al. |
| 2017/0020926 A1 | 1/2017 | Mata-Fink et al. |
| 2017/0066825 A1 | 3/2017 | Hubbell et al. |
| 2017/0066828 A1 | 3/2017 | Goldenberg et al. |
| 2017/0121379 A1 | 5/2017 | Zhang et al. |
| 2017/0137513 A1 | 5/2017 | Vallera et al. |
| 2017/0252417 A1 | 9/2017 | Irvine et al. |
| 2017/0320933 A1 | 11/2017 | Mannie |
| 2017/0326213 A1 | 11/2017 | Jajosky et al. |
| 2018/0000916 A1 | 1/2018 | Zurawski et al. |
| 2018/0094071 A1 | 4/2018 | Zurawski et al. |
| 2018/0100011 A1 | 4/2018 | Hubbell et al. |

(56) References Cited

U.S. PATENT DOCUMENTS

| | | |
|---|---|---|
| 2018/0104284 A1 | 4/2018 | Wallecha et al. |
| 2018/0117171 A1 | 5/2018 | Mooney et al. |

FOREIGN PATENT DOCUMENTS

| | | |
|---|---|---|
| EP | 0088695 | 6/1992 |
| EP | 0173629 | 6/1992 |
| EP | 0480041 | 6/1993 |
| EP | 0308208 | 12/1993 |
| EP | 0251455 | 5/1994 |
| EP | 0294294 | 5/1995 |
| EP | 0789715 | 8/1997 |
| EP | 0808366 | 11/1997 |
| EP | 0722340 | 4/1998 |
| EP | 0505357 | 3/1999 |
| EP | 0602290 | 8/1999 |
| EP | 0978564 | 2/2000 |
| EP | 1012308 | 6/2000 |
| EP | 630407 | 8/2000 |
| EP | 1046651 | 10/2000 |
| EP | 1093464 | 4/2001 |
| EP | 1301541 | 4/2003 |
| EP | 0743856 | 7/2003 |
| EP | 1370588 | 12/2003 |
| EP | 1409009 | 4/2004 |
| EP | 1292621 | 9/2006 |
| EP | 1838734 | 10/2007 |
| EP | 1853313 | 11/2007 |
| EP | 1028978 | 1/2008 |
| EP | 1086137 | 6/2008 |
| EP | 1938836 | 7/2008 |
| EP | 1440156 | 8/2008 |
| EP | 1619208 | 10/2008 |
| EP | 1996700 | 12/2008 |
| EP | 1996701 | 12/2008 |
| EP | 1045861 | 3/2009 |
| EP | 2125012 | 12/2009 |
| EP | 2178896 | 4/2010 |
| EP | 1516881 | 6/2010 |
| EP | 2238986 | 10/2010 |
| EP | 2315779 | 5/2011 |
| EP | 1417229 | 6/2011 |
| EP | 2344185 | 7/2011 |
| EP | 2344187 | 7/2011 |
| EP | 2394657 | 12/2011 |
| EP | 2394661 | 12/2011 |
| EP | 2406290 | 1/2012 |
| EP | 2428226 | 3/2012 |
| EP | 2478917 | 7/2012 |
| EP | 2066294 | 10/2012 |
| EP | 2527363 | 11/2012 |
| EP | 2598120 | 6/2013 |
| EP | 2618817 | 7/2013 |
| EP | 2620157 | 7/2013 |
| EP | 2630967 | 8/2013 |
| EP | 1904104 | 9/2013 |
| EP | 1991564 | 9/2013 |
| EP | 2115129 | 11/2013 |
| EP | 2684889 | 1/2014 |
| EP | 1443963 | 5/2014 |
| EP | 1664270 | 5/2014 |
| EP | 2115002 | 8/2014 |
| EP | 1605974 | 11/2014 |
| EP | 1850832 | 12/2014 |
| EP | 2114985 | 12/2014 |
| EP | 2283358 | 4/2015 |
| EP | 2213742 | 1/2016 |
| EP | 2982695 | 2/2016 |
| EP | 2983791 | 2/2016 |
| EP | 2989123 | 3/2016 |
| EP | 2346528 | 4/2016 |
| EP | 2406286 | 5/2016 |
| EP | 2205273 | 9/2016 |
| EP | 3091034 | 11/2016 |
| EP | 2406288 | 12/2016 |
| EP | 2406289 | 2/2017 |
| EP | 2217269 | 4/2017 |
| EP | 2344186 | 4/2017 |
| EP | 2630966 | 4/2017 |
| JP | H09-509572 | 9/1997 |
| JP | 2003-519619 | 6/2003 |
| JP | 2004-526452 | 9/2004 |
| JP | 2007-510915 | 4/2007 |
| JP | 2007-312776 | 12/2007 |
| JP | 2009-505049 | 2/2009 |
| JP | 2009-060894 | 3/2009 |
| JP | 2009-149664 | 7/2009 |
| JP | 2013-516967 | 5/2013 |
| WO | WO 1991/008770 | 6/1991 |
| WO | WO 1992/05801 | 4/1992 |
| WO | WO 1992/22310 | 12/1992 |
| WO | WO 1995/06737 | 3/1995 |
| WO | WO 1995/22977 | 8/1995 |
| WO | WO 1996/023882 | 8/1996 |
| WO | WO 1996/040245 | 12/1996 |
| WO | WO 1998/06737 | 2/1998 |
| WO | WO 1999/036437 | 7/1999 |
| WO | WO 2000/074717 | 12/2000 |
| WO | WO 2001/022995 | 4/2001 |
| WO | WO 2001/025793 | 4/2001 |
| WO | WO 2002/004522 | 1/2002 |
| WO | WO 2002/072799 A | 9/2002 |
| WO | WO 2002/083262 A | 10/2002 |
| WO | WO 2003/066820 | 8/2003 |
| WO | WO 2003/104273 | 12/2003 |
| WO | WO 2004/034966 A2 | 4/2004 |
| WO | WO 2004/035619 | 4/2004 |
| WO | WO 2004/098645 | 11/2004 |
| WO | WO 2005/045436 A | 5/2005 |
| WO | WO 2005/105129 | 11/2005 |
| WO | WO 2006/002382 | 1/2006 |
| WO | WO 2006/016247 | 2/2006 |
| WO | WO 2006/093524 | 9/2006 |
| WO | WO 2007/008300 | 1/2007 |
| WO | WO 2007/017556 A | 2/2007 |
| WO | WO 2007/097934 | 8/2007 |
| WO | WO 2007/098254 | 8/2007 |
| WO | WO 2007/099387 | 9/2007 |
| WO | WO 2007/099446 | 9/2007 |
| WO | WO 2007/150020 | 12/2007 |
| WO | WO 2008/063849 | 5/2008 |
| WO | WO 2009/019317 | 2/2009 |
| WO | WO 2009/056332 | 5/2009 |
| WO | WO 2009/078796 | 6/2009 |
| WO | WO 2009/086552 | 7/2009 |
| WO | WO 2010/045518 | 4/2010 |
| WO | WO 2010/060155 | 6/2010 |
| WO | WO 2010/076517 | 7/2010 |
| WO | WO 2010/085509 | 7/2010 |
| WO | WO 2011/012715 | 2/2011 |
| WO | WO 2011/051346 | 5/2011 |
| WO | WO 2011/086143 | 7/2011 |
| WO | WO 2011/092715 | 8/2011 |
| WO | WO 2012/021512 | 2/2012 |
| WO | WO 2012/057671 | 5/2012 |
| WO | WO 2012/083185 | 6/2012 |
| WO | WO 2012/112690 | 8/2012 |
| WO | WO 2012/167088 | 12/2012 |
| WO | WO 2013/121296 | 8/2013 |
| WO | WO 2013/160865 | 10/2013 |
| WO | WO 2014/011465 | 1/2014 |
| WO | WO 2014/023709 | 2/2014 |
| WO | WO 2014/052545 | 4/2014 |
| WO | WO 2014/135528 | 9/2014 |
| WO | WO 2014/169255 | 10/2014 |
| WO | WO 2015/140648 | 9/2015 |
| WO | WO 2015/157595 | 10/2015 |
| WO | WO 2015/171863 | 11/2015 |
| WO | WO 2015/175957 | 11/2015 |
| WO | WO 2016/022971 | 2/2016 |
| WO | WO 2016/044655 | 3/2016 |
| WO | WO 2016/044661 | 3/2016 |
| WO | WO 2016/070050 | 5/2016 |
| WO | WO 2016/210447 | 12/2016 |

(56) References Cited

FOREIGN PATENT DOCUMENTS

| WO | WO 2017/023779 | 2/2017 |
|---|---|---|
| WO | WO 2017/025889 | 2/2017 |
| WO | WO 2017/041053 | 3/2017 |
| WO | WO 2017/046652 | 3/2017 |
| WO | WO 2017/058996 | 4/2017 |
| WO | WO 2017/066484 | 4/2017 |
| WO | WO 2017/109134 | 6/2017 |
| WO | WO 2017/112899 | 6/2017 |
| WO | WO 2017/139498 | 8/2017 |
| WO | WO 2017/139787 | 8/2017 |
| WO | WO 2017/192785 | 11/2017 |
| WO | WO 2017/192786 | 11/2017 |

OTHER PUBLICATIONS

"EPFL School of Life Sciences—Annual Report SV 2011," 156 Pages (Dec. 31, 2011).

"SubName: Full=Phosphate ABC Transporter, Inner Membrane Subunit PstC;", XP002717162, Retrieved From EBI Accession No. UNIPROT:C7QKI6, Database Accession No. C7QKI6 (Oct. 13, 2009).

"SubName: Full=Putative Integron Gene Cassette Protein; Flags: Fragment", XP002717159, Retrieved From EBI Accession No. UNIPROT:B0BIT0, Database Accession No. B0BIT0 (Feb. 26, 2008).

"SubName: Full=Putative Transcriptional Regulator, ArsR Family;", XP002717163, Retrieved From EBI Accession No. UNIPROT:D2RZT2, Database Accession No. D2RZT2 (Mar. 2, 2010).

"SubName: Full=Putative Uncharacterized Protein;", XP002717158, Retrieved From EBI Accession No. UNIPROT: C0NJE0, Database Accession No. CONJE0 (May 5, 2009).

"SubName: Full=Putative Uncharacterized Protein;", XP002717160, Retrieved From EBI Accession No. UNIPROT:B9PUP0, Database Accession No. B9PUP0 (Mar. 24, 2009).

"SubName: Full=UncharacterizedProtein;", XP002717157, Retrieved From EBI Accession No. UNIPROT:B5E9K2 Database Accession No. B5E9K2 (Oct. 14, 2008).

Ahmed et al., "Carbohydrate-based materials for targeted delivery of drugs and genes to the liver." Nanomedicine (Lond.) (205) 10(14), 2263-2288.

Albert et al., "Immature dendritic cells phagocytose apoptotic cells Via vl35 and CD36, and cross-present antigens to cytotoxic T lymphocytes," Journal of Experimental Medicine, vol. 188(7): 1359-1368 (Oct. 5, 1998).

Andre et al., "Determination of modulation of ligand properties of synthetic complex-type biantennary N-glycans by introduction of bisecting GlcNAc in silico, in vitro and in vivo" Eur. J. Biochem. 2004;271(1):118-134.

Arnaboldi et al., "Suppression of Th 1 and Th17, but not Th2, responses in a CD8+ T cell-mediated model of oral tolerance," Mucosal Immunology, vol. 2(5):427-438 (Sep. 2009).

Bailon et al., "Rational design of a potent, long-lasting form of interferon: A 40 kDa branched polyethylene glycol-conjugated interferon-2a for the treatment of hepatitis C," Bioconjugate Chemistry, vol. 12(2):195-202 (2001).

Bielekova et al., "Expansion and Functional Relevance of High-Avidity Myelin-Specific CD4 T Cells in Multiple Sclerosis," J Immunol 2004; 172:3893-3904.

Bigbee et al., "Binding specificities of eight monoclonal antibodies to human glycophorin A—studies with McM, and MkEn(UK) variant human erythrocytes and M- and MNv-type chimpanzee erythrocytes," Dec. 1, 1984, J. Immunol., 133(6): 3149-3155 (1984).

Blancher et al., "Reactivity of anti-glycophorin monoclonal antibodies (Mabs) in tests with red cells of non-human primates," Jan. 1, 1997, Transfus Clin Biol 4, 81-85 (1997).

Brack et al., "Tumor-ta rgeting properties of novel antibodies specific to the large isoform of tenascin-C," Clinic Cancer Research, vol. 12(10):3200-3208 (May 15, 2006).

Bursch et al., "Langerhans cells are not required for the COB T cell response to epidermal self-antigens," Journal of Immunology, vol. 182(8):4657-4664 (Apr. 15, 2009).

Cao et al., "Molecular Beacon Aptamers for Protein Monitoring in Real-Time and in Homogeneous Solutions," Current Proteomics, 2:31-401, (2005).

Chasis et al., "Signal Transduction by Glycophorin A: Role of Extracellula Rand Cytoplasmic Domains in a Modulatable Process", The Journal of Cell Biology, 107:1351-1357, (Oct. 1988).

Chiarantini et al., "Red Blood Cells as DeliveRy System for Recombinant HSV-1 Glycoprotein B: Immunogenicity and Protection in Mice," Vaccine, 15(3):276-280, (1997).

Coulstock et al., "Liver-targeting of interferon-alpha with tissue-specific domain antibodies" PLOS One, Public Library of Science, US, vol. 8, No. 2, Jan. 1, 2013.

Craig et al., "Processing of C3b-Opsonized Immune Complexes Bound to Non-Complement Receptor 1 Sites on Red Cells: Phagocytosis, Transfer and Associations with CR1," J. Immunol.

Crispe et al., "Cellular and molecular mechanisms of liver tolerance," Immunol Rev., 213: 101-118 (2006).

Dane et al., "Isolation of cell specific peptide ligands using fluorescent bacterial display libraries-" Journal of Immunological Methods, vol. 309(1-2):120-129, (Jan. 2006).

Darrah et al., "IL-10 production differentially influences the magnitude, quality, and protective capacity of Th1 responses depending on the vaccine platform," Journal of Experimental Medicine, vol. 207(7):1421-1433 (2010).

Dennis et al.,"Albumin Binding as a General Strategy forImproving the Pha rmacokinetics of Proteins-" Journal of Biological Chemistry, vol. 277(38):35035-35043 (Sep. 20, 2002).

Devalapally et al., "Poly(ethylene oxide)-modified Poly(beta-amino ester) Nanoparticles as a pH-sensitive System for Tumor-targeted Delivery of Hydrophobic Drugs: Part 3. Therapeutic Efficacy and Safety Studies in Ovarian CanceRXenog Raft Model," Cancer Chemotherapy Pharmacology, 59:477-484, (2007).

Dhalluin et al.,"Structural and biophysical characterization of the 40 kDa PEG-interferon-2a and its individual positional isomers," Bioconjugate Chemistry, vol. 16(3):504-517 (2005).

Di Lorenzo et al., "Translational Mini-Review Series on Type 1 Diabetes: Systemic analysis of T cell epitopes in autoimmune diabetes," 2007, Clin Exp Immunol, vol. 148: 1-146.

Dienst et al., "Specific occlusion of mu rine and human tumor vasculature by VCAM-1-targeted recombinant fusion proteins," Journal of The National Cancer Institute, vol. 97(10):733-747, (2005).

Dieterich et al., "Identification of Tissue Transglutaminase as the Autoantigen of Celiac Disease," Nature Medicine vol. 3 p. 797-801 (1997).

Ducan, R. Development of HPMA copolymer-anticancer conjugates: Clinical experience and lessons learnt. Advanced Drug Delivery Reviews 61 (2009) pp. 1131-1148.

Ferguson et al., "Armed response: How dying cells influence T-cell functions," Immunology Review, vol. 241 (1 ):77-88 (May 2011 ).

Fife et al.,"Insulin-induced remission in new-onset NOD mice is maintained by the PD-1-PD-L 1 pathway," The Journal of Experimental Medicine, vol. 203(12):2737-2747, (Nov. 27, 2006).

Fishburn,"The pharmacology of PEGylation: balancing PD with PK to generate novel therapeutics," Journal of Pharmaceutical Sciences vol. 97(10):4167-4183 (Oct. 10, 2008).

Fonsatti et al.,"Targeting cancer vasculature via endoglin/CD105: A novel antibody-based diagnostic and therapeutic strategy in solid tumours," Cardiovascular Research, vol. 86(1):12-19, (2010).

Gadaleta et al.,"Trans-arterial chemoembolization as a therapy for liver tumours: New clinical developments and suggestions for combination with angiogenesis inhibitors," Critical Reviews in Oncology/Hematology, vol. 80:40-53 (2011).

Gao et al., "In situ growth of a stoichiometric PEG-like conjugate at a protein's N-terminus with significantly improved pharmacokinetics-" Proceedings of the National Academy Sciences vol. 106(36): 15231-15236 (Sep. 8, 2009).

Getts et al., "Have We Overestimated the Benefit of Human(ized) Antibodies?" Landes Bioscience, 2(6):682-694, (Nov./Dec. 2010).

(56) References Cited

OTHER PUBLICATIONS

Geng et al., "Site-directed conjugation of "clicked" glycopolymers for form glycoprotein mimics: binding to mammalian lectin and induction of immunological function." J Am Chem Soc. Dec. 12, 2007;129(49):15156-63.

Getz et al., "Protease-Resistant Peptide Ligands From a Knottin Scaffold Library," ACS Chemical Biology, 8 Pages, (May 26, 2011).

Godsel et al., "Prevention of autoimmune myocarditis through the induction of antigen-specific peripheral immune tolerance-" Circulation vol. 103(12):1709-1714 (2001).

Gorovits et al., "Proposed mechanism of off-target toxicity for antibody-drug conjugates driven by mannose receptor uptake," Cancer Immunol Immunother (2013) 62:217-233.

Gorzelany et al., "Protein replacement therapies for rare diseases: a breeze for regulatory approval?" Science Translational Medicine 5, 178fs10 (2013).

Green et al.,"Immunogenic and tolerogenic cell death," National Review of Immunology vol. 9(5):353-363, (May 2009).

Grimm et al., "Memory of tolerance and induction of regulatory T cells by erythrocyte-targeted antigens." Scientific Reports, 5:159907.

Gupta et al., "Expression, purification, and characterization of an anti-RBCFab-p24 fusion protein for hemagglutination-based rapid detection of antibodies to HIV in whole blood." Protein Expression and Purification 26 (2002) 162-170.

Hackel et al., "Picomolar affinity fibronectin domains engineered utilizing loop length diversity, recursive mutagenesis, and loop shuffling," Journal of Molecular Biolology, vol. 381(5):1238-1252, (Sep. 19, 2008).

Hall et al., "Identification of peptide ligands facilitating nanoparticle attachment toerythrocytes," Biotechnology Progess, vol. 23(3):749-754 (2007).

Hasselberg et al, "ADP-ribosylation controls the outcome of tolerance or enhanced priming following mucosal immunization" The Journal of Immunology, Aug. 24, 2016.

Holz et al., "CD8+ T cell tolerance following antigen recognition on hepatocytes," Journal of Autoimmunity, vol. 34 (1):15-22 (2010).

Huang et al., "Characterization of poly(ethylene glycol) and PEGylated products by LC/MS with postcolumn addition of amines," Analytical Chemistry, vol. 81(2):567-577 (Jan. 15, 2009).

Huang et al.,"Tumor infarction in mice by antibody-directed targeting of tissue factor to tumor vasculature," Science, vol. 275(5299):547-550 (Jan. 24, 1997).

Ichikawa et al., "Hepatic stellate cells function as regulatory bystanders," Journal of Immunology, vol. 186 (10):5549-5555 (May 15, 2011).

International Search Report and Written Opinion from corresponding PCT Application No. PCT/IB2013/000684, 12 pages, dated Jul. 9, 2013.

International Search Report for Application No. PCT/EP2014/054161 dated May 26, 2014.

International Search Report and Written Opinion from corresponding PCT Application No. PCT/US2011/047078, 13 pages, dated May 1, 2012.

Janeway et al., Immuno Biology, 8th Edtition, Garland Science (2012).

Janeway et al., "The complement system and innate immunity," Immunology: the Immune System in Health and Disease, 5th Edition. New York: Garland Science (2001).

Jewett et al., "Cu-free click cycloaddition reactions in chemical biology," Chem Soc Rev. Apr. 2010; 39(4): 1272-1279.

Jones et al., "Localization of Pectic Galactan in Tomato Cell Walls Using a Monoclonal Antibody Specific to (1->4)-β—D-Galactan" Plant Physiol. 1997; 113:1405-1412.

Julyan et al "Preliminary clinical study of the distribution of HPMA copolymers bearing doxorubicin and galactosamine" Journal of Controlled Release 57 (1999) pp. 281-290.

Kim et al "Imaging and therapy of liver fibrosis using bioreducible polyethylenimine/siRNA complexes conjugated with N-acetylglucosamine as a targeting moiety" Biomaterials 34:6504-6514 (2013).

King et al. "Antibody responses to bee melittin (Api m 4) and hornet antigen 5 (Dol m 5) in mice treated with the dominant T-cell Epitope peptides" Journal of Allergy and Clinical Immunology, vol. 101, Issue 3, Mar. 1998, pp. 397-403.

Lehrman et al., "The Binding of Fucose-containing Glycoproteins by Hepatic Lectins" The Journal of Biological Chemistry Jun. 5, 1986; 261, 7426-7432.

Murphy, "Antigen Recognition by B-Cell and T-cell Receptors," 2012, Janeway's Immuno Biology, 8th Edition, Chapter 4, Garland Science Taylor & Francis Goup, London and New York.

Keefe et al.,"Aptamers as therapeutics," Nature Reviews Drug Discovery, vol. 9(7):537-550 (2010).

Kenrick et al., "Bacterial Display Enables Efficient and Quantitative Peptide Affinity Maturation," Protein Engineering Design & Selection, vol. 23(1 ):9-17 (2010).

Khandelwal et al., "Assessment of survival of aging erythrocyte in circulation and attendant changes in size and CD147 expression by a novel two step biotinylation method," Experimental Gerontology, vol. 41(9):855-861 (Aug. 4, 2006).

Kim Et El., "Specific Binding of Glucose-derivatized Polymers to the Asialoglycoprotein Receptor of Mouse Primary Hepatocytes." The Journal of Biological Chemistry, vol. 276, No. 38, pp. 35312-35319, Sep. 21, 2001.

Kina et al.,"The Monoclonal Antibody TER-119 Recognizes a Molecule Associated with Glycophorin A and Specifically Marks the Late Stages of Murine Erythroid Lineage," British Journal of Haematolgy, vol. 109:280-287 (2000).

Kopecek et al. "HPMA copolymers: Origins, early developments, present, and future." Advanced Drug Delivery Reviews 62, (2010) pp. 122-149.

Kontos et al., "Engineering antigens for in situ erythrocyte binding induces T-cell deletion," PNAS, 2013, vol. 110, no. 1, p. E60-E68.

Kontos et al., "Improving Protein Pharmacokinetics by Engineering Erythrocyte Affinity," Molecular Pharmaceutics, 2010, vol. 7, No. 6, p. 2141-2147.

Kontos, "Improving Protein Pharmacokinetics by Engineering Erythrocyte Affinity", 1 Page, (2010) (Abstract Only).

Kontos, "Engineering Erythrocyte Affinity for Improved Pharmacokinetics and Immune Tolerogenesis", Thesis, 106 Pages (Jun. 23, 2011).

Kravtzoff et al., "Tolerance Evaluation of L-asparaginase loaded in red blood cells," 1996, Eur J Clin Pharmacol, vol. 51: 221-225.

Krebber et al., "Reliable Cloning of Functional Antibody Variable domains from Hybridomas and Spleen Cell Repertoires Employing a Reengineered Phage Display System," Journal of Immunological Methods, vol. 201 :35-55 (1997).

La Rosa, et al., "The Innate Immune System in Allograft Rejection and Tolerance," J. Immunol., 2007, 178:7503-7509.

Langer et al., "Optimization of the Rreparation Process for Human Serum Albumin (HSA) Nanoparticles," International Journal of Pharmaceutics, 257:169-180, (2003).

Lee et al., "Aptamers as Molecular Recognition Elements for Electrical Nanobiosensors," Analytical and Bioanalytical Chemistry, 390:1023-1032, (2008).

Lee et al., "Signaling pathways downstream of pattern—recognition receptors and their cross talk," Annual Review of Biochemistry, vol. 76:447-480 (Feb. 28, 2007).

Lepenies et al., "Targeting C-type lectin receptors with multivalent carbohydrate ligands." Adv. Drug Deliv. Rev. (2013).

Li et al., "Targeting self- and foreign antigens to dendritic cells via DC-ASGPR generates IL-10pproducing suppressive CD4+ T cells," Jan. 2, 2012, Journal of Experimental Medicine 209, 109-121 (2012).

Liu et al.,"Immune tolerance after delivery of dying cells to dendritic cells in situ," Journal of Experimental Medicine, vol. 196(8): 1091-1097 (Oct. 21, 2002).

Liu et al.,"Functional Nucleic Acid Sensors", Chemical Reviews, 109(5):1948-1998, (May 2009).

Liu et al. "Hapten may play an important role in food allergen-related intestinal immune inflammation," North American Journal of Medical Sciences, vol. 3. No. 3. (Mar. 2011).

Lorentz et al., "Engineered binding to erythrocytes induces immunological tolerance to E. coli asparaginase." Sci. Adv. 2015.

(56) References Cited

OTHER PUBLICATIONS

Luo et al., "ECDI-fixed allogeneic splenocytes induce donor-specific tolerance for long-term survival of islet transplants via two distinct mechanisms," Proceedings of National Academy of Science, vol. 105(38):14527-14532 (Sep. 23, 2008).
Lutolf et al.,"Synthesis and Physicochemical Characterization of End-Linked Poly(ethylene glycol)-co-peptide Hydrogels Formed by Michael-Type Addition," Biomacromolecules, 4:713-722, (Feb. 1, 2003).
Lutolf et al.,"Systematic modulation of Michael-type reactivity of thiols through the use of charged amino acids," Bioconjugate Chemistry vol. 12(6):1051-1056 (2001).
Lutterotti, A. et al., "Antigen-Specific Tolerance by Autologous Myelin Peptide-Coupled Cells: A Phase 1 Trial in Multiple Sclerosis," Science Translational Medicine 5, 188ra75-188ra75 (2013).
Magnani et al., "Red blood cells as an antigen-delivery system," Biotechnol Appl Biochem. Oct. 1992;16(2):188-94.
Maluccio et al., "Transcatheter arterial embolization with only particles for the treatment of unresectable hepatocellular carcinoma-" Journal of Vascular and Interventional Radiology, vol. 19(6):862-869 (2008).
Manidyala, S. et al, "Glycomimetic ligands for the human asialoglycoprotein receptor" J. Am Chem. Soc. Feb. 1, 2012, 134(4), pp. 1978-1981.
Maynard et al., "Antibody engineering," Annual Review of Biomedical Engineering, vol. 2:339-376 (2000).
Meager et al., "Anti-cytokine autoantibodies in autoimmunity: preponderance of neutralizing autoantibodies against interferon-alpha, interferon-omega and interleukin-12 in patients with thymoma and or myasthenia gravis" Clinical and Experimental Immunology, Wiley-Blackwell Publishing Ltd, GB, vol. 132, No. 1, Apr. 1, 2003.
Medina et al., "Targeting hepatic cancer cells with pegylated dendrimers displaying N-acetylgalactosamine and SP94 peptide ligands" Advanced Healthcare Materials, vol. 2, Issue 10, pp. 1337-1350, Oct. 2013.
Miller et al.,"Antigen-specific tolerance strategies for the prevention and treatment of autoimmune disease," Nature Reviews Immunology 7(9):665-677, (Sep. 2007).
Moghimi et al.,"Stealth liposomes and long circulating nanoparticles: critical issues in pharmacokinetics, opsonization and protein-binding properties," Progress in Lipid Research, vol. 42(6):463-478 (2003).
Mohandas et al.,"Red cell membrane: past, present, and future," Blood, vol. 112(10):3939-3948(Nov. 15, 2008).
Mueller,"Mechanisms maintaining peripheral tolerance," Nature Immunology, vol. 11(1):21-27 (Jan. 2010).
Murray et al.,"The Mouse Immune Response to Carrier Erythrocyte Entrapped Antigens," Vaccine, 24:6129-6139, (2006).
Muzykantov, "Drug Delivery by Red Blood Cells: Vascular Carriers Designed by Mother Nature", Expert Opinion Drug Delivery, 7(4):403-427, (Apr. 2010).
Nardin et al., "How are immune complexes bound to the primate erythrocyte complement receptor transferred to acceptor phagocytic cells," Mol. Immunol.
Nishikawa et al. "Galactosylated proteins are recognized by the liver according to the surface density of galactose moieties" The American journal of physiology Jun. 1995; 268(5 Pt 1):G849-56, Abstract.
O'Neil et al., "Extracellular matrix binding mixed micelles fordrug delivery applications," Journal of Control Release, vol. 137(2):146-151, (Mar. 27, 2009).
Parmeggiani et al., "Designed armadillo repeat proteins as general peptide-binding scaffolds: consensus design and computational optimization of the hydrophobic core," Journal of Molecular Biology, vol. 376(5):1282-1304 (2008).
Pasut et al.,"PEG conjugates in clinical development oruse as anticancer agents: An overview," Advanced Drug Delivery Reviews, vol. 61(13):1177-1188 (2009).
Qin, et al., Preparation and bioactivity of anti-hum red blood cell ScFv and CSFV E@ bifunctional fusion protein, Chin J. Biotech Jan. 25, 2010: 26(1): 28-34, Chinese Journal of Biotechnology (2010).
Reddy et al., "Exploiting lymphatic transport and complement activation in nanoparticle vaccines," Nature Biotechnology, vol. 25(10):1159-1164 (Oct. 2007).
Reddy et al., "In vivo targeting of dendritic cells in lymph nodes with poly(propylene sulfide) nanoparticles," Journal of Controlled Release, vol. 112(1):26-34, (Mar. 10, 2006).
Reinagel et al., "The Primate Erythrocyte Complement Receptor (CR1) as a Priveleged Site: Binding of Immunoglobulin G to Erythrocyte CR1 Does Not Target Erythrocytes for Phagocytosis," 1997, Blood, vol. 89: p. 1068-1077.
Rice et al., "Directed evolution of a biterminal bacterial display scaffold enhances the display of diverse peptides," Protein Engineering, Design & Selection, vol. 21(7):435-442 (2008).
Rigopoulou et al., "Asialoglycoprotein receptor (ASGPR) as target autoantigen in liver autoimmunity: Lost and found," Autoimmunity Reviews, 12 (2012) 260-269.
Rockey et al., "Synthesis and radiolabeling of chelator-RNA aptamerbioconjugates with copper-64 for targeted molecular imaging-" Bioorganic & Medicinal Chemistry, vol. 19(13):4080-4090 (2011).
Ruoslahti et al., "Targeting of drugs and nanoparticles to tumors," Journal of Cell Biology, vol. 188(6):759-768 (2010).
Rybak et al., "The extra-domain A of fibronectin is a vascular marker of solid tumors and metastases," Cancer Research, vol. 67(22):10948-10957 (2007).
Saibeni et al., "Antibodies to tissue-type plasminogen activator (t-PA) in patients with inflammatory bowel disease: high prevalence, interactions with functional domains oft-PA and possible implications in thrombosis," J. Thrombosis and Haemostasis, 4:1510-1516 (2006).
Saint-Lu, N. et al., "Targeting the allergen to oral dendritic cells with mucoadhesive chitosan particles enhances tolerance induction," Allergy, vol. 64(7):1003-1013 (2009).
Sakaguchi et al., "Regulatory T Cells and Immune Tolerance," Cell 133, May 30, 2008, 775-787.
Sampson, "Aptamers and SELEX: the technology," World Patent Information, vol. (25):123-129 (2003).
Savla et al., "Tumor targeted quantum dot-mucin 1 aptamer-doxorubicin conjugate for imaging and treatment of cancer," Journal of Controlled Release, vol. 153(1):16-22, Feb. 20, 2011.
Schliemann et al., "In vivo biotinylation of the vasculature in B-cell lymphoma identifies BST-2 as a target for antibody-based therapy," Vascular Blood, vol. 115(3):736-744 (Jan. 21, 2010).
Sehon et al., "Conversion of Antigens to Tolerogenic Derivatives by Conjugation with Monomethoxypolyethylene Glycol", The Pharmacology and Toxicology of Proteins, pp. 205-219 (1987).
Sehon et al., The Pharmacology and Toxicology of Proteins, Proceedings of Cetus—UCLA Symposium Held at Lake Tahoe, CA, Feb. 21-28, 1987, Alan r. Liss, Inc.—New York.
Seymour et al., "Hepatic Drug Targeting: Phase I evaluation of polymer-bound doxorubicin" Journal of Clinical Oncology, vol. 20, No. 6, Mar. 15, 2002, pp. 1668-1676.
Seymour et al., "N-(2-Hydroxypropyl)methacrylamide copolymers targeted to the hepatocyte galactose-receptor: pharmacokinetics in DBA2 mice." Br. J. Cancer (1991) 63, pp. 859-866.
Shan et al., "Structural Basis for Gluten Intolerance in Celiac Sprue," Science, 297, 2275 (2002).
Sheridan "Fresh from the biologic pipeline-2009," Nature Biotechnology, vol. 28(4):307-310 (Apr. 2010).
Silverman et al., "Engineered cystine-knot peptides that bind $v\beta3$ integrin with antibody-like affinities," Journal of Molecular Biology, vol. 382(4):1064-1075 (Jan. 30, 2009).
Sørensen et al., "Role of sialic acid for platelet life span: exposure of $\beta$-galactose results in the rapid clearance of platelets from the circulation by asialoglycoprotein receptor-expressing liver macrophages and hepatocytes." Blood, Aug. 20, 2009. vol. 114, No. 8.
Spitzer et al., "ScFv-Mediated in Vivo Targeting of DAF to Erythrocytes Inhibits Lysis by Complement," Molecular Immunology, vol. 40:911-919 (Oct. 30, 2003).

(56) References Cited

OTHER PUBLICATIONS

St. Clair et al., "New Reagents on the Horizon for Immune Tolerance," Sep. 20, 2006, Annu. Rev. Med. 2007. 58:329-46.
Staud et al., "Liver uptake and hepato-biliary transfer of galactosylated proteins in rats are determined by the extent of galactosylation" Biochimica et Biophysica Acta May 1999; 1427(2):183-192, Abstract.
Steiner et al., "Efficient selection of DARPins with sub-nanomolar affinities using SRP phage display," Journal of Molecular Biology, vol. 382(5):1211-1227 (2008).
Sun, et al, "Comparison between Ovalbumin and Ovalbumin Peptide 323-339 Responses in Allergic Mice: Humoral and Celluler Aspects," Scandinavian Journal of Immunology, vol. 71: 329-335 (Jan. 2010).
Supplementary European Search Report from corresponding PCT Application No. PCT/US2011047078, 21 Pages, dated Jan. 22, 2014.
Taneja et al., "Lessons from animal models for human autoimmune diseases," Sep. 1, 2001, Nature Immunology, vol. 2, No. 9, 781-784 (Sep. 2001).
Taylor et al., "Anti-glycophorin single-chain Fv fusion to low-affinity mutant erythropoietin improves red blood cell-lineage specificity", Protein Engineering, Design & Selection, vol. 23, No. 4 pp. 251-260, 2010.
Trahtenherts, A. et al, "An internalizing antibody specific for the human asialoglycoprotein receptor" Hybridoma, vol. 28, No. 4, Aug. 1, 2009.
Thijssen et al., "Galectin-1 is essential in tumor angiogenesis and is a target for antiangiogenesis therapy-", Proceeding of the Natinoal Academy Sciences, vol. 103(43):15975-15980 (2006).
Thomson et al., "Antigen-presenting cell function in the tolerogenic liver environment," National Reviews Immunology, vol. 10(11):753-766 (Nov. 2010).
Tobio et al., "Stealth PLA-PEG Nanoparticles as Protein Carriers for Nasal Administration," Pharmaceutical Research, 15(2):270-275, (1998).
Turley et al., "Prospects for Antigen-Specific Tolerance Based Therapies for the Treatment of Multiple Selerosis," Results and Problems in Cell Differentiation, 51 :217-235, (2010).
Updike et al., "Infusion of red blood cell-loaded asparaginase in monkey: Immunologic, metabolic, and toxicologic consequences," 1983, J Lab Clin Med, vol. 101(5): p. 679-691.
USPTO Office Action dated Oct. 30, 2013 for U.S. Appl. No. 13/206,304.
Van Der Vlies et al., "Synthesis of pyridyl disulfide-functionalized nanopa rticles for conjugating thiol-containing small molecules, peptides, and proteins," Bioconjugate Chemistry, vol. 21(4):653-662 (2010).
Velluto et al., "PEG-b-PPS Diblock Copolymer Aggregates for Hydrophobic Drug Solubilization and Release: Cyclosporin A as an Example," Molecular Pharmaceutics, 11 Pages, (May 2, 2008).
Vogl et al., "Review on transarterial chemoembolization in hepatocellular carcinoma: Palliative, combined, neoadjuvant, bridging, and symptomatic indications," European Journal Radiology, vol. 72(3):505-516 (2009).
Walker et al., "Anti-serum albumin domain antibodies in the development of highly potent, efficacious and long-acting interferon," Protein Engineering Design & Selection, vol. 23(4):271-278 (2010).
Wan, "Regulatory T cells: immune suppression and beyond," May 1, 2010, Cell Mol Immunol. May 2010; 7(3):204-210.
Weisser et al., "Applications of single-chain variable fragment antibodies in therapeutics and diagnostics," Biotechnology Advances, vol. 27(4):502-520 (2009).

Wilson et al., "Rapid Whole Blood Assay for HIV-1 Seropositivity Using An Fab-Peptide Conjugate," Journal of Immunological Methods, vol. 138:111-119 (1991).
Yamazaki et al., "CD8+ CD205+ splenic dendritic cells are specialized to induce Foxp3+ regulatory T cells," Journal of Immunology, vol. 181(10):6923-6933 (2008).
Yoo et al., "N-Acetylgalactosamino dendrons as clearing agents to enhance liver targeting of model antibody-fusion protein." Bioconjugate Chemistry, vol. 24, No. 12, Dec. 18, 2013, pp. 2088-2103.
Zaitsev et al., "Targeting of a Mutant Plasminogen Activator to Circulating Red Blood Cells for Prophylactic Fibrinolysis", The Journal of Pharmacology and Experimental Therapeutics, 332(3):1022-1031 and 976 (Nov. 30, 2009).
Zhao, X. et al "Construction and characterization of an anti-asialoglycoprotein receptor single-chain variable-fragment-targeted melittin" Biotechnol Appl. Biochem, Nov.-Dec. 2011; 58(6): pp. 405-411.
Zhong et al., Biomacromalecules 14:3723-3730 (2013).
Wang et al., J Polymer Sci. 49:3280-3290 (2011).
Qin et al., Bioconjugate Chem. 22:1503-1512 (2011).
Dornmair Klaus et al: "T-cell-mediated autoimmunity: Novel techniques to characterize autoreactive T-cell receptors", American Journal of Pathology, vol. 163, No. 4, Oct. 2003 (Oct. 2003-10), pp. 1215-1226, ISSN: 0002-9440.
Ciccocioppo, R. et al, "The immune recognition of gluten in coeliac disease", British Society for Immunology, Clinical and Experimental Immunology, Feb. 1, 2005, pp. 408-416.
Granoff et al., "A Novel Mimetic Antigen Eliciting Protective Antibody to Neisseria meningitidis" J Immunol 2001; 167:6487-6496.
"Integer", Meriam-Webster, available online at https://www.merriam-webster.com/dictionary/integer, 12 pages (2019) (Year: 2019).
Immunogenic, Definition of Immunogenic by Merriam-Webster, https://www.merriam-webster.com/dictionary/immunogenic[May 10, 2019 11:59:27 AM], retrieved on May 10, 2019, in 9 pages.
Mamidyala, et al., "Glycomimetic Ligands for the Human Asialoglycoprotein Receptor", Journal of the American Chemical Society, Jan. 24, 2012, vol. 134, p. 1978-1981.
Kontos, S: "Engineering Erythrocyte Affinity for Improved Pharmacokinetics and Immune Tolerogenesis", Thesis Ecole polytechnique federale de Lausanne EPFL , Jun. 23, 2011, 106 pages.
Loma et al., "Multiple Sclerosis: Pathogenesis and Treatment" Department of Neurology, Curr. NeuropharmacOLOGY, 9:409-416, Year 2011.
Meyer et al. Metformin and Insulin in Type 1 Diabetes; Diabetes Care 26:1655-1656, Year: 2003.
Moreau et al, "PEPOP: Computational design of immunogenic peptides" BioMed Central, Jan. 30, 2008, 15 pages.
Folgori A et al: "A general strategy to identify mimotopes of pathological antigens using only random peptide libraries and huamn sera", EMBO (European Molecular Biology Organization) Journal, vol. 13, No. 9, May 1, 1994 (May 1, 1994), pp. 2236-2243, ISSN: 0261-4189.
Seamons et al. Immune Tolerance to Myelin Proteins (Immunologic Research 2003; 28/3:201-221).
Teitelbaum et al., Immunomodulation of experimental autoimmune encephalomyelitis by oral administration of copolymer 1. Pro. Natl. Acad. Sci. USA vol. 96, pp. 3842-3847, Mar. 1999.
Tye-Din, et al. "Comprehensive, Quantitive Mapping of T Cell Epitopes in Gluten in Celiac Disease", www.ScienceTranslationalMedicine.org, Jul. 21, 2010, vol. 2 Issue 41, in 14 pages.
Yeste Ada et al: "Antigen Microarrays for the Study of Autoimmune Diseases", Clinical Chemistry, vol. 59, No. 7, Jul. 2013 (Jul. 2013), pp. 1036-1044, ISSN: 0009-9147(print).

A

B    C

ANTIGEN-SPECIFIC TOLERANCE AND COMPOSITIONS FOR INDUCTION OF SAME

CROSS REFERENCE TO RELATED APPLICATIONS

This application is a continuation of U.S. patent application Ser. No. 15/232,724, filed Aug. 9, 2016, which is a continuation of U.S. patent application Ser. No. 13/397,202, filed Feb. 15, 2012, which is a continuation-in-part of U.S. Ser. No. 13/206,034 filed Aug. 9, 2011 that claims priority to US provisional patent application U.S. Ser. No. 61/372,181 filed Aug. 10, 2010, which are hereby incorporated by reference herein.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is ANOK001P1C6_ST25.txt, the date of creation of the ASCII text file is Feb. 23, 2018, and the size of the ASCII text file is 32.7 KB. The information in the electronic format of the Sequence Listing is incorporated herein by reference in its entirety.

TECHNICAL FIELD OF THE INVENTION

The Technical Field relates to medical compositions and uses for ligands or antibodies that bind erythrocytes. Specific uses include immunotolerization, drug delivery, and cancer therapies.

BACKGROUND

The rejection of transplanted tissue and autoimmune diseases are pathological conditions that involve an immunorejection of a foreign biomolecule because of its antigenic nature. Many drugs and clinical processes are involved in suppressing or treating immunorejection. Vaccines take advantage of this process by stimulating an immune response to antigens on pathogenic biomolecules to build up the immune system response against proteins or other biomolecules that carry the antigen.

SUMMARY OF THE INVENTION

Tolerogenesis is a process of creating immunological tolerance to a substance. A patient, either human or non-human, that is treated to create tolerance of a substance will have a reduced adapative immune response to the substance. The reduction in an adaptive immune response can be measured by analyzing the amounts of circulating antibodies reactive to the substance, or by analyzing T-cell reactions to the substance and tolerizing agent. Compositions and methods for tolerization are provided herein. Many of the embodiments involve administering a fusion molecule that has a tolerizing antigen combined with an erythrocyte binding moiety. The fusion molecule binds to erythrocytes and begins a process of presenting the tolerizing antigen to the immune system in a manner that creates tolerance.

Peptides that specifically bind to erythrocytes (also known as red blood cells) have been discovered. These peptide ligands are erythrocyte-binding moieties that bind specifically to erythrocytes even in the presence of other factors present in blood. These ligands may be used in a variety of ways. One embodiment involves forming a molecular fusion of the ligand with a therapeutic agent. The ligand binds the erythrocytes in the body and the therapeutic agent is thus attached to the erythrocytes and circulates with them. Erythrocytes circulate in the bloodstream for prolonged periods of time, about 90 to 120 days in man, and they access many body compartments related to disease, such as tumor vascular beds, and physiology, such as the liver and the spleen. These features can be used to make the erythrocyte useful in therapeutic delivery, for example in prolonging the circulation of a therapeutic agent in the blood.

It has unexpectedly and surprisingly been found that these erythrocyte affinity ligands, or comparable antibodies, can be used to create immunotolerance. In this embodiment, a molecular fusion is made that comprises a tolerogenic antigen and an erythrocyte affinity ligand. The fusion is injected or otherwise administered in sufficient amounts until tolerance is observed. In contrast, prior reports have stated that immunorejection is created by attaching an antigen to a surface of an erythrocyte.

Embodiments are also directed to treating cancer by embolizing tumors. Many antigens for tumors and/or tumor microvasculature are known. Antibodies may readily be made that specifically bind these antigens. Such tumor-binding ligands are molecularly fused to ligands that bind erythrocytes, i.e., antibodies (or fragments thereof) or peptidic ligands. These fusions bind at the tumor site and also bind erythrocytes, causing blockage of blood supply to the tumor. These embodiments and others are described herein.

BRIEF DESCRIPTION OF THE FIGURES

FIG. 6 includes linker sequence GGGGS (SEQ ID NO: 18) that is repeated four times.

DETAILED DESCRIPTION OF PREFERRED EMBODIMENTS

Figure 1:
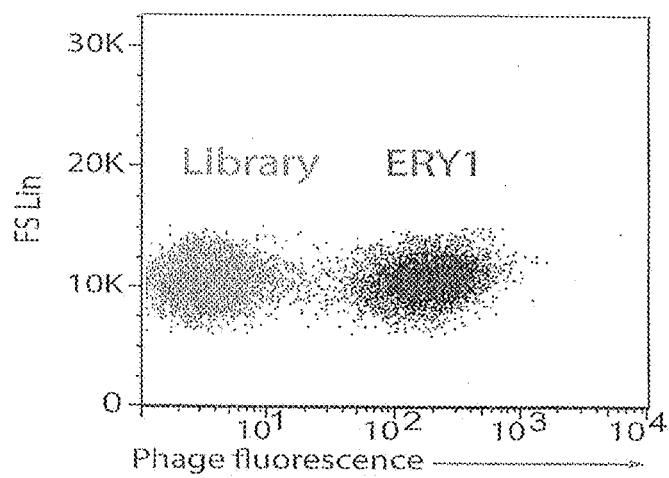
FIG. 1 is a scatter plot of a flow cytometric analysis of erythrocyte binding of ERY1 phage.

Molecular designs are provided for tolerogenesis. The protein or other molecular antigen to which tolerance is sought is formed as a conjugate with an erythrocyte binding moiety. The moiety may comprise a peptide ligand, an antibody, an aptamer, or an antibody fragment. The conjugate, also referred to as a molecular fusion, may be a fusion protein or may involve a linker, e.g., a polymer or polymer micelle or polymer nanoparticle conjugate.

Peptides that specifically bind erythrocytes are described herein. These are provided as peptidic ligands having sequences that specifically bind, or as antibodies or fragments thereof that provide specific binding, to erythrocytes. The peptides may be prepared as molecular fusions with therapeutic agents, tolerizing antigens, or targeting peptides. The therapeutic agents may advantageously have an increased circulating half-life in vivo when they are part of the fusion. Immunotolerance may be created by use of the fusions and choice of an antigen on a substance for which tolerance is desired. The term antigen, in this context, means the full size antigen, an antigenic fragment thereof, or a mimetic of the tolerogenic antigen. Fusions with targeting peptides direct the fusions to the target, for instance a tumor, where the erythrocyte-binding ligands reduce or entirely eliminate blood flow to the tumor by recruiting erythrocytes to the target.

Molecular designs involving erythrocyte binding are thus taught for extending the circulation half life of drugs, including protein drugs. The drug is formed as a conjugate, also referred to as a molecular fusion, for example a recombinant fusion or a chemical conjugate, with the erythrocyte binding ligand. Molecular designs are also taught for tumor embolization. The erythrocyte binding ligand is formed as a conjugate with a ligand for tumor vasculature; targeting to the tumor vasculature thus targets erythrocyte binding within the tumor vasculature.

Peptidic Sequences that Specifically Bind Erythrocytes

Peptides that specifically bind erythrocytes have been discovered. Example 1 describes the discovery of a peptide (ERY1) for specifically binding to an erythrocyte. Example 8 describes the discovery of six peptides (ERY19, ERY59, ERY64, ERY123, ERY141 and ERY162) that bind specifically to human erythrocytes. Example 20 details how peptidic ligands (ERY64, ERY123, and ERY141) were made part of a fusion protein with a fluorescent protein reporter and retained their specific binding properties. An embodiment of the invention is a substantially pure polypeptide comprising an amino acid sequence of ERY1, or one of the human erythrocyte binding peptides, or a conservative substitution thereof, or a nucleic acid encoding the same. Such polypeptides bind specifically erythrocytes and are a ligand for the same. Ligand is a term that refers to a chemical moiety that has specific binding to a target molecule. A target refers to a predetermined molecule, tissue, or location that the user intends to bind with the ligand. Thus targeted delivery to a tissue refers to delivering a molecule or other material such as a cell to the intended target tissue. Accordingly, embodiments include molecules or compositions comprising at least one of the ligands disclosed herein that are used to bind an erythrocyte. The binding activity of a polypeptide to an erythrocyte may be determined simply by following experimental protocols as described herein. Using such methods, the binding strengths of polypeptide variants relative to ERY1 or a human erythrocyte binding peptide under given physiological conditions can be determined, e.g., sequences made using conservative substitutions, addition or removal of flanking groups, or changes or additions for adjusting sequence solubility in aqueous solution.

Peptidic ligands may be generated specifically for one or more of the following targets or group of targets: an erythrocyte surface molecule (protein, glycoprotein), Band 3 (CD233), a glycophorin, more particularly glycophorin A (CD235a), glycophorin B (CD235b), glycophorin C (CD235c) & glycophorin D (CD235d), aquaporin-1, Glut-1, Kidd antigen, RhAg/Rh50 (CD241), Rh (CD240), Rh30CE (CD240CE), Rh30D (CD240D), Kx, Kell (CD238), Duffy/DARC (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, and H antigen (CD173). Erythrocytes cell-surface proteins, either purified preparations or a mixture of them, can be screened for peptidic ligands. Erythrocyte cell-surface proteins may be recombinantly expressed in their full form or as partial domains fused to tags that enhance expression or stability of the protein. The recombinant protein target may then be immobilized on a plate or bead, and used as the affinity target for the library screening process. Erythrocyte cell-surface proteins may also be isolated from cellular preparations of whole blood, from which purified or complex mixtures of membrane proteins may be immobilized on a solid matrix (bead, plate, or other), and used as affinity targets for the screening process. The entire screening process may be performed in the presence of a high concentration of serum albumin (e.g., 50 mg/mL) and at 37° C. to reduce non-specific binding events and to select for peptides with favorable binding characteristics in blood serum. Peptidic ligands are most preferably selected from Band 3 (CD233), glycophorin B (CD235b), glycophorin C (CD235c) and glycophorin D (CD235d).

As detailed in Example 2, peptidic ligands were observed to bind the erythrocyte cell surfaces without altering cell morphology and without cytoplasmic translocation. The ligands distributed across the cell surface and were free of clustering. Specific proteins that were the target of the ligands can be identified, as in Example 3, which identified glycophorin-A (GYPA) as the target of ERY-1. ERY-1 was reactive only with mouse and rat species (Example 4). Peptidic ligands that specifically bound human erythrocytes were specific for human erythrocytes and not other species (Example 9).

A naïve peptide library involving whole erythrocytes was screened to discover affinity partners, rather than screening against a purified erythrocyte cell-surface protein. Through the use of density gradient centrifugation and extensive washing, meticulous care was taken to minimize the number of unbound phage escaping round elimination. Furthermore, selection was halted and clones were analyzed early in the screening process so as to prohibit highly infective phage clones from dominating the population. The entire screening process was performed in the presence of a high concentration of serum albumin (50 mg/mL) and at 37° C. to reduce non-specific binding events and, perhaps more importantly, select for peptides with favorable binding characteristics in blood serum. In a first set of experiments (Example 1) clonal analysis revealed one phage clone displaying a high-affinity peptide, WMVLPWLPGTLD (SEQ ID NO:1 herein termed ERY1), towards the mouse erythrocyte cell surface (FIG. 1). When similarity searched using the BLAST algorithm in UniProt, no relevant protein sequence homology was identified towards the full peptide. Other experiments (Example 8) identified binding ligands for human erythrocytes as shown in Tables 1-2. Six sequences bound specifically to human erythrocytes. A seventh sequence, named ERY50, bound human erythrocytes and also bound epithelial/endothelial cells.

TABLE 1

Peptidic ligands that bind human erythrocytes

| Peptide Name | Human Erythrocyte Binding Peptide Sequence | Sequence Identifier |
| --- | --- | --- |
| ERY19 | GQSGQPNSRWIYMTPLSPGIYRGSSGGS | SEQ ID NO: 4 |
| ERY50 | GQSGQSWSRAILPLFKIQPVGSSGGS | SEQ ID NO: 5 |
| ERY59 | GQSGQYICTSAGFGEYCFIDGSSGGS | SEQ ID NO: 6 |
| ERY64 | GQSGQTYFCTPTLLGQYCSVGSSGGS | SEQ ID NO: 7 |
| ERY123 | GQSGHWHCQGPFANWVGSSGGS | SEQ ID NO: 8 |
| ERY141 | GQSGQFCTVIYNTYTCVPSSGSSGGS | SEQ ID NO: 9 |
| ERY162 | GQSGQSVWYSSRGNPLRCTGGSSGGS | SEQ ID NO: 10 |

Underlined sequence portions indicate linker sequences

TABLE 2

Peptidic ligands that bind mouse or human erythrocytes

| Peptide | | Sequence Identifier |
| --- | --- | --- |
| ERY19' | PNSRWIYMTPLSPGIYR | SEQ ID NO: 11 |
| ERY50'* | SWSRAILPLFKIQPV | SEQ ID NO: 12 |
| ERY59' | YICTSAGFGEYCFID | SEQ ID NO: 13 |
| ERY64' | TYFCTPTLLGQYCSV | SEQ ID NO: 14 |
| ERY123' | HWHCQGPFANWV | SEQ ID NO: 15 |
| ERY141' | FCTVIYNTYTCVPSS | SEQ ID NO: 16 |
| ERY162' | SVWYSSRGNPLRCTG | SEQ ID NO: 17 |
| ERY1** | WMVLPWLPGTLD | SEQ ID NO: 1 |

*not specific for erythrocytes
**for mouse

Embodiments of the invention include peptides that that specifically bind the surface of erythrocytes. The sequences were not optimized for minimum length. Such optimization is within the skill of the art and may be practiced using techniques described herein. For example, Kenrick et al. (Protein Eng. Des. Sel. (2010) 23(1):9-17) screened from a 15 residue library, and then identified minimal binding sequences 7 residues in length. Getz (ACS Chem. Biol., May 26, 2011 identified minimal binding domains as small as 5 residues in length. The erythrocyte binding peptides may be present in repeats of the same sequences, e.g., between 2 and 20 repeats; artisans will immediately appreciate that all the ranges and values within the explicitly stated ranges are contemplated. Moreover, the peptides may be present in combination, with two or more distinct sequences being in the same peptide or being part of a single molecular fusion.

The number of consecutive residues that provide specific binding is expected to be between about 4 and 12 residues. Accordingly, all peptides of four consecutive residues in length found in Table 2 are disclosed, as well as all peptides of, e.g., 5, 6, 7, or 8 consecutive residues. This number is based on the number of residues for other peptidic protein-binding ligands. Embodiments of the invention include minimum length sequences for one of the erythrocyte-binding SEQ IDs set for the herein, including Table 1. Accordingly, certain embodiments are directed to a composition comprising a peptide, or an isolated (or purified) peptide, comprising a number of consecutive amino acid sequences between 4 and 12 consecutive amino acid residues of a sequence chosen from the group consisting of SEQ ID NO:11, SEQ ID NO:13, SEQ ID NO:14, SEQ ID NO:15, SEQ ID NO:16, SEQ ID NO:17, SEQ ID NO:1, and conservative substitutions thereof, wherein said sequence specifically binds an erythrocyte. Alternatively the number of consecutive residues may be chosen to be between about 5 and about 18; artisans will immediately appreciate that all the ranges and values within the explicitly stated ranges are contemplated, e.g., 7, 8, 9, 10, or from 8 to 18. The erythrocyte-binding sequence may have, e.g., a conservative substitution of at least one and no more than two amino acids of the sequences, or 1, 2, or 3 substitutions, or between 1 and 5 substitutions. Moreover, the substitution of L-amino acids in the discovered sequence with D-amino acids can be frequently accomplished, as in Giordano. The peptide or composition may, in some embodiments, consist essentially of a sequence chosen from the group consisting of SEQ ID NO:11, SEQ ID NO:13, SEQ ID NO:14, SEQ ID NO:15, SEQ ID NO:16, SEQ ID NO:17, SEQ ID NO:1. The peptide may be limited in length, e.g., having a number of residues between about 10 and about 100; artisans will immediately appreciate that all the ranges and values within the explicitly stated ranges are contemplated, e.g., about 10 to about 50 or about 15 to about 80. A peptide erythrocyte-binding moiety may be provided that comprises a peptide ligand that has a dissociation constant of between about 10 µM and 0.1 nM as determined by equilibrium binding measurements between the peptide and erythrocytes; artisans will immediately appreciate that all the ranges and values within the explicitly stated ranges are contemplated, e.g., from about 1 µM to about 1 nM. The peptide may further comprise a therapeutic agent. The therapeutic agent may be, e.g., a protein, a biologic, an antibody fragment, an ScFv, or a peptide. The peptide may further comprise a tolerogenic antigen, e.g., a human protein used in a human deficient in that protein (e.g., blood factors such as factor VIII or factor IX), proteins with nonhuman glycosylation, synthetic proteins not naturally found in humans, human food allergens, or human autoimmune antigens.

Others have searched for peptidic ligands that specifically bind the surface of erythrocytes. A prior study attempted the discovery of erythrocyte-binding peptides by use of a novel bacterial surface displayed peptide library screening method (Hall, Mitragotri, et al., 2007). The focus of their study was to establish their novel bacterial peptide display system to screen naïve libraries for peptides with affinity for erythrocytes, and use the peptides to attach 0.22 µm particles to erythrocytes. Though they reported the identification of several peptides that accomplish this task, they did not characterize the binding phenomena to a sufficient degree required for applicable consideration. They did not report the cellular binding specificity of the peptides; the issue of what other cell types the peptides bind to is not addressed. Nor did they report the cell surface ligand of the peptides. Electron micrographs taken of the erythrocytes labeled with peptide-functionalized 0.22 µm particles depict erythrocytes with single clusters of particles per cell. Most potential binding sites would be expected to be broadly distributed over the cell surface and the fact that all of the tested ligands were localized to a small cell area indicates that these results are an experimental artifact. Such an artifact may be the result of the molar excess at which labeling was conducted, or other factors. No in vivo characterization of peptide-particle erythrocyte binding or pharmacokinetics was conducted. Taken together, the results described by Hall and colleagues do not suggest that peptide ligands to erythrocytes may be used as tools to improve the pharmacokinetics of therapeutics or in other medical or therapeutic fashion.

Polypeptides of various lengths may be used as appropriate for the particular application. In general, polypeptides that contain the polypeptide ligand sequences will exhibit specific binding if the polypeptide is available for interaction with erythrocytes in vivo. Peptides that have the potential to fold can be tested using methods described herein. Accordingly, certain embodiments are directed to polypeptides that have a polypeptide ligand but do not occur in nature, and certain other embodiments are directed to polypeptides having particular lengths, e.g., from 6 to 3000 residues, or 12-1000, or 12-100, or 10-50; artisans will immediately appreciate that every value and range within the explicitly articulated limits is contemplated.

Certain embodiments provide various polypeptide sequences and/or purified or isolated polypeptides. A polypeptide is a term that refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. As used herein, a "functional polypeptide" is a polypeptide that is capable of promoting the indicated function. Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

There are a variety of conservative changes that can generally be made to an amino acid sequence without altering activity. These changes are termed conservative substitutions or mutations; that is, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence may undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. The amino acid residues described herein employ either the single letter amino acid designator or the three-letter abbreviation. Abbreviations used herein are in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

In some cases a determination of the percent identity of a peptide to a sequence set forth herein may be required. In such cases, the percent identity is measured in terms of the number of residues of the peptide, or a portion of the peptide. A polypeptide of, e.g., 90% identity, may also be a portion of a larger peptide The term purified as used herein with reference to a polypeptide refers to a polypeptide that has been chemically synthesized and is thus substantially uncontaminated by other polypeptides, or has been separated or purified from other most cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, or a FLAG® tag) that facilitates the polypeptide to be purified or marked (e.g., captured onto an affinity matrix, visualized under a microscope). Thus a purified composition that comprises a polypeptide refers to a purified polypeptide unless otherwise indicated. The term isolated indicates that the polypeptides or nucleic acids of the invention are not in their natural environment. Isolated products of the invention may thus be contained in a culture supernatant, partially enriched, produced from heterologous sources, cloned in a vector or formulated with a vehicle, etc.

Polypeptides may include a chemical modification; a term that, in this context, refers to a change in the naturally-occurring chemical structure of amino acids. Such modifications may be made to a side chain or a terminus, e.g., changing the amino-terminus or carboxyl terminus. In some embodiments, the modifications are useful for creating chemical groups that may conveniently be used to link the polypeptides to other materials, or to attach a therapeutic agent.

Specific binding, as that term is commonly used in the biological arts, refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding. The peptide ERY1 and its derivatives and the human erythrocyte binding peptides and their derivatives may bind non-erythrocytes in some circumstances but such binding has been observed to be non-specific, as evidenced by the much greater binding of the peptides to the erythrocytes as opposed to other cells or proteins.

Thus, embodiments include a ligand that binds with specificity to an erythrocyte and does not specifically bind other blood components, e.g., one or more of: blood proteins, albumin, fibronectin, platelets, white blood cells, substantially all components found in a blood sample taken from a typical human. In the context of a blood sample, the term "substantially all" refers to components that are typically present but excludes incidental components in very low concentrations so that they do not effectively reduce the titer of otherwise bioavailable ligands.

Antibody Peptides

In addition to peptides that bind erythrocytes, proteins are also presented herein, specifically antibodies and especially single chain antibody fragments. Techniques for raising an antibody against an antigen are well known. The term antigen, in this context, refers to a site recognized by a host immune system that responds to the antigen. Antigen selection is known in the arts of raising antibodies, among other arts. Embodiments include use of these peptides in a molecular fusion and other methods presented herein. Antigens may be recombinantly expressed in their full form or as partial domains fused to tags that enhance expression or stability of the protein. The recombinant protein antigen may then be immobilized on a plate or bead, and used as the affinity target for the library screening process. Antigens may also be isolated from cellular preparations of whole blood, from which purified or complex mixtures of membrane proteins may be immobilized on a solid matrix (bead, plate, or other), and used as affinity targets for the screening process.

Artisans reading this disclosure will be able to create antibodies that specifically bind erythrocytes. Examples 15-17 relate to making antibodies or fragments thereof. Numerous parallel techniques are used to discover new antibodies or antibody fragments or to make compositions comprising such fragments active towards erythrocytes, including but not limited to phage display, yeast display, and bacterial display. Additional erythrocyte binding antibodies or antibody fragments, or scFvs may be generated specifically for one or more of the following targets or group of targets (collectively referred to herein as the Erythrocyte Target Group) chosen from the group consisting of Band 3 (CD233), aquaporin-1, Glut-1, Kidd antigen, RhAg/Rh50 (CD241), Rh (CD240), Rh30CE (CD240CE), Rh30D (CD240D), Kx, glycophorin A (CD235a), glycophorin B (CD235b), glycophorin C (CD235c), glycophorin D (CD235d), Kell (CD238), Duffy/DARC (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, and H antigen (CD173).

Additionally, new erythrocyte-specific antibodies may be generated by immunization of mice with intact, or protein preparations of, human erythrocytes. Following immunization with the target formulated in adjuvant, mice are sacrificed at pre-determined time points and their antibody repertoires are sequenced and/or their B cells isolated for hybridoma-based screening. These antibodies or antibody fragments may be optimized by several aforementioned in vitro techniques, for improved binding and/or stability parameters. Additional erythrocyte binding antibodies or antibody fragments may be generated by using antibody hybridoma clones previously discovered to bind erythrocytes. They may be generated, for instance, by using the method used to generate the TER119 scFv. As a template, or as an antibody source, the following hybridoma clones may be used, among others: BRIC 4, 5, 6, 10, 14, 18, 39, 66, 68, 69, 87, 108, 110, 111, 125, 126, 128, 145, 155, 157, 163, 170, 198, 203, 216, 220, 221, 222, 229, 230, 231, 235, or 256; BRAC 17, 18; BGRL 1, 2, 11, 100; BRAD 3; BIRMA D6, D10, K3, 84B; 6A7; COE; or KZ1.

The term peptide is used interchangeably with the term polypeptide herein. Antibodies and antibody fragments are peptides. The term antibody fragment refers to a portion of an antibody that retains the antigen-binding function of the antibody. The fragment may literally be made from a portion of a larger antibody or alternatively may be synthesized de novo. Antibody fragments include, for example, a single chain antibody fragment (scFv) An scFv is a fusion protein of the variable regions of the heavy (VH) and light chains (VL) of immunoglobulin, connected with a linker peptide, e.g., about 10 to about 50 amino acids. The linker can either connect the N-terminus of the VH with the C-terminus of the VL, or vice versa. The term scFv includes divalent scFvs, diabodies, triabodies, tetrabodies and other combinations of antibody fragments. Antibodies have an antigen-binding portion referred to as the paratope. The term peptide ligand refers to a peptide that is not part of a paratope.

The binding of erythrocytes, by antibodies and fragments thereof, by peptidic binding ligands, and by aptamers, may be performed without covalent bonding to the erythrocytes. The binding may be performed in vivo and without an ex vivo erythrocyte binding event. This binding event, including the resultant association of an antigen with the erythrocyte, can be performed without causing the erythrocytes to be apoptotic. The process may be performed so that the surface molecules of erythrocytes are not crosslinked to each other by a crosslinking agent and/or the binding event, and are not crosslinked by covalent bonds.

Aptamers for Specific Binding of Erythrocytes

In addition to peptide ligands that bind erythrocytes, nucleotide aptamer ligands for erythrocyte surface components are taught. Accordingly, aptamers are to be made and used as described herein for other erythrocyte-binging moieties. DNA and RNA aptamers may be used to provide non-covalent erythrocyte binding. As they are only composed of nucleotides, aptamers are promising biomolecular targeting moieties in that screening methodologies are well established, they are readily chemically synthesized, and pose limited side-effect toxicity and/or immunogenicity due to their rapid clearance in vivo (Keefe, Pai, et al., 2010). Furthermore, due to the non-canonical nature of the nucleotide-target protein interaction, any productive agonist signaling upon target binding in vivo is unlikely, thus contributing low immunogenicity and toxicity. As such, numerous aptamer-based molecules are currently in human clinical trials for a number of clinical indications, including leukemia, macular degeneration, thrombosis, and type 2 diabetes (Keefe, Pai, et al., 2010). Aptamers have also been used as targeting agents to deliver drug payloads to specific tissues in vivo, in applications such as cancer chemotherapy and fluorescence or radiological tumor detection techniques (Rockey, Huang, et al., 2011; Savla, Taratula, et al., 2011).

Aptamers are oligonucleic acids or peptides that bind to a specific target molecule. Aptamers are usually created to bind a target of interest by selecting them from a large random sequence pool. Aptamers can be classified as DNA aptamers, RNA aptamers, or peptide aptamers. Nucleic acid aptamers are nucleic acid species that have been engineered through repeated rounds of in vitro selection or Systematic Evolution of Ligands by Exponential Enrichment (SELEX) method (Archemix, Cambridge, Mass., USA) (Sampson, 2003) to specifically bind to targets such as small molecules, proteins, nucleic acids, cells, tissues and organisms. Peptide aptamers typically have a short variable peptide domain, attached at both ends to a protein scaffold. Peptide aptamers are proteins that are designed to interfere with other protein interactions inside cells. They consist of a variable peptide loop attached at both ends to a protein scaffold. This double structural constraint greatly increases the binding affinity of the peptide aptamer to be comparable to an antibody. The variable loop length is typically composed of about ten to about twenty amino acids, and the scaffold is a protein which has good solubility and is compact. For example the bacterial protein Thioredoxin-A is a scaffold protein, with the variable loop being inserted within the reducing active site, which is a -Cys-Gly-Pro-Cys-loop in the wild protein, the two Cysteines lateral chains being able to form a disulfide bridge.

Some techniques for making aptamers are detailed in Lu et al., Chem Rev 2009:109(5):1948-1998, and also in U.S. Pat. Nos. 7,892,734, 7,811,809, US 2010/0129820, US 2009/0149656, US 2006/0127929, and US 2007/0111222. Example 19 further details materials and methods for making and using aptamers for use with the embodiments disclosed herein.

Molecular Fusion

A molecular fusion may be formed between a first peptidic erythrocyte binding ligand and a second peptide. The fusion comprises the peptides conjugated directly or indirectly to each other. The peptides may be directly conjugated to each other or indirectly through a linker. The linker may be a peptide, a polymer, an aptamer, a nucleic acid, or a particle. The particle may be, e.g., a microparticle, a nanoparticle, a polymersome, a liposome, or a micelle. The polymer may be, e.g., natural, synthetic, linear, or branched. A fusion protein that comprises the first peptide and the second peptide is an example of a molecular fusion of the peptides, with the fusion protein comprising the peptides directly joined to each other or with intervening linker sequences and/or further sequences at one or both ends. The conjugation to the linker may be through covalent bonds. Other bonds include ionic bonds. Methods include preparing a molecular fusion or a composition comprising the molecular fusion, wherein the molecular fusion comprises peptides that specifically bind to erythrocytes and a therapeutic agent, tolerizing antigen, or other substance.

The term molecular fusion, or the term conjugated, refers to direct or indirect association by chemical bonds, including covalent, electrostatic ionic, charge-charge. The conjugation creates a unit that is sustained by chemical bonding. Direct conjugation refers to chemical bonding to the agent, with or without intermediate linkers or chemical groups. Indirect conjugation refers to chemical linkage to a carrier. The carrier may largely encapsulate the agent, e.g., a polymersome, a liposome or micelle or some types of nanoparticles, or have the agent on its surface, e.g., a metallic nanoparticle or bead, or both, e.g., a particle that includes some of the agent in its interior as well as on its exterior. The carrier may also encapsulate an antigen for immunotolerance. For instance a polymersome, liposome, or a particle may be made that encapsulates the antigen. The term encapsulate means to cover entirely, effectively without any portion being exposed, for instance, a polymersome may be made that encapsulates an antigen or an agent. Examples of therapeutic agents are single-chain variable fragments (scFv), antibody fragments, small molecule drugs, bioactive peptides, bioactive proteins, and bioactive biomolecules.

Conjugation may be accomplished by covalent bonding of the peptide to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, Biomacromolecules 2003; 4:713-22, Hermanson, Bioconjugate Techniques, London. Academic Press Ltd; 1996). In some embodiments, a soluble polymer linker is used, and may be administered to a patient in a pharmaceutically acceptable form. Or a drug may be encapsulated in polymerosomes or vesicles or covalently attached to the peptide ligand.

An embodiment is a conjugation of a non-protein therapeutic agent and a peptide ligand, antibody, antibody fragment, or aptamer that binds specifically to an erythrocyte. Application of the erythrocyte binding peptide methodology is not restricted to polypeptide therapeutics; rather it may be translated into other drug formulations, such as small molecules and polymeric particles. In the long history of small molecules and their application in medicine, short circulation half-lives and poor bioavailability have consistently plagued their efficacy in vivo. Polymeric micelles and nanoparticles represent a relatively newer generation of drug class, yet their pharmacokinetic behavior remains sub-optimal for reasons that include a high clearance rate via the action of the reticuloendothelial system (Moghimi and Szebeni, 2003). The erythrocyte-binding design can be extended to these other drug classes to increase their circulation half-lives and clinical efficacy.

The conjugate may comprise a particle. The erythrocyte binding peptide may be attached to the particle. An antigen, agent, or other substance may be in or on the particle. Examples of nanoparticles, micelles, and other particles are found at, e.g., US 2008/0031899, US 2010/0055189, US 2010/0003338, which applications are hereby incorporated by reference herein for all purposes, including combining the same with a ligand as set forth herein; in the case of conflict, however, the instant specification controls. Examples 11 and 12 describe the creation of certain particles in detail.

Nanoparticles may be prepared as collections of particles having an average diameter of between about 10 nm and about 200 nm, including all ranges and values between the explicitly articulated bounds, e.g., from about 20 to about 200, and from about 20 to about 40, to about 70, or to about 100 nm, depending on the polydispersity which is yielded by the preparative method. Various nanoparticle systems can be utilized, such as those formed from copolymers of poly (ethylene glycol) and poly(lactic acid), those formed from copolymers of poly(ethylene oxide) and poly(beta-amino ester), and those formed from proteins such as serum albumin. Other nanoparticle systems are known to those skilled in these arts. See also Devalapally et al., *Cancer Chemother Pharmacol.*, 07-25-06; Langer et al., *International Journal of Pharmaceutics*, 257:169-180 (2003); and Tobio et al., *Pharmaceutical Research*, 15(2):270-275 (1998).

Larger particles of more than about 200 nm average diameter incorporating the cartilage tissue-binding ligands may also be prepared, with these particles being termed microparticles herein since they begin to approach the micron scale and fall approximately within the limit of optical resolution. For instance, certain techniques for making microparticles are set forth in U.S. Pat. Nos. 5,227,165, 6,022,564, 6,090,925, and 6,224,794.

Functionalization of nanoparticles to employ targeting capability requires association of the targeting polypeptide with the particle, e.g., by covalent binding using a bioconjugation technique, with choice of a particular technique being guided by the particle or nanoparticle, or other construct, that the polypeptide is to be joined to. In general, many bioconjugation techniques for attaching peptides to other materials are well known and the most suitable technique may be chosen for a particular material. For instance, additional amino acids may be attached to the polypeptide sequences, such as a cysteine in the case of attaching the polypeptide to thiol-reactive molecules.

Figure 16:
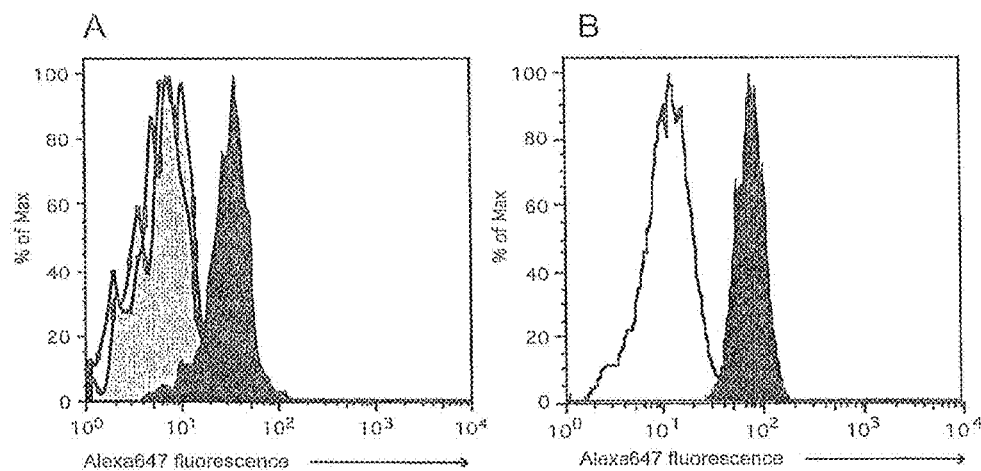
FIG. 16 presents experimental results wherein 8-arm PEG-ERY1 binds erythrocytes in vitro and in vivo; Panel (a) 8-arm PEG-ERY1 (black filled histogram), but not 8-arm PEG-MIS (grey filled histogram) or 8-arm PEG-pyridyldisulfide bind to mouse erythrocytes following in vitro incubation; Panel (b) 8-arm PEG-ERY1 (black filled histogram), but not 8-arm PEG-MIS (grey filled histogram) bind to circulating erythrocytes upon intravenous injection.
Figure 17:
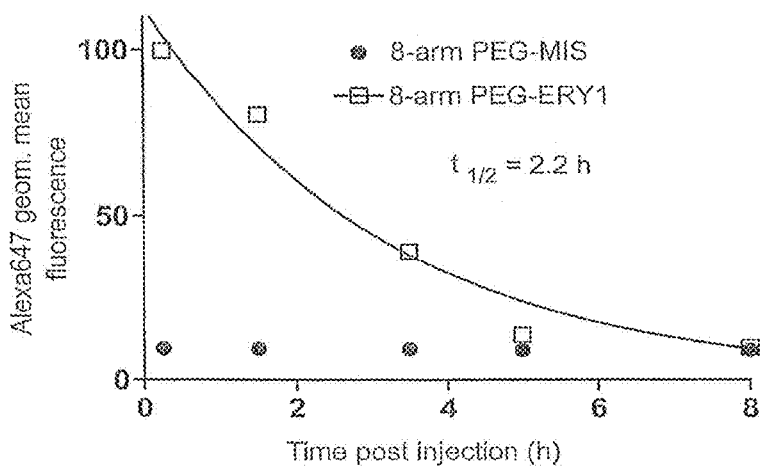
FIG. 17 presents experimental results depicting erythrocyte cell-surface half-life of 8-arm PEG-ERY1 (filled circles) and 8-arm PEG-MIS (empty boxes), determined by flow cytometry.

Example 18 details the creation of a multimeric branched polymer comprising erythrocyte specific biding moieties. To create a multimeric molecule capable of displaying multiple different bioactive molecules, a commercially available 8-arm PEG dendrimer was chemically modified to include reactive groups for facile conjugation reactions. The 8-arm PEG-pyridyldisulfide contained the pyridyldisulfide group that reacts readily with thiolates from small molecules and/or cysteine-containing peptides or proteins, resulting in a disulfide-bond between the attached bioactive moiety and the 8-arm PEG scaffold. The multimeric architecture of the 8-arm PEG allowed the conjugation of different peptides or molecules to the scaffold, thus creating a hetero-functionalized biomolecule with multiple activities by virtue of its attached moieties. Heterofunctionalized fluorescent 8-arm PEG constructs, capable of binding erythrocytes in vitro (FIG. 16A) and in vivo (FIG. 16B) were created. This binding was sequence specific to the ERY1 peptide, as conjugates harboring the non-specific MIS peptide demonstrated little to no binding to erythrocytes. The binding in vivo was long-lived, as fluorescent 8-arm PEG-ERY1-AL-EXAFLUOR647 was detected on circulating erythrocytes 5 h following intravenous administration, and displayed a cell-surface half-life of 2.2 h (FIG. 17). To demonstrate the induction of tolerance in an autoimmune diabetic mouse model, an 8-arm PEG conjugated with both ERY1 and the diabetes antigen chromogranin-A (CrA) was created. The modular nature of the 8-arm PEG-pyridyldisulfide scaffold made it possible to co-conjugate different of thiol-containing molecules by sequentially adding stoichiometrically defined quantities of the molecules.

The molecular fusion may comprise a polymer. The polymer may be branched or linear. The molecular fusion may comprise a dendrimer. In general, soluble hydrophilic biocompatbile polymers may be used so that the conjugate is soluble and is bioavailable after introduction into the patient. Examples of soluble polymers are polyvinyl alcohols, polyethylene imines, and polyethylene glycols (a term including polyethylene oxides) having a molecular weight of at least 100, 400, or between 100 and 400,000 (with all ranges and values between these explicit values being contemplated). Solubility in this context refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

In some embodiments, a polypeptide-polymer association, e.g., a conjugate, is prepared and introduced into the body as a purified composition in a pharmaceutically acceptable condition, or with a pharmaceutical excipient. The site of introduction may be, e.g., systemic, or at a tissue or a transplantation site.

Artisans may prepare fusion proteins using techniques known in these arts. Embodiments include preparing fusion proteins, isolating them, and administering them in a pharmaceutically acceptable form with or without other agents, e.g., in combination with an interleukin of TGF-beta. Embodiments include a vector for, and methods of, transfecting a cell to thereby engineer the cell to make the fusion protein in vivo, with the cell being transfected in vitro, ex vivo, or in vivo, and with the cell being a member of a tissue implant or distinct therefrom. The following U.S. patent applications are hereby incorporated by reference herein for all purposes, including the purposes of making fusion proteins, with the instant specification controlling in case of conflict: 5227293, 5358857, 5885808, 5948639, 5994104, 6512103, 6562347, 6905688, 7175988, 7704943, US 2002/0004037, US 2005/0053579, US 2005/0203022, US 2005/0250936, US 2009/0324538.

Embodiments of a molecular fusion include, for example, a molecular fusion that comprises a tolerogenic antigen and an erythrocyte-binding moiety that specifically binds an erythrocyte in the patient and thereby links the antigen to the erythrocyte, wherein the molecular fusion is administered in an amount effective to produce immunotolerance to a substance that comprises the tolerogenic antigen. Embodiments include, for example, a composition comprising an erythrocyte-binding moiety that specifically binds an erythrocyte joined to a carrier chosen from the group consisting of a polymer, a branched polymer, and a particle, wherein the carrier is joined to a therapeutic agent. The particle may be, e.g., a microparticle, a nanoparticle, a polymersome, a liposome, or a micelle. The erythrocyte-binding moiety may comprises a peptide comprising at least 5 consecutive amino acid residues of a sequence chosen from the group consisting of SEQ ID NO:11, SEQ ID NO:13, SEQ ID NO:14, SEQ ID NO:15, SEQ ID NO:16, SEQ ID NO:17, SEQ ID NO:1, and conservative substitutions thereof, wherein said sequence specifically binds an erythrocyte. The erythrocyte-binding moiety may comprise an antibody, antibody fragment, aptamer, scFv or peptide ligand. Embodiments of a molecular fusion include an erythrocyte binding moiety and a tolerogenic antigen, an antibody, an antibody fragment, an ScFv, a small molecule drug, a particle, a protein, a peptide, or an aptamer.

In a preferred aspect of the invention there is provided a molecular fusion that comprises a tolerogenic antigen and an erythrocyte-binding moiety selected from Band 3 (CD233), glycophorin B (CD235b), glycophorin C (CD235c) and glycophorin D (CD235d). The molecular fusion is particularly for use in producing immunotolerance. A preferred molecular fusion is one that comprises a tolerogenic antigen selected from: a protein, a portion of a protein, a human protein or portion thereof, a nonhuman protein or portion thereof, a glycan, a glycan of a protein that comprises nonhuman glycosylation, a human autoimmune antigen, a protein therapeutic for a human or a portion thereof, and a portion of a human food, proteins deficient by genetic disease, proteins with nonhuman glycosylation, nonhuman proteins, synthetic proteins not naturally found in humans, human food antigens, human transplantation antigens, and human autoimmune antigens; and an erythrocyte-binding moiety selected from Band 3 (CD233), glycophorin B (CD235b), glycophorin C (CD235c), glycophorin D (CD235d).

Erythrocyte Binding Ligands for Improved Pharmacokinetics

As many drugs are systemically delivered to the blood circulatory system, the answer to the problem of effective drug delivery often focuses on maintaining the drug in the blood for extended periods of time. Thus, the development of long-circulating (long half-life) therapeutics that remain biologically available in the blood for extended time periods will represent a new generation of drugs engineered for efficacy, safety, and economic feasibility.

Embodiments of the invention include molecular fusions of an erythrocyte-binding peptide and a therapeutic agent. Molecular fusions between peptides that specifically bind to erythrocytes and a therapeutic agent or other substance provide an increased circulation time (circulating half-life in blood in vivo) for the agent/substance. Examples 5 and 6 provide working examples of the same. The increase may be, for instance from about 1.5-fold to 20-fold increase in serum half-life, artisans will immediately appreciate that all the ranges and values within the explicitly stated ranges are contemplated, e.g., about 3-fold or about 6-fold or between about 3 fold and about 6-fold.

The molecular fusions may be accomplished by, for instance, recombinant addition of the peptide or adding the peptide by chemical conjugation to a reactive site on the therapeutic agent or associated molecule or particle. As solid-phase peptide synthesis can be used to synthesize high yields of pure peptide with varying terminal reactive groups, there exist multiple conjugation strategies for the attachment of the peptide onto the therapeutic. Though this functionalization method differs with the recombinant method used with proteins, the effect (erythrocyte binding leading to increased circulation half life) is postulated to be the same.

One embodiment of the invention involves functionalization of therapeutic agents with short peptide ligands that specifically bind to erythrocytes as tools for the improvement of pharmacokinetic parameters of the therapeutic agents. This half-life extension methodology takes into consideration pivotal parameters in therapeutic drug design, namely simplicity in manufacturing, modularity, and the ability to tune the extension effect. Using standard recombinant DNA techniques, proteins are easily altered at the amino acid level to contain new or altered functionalities. Generally, relying the use of shorter peptide domains for function is preferable to using larger polypeptide domains, for reasons that include ease in manufacturing, correct folding into a functional therapeutic protein, and minimal biophysical alterations to the original therapeutic itself. Polypeptides, e.g., ERY1, a human erythrocyte binding ligand, or antibodies or antibody fragments, may be engineered to bind specifically to erythrocytes and conjugated to a therapeutic agent to extend bioavailability, e.g., as measured by the circulating half-life of the agent.

The results reported herein provide opportunities to make molecular fusions to improve pharmacokinetic parameters of the therapeutic agents such as insulin, pramlintide acetate, growth hormone, insulin-like growth factor-1, erythropoietin, type 1 alpha interferon, interferon α2a, interferon α2b, interferon β1a, interferon β1b, interferon γ1b, β-glucocerebrosidase, adenosine deaminase, granulocyte colony stimulating factor, granulocyte macrophage colony stimulating factor, interleukin 1, interleukin 2, interleukin 11, factor VIIa, factor VIII, factor IX, exenatide, L-asparaginase, rasburicase, tumor necrosis factor receptor, and enfuvirtide.

Attempts by others to create passive half-life improvement methods focus on increasing the apparent hydrodynamic radius of the drug. The kidney's glomerular filtration apparatus is the primary site in the body where blood components are filtered. The main determinant of filtration is the hydrodynamic radius of the molecule in the blood; smaller molecules (<80 kDa) are filtered out of the blood to a higher extent than larger molecules. Researchers have used this generalized rule to modify drugs to exhibit a larger hydrodynamic radius and thus longer half-life, mainly via chemical conjugation to large molecular weight water-soluble polymers, such as polyethylene glycol (PEG). The success of this method is evident in the numerous PEGylated protein and small molecule therapeutics currently offered in the clinic (Pasut and Veronese, 2009; Fishbum, 2008). Though effective in many cases in increasing circulation half-life, especially as the hydrodynamic radius of the graft or fusion increases (Gao, Liu, et al., 2009), these methods offer challenges in manufacturing and maintenance of biological effector function. Heterogeneities in conjugation reactions can cause complex product mixtures with varying biological activities, due mostly to the utilization of site-unspecific chemistries. Extensive biochemical characterization often follows precise purification methods to retain a homogenous therapeutic product (Huang, Gough, et al., 2009; Bailon, Palleroni, et al., 2001; Dhalluin, Ross, et al., 2005). Furthermore, attachment of large moieties, such as branched PEGs, to reactive zones of proteins can lead to decreased receptor affinity (Fishburn, 2008).

Other work by others has provided for a therapeutic protein to bind to albumin for increased circulation of the drug (Dennis, 2002; Walker, Dunlevy, et al., 2010). Considering the same general aforementioned rule on kidney filtration, Dennis and colleagues hypothesized that increasing the apparent size of the therapeutic by engineering it to bind another protein in the blood (such as serum albumin) would decrease the rate of drug clearance. In this manner, the drug attains its large molecular size only after administration into the blood stream. The addition of affinity-matured serum albumin-binding peptides to antibody fragments increased their circulation time 24 fold in mice (Dennis, 2002). Though effective, this method is complicated by the dynamics of albumin recycle by the neonatal Fc receptor (FcRn) and the use of cysteine-constrained cyclic peptides for functionality. Walker and colleagues corroborate the results contributed by Dennis in 2002, namely that imparting serum albumin affinity to a protein increases its half-life. The method described by Walker and colleagues involves recombinant addition of large antibody fragments to the protein drug, which may cause structural as well as manufacturing complications. Though elegant and effective, the methods of Dennis and Walker are complicated by use of complex cyclic or large domains for functionality. Though the peptides discovered by Dennis and colleagues displayed high affinity for albumin, they require the physical constraint of correctly forming a cyclic structure prior to use. A more bulky approach, Walker's method of fusing larger antibody fragments may not be amendable to proteins with an already complex folding structure or low expression yield.

Single Chain Antibodies

An embodiment of the invention is a molecular fusion of an scFv with a peptide that specifically binds to an erythrocyte. An scFv may be used a therapeutic agent, and its combination with an erythrocyte binding peptide may be used to extend its circulating half-life and provide access to body compartments. Recombinant antibodies and recombinant antibody fragments have potential as therapeutics in the biologics industry (Sheridan, 2010).

Single-chain variable fragment (scFv) antibody fragments comprise of the entire antigen-binding domain of a full-length IgG, but lack the hinge and constant fragment regions (Maynard and Georgiou, 2000). Recombinant construction of a scFv involves fusing the variable heavy (VH) domain with the variable light (VL) domain with a short polypeptide linker consisting of tandem repeats of glycine and serine (e.g. $(GGGGS)_4$) (SEQ ID NO:18). Though the simplicity of scFv's is attractive for therapeutic applications, their main drawback the short circulation half lives which they exhibit, by virtue of their relatively small molecular weight of 26-28 kDa (Weisser and Hall, 2009).

Figure 6:
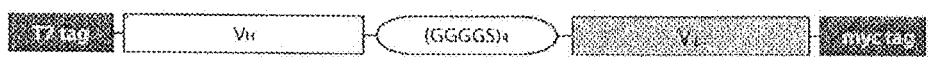
FIG. 6 is a schematic of scFv engineering designs; in panel A: linear representation of scFv domains from N to C terminus; in panel B: architecture of a folded scFv; in panel C: architecture of a folded scFv with chemically conjugated ERY1 peptides.
Figure 6:
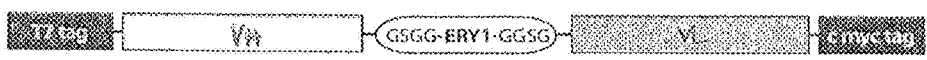
Figure 6:
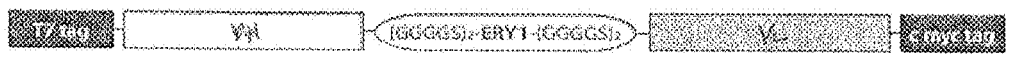
Figure 6:
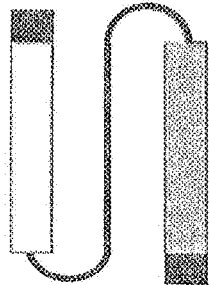
Figure 6:
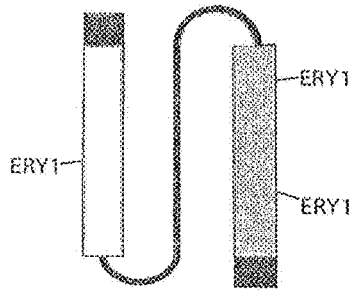

As the glycine-serine linker commonly used in scFv design is non-functional in nature, rather it exists as a physical bridge to ensure correct $V_H$-$V_L$ folding, linker domains were tested herein that exhibit a function of binding to erythrocytes in the blood. Thus, the engineered scFv may be multifunctional and bi-specific, displaying an affinity to its native antigen through the $V_H$-$V_L$ domains, and an affinity to erythrocytes in its linker domain. In binding to erythrocytes, the engineered scFv will exhibit a longer circulation half-life, as has been demonstrated for another model protein with this same functionality. An scFv antibody fragment may have a linker as described herein, or other linkers may be provided as is known to those of skill in these arts. An alternative embodiment provides for a free cysteine group engineered into the linker region of a scFv, and this cysteine thiol used to link by chemical conjugation an erythrocyte binding ligand.

scFv antibodies were engineered as detailed in Example 7. Design of the engineered scFv antibodies focused on the importance of linker domain length, as well as spacing of the erythrocyte binding peptide. As the wild-type variant was designed and validated for antigen binding with a $(GGGGS)_4$ linker (SEQ ID NO: 18), subsequent mutants were designed with a linker minimum linker length of 20 amino acids (FIG. 6A). As the linker domain can modulate correct folding of the scFv into its correct tertiary structure (FIG. 6B), two ERY1 containing mutants were designed. The REP mutant contains the ERY1 peptide centered in the linker domain, flanked by the correct number of Gly and Ser residues to maintain the parent 20 amino acid linker length. In the possible case where the hydrophobic nature of the ERY1 peptide does not linearly align, but clusters into a shorter assembled domain, the linker length of REP would be shorter and may thereby hinder correct folding. For such reasons, the INS mutant was designed to contain the ERY1 peptide added into the center of the parent linker domain, lengthening the linker to 32 amino acids. As the ERY1 peptide was discovered with a free N-terminus, it was unknown whether or not its presence in a constrained polypeptide conformation would effect erythrocyte binding. To address this potential behavior, a scFv variant was created by chemical conjugation with synthetic ERY1 peptide, whereby the N-terminus of the peptide is free and the C-terminus is conjugated to the scFv (FIG. 6C).

In this manner, the number of erythrocyte binding peptides, and thus the erythrocyte-binding capacity of an scFv, may be tuned stoichiometrically during the conjugation reaction. Accordingly, ScFv can be engineered to comprise the erythrocyte-binding peptides as taught herein. Embodiments include an scFv comprising a number of ligands ranging from 1 to 20; artisans will immediately appreciate that all the ranges and values within the explicitly stated ranges are contemplated, e.g, between 2 and 6.

Embodiments include scFv conjugated to a tolerogenic antigen to make a molecular fusion that induces tolerance, e.g., as in Example 17 describing details for creating tolerance as exemplified with creation of tolerance against OVA that is attached to an scFv. Example 17 also details materials and methods for making scFv protein constructs recombinantly fused to an immune recognition epitope of an antigen. The scFv is directed to recognition of erythrocytes. The antigen is an antigen as described herein, e.g., a tolerogenic antigen. Working examples reported herein describe results using murine models, with the use of murine TER119 scFv used as the antibody domain in the constructs. TER119 is an antibody that binds to mouse erythrocytes. The TER119 antibody domain may be replaced by other antibody domains, for instance domains directed to an erythrocyte in human or other animals. For instance, the 10F7 antibody domain may be used to create antibody-antigen constructs capable of binding human erythrocytes. Additional fusions of scFv from Ter-119 were made with three different antigens, as reported in Example 17, including the immunodominant MHC-I epitope of OVA, the chromogranin-A mimotope 1040-p31, and proinsulin.

Example 24 describes other embodiments of scFvs that have been made, including embodiments for testing in animal models and embodiments reactive for humans. These include those relating to the protein level: TER119-SIINFEKL, TER119-ChrA, and TER119-proinsulin. These also include those relating to the genetic level: TER119-SIINFEKL, TER119-ChrA, TER119-proinsulin, TER119-uricase, TER119-InsB9-23, TER119-ISQAVHAAHAEINEAGR (SEQ ID NO:87), TER119-H-2kb, TER119-H-2kd, 10F7-SIINFEKL, 10F7-ChrA, 10F7-proinsulin, and 10F7-uricase.

Embodiments include scFvs that bind a tumor marker and block blood flow to a tumor, as in Examples 10 and 13. For instance, the scFv may bind the tumor marker and further be part of a molecular fusion with an erythrocyte-binding peptide. These conjugates may also be used to treat cancer by blocking blood flow to a tumor.

Binding of Erythrocytes to Particular Sites, Such as Tumor Vasculature

In addition to increasing the half-life of a drug, the capacity of an engineered therapeutic to bind erythrocytes is useful in order to selectively bind and localize erythrocytes to a particular site in the body. In treatment of solid tumors, transarterial chemoembolization (TACE) may be used to limit blood supply to the tumor, thereby hindering its access to nutrients required for growth. TACE treatment involves the surgical insertion of polymeric solid microparticles upstream of the tumor blood supply. As the microparticles reach the tumor vascular bed, they become physically trapped in the blood vessel network thereby creating a blockage for blood supply to the tumor (Vogl, Naguib, et al., 2009).

Pursuant to the TACE theme, an embodiment herein is to use autologous erythrocytes circulating in the blood as natural microparticles for tumor embolization by engineering a tumor-homing therapeutic to contain an erythrocyte-binding peptide. In this manner, the therapeutic localizes to the tumor vascular bed and recruits passing erythrocytes to bind to the vessel, thereby limiting and blocking blood flow to the tumor mass. Such a treatment is less invasive than classical TACE: the drug would be simply injected intravenously and use natural erythrocytes already present in the blood as the embolization particle. The term tumor-binding or tumor-homing refers to a peptide that binds to a component accessible from the blood compartment in tumor vasculature or on tumor cells.

Discovery of specific tumor-homing therapeutics is known in the cancer research field. The paradigm of bioactive targeting of tumors relies on binding to protein markers specifically expressed in the tumor environment. These include, but are not limited to: RGD-directed integrins, aminopeptidase-A and -N, endosialin, cell surface nucleolin, cell surface annexin-1, cell surface p32/gC1q receptor, cell surface plectin-1, fibronectin EDA and EDB, interleukin 11 receptor a, tenascin-C, endoglin/CD105, BST-2, galectin-1, VCAM-1, fibrin, and tissue factor receptor. (Fonsatti, Nicolay, et al., 2010; Dienst, Grunow, et al., 2005; Ruoslahti, Bhatia, et al., 2010; Thijssen, Postel, et al., 2006; Schliemann, Roesli, et al., 2010; Brack, Silacci, et al., 2006; Rybak, Roesli, et al., 2007). A therapeutic targeted towards any of these molecules may be a vector to carry an erythrocyte-binding peptide to the tumor vasculature to cause specific occlusion.

An embodiment is a first ligand that specifically binds erythrocytes conjugated with a second ligand that specifically binds to a cancerous cell or the tumor vasculature or a component of the tumor vasculature, such as a protein in the subendothelium (which is partially exposed to the blood in a tumor) or a protein on the surface of a tumor endothelial cell. The ligand may be part of a pharmaceutically acceptable composition that is introduced into a patient, e.g., into the bloodstream. The ligands bind to erythrocytes and the tumor-homing ligand binds to a site at or near the tumor or tumor vasculature, or to a cancerous cell. The erythrocytes collect at the targeted site and block access of the target site to nutrients, e.g., by embolizing a blood vessel. Given that the embolization is mechanical, being determined by the physical size of the erythrocyte, embolization will be sudden.

Solid tumors depend heavily on their vascular supply, and biomolecular therapeutics as well as material therapeutics have been developed to either block growth of their vascular supply or to block flow to their vascular supply. An embodiment is a biomolecular formulation or a biomolecular-nanoparticulate formulation that is to be systemically injected to rapidly occlude the vasculature of solid tumors, in the primary tumor or in the metastases at known or unknown locations.

Tumor embolization has been approached in a number of ways, including the use of particle and biomolecular based methods. Biomaterial particles, including those made of polyvinyl alcohol, are of a diameter greater than the tumor microvasculature, e.g. 50-500 micrometers in diameter, and have been developed for use clinically in transcatheter arterial embolization, or TACE (Maluccio, Covey, et al., 2008). A parallel approach includes chemotherapeutics loaded inside the particles for slow release in transarterial chemoembolization (TACE) used mainly for the treatment for hepatocellular carcinoma (Gadaleta and Ranieri, 2010). In both cases, when particles are injected into the arterial circulation, usually by an interventional radiologist under radiographic guidance, these particles can flow into the tumor vasculature and occlude them, blocking flow (Maluccio, Covey, et al., 2008). With these local approaches, only the tumor that is directly targeted by the placement of the catheter is treated, and other tumors, such as metastases at known or unknown locations, go untreated since the particles are not easily targeted in the vessels. More recently, biomolecular approaches have been explored, for example using bispecific antibodies that recognize both a thrombosis factor and a tumor vascular endothelial marker not present in normal vasculature. After binding specifically to the tumor vasculature, the antibody accumulates and initiates the formation of blood clots within the tumor vessels to block them; this effect was only induced when the antibody was targeted to the tumor (Huang, Molema, et al., 1997). These biomolecular approaches have a benefit of targeting both primary and secondary tumors from intravenous infusions if specific tumor vascular signatures can be identified; yet they have a disadvantage of not providing sudden mechanical occlusion to the tumor.

Embodiments of the invention include a method of embolizing a tumor in a patient comprising administering a composition to a patient that comprises an erythrocyte-binding moiety coupled to a targeting moiety, wherein the targeting moiety is an antibody, antibody fragment, or peptide that is directed to a target chosen from the group consisting of a tumor and tumor microvasculature, and wherein the erythrocyte-binding moiety comprises a peptide, an antibody, an antibody fragment, or an aptamer that specifically binds erythrocytes. The peptide may be, e.g., a sequence as set forth herein.

Antigen-Specific Immunological Tolerance

In addition to improving the pharmacokinetic behavior of a therapeutic agent, it has been discovered that erythrocyte affinity may be used in methods of creating antigen-specific tolerance. Certain working and prophetic embodiments are set forth in the Examples. Tolerogenesis, as demonstrated herein, can result in elimination of circulating antibodies against an antigen, or reduction of circulating antibodies against an antigen by a factor of at least 10, i.e., at least 100, at least 1000, or more than 10,000. Tolerogenesis can prevent, cure, or slow disease progression, reduce or eliminate rejection of a transplanted tissue, and reduce or eliminate an allergic reaction to a substance.

Examples 14 and 21-23 detail how tolerance was created in mouse animal models predictive of human behavior. Example 14 showed the creation of tolerance using a test antigen (ovalbumin) connected to a peptide ligand that binds an erythrocyte surface. Examples 21-23 corroborate the results of Example 14 and provide further working examples showing creation of tolerance using ovalbumin attached to an scFv and asparaginase attached to a peptidic ligand. A working example showing creation of tolerance that reverses pre-existing immunorejection is provided in Example 23. Accordingly, embodiments include a fusion molecule for tolerogenesis comprising asparaginase, an antigenic asparaginase fragment, of an antigenic mimotope of asparaginase and an erythrocyte-binding moiety, with the erythrocyte-binding moiety specifically binding, for instance, glycophorin A or a target chosen from the group consisting of Band 3, glycophorin B, glycophorin C or other members of the Erythrocyte Target Group. The erythrocyte-binding moiety may be, for instance, chosen from the group consisting of antibodies, antibody fragments, scFvs, peptide ligands and aptamers and/or from the group consisting of ERY19, ERY59, ERY64, ERY123, ERY141, ERY162, ERY19', ERY59', ERY64', ERY123', ERY141', and ERY162' and conservative substitutions thereof. These fusion molecules may be applied prophylacticly before a first administration of asparaginase, during a course of treatment with asparaginase, and/or after a course of treatment with asparaginase. These fusion molecules may be applied before an immune response to asparaginase drug is observed, or after such a response is observed.

In Example 14, a peptide the binds mouse erythrocytes, ERY1, had been discovered. A molecular fusion of ERY1 was made with a test antigen, ovalbumin (OVA). The fusion bound specifically bound to erythrocytes in vivo and did not bind other molecules, including those in blood or the vasculature. A lengthy circulating half-life was observed. Erythrocyte binding of ERY1-OVA was observed to lead to efficient cross-presentation of the OVA immunodominant MHC I epitope (SIINFEKL) by antigen-presenting cells (APCs) and corresponding cross-priming of reactive T cells. ERY1-OVA induced much higher numbers of annexin-$V^+$ proliferating OT-I $CD8^+$ T cells than OVA (FIG. 12*d*), suggesting an apoptotic fate that would eventually lead to clonal deletion. Using an established OT-I challenge-to-tolerance model (Liu, Iyoda, et al., 2002) (FIG. 14*a*), ERY1-OVA was demonstrated to prevent subsequent immune responses to vaccine-mediated antigen challenge, even with a very strong bacterially-derived adjuvant. Intravenous administration of ERY1-OVA resulted in profound reductions in OT-I $CD8^+$ T cell populations in the draining lymph nodes (FIG. 14; gating in FIG. 14*b*) and spleens compared with mice administered unmodified OVA prior to antigen challenge with LPS (FIG. 14*c*), demonstrating deletional tolerance. This effective clonal deletion exhibited in mice administered ERY1-OVA supported earlier observations of enhanced OT-I $CD8^+$ T cell cross-priming (FIG. 12) and furthermore shows that cross-priming occurred in the absence of APC presentation of co-stimulatory molecules to lead to deletional tolerance. Intravenous administrations of ERY1-OVA caused a 39.8-fold lower OVA-specific serum IgG levels 19 d after the first antigen administration (FIG. 15) as compared to OVA-treated mice. To further validate the induction of antigen-specific immune tolerance, the OT-I challenge-to-tolerance model was combined with an OVA-expressing tumor graft model (FIG. 14), with favorable results. The results detailed in this Example demonstrate that erythrocyte binding by ERY1-OVA induces antigen-specific immune tolerance. This was shown in response to a strongly adjuvanted challenge as well as implanted cellular grafts expressing a xeno-antigen. Moreover, tolerance was achieved by functional inactivation and deletion of reactive $CD8^+$ T cells through interaction with antigen present on circulating erythrocytes, independent of direct $CD4^+$ T cell regulation. These detailed experiments with ERY1, a mouse erythrocyte binding peptide, are predictive of similar results in humans using human erythrocyte binding peptides, several of which are taught herein. Moreover, having shown that peptide ligands are effective, similar results may be made using conjugates with other erythrocyte binding ligands, e.g., antibodies, antibody fragments, or aptamers, with these moieties binding a surface molecule of an erythrocyte, for example, one of the surface proteins or antigens set forth herein.

Example 21 further demonstrated the creation of tolerance to a tolerogenic antigen by fusing the tolerogenic antigen to an scFv that binds an erythrocyte, and preparing the fusion molecule as a medicament for administration to a patient. Example 21 demonstrates induction of tolerance to the MHC-I immunodominant domain of OVA, which is the peptide SIINFEKL (SEQ ID NO:3). This antigen was fused to the scFv TER-119, which is known to bind to mouse erythrocytes. OT-I $CD8^+$ T cell proliferation, determined by dilution of the fluor CFSE as measured by flow cytometry, was markedly enhanced in mice administered TER119-SIINFEKL compared to ERY1-OVA or OVA (FIG. 20), demonstrating that erythrocyte-binding increased antigen-specific $CD8^+$ T cell cross-priming compared to the soluble antigen SIINFEKL. Furthermore, these data demonstrate that antibody fragments designed to bind erythrocytes and display immune epitopes are efficiently processed by immune cells to cross-prime antigen specific T cells. These results on cross-presentation and cross-priming are consistent with other studies concerning tolerogenic antigen presentation on MHC I by APCs engulfing antigen from apoptotic cells (Albert 1998, Green 2009). TER119-SIINFEKL and ERY1-OVA induced much higher numbers of annexin-$V^+$ and PD-$1^+$ proliferating OT-I $CD8^+$ T cells than OVA (FIG. 21), indicating an exhausted and apoptotic fate that leads to clonal deletion. This phenotype of proliferating $CD8^+$ T cells is consistent with other reported OT-I adoptive transfer models in which regulated antigen-specific T cell receptor engagement by APCs fails to induce inflammatory responses (Bursch, Rich, et al., 2009).

Referring to Example 21, the ability of TER119-SIINFEKL and ERY1-OVA to prevent subsequent immune responses to a vaccine-mediated antigen challenge were demonstrated—even when challenged with a very strong bacterially-derived adjuvant. Fusion molecules with either an scFv or a peptide ligand for binding an erythrocyte were thus effective to produce tolerance.

Example 22 shows that it is possible to induce antigen-specific immune tolerance towards therapeutic proteins and proteins with therapeutic potential. Many therapeutic proteins induce immune reactions, rendering their clinical use dangerous or ineffective. Asparaginase is a microbially-derived therapeutic enzyme used to treat acute lymphoblastic leukemia, yet also induces dangerous immune responses that obviate its repeated use. A mouse model was used. A fusion molecule of asparaginase and an erythrocyte-binding moiety (the peptide ERY1) was administered to mice and compared to mice treated with the clinical drug asparaginase. The drug asparaginase produced antibodies but the fusion molecule did not; this test established that antibody levels could be used as a measure of tolerance. Tolerance was then proven by administering the fusion molecule to mice followed by repeated administration of the clinical drug asparaginase, and observing that there was no potent antibody response, even after a very aggressive challenge by repeated dosing with the drug. In contrast, mice that received the drug but not the fusion molecule became immunoreactive and dangerously hypersensitive.

Example 23 shows that immunoreversal is possible. Mice that were immunoreactive to a protein were treated to become tolerant of the protein. The asparaginase mouse model of Example 22 was used. Mice that were immunoreactive to the drug asparaginase were treated with the fusion molecule (asparaginase-and-erythrocyte binder) and became tolerant of the drug asparaginase.

In contrast, prior reports teach that immunorejection is created by attaching an antigen to a surface of an erythrocyte to thereby make a vaccine, and other reports have used antigens encapsulated within erythrocytes to create vaccines. For instance when antigen is encapsulated within an erythrocyte, a vaccine is thereby made (Murray et al., Vaccine 24: 6129-6139 (2006)). Or antigens conjugated to an erythrocyte surface were immunogenic and proposed as vaccines (Chiarantini et al., Vaccine 15(3): 276-280 (1997)). These references show that the erythrocyte delivery approach an immune response as good as those obtained with normal vaccines with adjuvants. Others have reported that placement within an erythrocyte is needed for inducing tolerance, as in patent application WO 2011/051346, which also teaches several means by which to alter the erythrocyte surface to enhance clearance by Kupffer cells in the liver. This same application also teaches binding antibodies to erythrocyte surface proteins such as glycophorin A, but for the purpose of making immune complexes on the erythrocyte to enhance its clearance by Kupffer cells.

Embodiments set forth herein provide for a method of producing immunotolerance, the method comprising administering a composition comprising a molecular fusion that comprises a tolerogenic antigen and an erythrocyte-binding moiety that specifically binds an erythrocyte in the patient and thereby links the antigen to the erythrocyte, wherein the molecular fusion is administered in an amount effective to produce immunotolerance to a substance that comprises the tolerogenic antigen. The erythrocyte, and patient, may be free of treatments that cause other alterations to erythrocytes, and free of erythrocyte crosslinking, chemical covalent conjugations, coatings, and other alterations other than the specific binding of the peptide. The molecular fusion may comprise, or consist of, the erythrocyte-binding moiety directly covalently bonded to the antigen. The molecular fusion may comprise the erythrocyte-binding moiety attached to a particle that is attached to the antigen. The particle may comprise a microparticle, a nanoparticle, a liposome, a polymersome, or a micelle. The tolerogenic antigen may comprise a portion of a therapeutic protein, e.g., a blood factor administered to a patient suffering from a lack of production of the factor. Embodiments include the instances wherein: the patient is a human and the tolerogenic antigen is a human protein of which the patient is genetically deficient; wherein the patient is a human and the tolerogenic antigen comprises a portion of a nonhuman protein; wherein the patient is a human and the tolerogenic antigen comprises a portion of an engineered therapeutic protein not naturally found in a human; wherein the patient is a human and the tolerogenic antigen comprises a portion of a protein that comprises nonhuman glycosylation; wherein the tolerogenic antigen comprises a portion of a human autoimmune disease protein; wherein the tolerogenic antigen is an antigen in allograft transplantation; wherein the tolerogenic antigen comprises a portion of a substance chosen from the group consisting of human food; and/or wherein the erythrocyte-binding moiety is chosen from the group consisting of a peptide, an antibody, and an antibody fragment. Embodiments include tolerization materials and methods wherein the erythrocyte-binding moiety comprises a peptide comprising at least 5 consecutive amino acid residues of a sequence chosen from the group consisting of SEQ ID NO:11, SEQ ID NO:13, SEQ ID NO:14, SEQ ID NO:15, SEQ ID NO:16, SEQ ID NO:17, SEQ ID NO: 1, and conservative substitutions thereof, wherein said sequence specifically binds an erythrocyte.

The molecular fusion may be chosen to place the antigen on the inside or the outside of the erythrocyte. Without being bound to a particular mechanism of action, the following theory is presented. In man, approximately 1% of erythrocytes become apoptotic (eryptotic) and are cleared each day, a large number of cells, and their proteins are processed in a manner so as to maintain tolerance to the erythrocyte self-antigens. An antigen engineered to bind to erythrocytes through the use of the ERY1 peptide or a human erythrocyte binding peptide, an erythrocyte-binding single chain antibody or antibody, an erythrocyte-binding aptamer, or another erythrocyte-binding agent may also elicit the same tolerogenic response. Given that the current state-of-the-art method developed by Miller and colleagues (see above) is cumbersome, in that it requires harvesting and reacting donor splenocytes for re-administration, our non-covalent erythrocyte-binding method provides a simpler alternative. As the ERY1-erythrocyte or human erythrocyte binding peptide-erythrocyte or other affinity biomolecule (single chain antibody, antibody, or aptamer, for example) interaction occurs spontaneously after introduction of the antigen conjugate or fusion in vivo, the engineered antigen is simply administered by injection, and binding occurs in situ.

In some cases, the tolerogenic antigen is derived from a therapeutic agent protein to which tolerance is desired. Examples are protein drugs in their wild type, e.g., human factor VIII or factor IX, to which patients did not establish central tolerance because they were deficient in those proteins; or nonhuman protein drugs, used in a human. Other examples are protein drugs that are glycosylated in nonhuman forms due to production, or engineered protein drugs, e.g., having non-native sequences that can provoke an unwanted immune response. Examples of tolerogenic antigens that are engineered therapeutic proteins not naturally found in humans include human proteins with engineered mutations, e.g., mutations to improve pharmacological characteristics. Examples of tolerogenic antigens that comprise nonhuman glycosylation include proteins produced in yeast or insect cells.

Embodiments include administering a protein at some frequency X or dose Y and also administering an antigen from that protein at a lesser frequency and/or dose, e.g., a frequency that is not more than 0.2X or a dose that is not more than 0.2Y; artisans will immediately appreciate that all the ranges and values within the explicitly stated ranges are contemplated, e.g., 0.01 or 005 X or some range therebetween.

Embodiments include choosing the tolerogenic antigen from proteins that are administered to humans that are deficient in the protein. Deficient means that the patient receiving the protein does not naturally produce enough of the protein. Moreover, the proteins may be proteins for which a patient is genetically deficient. Such proteins include, for example, antithrombin-III, protein C, factor VIII, factor IX, growth hormone, somatotropin, insulin, pramlintide acetate, mecasermin (IGF-1), β-gluco cerebrosidase, alglucosidase-α, laronidase (α-L-iduronidase), idursuphase (iduronate-2-sulphatase), galsulphase, agalsidase-β (α-galactosidase), α-1 proteinase inhibitor, and albumin. Accordingly, embodiments include a fusion molecule for tolerogenesis comprising an erythrocyte-binding moiety and at least one antigen, antigenic fragment, or antigenic mimotope of one or more of these proteins, with the erythrocyte-binding moiety specifically binding, for instance, glycophorin A or a target chosen from the group consisting of Band 3, glycophorin B, glycophorin C or other members of the Erythrocyte Target Group. The erythrocyte-binding moiety may be, for instance, chosen from the group consisting of antibodies, antibody fragments, scFvs, peptide ligands and aptamers.

Embodiments include choosing the tolerogenic antigen from therapeutic antibodies and antibody-like molecules, including antibody fragments and fusion proteins with antibodies and antibody fragments. These include nonhuman (such as mouse) antibodies, chimeric antibodies, and humanized antibodies. Immune responses to even humanized antibodies have been observed in humans (Getts, 2010). Accordingly, embodiments include a fusion molecule for tolerogenesis comprising an erythrocyte-binding moiety and at least one antigen, antigenic fragment, or antigenic mimotope of one or more of these proteins, with the erythrocyte-binding moiety specifically binding, for instance, glycophorin A or a target chosen from the group consisting of Band 3, glycophorin B, glycophorin C or other members of the Erythrocyte Target Group. The erythrocyte-binding moiety may be, for instance, chosen from the group consisting of antibodies, antibody fragments, scFvs, peptide ligands and aptamers.

Embodiments include choosing the tolerogenic antigen from proteins that are nonhuman. Examples of such proteins include adenosine deaminase, pancreatic lipase, pancreatic amylase, lactase, botulinum toxin type A, botulinum toxin type B, collagenase, hyaluronidase, papain, L-Asparaginase, rasburicase, lepirudin, streptokinase, anistreplase (anisoylated plasminogen streptokinase activator complex), antithymocyte globulin, crotalidae polyvalent immune Fab, digoxin immune serum Fab, L-arginase, and L-methionase.

Embodiments include choosing the tolerogenic antigen from human allograft transplantation antigens. Examples of these antigens are the subunits of the various MHC class I and MHC class II haplotype proteins, and single-amino-acid polymorphisms on minor blood group antigens including RhCE, Kell, Kidd, Duffy and Ss. A In some cases, the tolerogenic antigen is a self antigen against which a patient has developed an autoimmune response or may develop an autoimmune response. Examples are proinsulin (diabetes), collagens (rheumatoid arthritis), myelin basic protein (multiple sclerosis).

For instance, Type 1 diabetes mellitus (T1D) is an autoimmune disease whereby T cells that recognize islet proteins have broken free of immune regulation and signal the immune system to destroy pancreatic tissue. Numerous protein antigens that are targets of such diabetogenic T cells have been discovered, including insulin, GAD65, chromogranin-A, among others. In the treatment or prevention of T1D, it would be useful to induce antigen-specific immune tolerance towards defined diabetogenic antigens to functionally inactivate or delete the diabetogenic T cell clones. Example 25 details how a fusion molecule presenting the chromogranin-A (ChrA) mimotope as a tolerogenic antigen successfully created tolerogenesis to ChrA, based on T-cell data that was established as predictive in the other Examples. Accordingly, embodiments include a fusion molecule for tolerogenesis comprising chromogranin-A, an antigen or antigenic portion thereof, or a mimotope of the same with an erythrocyte-binding moiety, with the erythrocyte-binding moiety specifically binding, for instance, glycophorin A or a target chosen from the group consisting of Band 3, glycophorin B, glycophorin C or other members of the Erythrocyte Target Group. The erythrocyte-binding moiety may be, for instance, chosen from the group consisting of antibodies, antibody fragments, scFvs, peptide ligands and aptamers and/or from the group consisting of ERY19, ERY59, ERY64, ERY123, ERY141, ERY162, ERY19', ERY59', ERY64', ERY123', ERY141', ERY162' and conservative substitutions thereof.

Accordingly, tolerance and/or delay of onset or progression of autoimmune diseases may be achieved for various of the many proteins that are human autoimmune proteins, a term referring to various autoimmune diseases wherein the protein or proteins causing the disease are known or can be established by routine testing.

Embodiments include testing a patient to identify an autoimmune protein and creating an antigen for use in a molecular fusion and creating immunotolerance to the protein. Embodiments include an antigen, or choosing an antigen from, one or more of the following proteins. In type 1 diabetes mellitus, several main antigens have been identified: insulin, proinsulin, preproinsulin, glutamic acid decarboxylase-65 (GAD-65), GAD-67, insulinoma-associated protein 2 (IA-2), and insulinoma-associated protein 2β (IA-2β); other antigens include ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor. In Addison's disease, main antigens include 21-hydroxylase, 17α-hydroxylase, and P450 side chain cleavage enzyme (P450scc); other antigens include ACTH receptor, P450c21 and P450c17. In premature ovarian failure, main antigens include FSH receptor and α-enolase. In autoimmune hypophysitis, or pituitary autoimmune disease, main antigens include pituitary gland-specific protein factor (PGSF) 1a and 2; another antigen is type 2 iodothyronine deiodinase. In multiple sclerosis, main antigens include myelin basic protein, myelin oligodendrocyte glycoprotein and proteolipid protein. In rheumatoid arthritis, a main antigen is collagen II. In immunogastritis, a main antigen is $H^+$, $K^+$-ATPase. In pernicious angemis, a main antigen is intrinsic factor. In celiac disease, main antigens are tissue transglutaminase and gliadin. In vitiligo, a main antigen is tyrosinase, and tyrosinase related protein 1 and 2. In myasthenia gravis, a main antigen is acetylcholine receptor. In pemphigus vulgaris and variants, main antigens are desmoglein 3, 1 and 4; other antigens include pemphaxin, desmocollins, plakoglobin, perplakin, desmoplakins, and acetylcholine receptor. In bullous pemphigoid, main antigens include BP180 and BP230; other antigens include plectin and laminin 5. In dermatitis herpetiformis Duhring, main antigens include endomysium and tissue transglutaminase. In epidermolysis bullosa acquisita, a main antigen is collagen VII. In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jol, NAG-2, centromere proteins, topoisomerase I, nucleolar proteins, RNA polymerase I, II and III, PM-Slc, fibrillarin, and B23. In mixed connective tissue disease, a main antigen is U1snRNP. In Sjogren's syndrome, the main antigens are nuclear antigens SS-A and SS-B; other antigens include fodrin, poly(ADP-ribose) polymerase and topoisomerase. In systemic lupus erythematosus, main antigens include nuclear proteins including SS-A, high mobility group box 1 (HMGB1), nucleosomes, histone proteins and double-stranded DNA. In Goodpasture's syndrome, main antigens include glomerular basement membrane proteins including collagen IV. In rheumatic heart disease, a main antigen is cardiac myosin. Other autoantigens revealed in autoimmune polyglandular syndrome type 1 include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega. Example 26 provides detailed guidance for tolerogenesis to such proteins, and specifically describes a process with insulin as an example.

In some cases, the tolerogenic antigen is a foreign antigen against which a patient has developed an unwanted immune response. Examples are food antigens. Embodiments include testing a patient to identify foreign antigen and creating a molecular fusion that comprises the antigen and treating the patient to develop immunotolerance to the antigen or food. Examples of such foods and/or antigens are provided. Examples are from peanut: conarachin (Ara h 1), allergen II (Ara h 2), *arachis* agglutinin, conglutin (Ara h 6); from apple: 31 kda major allergen/disease resistance protein homolog (Mal d 2), lipid transfer protein precursor (Mal d 3), major allergen Mal d 1.031) (Mal d 1); from milk: α-lactalbumin (ALA), lactotransferrin; from kiwi: actinidin (Act c 1, Act d 1), phytocystatin, thaumatin-like protein (Act d 2), kiwellin (Act d 5); from mustard: 2S albumin (Sin a 1), 11S globulin (Sin a 2), lipid transfer protein (Sin a 3), profilin (Sin a 4); from celery: profilin (Api g 4), high molecular weight glycoprotein (Api g 5); from shrimp: Pen a 1 allergen (Pen a 1), allergen Pen m 2 (Pen m 2), tropomyosin fast isoform; from wheat and/or other cerials: high molecular weight glutenin, low molecular weight glutenin, alpha- and gamma-gliadin, hordein, secalin, avenin; from strawberry: major strawberry allergy Fra a 1-E (Fra a 1), from banana: profilin (Mus xp 1).

Many protein drugs that are used in human and veterinary medicine induce immune responses, which creates risks for the patient and limits the efficacy of the drug. This can occur with human proteins that have been engineered, with human proteins used in patients with congenital deficiencies in production of that protein, and with nonhuman proteins. It would be advantageous to tolerize a recipient to these protein drugs prior to initial administration, and it would be advantageous to tolerize a recipient to these protein drugs after initial administration and development of immune response. In patients with autoimmunity, the self-antigen(s) to which autoimmunity is developed are known. In these cases, it would be advantageous to tolerize subjects at risk prior to development of autoimmunity, and it would be advantageous to tolerize subjects at the time of or after development of biomolecular indicators of incipient autoimmunity. For example, in Type 1 diabetes mellitus, immunological indicators of autoimmunity are present before broad destruction of beta cells in the pancreas and onset of clinical disease involved in glucose homeostasis. It would be advantageous to tolerize a subject after detection of these immunological indicators prior to onset of clinical disease.

Recent work by headed by Miller and colleagues has shown that covalently conjugating an antigen to allogenic splenocytes ex vivo creates antigen-specific immune tolerance when administered intravenously in mice (Godsel, Wang, et al., 2001; Luo, Pothoven, et al., 2008). The process involves harvesting donor splenic antigen-presenting cells and chemically reacting them in an amine-carboxylic acid crosslinking reaction scheme. The technique has proven effective in inducing antigen-specific tolerance for mouse models of multiple sclerosis (Godsel, Wang, et al., 2001), new onset diabetes type 1 (Fife, Guleria, et al., 2006), and allogenic islet transplants (Luo, Pothoven, et al., 2008). Though the exact mechanism responsible for the tolerogenic response is not known, it is proposed that a major requirement involves antigen presentation without the expression of co-stimulatory molecules on apoptotic antigen-coupled cells (Miller, Turley, et al., 2007). It has also been contemplated to encapsulate antigens within erythrocyte ghosts, processing the erythrocytes ex vivo and re-injecting them, as in WO2011/051346.

Administration

Many embodiments of the invention set forth herein describe compositions that may be administered to a human or other animal patient. Embodiments of the invention include, for example, molecular fusions, fusion proteins, peptide ligands, antibodies, scFv, that recognize antigens on erythrocytes or tumors or tumor vasculature, as well as combinations thereof. These compositions may be prepared as pharmaceutically acceptable compositions and with suitable pharmaceutically acceptable carriers or excipients.

The compositions that bind erythrocytes may do so with specificity. This specificity provides for in vivo binding of the compositions with the erythrocytes, as well as alternative ex vivo processes. Accordingly, the compositions may be directly injected into a vasculature of the patient. An alternative is injection into a tissue, e.g., muscle, dermal, or subcutaneous, for subsequent erythrocyte contact and uptake. An embodiment of the invention is a method of inducing tolerogenesis in a patient comprising administering a tolerizing antigen to the patient in association with an erythrocyte-binding moiety to thereby attach the antigen to an erythrocyte in vivo; the in vivo attachment can thus be performed without ex vivo processing of erythrocytes. This process may be performed wherein the erythrocyte is not made to be apoptotic as a result of the process. This process may be performed so that it is free of (does not involve) exposing the erythrocytes to one or more of: a crosslinking agent; a crosslinking agent that crosslinks surface molecules of an erythrocyte; a crosslinking agent comprising at least two functional groups; a crosslinking agent that forms a covalent bind with an erythrocyte; functional groups that form a covalent bond with an erythrocyte; and an antigen and/or antigenic substance that covalently bonds to the erythrocyte. The process may be performed so that the erythrocytes and/or the antigens are free of 1-ethyl-3-(3-dimethylaminopropyl) carbodiimide) (EDC; also EDAC or EDCI) and may also be free of any reactions with a carbodiimide. This process may be performed with autologous erythrocytes and may be free of allogeneic erythrocytes.

Pharmaceutically acceptable carriers or excipients may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a pharmaceutically acceptable carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts. Thus pharmaceutically acceptable compositions are highly purified to be free of contaminants, are biocompatible and not toxic, are suited to administration to a patient. In the case of water as the carrier, the water is highly purified and processed to be free of contaminants, e.g., endotoxins.

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

EXAMPLES

Example 1: Screening for Erythrocyte-Binding Peptides with Mouse Erythrocytes

The PhD naïve 12 amino acid peptide phage library commercially available from New England Biolabs (NEB) was used in the selection. In each round of screening, $10^{11}$ input phage were incubated with mouse erythrocytes in PBS with 50 mg/mL BSA (PBSA-50). After 1 h at 37° C., unbound phage were removed by centrifugation in PERCOLL (GE Life Sciences) at 1500 g for 15 min. A subsequent dissociation step was carried out in PBSA-50 in order to remove low-affinity binding phage. Dissociation duration and temperature were increased in later rounds of screening to increase stringency of the selection process. In round 1, phage binding was followed by a 2 min dissociation step at room temperature prior to washing and elution. In round 2, phage binding was followed by a 10 min dissociation at 37° C. In rounds 3 and 4, two separate and sequential dissociation steps were conducted at 37° C.: 10 min followed by 15 min in round 3, and 10 min followed by 30 min in round 4. Erythrocyte-associated phage were eluted with 0.2 M glycine, pH 2.2 for 10 min, and the solution neutralized with 0.15 volumes of 1 M Tris, pH 9.1. Applying 4 rounds of selection against whole erythrocytes substantially enriched the library towards high-affinity phage clones, as illustrated by flow cytometry. Infective or plaque forming units were calculated by standard titering techniques. Phage samples were serially diluted into fresh LB media, and 10 µL of the phage dilution was added to 200 µL of early-log phase ER2738 E. coli (NEB). Following a 3 minute incubation at room temperature, the solution was added to 3 mL of top agar, mixed, and poured onto LB plates containing IPTG and XGal. Following incubation overnight at 37° C., blue colonies were counted as plaque forming units (pfu).

Example 2: Characterizing of Binding to Mouse Erythrocytes

Result: Microscopy confirmed that the ERY1 phage binds the erythrocyte cell surface without altering cell morphology and without cytoplasmic translocation. Fluorescence and phase contrast images reiterated the erythrocyte-binding capacity of ERY1 phage relative to the non-selected library. High-resolution confocal imaging revealed that ERY1 phage are distributed across the cell surface (as opposed to being clustered at a single site) and bind preferentially to the equatorial periphery of the cell surface, and that binding was homogeneous among erythrocytes (FIG. 1).

Method: For all samples sample, $10^{11}$ input phage were incubated with mouse erythrocytes in PBS-50. After 1 h at 37° C., unbound phage were removed by centrifugation at 200 g for 3 min. For regular fluorescence microscopy samples, cells were incubated with anti-M13 coat protein-PE antibody (Santa Cruz Biotechnology) at a 1:20 dilution in PBSA-5 for 1 h at room temperature. Cells were spun at 200 g for 3 min, resuspended in 10 µL of hard-set mounting medium (VECTASHIELD), applied to a microscope slide, covered with a cover slip, and visualized. For confocal microscope samples, cells were incubated with rabbit anti-fd bacteriophage (Sigma) and anti-rabbit ALEXAFLUOR conjugate (Invitrogen).

Example 3: Characterizing the Molecular Target of Binding to Mouse Erythrocytes

Figure 2:
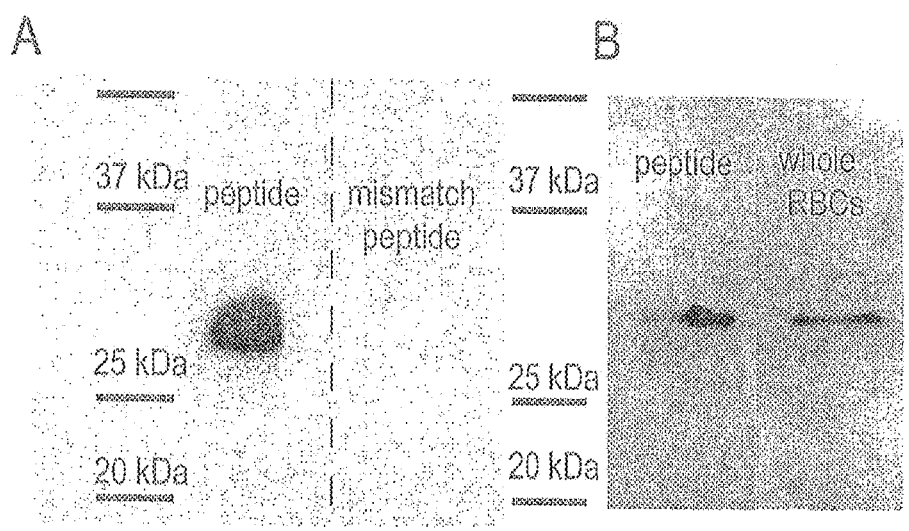
FIG. 2 is a photo montage of an affinity pull-down with soluble biotinylated ERY1 peptide: In panel A: streptavidin-HRP Western blot of eluted sample using the ERY1 and mismatched peptides; In panel B: anti-mouse GYPA Western blot of eluted sample using the ERY1 peptide compared to whole erythrocyte lysate.

Result: To search for the molecular target for the ERY1 peptide, affinity pull-down techniques using a biotinylated soluble peptide were employed; this method revealed glycophorin-A (GYPA) as the ERY1 ligand on the erythrocyte membrane. When whole erythrocytes were incubated with ERY1 peptide functionalized with biotin and a photoactivatable crosslinker, a single 28 kDa protein was conjugated with the peptide-biotin complex, as detected by a streptavidin Western blot (FIG. 2A). The reaction lysate was extensively washed and purified using streptavidin magnetic beads to ensure no unlabeled proteins from the erythrocyte lysate remained. As expected, the mismatch peptide failed to conjugate to any erythrocyte proteins. The mismatch peptide, PLLTVGMDLWPW (SEQ ID NO:2), was designed to contain the same amino acid residues as ERY1, and to match its hydrophobicity topography. Evidence of the apparent size of the interacting protein suggested several smaller, single pass membrane proteins as likely ligands, namely the glycophorins. Anti-GYPA Western blotting of the same purified samples from the crosslinking reaction confirmed that the candidate biotinlyated protein was indeed GYPA (FIG. 2B).

Co-localization of ERY1 phage with GYPA was analyzed by high-resolution confocal microscopy. GYPA is naturally expressed and presented as part of a complex comprised of several membrane and cytoskeletal proteins (Mohandas and Gallagher, 2008). This is visually evident in GYPA staining, whereby non-uniform labeling was seen at the cell equatorial periphery. Labeling with ERY1 phage produced extremely similar staining topographies. A high overlap coefficient of 0.97 in co-localization analysis, corroborated the conclusion that ERY1 phage and anti-GYPA bind to the same protein. GYPA clustering was also witnessed in erythrocytes labeled with library phage, yet no phage binding thus no co-localization was evident.

Method: The ERY1 ($H_2N$-WMVLPWLPGTLDGGS-GCRG-$CONH_2$) (SEQ ID NO:19) and mismatch ($H_2N$-PLLTVGMDLWPWGGSGCRG-$CONH_2$) (SEQ ID NO:20) peptides were synthesized using standard solid-phase f-moc chemistry on TGR resin. The peptide was cleaved from the resin in 95% tri-fluoroacetic acid, 2.5% ethanedithiol, 2.5% water, and precipitated in ice-cold diethyl ether. Purification was conducted on a Waters preparative HPLC-MS using a C18 reverse phase column.

The ERY1 and mismatch peptide were conjugated to Mts-Atf-biotin (Thermo Scientific) as suggested by the manufacturer. In brief, peptides were solubilized in PBS/DMF and reacted with 1.05 equivalents of Mts-atf-biotin overnight at 4° C. Following clarification of the reaction by centrifugation, biotinylated peptide was incubated with erythrocytes at in PBSA-50 for 1 h at 37° C., cells were washed twice in fresh PBS, and were UV irradiated at 365 nm for 8 min at room temperature. Cells were lysed by sonication and the lysate was purified using streptavidin-coated magnetic beads (Invitrogen). The eluate was run on an SDS-PAGE and transferred to a PVDF membrane, and immunoblotted with streptavidin-HRP (R&D Systems) or anti-mouse GYPA.

Figure 3:
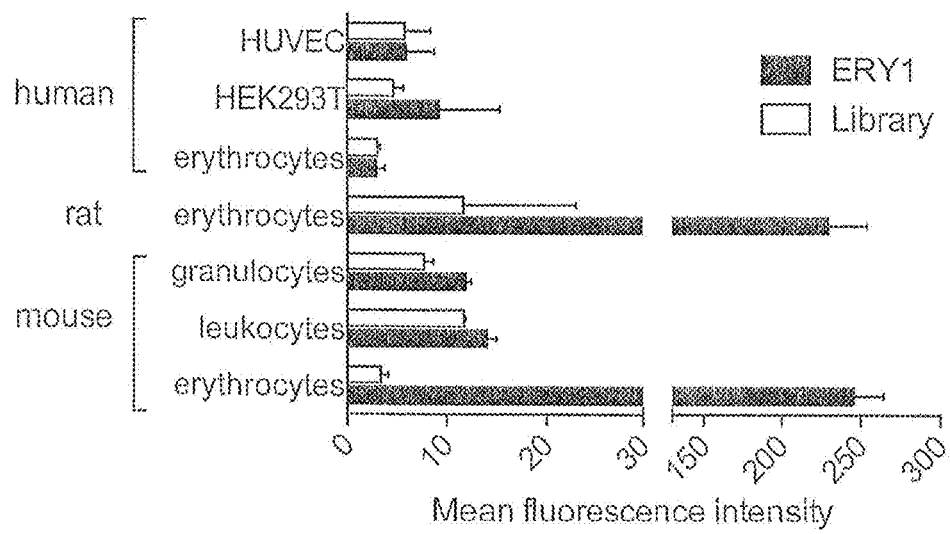
FIG. 3 is a plot of a cell binding panel.

Example 4: Characterizing Binding or the Lack of Binding of ERY1 to Other Mouse Cells and Erythrocytes from Other Species Result: Flow cytometric screening of a panel of interspecies cell lines demonstrated the ERY1 phage was specific for mouse and rat erythrocytes, with no measurable binding to mouse leukocytes or human cells (FIG. 3). These data suggested that the specific membrane protein acting as the ERY1 ligand was found solely in erythroid cells, and not in myeloid or lymphoid cell lineages. Furthermore, this validated the screening method of using freshly isolated blood with little prior purification other than centrifugation for a target.

Method: To determine phage binding, approximately $10^{10}$ phage particles were used to label $5\times10^5$ cells in PBSA-50 for 1 h at 37° C. Following a 4-min centrifugation at 200 g, cells were resuspended in PBSA-5 and anti-phage-PE was added at a 1:20 dilution for 1 h at room temperature. After a final spin/wash cycle, cells were resuspended in PBSA-5 and analyzed on a flow cytometer.

Example 5: Characterizing Intravascular Pharmacokinetics with a Model Protein

Figure 4:
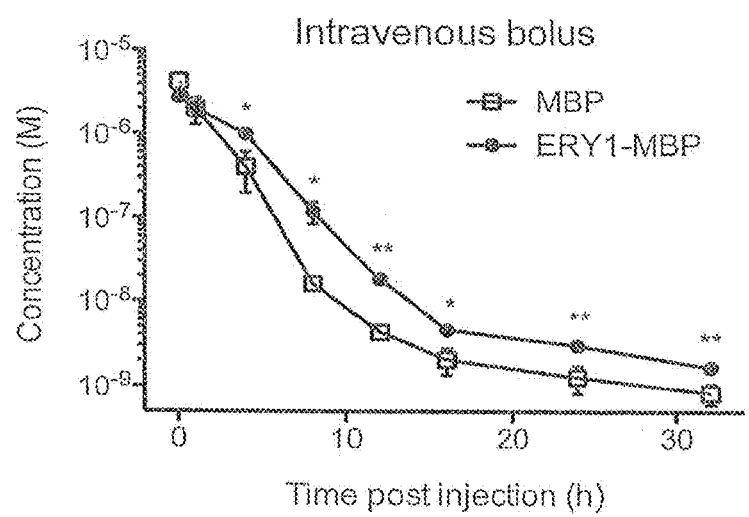
FIG. 4 is a semi logarithmic plot of an intravenous bolus of ERY1-MBP showing plasma MBP concentration following intravenous administration and concentration versus time of ERY1-MBP compared to MBP.

Result: To characterize the effect of the ERY1 peptide upon the pharmacokinetics of a protein, we expressed the model protein maltose binding protein (MBP) as an N-terminal fusion with the ERY1 peptide (ERY1-MBP). Upon intravascular administration, the ERY1-MBP variant exhibited extended circulation relative to the wild-type protein (FIG. 4). Blood samples at time points taken immediately following injection confirmed that initial concentrations, and thus the dose, were identical in both formulations. Beginning 4 h after intravenous injection, ERY1-MBP was cleared from circulation at a statistically significant slower rate than the non-binding wild-type MBP.

ERY1-MBP demonstrated a 3.28 (for a single-compartment model) to 6.39 fold (for a two-compartment model) increase in serum half-life and a 2.14 fold decrease in clearance as compared to the wild-type MBP. Analyzing concentrations using a standard one-compartment pharmacokinetic model yielded a half-life of 0.92 h and 3.02 h for the wild-type and ERY1 variants, respectively. The data were also accurately fit to a two-compartment model ($R^2 \geq 0.98$) to obtain a and 3 half lives of 0.41 h and 1.11 h, and 2.62 h and 3.17 h, for the wild-type and ERY1 variants, respectively. Accordingly, a half-life extension with human erythrocyte binding peptides and other erythrocyte binding ligands as taught herein may be expected.

Method: Clonal replicative form M13KE DNA was extracted using a standard plasmid isolation kit. The resultant plasmid was digested with Acc65I and EagI to obtain the gIII fusion gene and then ligated into the same sites in pMAL-pIII, yielding the plasmid herein termed pMAL-ERY1. Sequence verified clones were expressed in BL21 *E. coli*. In brief, mid-log BL21 cultures were induced with IPTG to a final concentration of 0.3 mM for 3 h at 37° C. An osmotic shock treatment with 20 mM Tris, 20% sucrose, 2 mM EDTA for 10 min, followed by a second treatment in 5 mM $MgSO_4$ for 15 min at 4° C., allowed for the periplasmically expressed MBP fusion to be isolated from the cell debris. Purification of the fusion protein was conducted on amylose SEPHAROSE and analyzed for purity by SDS-PAGE.

The Swiss Vaud Veterinary Office previously approved all animal procedures. While under anesthesia with ketamine/xylasine, the mouse tail was warmed in 42° C. water and 150 μg of protein was injected in a 100 μL volume directly into the tail vein. Care was taken to ensure mice were kept at 37° C. while under anesthesia. Blood was drawn by a small scalpel incision on the base of the tail, and diluted 10-fold in PBSA-5, 10 mM EDTA, and stored at −20° C. until further analysis. Blood samples were analyzed for MBP concentration by sandwich ELISA. In brief, monoclonal mouse anti-MBP was used as the capture antibody, polyclonal rabbit anti-MBP as the primary antibody, and goat anti-rabbit-HRP as the secondary antibody. The data were analyzed in PRISM4 using standard pharmacokinetic compartmental analysis, using Eq. 1 and Eq. 2

$$A = A_0 e^{-Kt}$$ Equation 1: Standard one-compartment model where A is the amount of free drug in the body at time t and $A_0$ is the initial amount of drug at time zero.

$$A = ae^{-\alpha t} + be^{-\beta t}$$ Equation 2: Standard two-compartment model where A is the amount of free drug in the central compartment at time t.

Figure 5:
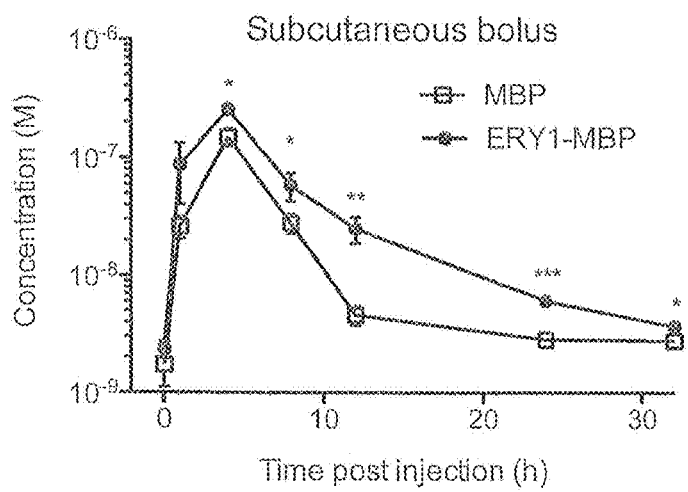
FIG. 5 is a semi logarithmic plot of a subcutaneous bolus of ERY1-MBP showing plasma MBP concentration following subcutaneous administration; concentration versus time for MBP versus ERY1-MBP.

Example 6: Characterizing Subcutaneous Pharmacokinetics with a Model Protein Result: Upon extravascular administration, the ERY1-MBP variant exhibited extended circulation relative to the wild-type protein (FIG. 5). Blood samples at time points taken immediately following injection confirmed that initial concentrations, and thus the dose, were identical in both formulations. Following subcutaneous injection, similar trends of heightened blood concentrations of ERY1-MBP were seen sustained throughout the experimental duration. Analyzing blood concentrations revealed that the ERY1-MBP variant demonstrated a 1.67 increase in bioavailability as compared to wild-type MBP. Accordingly, half-life extension is possible with human erythrocyte binding peptides and other erythrocyte binding ligands as taught herein.

Method: Clonal replicative form M13KE DNA was extracted using a standard plasmid isolation kit. The resultant plasmid was digested with Acc651 and EagI to obtain the gIII fusion gene and then ligated into the same sites in pMAL-pIII, yielding the plasmid herein termed pMAL-ERY1. Sequence verified clones were expressed in BL21 *E. coli*. In brief, mid-log BL21 cultures were induced with IPTG to a final concentration of 0.3 mM for 3 h at 37° C. An osmotic shock treatment with 20 mM Tris, 20% sucrose, 2 mM EDTA for 10 min, followed by a second treatment in 5 mM MgSO$_4$ for 15 min at 4° C., allowed for the periplasmically expressed MBP fusion to be isolated from the cell debris. Purification of the fusion protein was conducted on amylose Sepharose and analyzed for purity by SDS-PAGE.

The Swiss Vaud Veterinary Office previously approved all animal procedures. While under anesthesia with isoflurane, 150 µg of protein was injected in a 100 µL volume directly into the back skin of mice. Care was taken to ensure mice were kept at 37° C. while under anesthesia. Blood was drawn by a small scalpel incision on the base of the tail, and diluted 10-fold in PBSA-5, 10 mM EDTA, and stored at −20 C until further analysis. Blood samples were analyzed for MBP concentration by sandwich ELISA. In brief, monoclonal mouse anti-MBP was used as the capture antibody, polyclonal rabbit anti-MBP as the primary antibody, and goat anti-rabbit-HRP as the secondary antibody. The data were analyzed in Prism4 using standard pharmacokinetic compartmental analysis, using Eq. 3.

Bioavailability Equation 3

$$B = \frac{AUC_\infty^{s.c.}}{AUC_\infty^{i.v.}}$$

where AUC is the area under the curve of the plasma concentration vs. time graph, s.c. is subcutaneous and i.v. is intravenous.

Example 7: Engineering the Linker Domain of scFv Antibodies

Method: The gene encoding for the scFv fragment against the extra domain A of fibronectin was ordered synthesized from DNA 2.0 (Menlo Park, Calif., USA):

(SEQ ID NO: 21)
5'ATGGCAAGCATGACCGGTGGCCAACAAATGGGTACGGAAGTGCAACTG
CTGGAGTCTGGCGGTGGCCTGGTTCAGCCGGGTGGCAGCTTGCGCCTGAG
CTGTGCGGCGTCTGGCTTCACCTTTAGCGTCATGAAAATGAGCTGGGTTC
GCCAGGCACCAGGTAAAGGCCTGGAGTGGGTGTCGGCAATCAGCGGTTCC
GGTGGTAGCACCTATTACGCTGACAGCGTGAAAGGCCGTTTTACGATTTC
GCGTGATAACAGCAAGAACACGCTGTACTTGCAAATGAATAGCCTGCGTG
CAGAGGACACGGCAGTGTACTATTGTGCGAAGAGCACTCACCTGTACTTG
TTTGATTACTGGGGTCAAGGCACCCTGGTTACCGTTAGCAGCGGCGGTGG
TGGCTCCGGTGGTGGTGGTAGCGGTGGCGGTGGTTCTGGTGGTGCGCGGC
TCTGAAATTGTCCTGACTCAGAGCCCTGGCAGCTGAGCCTGAGCCCGGGT
GAGCGCGCGACGCTGAGCTGCCGTGCGAGCCAGTCCGTTAGCAACGCGTT
CCTGGCTTGGTATCAACAGAAACCGGGTCAGGCCCCTCGCCTGCTGATTT
ACGGTGCCAGCTCCCGTGCGACGGGCATCCCGGACCGTTTTCCGGCTCC
GGTAGCGGCACCGACTTCACCCTGACCATCAGCCGCCTGGAGCCGGAGGA
TTTCGCGGTGTATTACTGCCAGCAAATGCGTGGCCGTCCGCCGACCTTCG
GTCAGGGTACCAAGGTCGAGATTAAGGCTGCGGCCGAACAGAAACTGATC
AGCGAAGAAGATTTGAATGGTGCCGCG-3'.

For construction of an expression plasmid containing the wild-type scFv, primers SK01 and SK02 were used to PCR amplify the gene and add HindIII (5' end) and XhoI (3' end) restriction sites, as well as two stop codons at the 3' end. For construction of the REP mutant scFv containing the ERY1 peptide in the linker region of the scFv, overlap extension PCR was used. Using primers SK01 and SK03, a gene fragment comprising of the 5' half of the scFv followed by an ERY1 gene fragment was created by PCR. Using primers SK02 and SK04, a gene fragment comprising of an ERY1 gene fragment (complimentary to the aforementioned fragment) followed by the 3' half of the scFv was created by PCR. The gene fragments were purified following agarose electrophoresis using a standard kit (Zymo Research, Orange, Calif., USA), and the two fragments were fused using PCR. A final amplification PCR using SK01 and SK02 primers was conducted to create the correct restriction sites and stop codons. Construction of the INS mutant scFv was conducted in exactly the same manner as the REP mutant, except primer SK05 was used in place of SK03, and SK06 was used in place of SK04. Each final completed scFv gene product was digested with HindIII and XhoI (NEB, Ipswich, Mass., USA), and ligated into the same sites on the pSec-TagA mammalian expression plasmid (Invitrogen, Carlsbad, Calif., USA).

| SEQ ID NO | Primer name | Primer sequence (5' to 3') |
|---|---|---|
| SEQ ID NO: 22 | SK01 | TCTAAGCTTGATGGCAAGCATGACCGGTGG |

-continued

| SEQ ID NO | Primer name | Primer sequence (5' to 3') |
|---|---|---|
| SEQ ID NO: 23 | SK02 | TCGCTCGAGTCATCACGCGGCACCATTCAAATCTT |
| SEQ ID NO: 24 | SK03 | CAACGTACCAGGCAGCCACGGAAGCACCATCCAGCTACCACCACCACCGGAGCCA |
| SEQ ID NO: 25 | SK04 | GTGCTTCCGTGGCTGCCTGGTACGTTGGATGGTGGCGGTGGTTCTGGTGGTG |
| SEQ ID NO: 26 | SK05 | ACGTACCAGGCAGCCACGGAAGCACCATCCAACCACCGGAGCCGCTGCTAACGGTAACCAGGGTG |
| SEQ ID NO: 27 | SK06 | GGTGCTTCCGTGGCTGCCTGGTACGTTGGATGGTGGCTCTGGTGAAATTGTCCTGACTCAGAGCC |

Sequence verified clones were amplified and their plasmid DNA purified for expression in human embryonic kidney (HEK) 293T cells. The expression plasmid contains an N-terminal signal sequence for secretion of the recombinant protein of interest into the media. Following 7 days of expression, cells were pelleted, the media harvested, and scFv was purified using size exclusion chromatography on a SUPERDEX 75 column (GE Life Sciences, Piscataway, N.J., USA).

The ERY1 peptide containing a C-terminal cysteine was conjugated to the wild type scFv using succinimidyl-4-(N-maleimidomethyl)cyclohexane-1-carboxylate (SMCC, CAS#64987-85-5, Thermo Scientific) as a crosslinker. SMCC was dissolved in dimethyl formamide and added to the scFv in phosphate buffered saline (PBS) at a 30-fold molar excess. Following 2 h at 4° C., the reaction was desalted on a ZEBASPIN desalting column (Thermo Scientific), and the product was reacted with ERY1 peptide at a 5 molar excess of peptide. Following 2 h at 4° C., the reaction was dialyzed against PBS in 10 kDa MWCO dialysis tubing for 2 days at 4° C. The conjugated scFv was analyzed by SDS-PAGE, Western blotting, and MALDI.

Example 8: Screening for Erythrocyte-Binding Peptides with Human Erythrocytes

Result: For the selection of seven novel peptides binding to human erythrocytes, an E. coli surface display library was employed. The screening process was performed in washed whole blood in a high concentration of serum albumin (50 mg/mL) and at 4° C. to reduce non-specific binding to leukocytes. The peptide library was initially enriched in 3 rounds through incubation with blood followed by careful separation of erythrocytes with bacteria bound from other cells through extensive washing and density gradient centrifugation. Subsequently, bacterial plasmids encoding for the selected peptides were transformed into bacteria expressing a green fluorescent protein variant. This allowed for green bacteria bound to erythrocytes to be sorted by high throughput FACS, and individual bacterial clones recovered were assayed for binding to erythrocytes using cytometry. Seven unique erythrocyte-binding peptides were identified, as shown in Table 1. These peptides did not contain consensus motifs nor were relevant protein sequence homologies found when analyzing against known proteins using the BLAST algorithm in UniProt.

Method: The E. coli surface display was comprised of over a billion different bacteria, each displaying approximately 1000 copies of a random 15mer peptide on the N-terminus of a scaffold protein, eCPX, a circularly permuted variant of outer membrane protein X (Rice and Daugherty, 2008). For the first three cycles of selection, bacteria binding to human erythrocytes were selected using co-sedimentation, followed by one round of FACS (Dane, Chan, et al., 2006). Frozen aliquots of $10^{11}$ cells containing the eCPX surface display library were thawed and grown overnight in Luria Bertani (LB) broth supplemented with 34 µg/mL chloramphenicol (Cm) and 0.2% D-(+)-glucose at 37° C. The bacteria were subcultured 1:50 for 3 h in LB supplemented with Cm and induced with 0.02% L-(+)-arabinose for 1 h. Human blood (type B) from a healthy donor was washed twice with 5% HSA, 2% FBS in PBS (HFS), resuspended in conical tubes, and co-incubated with $10^{11}$ bacterial cells for 1 h on an inversion shaker at 4° C. Cell suspensions were centrifuged at 500 g for 5 min and non-binding bacteria in the supernatant were removed. Erythrocytes were washed three times in 50 mL HFS and resuspended in LB for overnight growth of binding bacteria. Recovered bacterial clones were counted by plating on LB-agar plates supplemented with Cm. For the second and third rounds, $10^8$ and $5 \times 10^7$ bacteria were added, respectively, and washed once as above, erythrocytes were separated using a 70% Percoll (GE Life Sciences) gradient at 1000 g for 10 min. For flow cytometric sorting, plasmids of the selected eCPX library populations were extracted from bacterial cells using Zyppy Miniprep kits. Subsequently, these plasmids were transformed into E. coli MC1061/pLAC22Grn1 for inducible GFP expression. GFP expression was induced with 1 mM IPTG for 2 h followed by induction of peptide surface expression with 0.02% L-(+)-arabinose for 1 h, both at 37° C. Sample preparation for FACS was performed using similar techniques as described above and the fluorescent round three population binding to erythrocytes was sorted using a FACSAria (BD Biosciences).

Example 9: Characterizing of Binding to Human Erythrocytes

Figure 7:
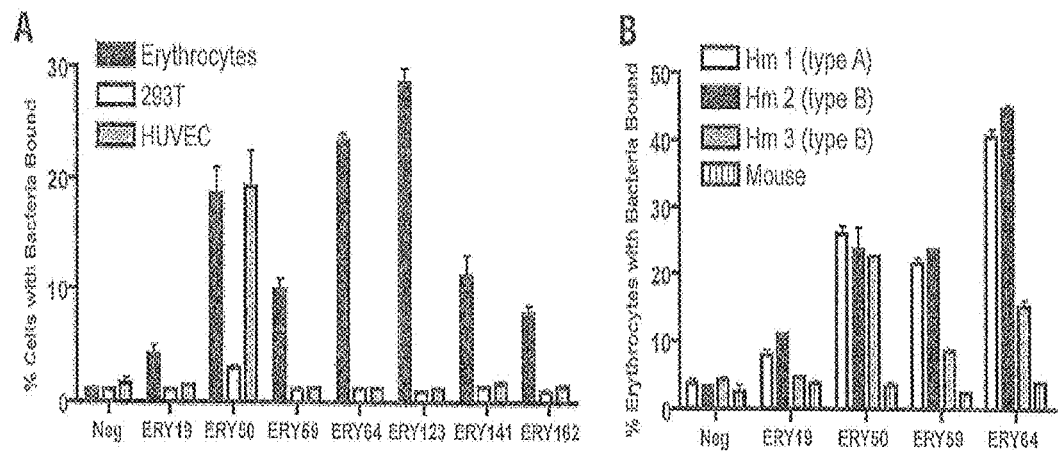
FIG. 7 is a montage of bar graphs showing a percentage of cells that have bacteria bound as determined by flow cytometry; in panel (A) Peptides on the surface of bacteria bind to erythrocytes but not to epithelial 293T or endothelial HUVECs, with the exception of ERY50; in panel (B) Peptides bind to multiple human samples, but not to mouse blood.

Result: To characterize the selected peptides that bound to human erythrocytes, bacteria displaying each individual peptide were subjected to binding assays with multiple cell types. Six (ERY19, ERY59, ERY64, ERY123, ERY141 and ERY162) of seven peptides bound specifically to human erythrocytes as compared to binding towards human epithelial 293T cells and human endothelial HUVECs (FIG. 7A). Additionally, peptides bound to human blood types A and B, but not to mouse blood (FIG. 7B) indicating that these peptides were specific to human blood, but not dependent on the common blood group antigens. Peptides are synthesized using standard solid-phase f-moc chemistry, conjugated to nanoparticles, and analyzed for binding to individual cell types as above. Binding to erythrocyte surfaces is studied using both microscopy and flow cytometry.

Method: To characterize specificity, individual sequenced clones were analyzed using cytometry for binding toward human erythrocytes (type A and B), mouse erythrocytes, HEK293T cells and HUVECs. For binding assays, $10^6$ mammalian cells were scanned on an AccuriA6 after co-incubation with $5 \times 10^7$ bacteria for 1 h at 4° C. followed by three washes in HFS (5% HSA, 2% FBS in PBS). The percentage of cells with green bacteria bound was calculated using FLOWJO Software.

Example 10: Engineering the Linker Domain of scFv Antibodies

Figure 8:
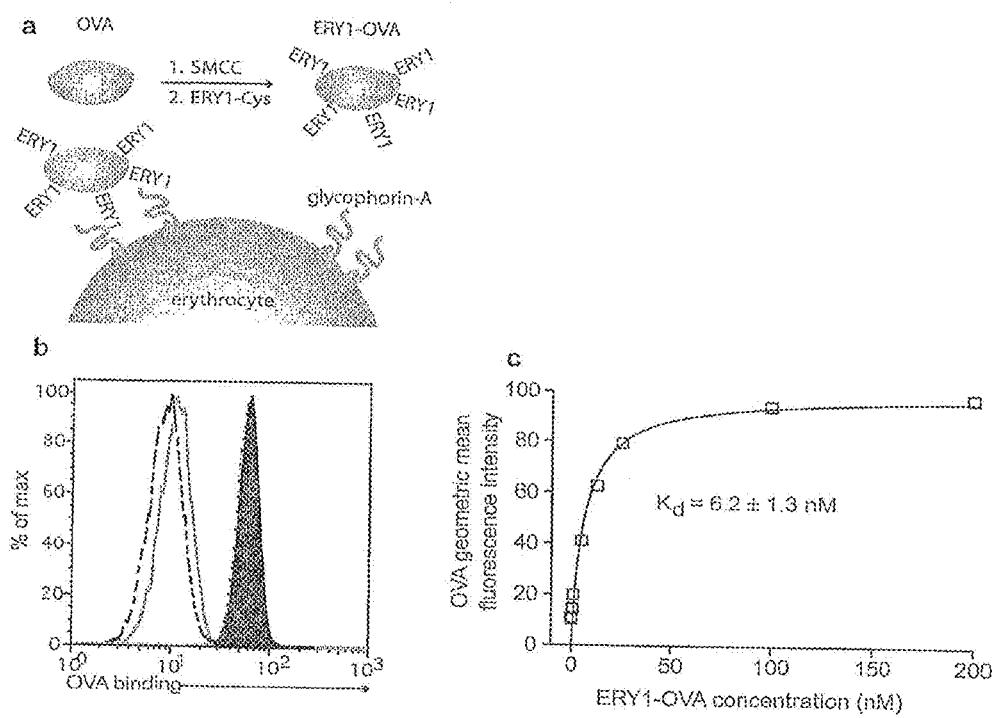
FIG. 8 shows the experimental scheme and results for the molecular fusion of ERY 1 and ovalbumin (OVA), wherein the ERY1-OVA fusion binds the equatorial periphery of mouse erythrocytes with high affinity; Panel (a) Schematic of conjugation of ERY1 peptide to ovalbumin (OVA), resulting in binding to erythrocyte-surface glycophorin-A; Panel (b) Binding of each OVA conjugate and intermediate, characterized by flow cytometry; black filled histogram, ERY1-OVA; empty histogram, SMCC-OVA; dotted histogram, MIS-OVA; ERY1=erythrocyte-binding peptide WMVLP-WLPGTLD (SEQ ID NO:1), MIS=mismatch peptide PLLT-VGMDLWPW (SEQ ID NO:2), SMCC=sulfosuccinimidyl-4-(N-maleimidomethyl) cyclohexane-1-carboxylate, used to conjugate ERY1 to OVA; Panel (c) Equilibrium binding of ERY1-OVA to erythrocytes demonstrating the low dissociation constant of ERY1-OVA ($R^2$=0.97, one-site binding), determined by flow cytometry.

Engineered scFvs against the tumor vascular marker fibronectin EDA (EDA) may be created as fusions to the peptides that bind specifically to human erythrocytes. A plurality of, or each, peptide from Example 8 is to be inserted in to the (GGGGS)$_4$ (SEQ ID NO:18) linker region, or comparable region, similar to the two ERY1 containing mutants that were designed; as such, peptides ERY19, ERY50, ERY59, ERY64, ERY123, ERY141, ERY162 will be added in place of ERY1 in the sequences in the REP and INS mutants (FIG. 6A). As the human ERY peptides were discovered tethered to the N-terminus of the scaffold protein eCPX, these constructs inserted into a linker region may affect erythrocyte binding. To address this, scFv variants are to be created by chemical conjugation with synthetic human ERY peptides, similar to ERY1 (FIG. 6C). This will allow for the optimum number of ERY peptides, alone or in combination, to be added to the scFv to stimulate erythrocyte binding.

Example 11: Characterizing Pharmacokinetics and Biodistribution of Polymeric Nanoparticles and Micelles The inventive laboratory has previously developed numerous polymer-based nanoparticles and micelles for use in drug delivery and immunomodulation. This technology is robust in that it allows for facile site-specific conjugation of thiol-containing molecules to the nanoparticle in a quantifiable manner (van der Vlies, O'Neil, et al., 2010). This laboratory has also developed micelle formulations displaying multiple chemical groups on a single micelle, and formulations capable of controlled delivery of hydrophobic drugs (O'Neil, van der Vlies, et al., 2009; Velluto, Demurtas, et al., 2008). This laboratory has also explored the use of its nanoparticle technology as a modulator of the immune response, as they target antigen presenting cells in the lymph node (Reddy, Rehor, et al., 2006; Reddy, van der Vlies, et al., 2007). Micellar and particle technologies for combination with materials and methods herein include US 2008/0031899, US 2010/0055189, and US 2010/0003338, which are hereby incorporated by reference herein.

Adding the ERY1 peptide or human erythrocyte binding peptides to these nanoparticle and micelle platforms improves their pharmacokinetic behavior, thereby enhancing their performance as circulating drug carriers. ERY1 or human erythrocyte binding peptide conjugation to any variant of nanoparticle or micelle may be performed by various reaction schemes, and conjugation of a detection molecule to the end product may be accomplished using an orthogonal chemistry. Validation of nanoparticle or micelle binding to erythrocytes, due to presence of the ERY1 or human erythrocyte binding peptide group, can be verified by flow cytometry and microscopy, and further validation by in vivo characterization may be performed by quantifying the detection molecule at varying time points following administration in mice.

Example 12: Engineering Polymer Nanoparticles and Micelles for Occlusion of Tumor Vasculature Engineered polymer nanoparticles and micelles, designed for dual specificity for both erythrocytes and a tumor vascular marker may be prepared that cause an aggregation event of erythrocytes in the tumor vascular bed and specifically occlude its blood supply. Several tumor-targeting markers can be evaluated and utilized, including modified scFv's for fibronectin EDA that include a cysteine in the linker region, a fibrinogen binding peptide containing the GPRP peptide motif, and a truncated tissue factor fusion protein, each with either an engineered cysteine or biotin to allow for attachment to particles. These tumor targeting ligands may be put in combination with the erythrocyte-binding peptides or glycophorin A scFvs on nanoparticles and micelles at optimum ratios to achieve dual targeting; multiple ligands may be attached to particles through disulfide linkages or avidin-biotin interactions. By way of verification, a standard mouse solid tumor model could be employed whereby mouse tumor cells are injected into the back skin of mice, and allowed to grow a predetermined period of time, at which point the mice would be administered with nanoparticles or micelles. Dosage and treatment regimens may be determined following characterization of the pharmacokinetics of the therapeutics. For further verification, at varying time points following treatment, tumor volume could be compared between treatment groups to assess the therapeutic's potential to block further growth of the tumor mass. Further confirmation of erythrocyte-mediated blockage of the tumor vasculature could be assessed by perfusion experiments in live tumor-bearing mice. A positive correlation between the therapeutic's affinity for erythrocytes and tumor vascular occlusion would be observed.

Example 13: Engineering scFv Antibodies for Occlusion of Tumor Vasculature

Engineered scFvs specific for the tumor vascular marker EDA and for erythrocytes can cause an aggregation event of erythrocytes in the tumor vascular bed and specifically occlude its blood supply. The modified scFv's for EDA includes the human ERY binding peptides as fusions in the linker region or as conjugates to the scFv. A standard mouse solid tumor model may be employed whereby mouse tumor cells are injected into the back skin of mice, allowed to grow a predetermined period of time, at which point the mice are administered with nanoparticles or micelles. Dosage and treatment regimens are to be determined following characterization of the pharmacokinetics of the therapeutics. At varying time points following treatment, tumor volume may be compared between treatment groups to assess the therapeutic's potential to block further growth of the tumor mass. Confirmation of erythrocyte-mediated blockage of the tumor vasculature may be assessed by perfusion experiments in live tumor-bearing mice. The therapeutic's affinity for erythrocytes will correlate to tumor vascular occlusion.

Example 14: Inducing Antigen-Specific Immunological Tolerance Through Non-Covalent Erythrocyte-Binding with ERY1 Peptide-Conjugated Antigen or Human Erythrocyte Binding Peptide-Conjugated Antigen To obtain strong and specific biophysical binding of an antigen to erythrocytes, we used a synthetic 12 amino acid peptide (ERY1) that we discovered by phage display to specifically bind to mouse glycophorin-A (Kontos and Hubbell, 2010). In this investigation, the model antigen OVA was used with a transgenic mouse strain (OT-I) whose $CD8^+$ T cell population expresses the T cell receptor specific for the MHC I immunodominant OVA peptide SIINFEKL (SEQ ID NO:3). The ERY1 peptide was chemically conjugated to OVA to create an OVA variant (ERY1-OVA) that binds mouse erythrocytes with high affinity and specificity (FIG. 8a). High-resolution confocal microscopy confirmed earlier observations concerning ERY1 binding (Kontos and Hubbell, 2010), namely localization to the cell membrane equatorial periphery, with no intracellular translocation of the ERY1-conjugated protein. ERY1-mediated binding to glycophorin-A was sequence-specific, as an OVA variant conjugated with a mismatch peptide (MIS-OVA), containing identical amino acids to ERY1 but scrambled in primary sequence, displayed negligible binding (FIG. 8b). OVA conjugated with only the crosslinking molecule used to conjugate the peptide did not display any measureable affinity towards erythrocytes, confirming that ERY1-OVA binding resulted from non-covalent interaction between the ERY1 peptide and glycophorin-A on the erythrocyte surface. Furthermore, ERY1-OVA bound to erythrocytes with high affinity, exhibiting an antibody-like dissociation constant ($K_d$) of 6.2±1.3 nM, as determined by equilibrium binding measurements (FIG. 8c).

Figure 9:
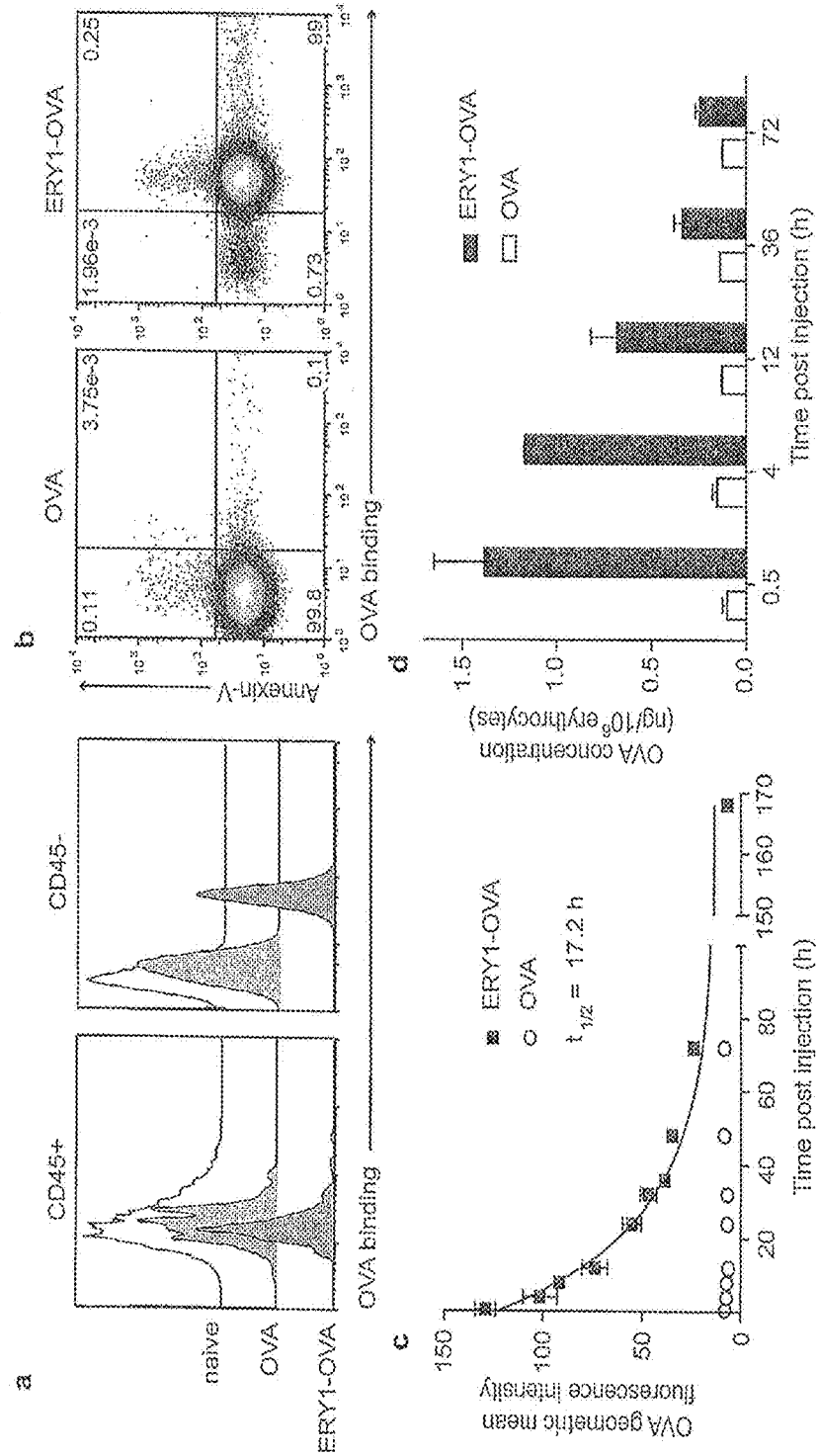
FIG. 9 shows the experimental scheme and results for the binding and circulation of the molecular fusion of ERY1-conjugated antigen: the fusion biospecifically binds circulating healthy and eryptotic erythrocytes upon intravenous administration, inducing uptake by specific antigen presenting cell subsets; Panel (a) OVA (grey filled histogram) and ERY1-OVA (black filled histogram) binding to erythrocyte ($CD45^-$) and nonbinding to leukocyte ($CD45^+$) populations in vivo as compared to non-injected mice (empty histogram), determined by flow cytometry; Panel (b) ERY1-OVA binding and OVA nonbinding to circulating eryptotic (annexin-$V^+$) and healthy (annexin-V) erythrocytes, determined by flow cytometry; Panel (c) Cell surface half-life of bound ERY1-OVA to circulating erythrocytes, determined by geometric mean fluorescence intensity of flow cytometry measurements (n=2, $R^2$=0.98, one-phase exponential decay); Panel (d) Time-dependent ERY1-OVA cell-surface concentration, determined by ELISA, at an administered dose of 150 µg (n=2).

ERY1-OVA binding was validated in vivo to circulating erythrocytes following intravenous administration in mice. Whole blood samples taken 30 min following injection of 150 µg of either OVA or ERY1-OVA confirmed the specific erythrocyte-binding capability of ERY1-OVA even amidst the complex heterogeneous milieu of blood and the vasculature (FIG. 9a). Consistent with glycophorin-A association, ERY1-OVA bound to erythrocytes (CD45$^-$) but not to leukocytes (CD45$^+$). ERY1-OVA binding was unbiased as to the apoptotic state of the erythrocytes, binding strongly to both annexin-V$^+$ and annexin-V$^-$ CD45$^-$ populations (FIG. 9b). Pharmacokinetic studies of the OVA conjugate demonstrated that ERY1-OVA erythrocyte binding was long-lived in vivo, exhibiting a cell-surface half-life of 17.2 h (FIG. 9c). ERY1-OVA remained bound to erythrocytes for as long as 72 h following administration; during this time frame, approximately 13% of erythrocytes are cleared in the mouse (Khandelwal and Saxena, 2006). Quantification of erythrocyte-bound ERY1-OVA in vivo showed a relatively high loading of 0.174±0.005 ng of OVA per $10^6$ erythrocytes.

Figure 10:
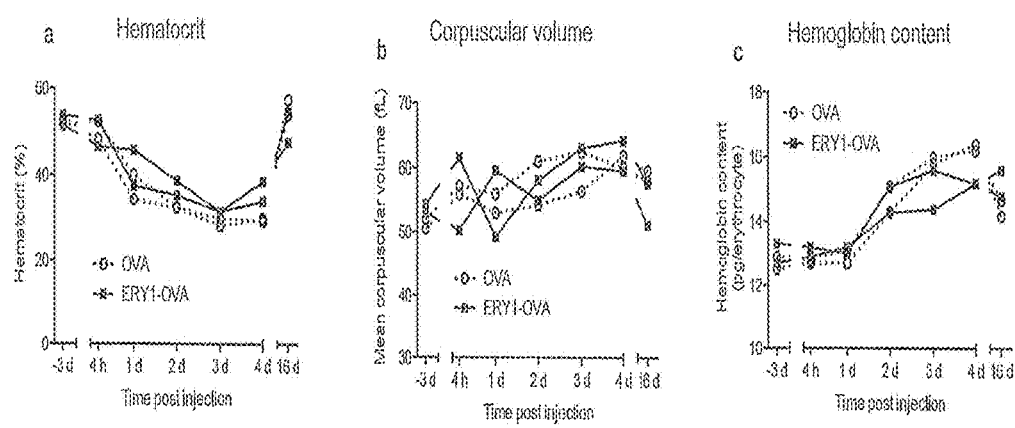
FIG. 10 is a montage of plots showing that erythrocyte binding does not alter hematological behavior; Panel (a) Hematocrit; Panel (b) mean corpuscular volume, and Panel (c) erythrocyte hemoglobin content measured at varying time points following administration of either 10 µg OVA (open circles) or ERY1-OVA (closed circles).

To exclude any potential physiological effects of OVA loading on erythrocyte function, hematological parameters were characterized at varying time points following intravenous administration of either ERY1-OVA or OVA. Erythrocyte binding by ERY1-OVA elicited no detectable differences in hematocrit, corpuscular volume, or erythrocyte hemoglobin content, as compared with administration of OVA (FIG. 10). These results demonstrate that glycophorin-A-mediated erythrocyte binding with antigen did not alter their hematological parameters.

Figure 11:
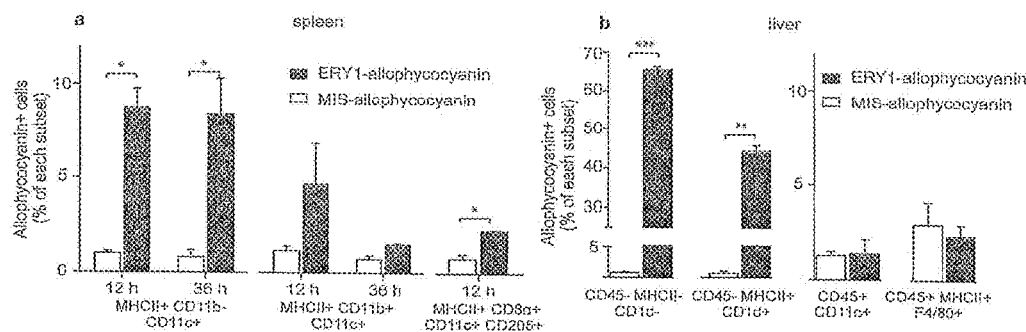
FIG. 11 is a bar graph of results wherein an ERY1-conjugated antigen biospecifically induces uptake by specific antigen presenting cell subsets: Panel (a) Increased cellular uptake of ERY1-allophycocyanin by $MHCII^+$ $CD11b^-$ $CD11c^+$ and $MHCII^+$ $CD8\alpha^+$ $CD11c^+$ $CD205^+$ splenic dendritic cells (DCs) at 12 and 36 h post-injection, as compared with MIS-allophycocyanin; Panel (b) Increased cellular uptake of ERY1-allophycocyanin in the liver by hepatocytes ($CD45^-$ $MHCII^-$ $CD1d^-$) and hepatic stellate cells ($CD45^-$ $MHCII^+$ $CD1d^+$), but not liver DCs ($CD45^+$ $CD11c^+$) or Kupffer ($CD45^+$ $MHCII^+$ $F4/80^+$) cells, as compared with MIS-allophycocyanin, 36 h following intravenous administration. (n=2, *$P\leq0.05$, $P\leq0.01$, *$P\leq0.001$). Data represent mean±SE.

To reveal the cellular targets of erythrocyte-bound antigen upon administration, mice were intravenously injected with the highly fluorescent allophycocyanin protein, conjugated to either ERY1 (ERY1-allophycocyanin) or MIS peptide (MIS-allophycocyanin). Flow cytometric analysis of splenic DC populations 12 and 36 h following administration showed 9.4-fold enhanced uptake of ERY1-allophycocyanin by MHCII$^+$ CD11b$^-$ CD11c$^+$ DCs as compared with MIS-allophycocyanin, yet similar uptake of ERY1-allophycocyanin and MIS-allophycocyanin by MHCII$^+$ CD11b$^+$ CD11c$^+$ DCs (FIG. 11a). Additionally, MHCII$^+$ CD8α$^+$ CD11c$^+$ CD205$^+$ splenic DCs were found to uptake ERY1-allophycocyanin to a 3.0-fold greater extent than MIS-allophycocyanin, though the absolute magnitude was markedly lower than for other DC populations in the spleen. Such targeting of antigen towards non-activated and CD8α$^+$ CD205$^+$ splenic DCs could strengthen the tolerogenic potential of erythrocyte binding, as these populations have been extensively implicated in apoptotic cell-driven tolerogenesis (Ferguson, Choi, et al., 2011; Yamazaki, Dudziak, et al., 2008). In the liver, ERY1-allophycocyanin also greatly enhanced uptake by hepatocytes (CD45$^-$ MHCII$^-$ CD1d$^-$; by 78.4-fold) and hepatic stellate cells (CD45$^-$ MHCII$^+$ CD1d$^+$; by 60.6-fold) as compared with MIS-allophycocyanin (FIG. 11b); both populations have been reported as antigen-presenting cells that trigger CD8$^+$ T cell deletional tolerance (Holz, Warren, et al., 2010; Ichikawa, Mucida, et al., 2011; Thomson and Knolle, 2010). Interestingly, such uptake was not seen in liver DCs (CD45$^+$ CD11c$^+$) or Kupffer cells (CD45$^+$ MHCII$^+$ F4/80$^+$), which serve as members of the reticuloendothelial system that aid in clearance of erythrocytes and complement-coated particles. Increased uptake of erythrocyte-bound antigen by the tolerogenic splenic DC and liver cell populations suggests the potential for a complex interconnected mechanism of antigen-specific T cell deletion driven by non-lymphoid liver cell and canonical splenic cell cross-talk.

Figure 12:
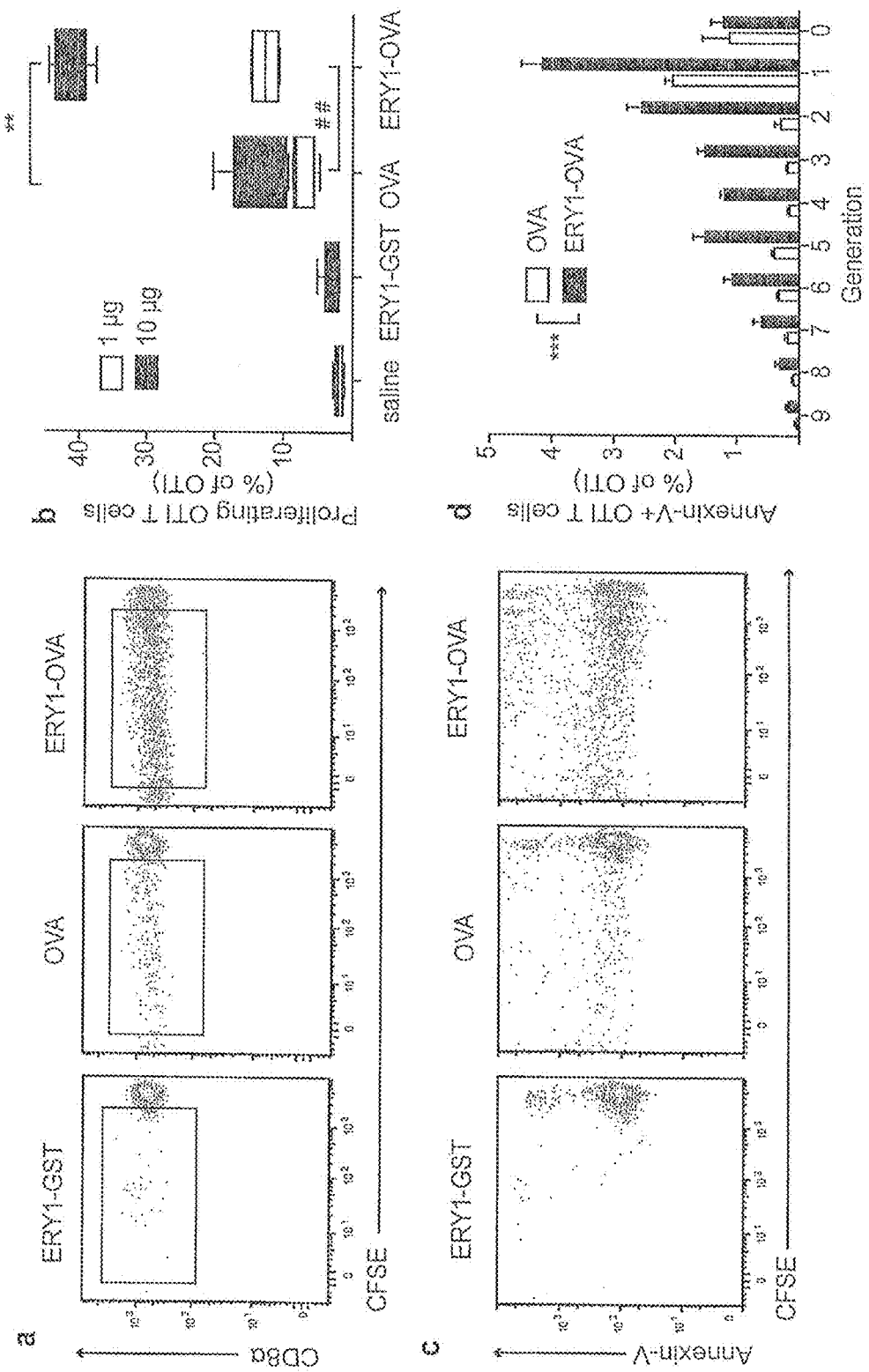
FIG. 12 is a montage of results showing that a molecular fusion of ERY1-OVA enhances cross-priming and apoptotic-fate deletional proliferation of antigen-specific OTI $CD8^+$ T cells in vivo: Panel (a) Proliferation of carboxyfluorescein succinimidyl ester (CFSE)-labeled splenic OTI $CD8^+$ T cells ($CD3\varepsilon^+$ $CD8\alpha^+$ $CD45.2^+$) 5 d following intravenous administration of 10 µg ERY1-glutathione-S-transferase (ERY1-GST, left panel), 10 µg OVA (middle panel), or 10 µg ERY1-OVA (right panel); Panel (b) Dose-dependent quantified proliferative populations of OTI $CD8^+$ T cell proliferation from A, as well as an identical 1 µg dosing study, data represent median±min to max (n=5, $P\leq0.01$, ##$P\leq0.01$); Panel (c) OTI $CD8^+$ T cell proliferation generations exhibiting larger annexin-$V^+$ populations upon ERY1-OVA administration (right panel), as compared with OVA (middle panel) or ERY1-GST (left panel); Panel (d) Quantified annexin-$V^+$ OTI $CD8^+$ T cell proliferation generations demonstrating ERY1-OVA induced OTI $CD8^+$ T cell apoptosis, data represent mean±SE (n=5, *$P\leq0.0001$). All data determined by multi-parameter flow cytometry.

Erythrocyte binding of ERY1-OVA was observed to lead to efficient cross-presentation of the OVA immunodominant MHC I epitope (SIINFEKL) (SEQ ID NO:3) by APCs and corresponding cross-priming of reactive T cells. CFSE-labeled OT-I CD8$^+$ T cells (CD45.2$^+$) were adoptively transferred into CD45.1$^+$ mice. Measurements were made of the proliferation of the OT-I CD8$^+$ T cells over 5 d following intravenous administration of 10 µg of OVA, 10 µg ERY1-OVA, or 10 µg of an irrelevant erythrocyte-binding antigen, ERY1-glutathione-S-transferase (ERY1-GST). OT-I CD8$^+$ T cell proliferation, determined by dilution of the fluor CFSE as measured by flow cytometry (FIG. 12a), was markedly enhanced in mice administered ERY1-OVA compared to OVA (FIG. 12b), demonstrating that erythrocyte-binding increased antigen-specific CD8$^+$ T cell cross-priming compared to the soluble antigen. Similar results were also obtained by administration of a 10-fold lower antigen dose of 1 µg, demonstrating the wide dynamic range of efficacy of OT-I CD8$^+$ T cell proliferation induced by erythrocyte-bound antigen. The results on cross-presentation and cross-priming are consistent with other studies concerning tolerogenic antigen presentation on MHC I by APCs engulfing antigen from apoptotic cells (Albert, Pearce, et al., 1998; Green, Ferguson, et al., 2009).

Figure 13:
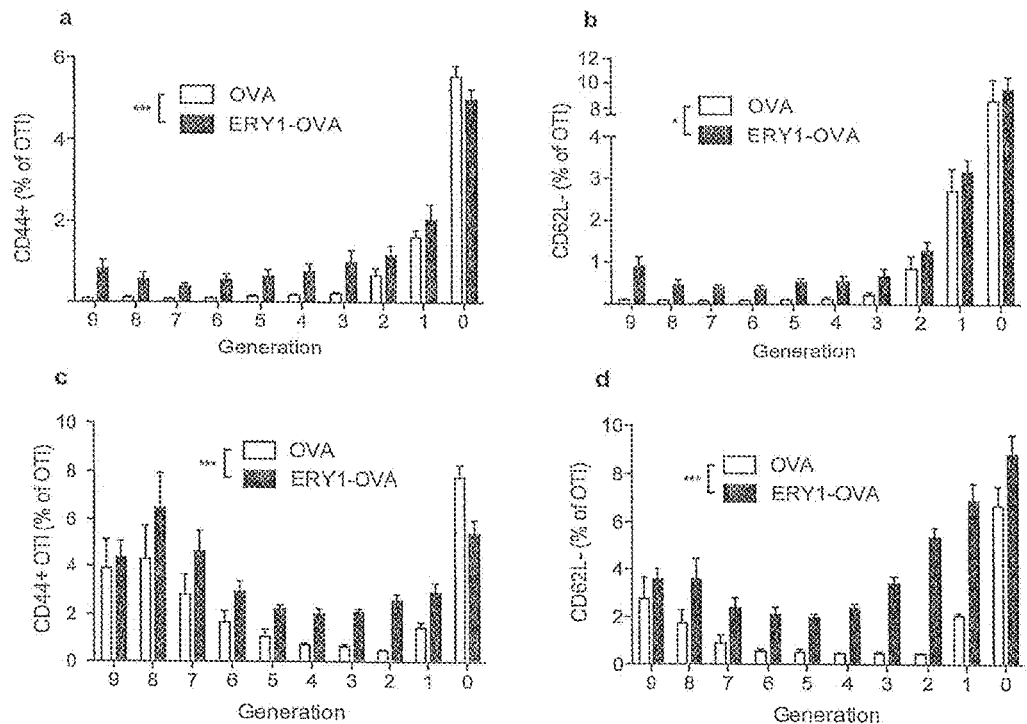
FIG. 13 is a montage of results presented as bar graphs showing that a molecular fusion of ERY1-OVA induces OTI $CD8^+$ T cell proliferation to an antigen-experienced phenotype; Panel (a) Quantification of $CD44^+$ OTI $CD8^+$ T cells ($CD3\varepsilon^+$ $CD8\alpha^+$ $CD45.2^+$ $CD44^+$) in the spleen 5 d following administration of 1 µg OVA or 1 µg ERY1-OVA, (***$P\leq0.0001$); Panel (b) Quantification of $CD62L^-$ OTI $CD8^+$ T cells ($CD3\varepsilon^+$ $CD8\alpha^+$ $CD45.2^+$ $CD62L^-$ in the spleen 5 d following administration of 1 µg OVA or 1 µg ERY1-OVA, (*$P\leq0.05$); Panel (c) Quantification of $CD44^+$ OTI $CD8^+$ T cells ($CD3\varepsilon^+$ $CD8\alpha^+$ $CD45.2^+$ $CD44^+$) in the spleen 5 d following administration of 10 µg OVA or 10 µg ERY1-OVA, (*P=0.0005); Panel (d) Quantification of $CD62L^-$ OTI $CD8^+$ T cells ($CD3\varepsilon E$ $CD8\alpha^+$ $CD45.2^+$ $CD62L^-$ in the spleen 5 d following administration of 10 µg OVA or g ERY1-OVA, (*$P\leq0.0001$). Data represent mean±SE, n=5.

To distinguish T cells being expanded into a functional effector phenotype from those being expanded and deleted, the proliferating OT-I CD8$^+$ T cells for annexin-V were analyzed as a hallmark of apoptosis and thus deletion (FIG. 12c). ERY1-OVA induced much higher numbers of annexin-V$^+$ proliferating OT-I CD8$^+$ T cells than OVA (FIG. 12d), suggesting an apoptotic fate that would eventually lead to clonal deletion. The same proliferating OT-I CD8$^+$ T cells induced by ERY1-OVA administration exhibited an antigen-experienced phenotype at both 1 and 10 µg doses, displaying upregulated CD44 and downregulated CD62L (FIG. 13). This phenotype of proliferating CD8$^+$ T cells is consistent with other reported OT-I adoptive transfer models in which regulated antigen-specific T cell receptor engagement by APCs fails to induce inflammatory responses (Bursch, Rich, et al., 2009).

Figure 14:
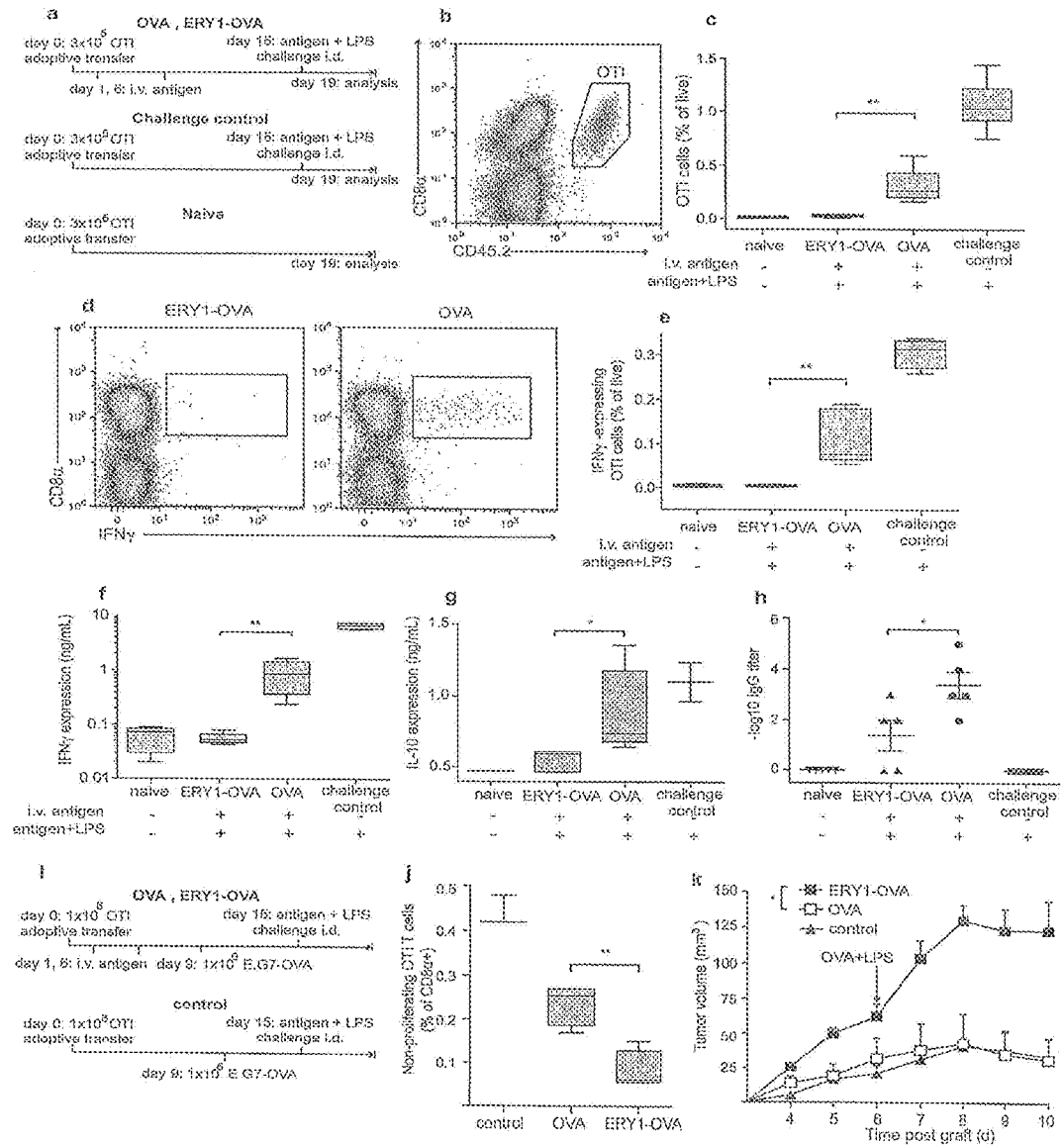
FIG. 14 is a montage of results showing that erythrocyte-binding induces tolerance to antigen challenge: Panel (a) The OTI $CD8^+$ T cell adoptive transfer tolerance model, displaying experimental protocol for experimental as well as challenge and naive control groups (n=5); Panel (b) Flow cytometric detection of OTI $CD8^+$ T cell populations ($CD3\varepsilon^+$ $CD8\alpha^+$ $CD45.2^+$); Panel (c) OTI $CD8^+$ T cell population quantification in the draining lymph nodes (inguinal and popliteal) 4 d following antigen challenge in $CD45.1^+$ mice ($P\leq0.01$); Panel (d) Flow cytometric detection of IFNγ-expressing OTI $CD8^+$ T cells; Panel (e) IFNγ-expressing OTI $CD8^+$ T cells in the draining lymph nodes 4 d following antigen challenge and restimulation with SIINFEKL peptide (SEQ ID NO:3) (P<0.01); Panel (f) IFNγ concentrations in lymph node cell culture media 4 d following restimulation with SIINFEKL peptide (SEQ ID NO:3), determined by ELISA (**P<0.01); Panel (g) IL-10 concentrations in lymph node cell culture media 4 d following restimulation with OVA, determined by ELISA (*$P\leq0.05$). Data represent median±min to max; Panel (h) OVA-specific serum IgG titers at day 19, (*$P\leq0.05$) data represent mean±SE; Panel (i) The combination OTI and OVA-expressing EL4 thymoma (E.G7-OVA) tumor tolerance model, displaying experimental protocol for experimental as well as control groups (n=4, 3, respectively); Panel (j) Quantification of non-proliferating (generation 0) OTI $CD8^+$ T cells circulating in blood 5 d following adoptive transfer; data represent median±min to max (**P<0.01); Panel (k) Growth profile of E.G7-OVA tumors, subcutaneously injected 9 d following OTI adoptive transfer, data represent mean±SE (*P<0.05).

Using an established OT-I challenge-to-tolerance model (Liu, Iyoda, et al., 2002) (FIG. 14a), ERY1-OVA was demonstrated to prevent subsequent immune responses to vaccine-mediated antigen challenge, even with a very strong bacterially-derived adjuvant. To tolerize, we intravenously administered 10 μg of either OVA or ERY1-OVA 1 and 6 d following adoptive transfer of OT-I CD8+ (CD45.2+) T cells to CD45.1+ mice. After 9 additional days to allow potential deletion of the transferred T cells, we then challenged the recipient mice with OVA adjuvanted with lipopolysaccharide (LPS) by intradermal injection. Characterization of draining lymph node and spleen cells as well as their inflammatory responses 4 d after challenge allowed us to determine if deletion actually took place.

Intravenous administration of ERY1-OVA resulted in profound reductions in OT-I CD8+ T cell populations in the draining lymph nodes (FIG. 14; gating in FIG. 14b) and spleens compared with mice administered unmodified OVA prior to antigen challenge with LPS (FIG. 14c), demonstrating deletional tolerance. Draining lymph nodes from ERY1-OVA-treated mice contained over 11-fold fewer OT-I CD8+ T cells as compared to OVA-treated mice, and 39-fold fewer than challenge control mice that did not receive intravenous injections of antigen; responses in spleen cells were similar. This effective clonal deletion exhibited in mice administered ERY1-OVA supported earlier observations of enhanced OT-I CD8+ T cell cross-priming (FIG. 12) and furthermore shows that cross-priming occurred in the absence of APC presentation of co-stimulatory molecules to lead to deletional tolerance.

Figure 15:
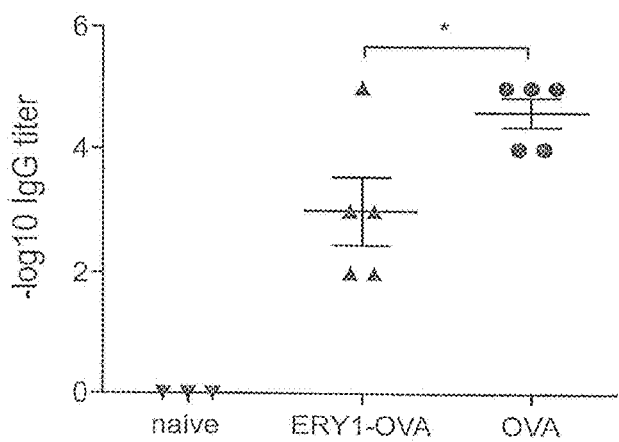
FIG. 15 is a bar graph showing how erythrocyte binding attenuates antigen-specific humoral responses in C57BL/6 mice. OVA-specific IgG detection in serum 19 days following two administrations of 1 µg OVA or 1 µg ERY1-OVA 6 d apart in C57BL/6 mice (*$P\leq0.05$).

To further evaluate the immune response following antigen challenge, the inflammatory nature of resident lymph node and spleen cells was characterized by expression of interferon-γ (IFNγ) by OT-I CD8+ T cells (FIG. 14d). Following challenge with OVA and LPS, the lymph nodes of mice previously treated with ERY1-OVA harbored 53-fold fewer IFNγ-expressing cells compared to challenge control mice (previously receiving no antigen), and over 19-fold fewer IFNγ-expressing cells compared to mice previously treated with an equivalent dose of OVA (FIG. 14e), demonstrating the importance of erythrocyte binding in tolerogenic protection to challenge; responses in spleen cells were similar. In addition, of the small OT-I CD8+ T cell population present in the lymph nodes and spleens of mice previously treated with ERY1-OVA, a lower percentage expressed IFNγ, suggesting clonal inactivation. Furthermore, the magnitude of total IFNγ levels produced by cells isolated from the draining lymph nodes upon SIINFEKL restimulation was substantially reduced in mice previously treated with ERY1-OVA (FIG. 14f), erythrocyte binding reducing IFNγ levels 16-fold compared to OVA administration and over 115-fold compared to challenge controls. Of note, the suppressive phenomenon was also correlated with downregulated interleukin-10 (IL-10) expression, as lymph node cells from mice previously treated with ERY1-OVA expressed 38% and 50% less IL-10 as compared with previously OVA-treated and challenge control mice, respectively (FIG. 14g). Typically considered a regulatory CD4+ T cell-expressed cytokine in the context of APC-T cell communication to dampen Th1 responses (Darrah, Hegde, et al., 2010; Lee and Kim, 2007), IL-10 expression was dispensible for desensitization to challenge. Similar IL-10 downregulation has been implicated in CD8+ T cell mediated tolerogenesis (Fife, Guleria, et al., 2006; Arnaboldi, Roth-Walter, et al., 2009; Saint-Lu, Tourdot, et al., 2009). Erythrocyte-binding also substantially attenuated humoral immune responses against antigen, as mice treated with ERY1-OVA exhibited 100-fold lower antigen-specific serum IgG titers compared with mice treated with soluble OVA (FIG. 14h). A similar reduction in OVA-specific IgG titer reduction as a result of erythrocyte binding was seen in non-adoptively transferred C57BL/6 (CD45.2+) mice. Following two intravenous administrations of 1 μg OVA or ERY1-OVA 7 d apart, ERY1-OVA treated mice exhibited 39.8-fold lower OVA-specific serum IgG levels 19 d after the first antigen administration (FIG. 15). This apparent reduction in B cell activation, following erythrocyte ligation by the antigen, corroborates current hypotheses concerning non-inflammatory antigen presentation during tolerance induction (Miller, Turley, et al., 2007; Green, Ferguson, et al., 2009; Mueller, 2010).

To further validate the induction of antigen-specific immune tolerance, the OT-I challenge-to-tolerance model was combined with an OVA-expressing tumor graft model (FIG. 14i). Similar to the previous experimental design, mice were tolerized by two intravenous administrations of 10 μg ERY1-OVA or 10 μg OVA following adoptive transfer of OT-I CD8+ T cells. Marked T cell deletion was detected 5 d following the first antigen administration, as ERY1-OVA injected mice harbored 2.9-fold fewer non-proliferating (generation 0) OT-I CD8+ T cells in the blood (FIG. 14j). To determine the functional responsiveness of proliferating OT-I CD8+ T cells in the absence of a strong exogenously administered adjuvant, OVA-expressing EL-4 thymoma cells (E.G7-OVA) were intradermally injected into the back skin of mice 9 d following adoptive transfer. To assess the tolerogenic efficacy of erythrocyte-bound antigen, tumor-bearing mice were challenged with LPS-adjuvanted OVA 6 d following tumor grafting, analogous in dose and schedule to the challenge-to-tolerance model. Robust tumor growth was continuously observed in ERY1-OVA treated mice as compared to OVA-treated or non-treated control mice through to 8 d following tumor grafting (FIG. 14k), confirming that ERY1-OVA driven OT-I CD8+ T cell proliferation induced functional immune non-responsiveness to OVA. That tumor size was arrested to a steady state 8 d following grafting may be indicative of residual OT-I CD8+ T cells that had yet to undergo ERY1-OVA-driven deletional tolerance.

Animals

Swiss Veterinary authorities previously approved all animal procedures. 8-12 wk old female C57BL/6 mice (Charles River) were used for in vivo binding studies and as E.G7-OVA tumor hosts. C57BL/6-Tg(TcraTcrb) 1100Mjb (OT-I) mice (Jackson Labs) were bred at the EPFL Animal Facility, and females were used for splenocyte isolation at 6-12 wk old. 8-12 week old female B6.SJL-Ptprc$^a$Pepc$^b$/Boy (CD45.1) mice (Charles River) were used as recipient hosts for OT-I CD8+ T cell adoptive transfer and tolerance induction studies.

Peptide Design and Synthesis

The

```
                                                    (SEQ ID NO: 19)
ERY1 (H2N-WMVLPWLPGTLDGGSGCRG-CONH2)
``` and mismatch (H2N-PLLTVGMDLWPWGGSGCRG-CONH2) (SEQ ID NO:20) peptides were synthesized using standard solid-phase f-moc chemistry using TGR resin (Nova Biochem) on an automated liquid handler (CHEMSPEED). The underlined sequence is the ERY1 12-mer sequence that we previously discovered by phage display as a mouse glycophorin-A binder (Kontos and Hubbell, 2010). The GGSG region served as a linker to the cysteine residue used for conjugation; the flanking arginine residue served to lower the pKa and thus increase the reactivity of the cysteine residue (Lutolf, Tirelli, et al., 2001). The peptide was cleaved from the resin for 3 h in 95% tri-fluoroacetic acid, 2.5% ethanedithiol, 2.5% water, and precipitated in ice-cold diethyl ether. Purification was conducted on a preparative HPLC-MS (Waters) using a C18 reverse phase column (PerSpective Biosystems).

ERY1-Antigen Conjugation 10 molar equivalents of succinimidyl-4-(N-maleimidomethyl)cyclohexane-1-carboxylate (SMCC, CAS#64987-85-5, Thermo Scientific) dissolved in dimethylformamide were reacted with 5 mg/mL endotoxin-free (<1 EU/mg) OVA (Hyglos GmbH) in PBS for 1 h at room temperature. Following desalting on a 2 mL ZEBA Desalt spin column (Thermo Scientific), 10 equivalents of ERY1 or MIS peptide dissolved in 3 M guanidine-HCl were added and allowed to react for 2 h at room temperature. The conjugate was desalted using 2 mL ZEBA Desalt spin columns, 0.2 m sterile filtered, dispensed into working aliquots, and stored at −20 C. Protein concentration was determined via BCA Assay (Thermo Scientific). The scheme results in conjugation of the cysteine side chain on the peptide to lysine side-chains on the antigen. Glutathione-S-transferase (GST) was expressed in BL21 *Escherichia coli* and purified using standard glutathione affinity chromatography. On-column endotoxin-removal was performed by extensive Triton-X114 (Sigma Aldrich) washing, and endotoxin removal was confirmed with THP-1X Blue cells (InvivoGen). The same reaction procedure was used to conjugate ERY1 to GST. Maleimide-activated allophycocyanin (Innova Biosciences) was dissolved in PBS, and conjugated with ERY1 or MIS as described above.

Microscopy of Binding to Erythrocytes $5 \times 10^5$ freshly isolated mouse erythrocytes were exposed to 100 nM of ERY1-OVA or OVA in PBS containing 10 mg/mL BSA for 1 h at 37 C. Following centrifugation and washing, cells were labeled with 1:200 diluted goat anti-mouse glycophorin-A (Santa Cruz) and rabbit anti-OVA (AbD SEROTEC) for 20 min on ice. Following centrifugation and washing, cells were labeled with 1:200 ALEX-AFLUOR488 anti-goat IgG (Invitrogen) and AlexaFluor546 anti-rabbit IgG (Invitrogen) for 20 min on ice. Following a final spin/wash cycle, cells were hard set mounted and imaged on a Zeiss LSM700 inverted confocal microscope with a 63× oil immersion objective. Image analysis was conducted in IMAGEJ (NIH), with identical processing to both images.

In Vivo Binding and Biodistribution

150 µg of ERY1-OVA or OVA in 0.9% saline (B. Braun) in a volume of 100 µL was injected intravenously into the tail of 8-12 week old female C57BL/6 mice while under anesthesia with isoflurane. Care was taken to ensure mice were kept at 37 C with a heating pad during experimentation. At predetermined time points, 5 µL of blood was taken from a small incision on the tail, diluted 100-fold into 10 mM EDTA in PBS, washed three times with PBS with 10 mg/mL BSA, and analyzed for OVA content by flow cytometry and ELISA. OVA was quantified by sandwich ELISA, using a mouse monoclonal anti-OVA antibody (Sigma) for capture, a polyclonal rabbit anti-OVA antibody (AbD SEROTEC) for detection, a goat anti-rabbit-IgG-HRP antibody (BioRad) for final detection, followed by TMB substrate (GE Life Sciences). Hematological characterization was performed on an ADVIVA 2120 Hematology System (Siemens). Erythrocyte-bound ERY1-GST was detected by incubating labeled cells with goat anti-GST (GE Healthcare Life Sciences), followed by incubation with AlexaFluor488 donkey anti-goat (Invitrogen), and analyzed by flow cytometry. For biodistribution studies, 20 µg of ERY1-APC or MIS-APC was injected intravenously into the tail vein of 8-12 week old female C57BL/6 mice as described above. Mice were sacrificed at predetermined time points, and the spleen, blood, and liver were removed. Each organ was digested with collagenase D (Roche) and homogenized to obtain a single-cell suspension for flow cytometry staining.

T Cell Adoptive Transfer

CD8$^+$ T cells from OT-I (CD45.2$^+$) mouse spleens were isolated using a CD8 magnetic bead negative selection kit (Miltenyi Biotec) as per the manufacturer's instructions. Freshly isolated CD8$^+$ OT-I cells were resuspended in PBS and labeled with 1 M carboxyfluorescein succinimidyl ester (CFSE, Invitrogen) for 6 min at room temperature, and the reaction was quenched for 1 min with an equal volume of IMDM with 10% FBS (Gibco). Cells were washed, counted, and resuspended in pure IMDM prior to injection. $3 \times 10^6$ CFSE-labeled CD8$^+$ OT-I cells were injected intravenously into the tail vein of recipient CD45.1$^+$ mice. For short-term proliferation studies, 10 µg of ERY1-OVA or OVA in 100 µL volume was injected 24 h following adoptive transfer. Splenocytes were harvested 5 d following antigen administration and stained for analysis by flow cytometry.

OT-I Tolerance and Challenge Model $3 \times 10^5$ CFSE-labeled OT-I CD8$^+$ T cells were injected into CD45.1$^+$ recipient mice as described above. 1 and 6 d following adoptive transfer, mice were intravenously administered 10 µg of ERY1-OVA or OVA in 100 µL saline into the tail vein. 15 d following adoptive transfer, mice were challenged with 5 µg OVA and 25 ng ultra-pure *Escherichia coli* LPS (InvivoGen) in 25 µL intradermally into each rear leg pad (Hock method, total dose of 10 µg OVA and 50 ng LPS). Mice were sacrificed 4 d following challenge, and spleen and draining lymph node cells were isolated for restimulation. For flow cytometry analysis of intracellular cytokines, cells were restimulated in the presence of 1 mg/mL OVA or 1 µg/mL SIINFEKL (SEQ ID NO:3) peptide (Genscript) for 3 h. Brefeldin-A (Sigma, 5 µg/mL) was added and restimulation resumed for an additional 3 h prior to staining and flow cytometry analysis. For ELISA measurements of secreted factors, cells were restimulated in the presence of 100 µg/mL OVA or 1 µg/mL SIINFEKL (SEQ ID NO:3) peptide for 4 d. Cells were spun and the media collected for ELISA analysis using IFNγ and IL-10 Ready-Set-Go kits (eBiosciences) as per the manufacturer's instructions. OVA-specific serum IgG was detected by incubating mouse serum at varying dilutions on OVA-coated plates, followed by a final incubation with goat anti-mouse IgG-HRP (Southern Biotech).

OT-IE.G7-OVA Tolerance Model $1 \times 10^6$ CFSE-labeled OT-I CD8+ T cells were injected into 8-12 wk old female C57BL/6 mice as described above. 1 and 6 d following adoptive transfer, mice were intravenously administered 10 µg of ERY1-OVA or 10 µg OVA in 100 µL saline into the tail vein. Blood was drawn 5 d following adoptive transfer for characterization of OT-I CD8+ T cell proliferation by flow cytometry. OVA-expressing EL-4 thymoma cells (E.G7-OVA, ATCC CRL-2113) were cultured as per ATCC guidelines. In brief, cells were cultured in RPMI 1640 medium supplemented with 10% fetal bovine serum, 10 mM HEPES, 1 mM sodium pyruvate, 0.05 mM β-mercaptoethanol, 1% puromycin/streptomycin (Invitrogen Gibco), and 0.4 mg/mL G418 (PAA Laboratories). Just prior to injection, cells were expanded in media without G418 and resuspended upon harvest in HBSS (Gibco). 9 d following adoptive transfer, mice were anesthetized with isoflurane, the back area was shaved, and $1 \times 10^6$ E.G7-OVA cells were injected intradermally between the shoulder blades. 4 d following E.G7-OVA graft, tumor dimensions were measured every 24 h with a digital caliper, and tumor volume was calculated as an ellipsoid (V=(□/6) 1*w*h), where V is volume, 1 is length, w is width, and h is the height of the tumor). 15 d following adoptive transfer, mice were challenged with 5 μg OVA and 25 ng ultra-pure *Escherichia coli* LPS (InvivoGen) in 25 μL intradermally into each front leg pad (total dose of 10 μg OVA and 50 ng LPS).

Antibodies and Flow Cytometry

The following anti-mouse antibodies were used for flow cytometry: CD1d Pacific Blue, CD3ε PerCP-Cy5.5, CD8αPE-Cy7, CD11b PE-Cy7, CD11c Pacific Blue, biotinylated CD45, CD45.2 Pacific Blue, CD45 Pacific Blue, IFNγ-APC, CD8αAPC-eF780, CD44 PE-Cy5.5, CD62L PE, CD205 PE-Cy7, F4/80 PE, I-A/I-E MHCII FITC (all from eBioscience), in addition to fixable live/dead dye (Invitrogen), annexin-V-Cy5 labeling kit (BioVision), streptavidin Pacific Orange (Invitrogen), and anti-OVA-FITC (Abcam). Samples were analyzed on a CyAn ADP flow cytometer (Beckman Coulter). Cells were washed first with PBS, stained for 20 min on ice with live/dead dye, blocked for 20 min on ice with 24G2 hybridoma medium, surface stained for 20 min on ice, fixed in 2% paraformaldehyde for 20 min ice, intracellularly stained in the presence of 0.5% saponin for 45 min on ice, followed by a final wash prior to analysis. For apoptosis staining, annexin-V-Cy5 was added 5 min prior to analysis. For CD45 staining, cells were stained with streptavidin Pacific Orange for 20 min on ice, washed, and analyzed.

Implementation with Particles

The ERY1 peptide has also been implemented for tolerogenesis in the form of nanoparticles, to which the ERY1 peptide and the tolerogenic antigen are both conjugated.

To form conjugates of ERY1 with a polymer nanoparticle, which is also conjugated to the peptide or protein antigen, stoichiometric amounts of each component may be added consecutively to control conjugation conversions. To form a nanoparticle conjugated with both OVA and ERY1 or mismatch peptide, the peptides were first dissolved in aqueous 3M guanidine HCl, and 0.5 equivalents were added to nanoparticles containing a thiol-reactive pyridyldisulfide group. Absorbance measurements were taken at 343 nm to monitor the reaction conversion, as the reaction creates a non-reactive pyridine-2-thione species with a high absorbance at this wavelength. Following 2 h at room temperature, the absorbance at 343 nm had stabilized and OVA was dissolved in aqueous 3M guanidine HCl, and added to the nanoparticle solution at a 2-fold molar excess. Following 2 h at room temperature, the absorbance at 343 nm had once again stabilized to a higher value, and the concentrations of both the peptide and OVA in the solution were calculated. The bifunctionalized nanoparticles were purified from non-reacted components by gel filtration on a Sepharose CL6B packed column. Each 0.5 mL fraction was analyzed for the presence of protein and/or peptide by fluorescamine, and nanoparticle size was assessed by dynamic light scattering (DLS).

Should the antigen not contain any free thiol groups to perform such a reaction, they may be introduced by recombinant DNA technology to create a mutant that could then be expressed and purified recombinantly. Alternatively, amine-carboxylic acid crosslinking could be performed between the nanoparticle and antigen using 1-ethyl-3-(3-dimethylaminopropyl) carbodiimide (EDC).

To form conjugates of ERY1 with a polymer micelle, which is also conjugated to the peptide or protein antigen, similar reactions would be used as described with polymeric nanoparticles. The micelle would be formed to contain functional groups desired for the appropriate conjugation scheme. Given that our nanoparticles and micelles may be synthesized to contain many different chemical group functionalizations, there exist numerous possibilities of conjugation schemes to employ in creating the nanoparticle/micelle-antigen-ERY1 complex.

Example 15: Development of Antibodies and Antibody-Fragments with that Bind Mouse and/or Human Erythrocytes As another method to non-covalently bind erythrocytes, an erythrocyte-binding antibody may also be used to induce antigen-specific immunological tolerance. Antibodies displaying high affinity towards erythrocyte surface proteins may be isolated by screening antibody libraries using state-of-the art display platforms, including but not limited to bacteriophage display, yeast and *E. coli* surface display. Upon discovery of the novel erythrocyte-binding antibody, similar biochemical characterization of binding may be assessed as was performed with the ERY1 peptide. In order to create higher-affinity mutants with improved binding characteristics, affinity maturation is conducted on the antibody fragments discovered to bind erythrocytes from the initial library screening. Using standard recombinant DNA techniques, such as error-prone PCR and site-directed mutagenesis, a new library is created from the parent binding sequence. The affinity maturation library is then displayed using state-of-the-art display platforms, as described above, for other antibody fragments with enhanced affinity for erythrocytes as compared with the parent binding sequence.

Affinity maturation is also performed on existing antibodies that bind either mouse erythrocytes or human erythrocytes. The rat monoclonal TER-119 clone antibody (Kina et al, Br J Haematol, 2000) binds mouse erythrocytes at a site yet to be fully determined, yet its specificity has led to its common use in removal of erythrocytes from heterogeneous cellular populations. Affinity maturation is performed on the TER-119 antibody, either as a full-length antibody or as an antibody fragment such as an scFv, to discover new antibodies with increased affinity towards mouse erythrocytes. The mouse monoclonal 10F7 clone antibody (Langlois et al, J Immunol 1984) binds to human glycophorin-A on the human erythrocyte cell surface. Affinity maturation is performed on the 10F7 antibody, either as a full-length antibody or as an antibody fragment such as an scFv, to discover new antibodies with increased affinity towards human erythrocytes.

To determine the primary sequence of the TER-119 antibody, we cloned the antibody-specific isolated cDNA from the TER-119 hybridoma into a plasmid allowing for facile sequencing of the gene fragments. A specific set of primers were used for the PCR amplification process of the antibody genes that allows for amplification of the multiple variable domains of the gene segments (Krebber et al., 1997; Reddy et al., 2010). The DNA sequence of the antibody domains allowed us to determine the variable regions of the heavy and light chains of the TER-119 IgG antibody. To construct an scFv version of the TER-119 IgG, we used assembly PCR to create a gene comprising of the variable heavy chain of TER-119, followed by a (Gly-Gly-Gly-Gly-Ser)$_4$ (SEQ ID NO:18) linker, followed by the variable light chain of TER-119.

Standard reverse transcriptase PCR (RT-PCR) was performed on mRNA from the TER-119 hybridoma clone using the Superscript III First Strand Synthesis System (Invitrogen) to create complimentary DNA (cDNA) of the clone.

PCR was then conducted using the following set of primers to specifically amplify the DNA sequences of the variable heavy (VH) and variable light (VL) regions of the antibody:

| Primer name | Primer sequence (5' to 3') | SEQ ID NO |
|---|---|---|
| VL-FOR1 | AGC CGG CCA TGG CGG AYA TCC AGC TGA CTC AGC C | SEQ ID NO: 28 |
| VL-FOR2 | AGC CGG CCA TGG CGG AYA TTG TTC TCW CCC AGT C | SEQ ID NO: 29 |
| VL-FOR3 | AGC CGG CCA TGG CGG AYA TTG TGM TMA CTC AGT C | SEQ ID NO: 30 |
| VL-FOR4 | AGC CGG CCA TGG CGG AYA TTG TGY TRA CAC AGT C | SEQ ID NO: 31 |
| VL-FOR5 | AGC CGG CCA TGG CGG AYA TTG TRA TGA CMC AGT C | SEQ ID NO: 32 |
| VL-FOR6 | AGC CGG CCA TGG CGG AYA TTM AGA TRA MCC AGT C | SEQ ID NO: 33 |
| VL-FOR7 | AGC CGG CCA TGG CGG AYA TTC AGA TGA YDC AGT C | SEQ ID NO: 34 |
| VL-FOR8 | AGC CGG CCA TGG CGG AYA TYC AGA TGA CAC AGA C | SEQ ID NO: 35 |
| VL-FOR9 | AGC CGG CCA TGG CGG AYA TTG TTC TCA WCC AGT C | SEQ ID NO: 36 |
| VL-FOR10 | AGC CGG CCA TGG CGG AYA TTG WGC TSA CCC AAT C | SEQ ID NO: 37 |
| VL-FOR11 | AGC CGG CCA TGG CGG AYA TTS TRA TGA CCC ART C | SEQ ID NO: 38 |
| VL-FOR12 | AGC CGG CCA TGG CGG AYR TTK TGA TGA CCC ARA C | SEQ ID NO: 39 |
| VL-FOR13 | AGC CGG CCA TGG CGG AYA TTG TGA TGA CBC AGK C | SEQ ID NO: 40 |
| VL-FOR14 | AGC CGG CCA TGG CGG AYA TTG TAA CYC AGG A | SEQ ID NO: 41 |
| VL-FOR15 | AGC CGG CCA TGG CGG AYA TTG TGA TGA CCC AGW T | SEQ ID NO: 42 |
| VL-FOR16 | AGC CGG CCA TGG CGG AYA TTG TGA TGA CAC AAC C | SEQ ID NO: 43 |
| VL-FOR17 | AGC CGG CCA TGG CGG AYA TTT TGC TGA CTC AGT C | SEQ ID NO: 44 |
| VL-FOR18 | AGC CGG CCA TGG CGG ARG CTG TTG TGA CTC AGG AAT C | SEQ ID NO: 45 |
| VL-REV1 | GAT GGT GCG CCG CA GTA CGT TTG ATT TCC AGC TTG G | SEQ ID NO: 46 |
| VL-REV2 | GAT GGT GCG CCG CA GTA CGT TTT ATT TCC AGC TTG G | SEQ ID NO: 47 |
| VL-REV3 | GAT GGT GCG CCG CA GTA CGT TTT ATT TCC AAC TTT G | SEQ ID NO: 48 |
| VL-REV4 | GAT GGT GCG CCG CA GTA CGT TTC AGC TCC AGC TTG G | SEQ ID NO: 49 |
| VL-REV5 | GAT GGT GCG CCG CA GTA CCT AGG ACA GTC AGT TTG G | SEQ ID NO: 50 |
| VL-REV6 | GAT GGT GCG CCG CA GTA CCT AGG ACA GTG ACC TTG G | SEQ ID NO: 51 |
| VH-FOR1 | GTT ATT GCT AGC GGC TCA GCC GGC AAT GGC GGA KGT RMA GCT TCA GGA GTC | SEQ ID NO: 52 |
| VH-FOR2 | GTT ATT GCT AGC GGC TCA GCC GGC AAT GGC GGA GGT BCA GCT BCA GCA GTC | SEQ ID NO: 53 |
| VH-FOR3 | GTT ATT GCT AGC GGC TCA GCC GGC AAT GGC GCA GGT GCA GCT GAA GSA STC | SEQ ID NO: 54 |
| VH-FOR4 | GTT ATT GCT AGC GGC TCA GCC GGC AAT GGC GGA GGT CCA RCT GCA ACA RTC | SEQ ID NO: 55 |
| VH-FOR5 | GTT ATT GCT AGC GGC TCA GCC GGC AAT GGC GCA GGT YCA GCT BCA GCA RTC | SEQ ID NO: 56 |
| VH-FOR6 | GTT ATT GCT AGC GGC TCA GCC GGC AAT GGC GCA GGT YCA RCT GCA GCA GTC | SEQ ID NO: 58 |
| VH-FOR7 | GTT ATT GCT AGC GGC TCA GCC GGC AAT GGC GCA GGT CCA CGT GAA GCA GTC | SEQ ID NO: 59 |
| VH-FOR8 | GTT ATT GCT AGC GGC TCA GCC GGC AAT GGC GGA GGT GAA SST GGT GGA ATC | SEQ ID NO: 60 |
| VH-FOR9 | GTT ATT GCT AGC GGC TCA GCC GGC AAT GGC GGA VGT GAW GYT GGT GGA GTC | SEQ ID NO: 61 |
| VH-FOR10 | GTT ATT GCT AGC GGC TCA GCC GGC AAT GGC GGA GGT GCA GSK GGT GGA GTC | SEQ ID NO: 62 |
| VH-FOR11 | GTT ATT GCT AGC GGC TCA GCC GGC AAT GGC GGA KGT GCA MCT GGT GGA GTC | SEQ ID NO: 63 |
| VH-FOR12 | GTT ATT GCT AGC GGC TCA GCC GGC AAT GGC GGA GGT GAA GCT GAT GGA RTC | SEQ ID NO: 64 |
| VH-FOR13 | GTT ATT GCT AGC GGC TCA GCC GGC AAT GGC GGA GGT GCA RCT TGT TGA GTC | SEQ ID NO: 65 |
| VH-FOR14 | GTT ATT GCT AGC GGC TCA GCC GGC AAT GGC GGA RGT RAA GCT TCT CGA GTC | SEQ ID NO: 66 |
| VH-FOR15 | GTT ATT GCT AGC GGC TCA GCC GGC AAT GGC GGA AGT GAA RST TGA GGA GTC | SEQ ID NO: 67 |
| VH-FOR16 | GTT ATT GCT AGC GGC TCA GCC GGC AAT GGC GCA GGT TAC TCT RAA AGW GTS TG | SEQ ID NO: 68 |
| VH-FOR17 | GTT ATT GCT AGC GGC TCA GCC GGC AAT GGC GCA GGT CCA ACT VCA GCA RCC | SEQ ID NO: 69 |
| VH-FOR18 | GTT ATT GCT AGC GGC TCA GCC GGC AAT GGC GGA TGT GAA CTT GGA AGT GTC | SEQ ID NO: 70 |
| VH-FOR19 | GTT ATT GCT AGC GGC TCA GCC GGC AAT GGC GGA GGT GAA GGT CAT CGA GTC | SEQ ID NO: 71 |
| VH-REV1 | CCC TTG AAG CTT GCT GAG GAA ACG GTG ACC GTG GT | SEQ ID NO: 72 |
| VH-REV2 | CCC TTG AAG CTT GCT GAG GAG ACT GTG AGA GTG GT | SEQ ID NO: 73 |
| VH-REV3 | CCC TTG AAG CTT GCT GCA GAG ACA GTG ACC AGA GT | SEQ ID NO: 74 |
| VH-REV4 | CCC TTG AAG CTT GCT GAG GAG ACG GTG ACT GAG GT | SEQ ID NO: 75 |

The amplified VH and VL genes were then digested with restriction endonucleases (NcoI and NotI for VL, NdeI and HindIII for VH), the gene fragments were purified following agarose electrophoresis using a standard kit (Zymo Research, Orange, Calif., USA), and ligated into a cloning plasmid pMAZ360. The plasmid containing either the VH or VL gene was sequenced, and a new gene was constructed using assembly PCR to create the TER-119 scFv sequence:

5'-GAGGTGAAGCTGCAGGAGTCTGGAGGAGGCT-
TGGTGCAACC TGGGGGGTCTCTGAAACTCTCCT-
GTGTAGCCTCAGGATTCACTTTCAGGGACCAC
TGGATGAATTGGGTCCGGCAGGCTCCCG-
GAAAGACCATGGAGTGGATTGGAGAT ATTAGACCT-
GATGGCAGTGACACAAACTATGCACCATCTGTGAG-
GAATAGATTC
ACAATCTCCAGAGACAATGCCAGGAGCATCCTG-
TACCTGCAGATGAGCAATATG AGATCTGATTA-
CACAGCCACTTATTACTGTGTTAGAGACTCAC-
CTACCCGGGCTG
GGCTTATGGATGCCTGGGGTCAAGGAACCTCAGT-
CACTGTCTCCTCAGCCGGTGG TGGTGGTTCTG-
GTGGTGGTGGTTCTGGCGGCGGCGGCTCCGGTG-
GTGGTGGATCC
GACATTCAGATGACGCAGTCTCCTTCAGTCCT-
GTCTGCATCTGTGGGAGACAGAG TCACTCT-
CAACTGCAAAGCAAGTCAGAATATTAACAAGTACT-
TAAACTGGTATCA
GCAAAAGCTTGGAGAAGCTCCCAAAGTCCTGA-
TATATAATACAAACAATTTGCA AACGGGCATCCCAT-
CAAGGTTCAGTGGCAGTGGATCTGGTACA-
GATTTCACACTC
ACCATCAGTAGCCTGCAGCCTGAAGATTTTGCCA-
CATATTTCTGCTTTCAGCATT ATACTTGGC-
CCACGTTTGGAGGTGGGACCAAGCTGGAAAT-
CAAACGTACT-3' (SEQ ID NO:76), which encodes for the VH region of the TER-119 clone at the N terminus of the translated protein, followed by a (Gly-Gly-Gly-Gly-Ser)$_4$ (SEQ ID NO:18) linker domain, followed by the VL region of the TER-119 clone at the C terminus of the translated protein. The TER-119 scFv gene was constructed by amplifying the TER-119 cDNA with primers SK07 and SK08, specific for the VH region, and SK09 and SK10, specific for the VL region:

| Primer name | Primer sequence (5' to 3') | SEQ ID NO |
|---|---|---|
| SK07 | ACT CGC GGC CCA GCC GGC CAT GGC GGA GGT GAA GCT GCA GGA GTC | SEQ ID NO: 77 |
| SK08 | GGA GCC GCC GCC GCC AGA ACC ACC ACC ACC AGA ACC ACC ACC ACC GGC TGA GGA GAC AGT GAC TG | SEQ ID NO: 78 |
| SK09 | GGC GGC GGC GGC TCC GGT GGT GGT GGA TCC GAC ATT CAG ATG ACG CAG TC | SEQ ID NO: 79 |
| SK10 | GAC TAC TAG GCC CCC GAG GCC AGT ACG TTT GAT TTC CAG CT | SEQ ID NO: 80 |

Each final completed scFv gene product was digested with SfiI and XhoI (NEB, Ipswich, Mass., USA), and ligated into the same sites on the pSecTagA mammalian expression plasmid (Invitrogen, Carlsbad, Calif., USA).

To affinity mature the 10F7 scFv that binds to human glycophorin-A, the gene was commercially synthesized and obtained from DNA2.0 (Menlo Park, Calif., USA) as the following sequence:

(SEQ ID NO: 81)

```
5'-GTTATTACTCGCGGCCCAGCCGGCCATGGCGGCGCAGGTGAA

ACTGCAGCAGAGCGGCGCGGAACTGGTGAAACCGGGCGCGAGCGTGAAACT
```

-continued

```
GAGCTGCAAAGCGAGCGGCTATACCTTTAACAGCTATTTTATGCATTGGAT

GAAACAGCGCCCGGTGCAGGGCCTGGAATGGATTGGCATGATTCGCCCGAA

CGGCGGCACCACCGATTATAACGAAAAATTTAAAAACAAAGCGACCCTGAC

CGTGGATAAAAGCAGCAACACCGCGTATATGCAGCTGAACAGCCTGACCAG

CGGCGATAGCGCGGTGTATTATTGCGCGCGCTGGGAAGGCAGCTATTATGC

GCTGGATTATTGGGGCCAGGGCACCACCGTGACCGTGAGCAGCGGCGGCGG

CGGCAGCGGCGGCGGCGGCAGCGGCGGCGGCGGCAGCGATATTGAACTGAC

CCAGAGCCCGGCGATTATGAGCGCGACCCTGGGCGAAAAAGTGACCATGAC

CTGCCGCGCGAGCAGCAACGTGAAATATATGTATTGGTATCAGCAGAAAAG

CGGCGCGAGCCCGAAACTGTGGATTTATTATACCAGCAACCTGGCGAGCGG

CGTGCCGGGCCGCTTTAGCGGCAGCGGCAGCGGCACCAGCTATAGCCTGAC

CATTAGCAGCGTGGAAGCGGAAGATGCGGCGACCTATTATTGCCAGCAGTT

TACCAGCAGCCCGTATACCTTTGGCGGCGGCACCAAACTGGAAATTAAACG

CGCGGCGGCGGCCTCGGGGGCCGAGGGCGGCGGTTCT-3'.
```

Similar affinity maturation using recombinant DNA techniques described above for TER-119 is performed on the 10F7 gene to obtain a library of mutants to enable screening for enhanced binding towards human erythrocytes.

Example 16: Inducing Antigen-Specific Immunological Tolerance Through Non-Covalent Erythrocyte-Binding with Antibody-Conjugated Antigen The antibody may be conjugated with the antigen using standard crosslinking reactions as mentioned in Example 14 and elsewhere herein. The purified antibody-antigen conjugate will exhibit induction of tolerance towards the antigen in standard mouse models of type 1 diabetes, multiple sclerosis, islet transplantation, and OVA model antigen.

In order to demonstrate the induction of tolerance towards OVA, the OVA-antibody conjugate or OVA-nanoparticle-antibody conjugate may be administered either intravenously or extravascularly to mice. At a predetermined number of days following administration, mice are to be sacrificed and lymph nodes, spleen, and blood harvested for analysis. Splenocytes and lymph node derived cells are plated and re-stimulated for 3 days ex vivo with OVA and/or SIINFEKL peptide, and their down-regulation of IFNγ, IL-17a, IL-2, and IL-4 expression, and up-regulation of TGF-β1, which are established evidence of tolerance, are measured by ELISA. Intracellular staining of IFNγ, IL-17a, IL-2, and IL-4 are performed using flow cytometry on splenocytes and lymph node derived cells following 6 h of ex vivo re-stimulation with OVA and/or SIINFEKL peptide. Furthermore, flow cytometry is used to characterize the expression profiles of CD4, CD8, and regulatory T-cells from lymph node, spleen, and blood derived cells. Additionally, blood samples are taken from mice at varying time points to measure humoral antibody responses towards the OVA antigen. A variant experiment of the ex vivo re-stimulation is performed to determine if systemic tolerance has been established. Mice are administered with OVA-antibody conjugate or OVA-antibody-nanoparticle conjugate as described above, OVA is re-administered 9 days later with an adjuvant (lipopolysaccharide, complete Freud's adjuvant, alum, or other), and splenocyte responsiveness to the OVA antigen is assessed by ELISA and/or flow cytometry as described above. The OVA-antibody conjugate and/or OVA-antibody-nanoparticle formulation will render splenocytes non-responsive to the second challenge with OVA and adjuvant, which is one method to demonstrate effective establishment of systemic tolerance. Following initial administration with OVA-antibody conjugate and/or OVA-antibody-nanoparticle formulations, similar in vivo challenge experiments may be conducted with transgenic cell lines as a further demonstration of tolerance, such as adoptive transfer with OT-I T cells, similar to studies described in detail in Example 14. To demonstrate immune tolerance in mouse models of autoimmunity or deimmunization of therapeutic molecules, analogous antibody conjugates may be made to the relevant antigens as was described herein with OVA.

Example 17: Inducing Antigen-Specific Immunological Tolerance Through Non-Covalent Erythrocyte-Binding with Single Chain Antibody-Fused Antigen Single chain antibody fragments (scFv's) may be used as non-covalent binders to erythrocytes. ScFv's displaying high affinity towards erythrocyte surface proteins may be isolated by screening scFv libraries using state-of-the-art display platforms, as discussed in Example 13. Upon discovery of the novel erythrocyte-binding antibody fragment, similar biochemical characterization of binding are to be assessed as was performed with the ERY1 peptide. As the scFv has one polypeptide chain, it will be fused to the antigen in a site-specific recombinant manner using standard recombinant DNA techniques. Depending on the nature of the antigen fusion partner, the scFv is fused to the N- or C-terminus of the antigen to create the bifunctional protein species. In the case where the major histocompatibility complex (MHC) peptide recognition sequence is known for the antigen, the peptide is also inserted into the linker domain of the scFv, thus creating a new bifunctional antibody/antigen construct containing the native termini of the scFv.

In order to demonstrate the induction of tolerance towards OVA, an OVA-scFv or OVA-nanoparticle-scFv conjugate may be administered either intravenously or extravascularly to mice. At a predetermined number of days following administration, mice are to be sacrificed and lymph nodes, spleen, and blood are to be harvested for analysis. Splenocytes and lymph node derived cells are to be plated and re-stimulated for 3 days ex vivo with OVA and/or SIINFEKL peptide (SEQ ID NO:3), and their down-regulation of IFNγ, IL-17a, IL-2, and IL-4 expression, and up-regulation of TGF-β1, which are established evidence of tolerance, are to be measured, e.g., by ELISA. Intracellular staining of IFNγ, IL-17a, IL-2, and IL-4 is performed using flow cytometry on splenocytes and lymph node derived cells following 6 h of ex vivo re-stimulation with OVA and/or SIINFEKL peptide (SEQ ID NO:3). Furthermore, flow cytometry may be used to characterize the expression profiles of CD4, CD8, and regulatory T-cells from lymph node, spleen, and blood derived cells. Additionally, blood samples are taken from mice at varying time points to measure humoral antibody responses towards the OVA antigen. A variant experiment of the ex vivo re-stimulation is performed to determine if systemic tolerance has been established. Mice are administered with OVA-scFv or OVA-nanoparticle-scFv conjugate as described above, OVA is re-administered 9 days later with an adjuvant (lipopolysaccharide, complete Freud's adjuvant, alum, or other), and splenocyte responsiveness to the OVA antigen is assessed by ELISA and/or flow cytometry as described above. The OVA-scFv and/or OVA-scFv-nanoparticle formulation will render splenocytes non-responsive to the second challenge with OVA and adjuvant, thereby illustrating effective establishment of systemic tolerance. Following initial administration with OVA-scFv and/or OVA-scFv-nanoparticle formulations, similar in vivo challenge experiments may be conducted with transgenic cell lines to demonstrate tolerance, such as adoptive transfer with OT-I T cells, similar to studies described in detail in Example 14. To demonstrate immune tolerance in mouse models of autoimmunity or deimmunization of therapeutic molecules, analogous scFv fusions may be made to the relevant antigens as was described here with OVA.

Standard recombinant DNA techniques were used to create an antibody construct that both binds mouse erythrocytes and displays the immunodominant MHC-I epitope of OVA (SGLEQLESIINFEKL) (SEQ ID NO:82). Using overlap extension PCR, we first created a DNA fragment that encoded for the terminal 3' domain, including the SGLEQLESIINFEKL (SEQ ID NO:82) peptide with an overlapping 5' domain that is complimentary to the 3' terminus of the TER119 sequence. This DNA fragment was used as a reverse primer, along with a complimentary forward 5' primer, in a standard PCR to create the entire DNA fragment encoding for TER119-SGLEQLESIINFEKL (SEQ ID NO:82):

(SEQ ID NO: 83)

```
5'-GAGGTGAAGCTGCAGGAGTCTGGAGGAGGCTTGGTGCAACCTGGGGGG
TCTCTGAAACTCTCCTGTGTAGCCTCAGGATTCACTTTCAGGGACCACTGG
ATGAATTGGGTCCGGCAGGCTCCCGGAAAGACCATGGAGTGGATTGGAGAT
ATTAGACCTGATGGCAGTGACACAAACTATGCACCATCTGTGAGGAATAGA
TTCACAATCTCCAGAGACAATGCCAGGAGCATCCTGTACCTGCAGATGAGC
AATATGAGATCTGATTACACAGCCACTTATTACTGTGTTAGAGACTCACCT
ACCCGGGCTGGGCTTATGGATGCCTGGGGTCAAGGAACCTCAGTCACTGTC
TCCTCAGCCGGTGGTGGTGGTTCTGGTGGTGGTGGTTCTGGCGGCGGCGGC
TCCGGTGGTGGTGGATCCGACATTCAGATGACGCAGTCTCCTTCAGTCCTG
TCTGCATCTGTGGGAGACAGAGTCACTCTCAACTGCAAAGCAAGTCAGAAT
ATTAACAAGTACTTAAACTGGTATCAGCAAAAGCTTGGAGAAGCTCCCAAA
GTCCTGATATATAATACAAACAATTTGCAAACGGGCATCCCATCAAGGTTC
AGTGGCAGTGGATCTGGTACAGATTTCACACTCACCATCAGTAGCCTGCAG
CCTGAAGATTTTGCCACATATTTCTGCTTTCAGCATTATACTTGGCCCACG
TTTGGAGGTGGGACCAAGCTGGAAATCAAACGTACTCATCATCACCATCAT
CACGGTGGCGGTTCTGGCCTGGAGCAGCTGGAGTCTATTATTAATTTCGAA
AAACTG-3'.
```

The underlined sequence denotes the gene segment encoding for SGLEQLESIINFEKL. The DNA fragment was inserted into a mammalian and prokaryotic expression vector for recombinant expression.

Standard recombinant DNA techniques were used to create an antibody construct that both binds mouse erythrocytes and displays the chromogranin-A mimetope 1040-p31 (YVRPLWVRME) (SEQ ID NO:84). Using overlap extension PCR, a DNA fragment was created that encoded for the terminal 3' domain, including the YVRPLWVRME (SEQ ID NO:84) peptide with an overlapping 5' domain that is complimentary to the 3' terminus of the TER119 sequence. This DNA fragment was used as a primer, along with a complimentary forward 5' primer, in a standard PCR to create the entire DNA fragment encoding for TER119-YVRPLWVRME:

(SEQ ID NO: 85)
5'-GAGGTGAAGCTGCAGGAGTCAGGAGGAGGCTTGGTGCAACCTGGGGGG

TCTCTGAAACTCTCCTGTGTAGCCTCAGGATTCACTTTCAGGGACCACTGG

ATGAATTGGGTCCGGCAGGCTCCCGGAAAGACCATGGAGTGGATTGGGGAT

ATTAGACCTGATGGCAGTGACACAAACTATGCACCATCTGTGAGGAATAGA

TTCACAATCTCCAGAGACAATACCAGGAGCATCCTGTACCTGCAGATGGGC

AATATGAGATCTGATTACACAGCCACTTATTACTGTGTTAGAGACTCACCT

ACCCGGGCTGGGCTTATGGATGCCTGGGGTCAAGGAACCTCAGTCACTGTC

TCCTCAGCCGGTGGTGGTGGTTCTGGTGGTGGTGGTTCTGGCGGCGGCGGC

TCCGGTGGTGGTGGATCCGACATTCAGATGACGCAGTCTCCTTCAGTCCTG

TCTGCATCTGTGGGAGACAGAGTCACTCTCAACTGCAAAGCAAGTCAGAAT

ATTAACAAGTACTTAAACCGGTATCAGCAAAAGCTTGGAGAAGCTCCCAAA

GTCCTGGTATATAATACAAACAATTTGCAAACGGGCATCCCATCAAGGTTC

AGTGGCAGTGGATCTGGCACAGATTTCACACTCACCATCAGTAGCCTGCAG

CCTGAAGATTTTGCCACATATTTCTGCTTTCAGCATTATACTTGGCCCACG

TTTGGAGGTGTGACCAAGCTGGAAATCAAACGTACTCATCATCACCATCAT

CACGGTGGCGGT<u>TATGTCAGACCTCTGTGGGTCAGAATGGAA</u>-3'.

The underlined sequence denotes the gene segment encoding for the chromogranin-A (1040-p31) mimetope (YVRPLWVRME) (SEQ ID NO:84). The DNA fragment was inserted into a mammalian and prokaryotic expression vector for recombinant expression.

Standard recombinant DNA techniques were used to create an antibody construct that both binds mouse erythrocytes and displays mouse proinsulin, a major diabetes autoantigen in the NOD mouse. Using overlap extension PCR, we first created a DNA fragment that encoded for the terminal 3' domain, including the entire proinsulin protein, with an overlapping 5' domain that is complimentary to the 3' terminus of the TER119 sequence. This DNA fragment was used as a primer, along with a complimentary forward 5' primer, in a standard PCR to create the entire DNA fragment encoding for TER119-proinsulin:

(SEQ ID NO: 86)
5'-GAGGTGAAGCTGCAGGAGTCAGGAGGAGGCTTGGTGCAACCTGGGGGG

TCTCTGAAACTCTCCTGTGTAGCCTCAGGATTCACTTTCAGGGACCACTGG

ATGAATTGGGTCCGGCAGGCTCCCGGAAAGACCATGGAGTGGATTGGAGAT

ATTAGACCTGATGGCAGTGACACAAACTATGCACCATCTGTGAGGAATAGA

TTCACAATCTCCAGAGACAATGCCAGGAGCATCCTGTACCTGCAGATGAGC

AATATGAGATCTGATTACACAGCCACTTATTACTGTGTTAGAGACTCACCT

ACCCGGGCTGGGCTTATGGATGCCTGGGGTCAAGGAACCTCAGTCACTGTC

TCCTCAGCCGGTGGTGGTGGTTCTGGTGGTGGTGGTTCTGGCGGCGGCGGC

TCCGGTGGTGGTGGATCCGACATTCAGATGACGCAGTCTCCTTCAGTCCTG

TCTGCATCTGTGGGAGACAGAGTCACTCTCAACTGCAAAGCAAGTCAGAAT

ATTAACAAGTACTTAAACTGGTATCAGCAAAAGCTTGGAGAAGCTCCCAAA

GTCCTGATATATAATACAAACAATTTGCAAACGGGCATCCCATCAAGGTTC

AGTGGCAGTGGATCTGGTACAGATTTCACACTCACCATCAGTAGCCTGCAG

CCTGAAGATTTTGCCACATATTTCTGCTCTCAGCATTATACTTGGCCCACG

TTTGATGGTGGGACCAAGCTGGAAATCAAACGTACTCATCATCACCATCAT

CACGGTGGCGGT<u>TTTGTGAAACAGCATCTGTGCGGTCCGCATCTGGTGGAA

GCGCTGTATCTGGTGTGCGGCGAACGTGGCTTTTTTTATACCCCGAAAAGC

CGTCGTGAAGTGGAAGATCCGCAGGTGGAACAGCTGGAACTGGGCGGCAGC

CCGGGTGATCTGCAGACCCTGGCCCTGGAAGTGGCGCGTCAGAAACGTGGC

ATTGTGGATCAGTGCTGCACCAGCATTTGCAGCCTGTATCAGCTGGAAAAC

TATTACAAC</u>-3'.

The underlined sequence denotes the proinsulin gene segment of the construct. The DNA fragment was inserted into a mammalian and prokaryotic expression vector for recombinant expression.

Example 18: Synthesis of Branched Polymers Comprising Erythrocyte Binding Ligands and Other Functions For the synthesis of 8-arm PEG-thioacetate, 8-arm PEG-OH (Nektar) was dissolved in toluene and reacted for 18 h with 10 equivalents of triethylamine (Sigma Aldrich, CAS#121-44-8) and 10 equivalents of methanesulfonyl chloride (Sigma Aldrich, CAS#124-63-0) at room temperature under argon. The residue was filtered and the filtrate concentrated under reduced pressure, dissolved in dimethylformamide (DMF), and 10 equivalents of potassium thioacetate (Sigma Aldrich, CAS#10387-40-3) was added. After 18 h at room temperature, the residue was filtered, the filtrate was concentrated under reduced pressure and precipitated in diethyl ether. The precipitate was filtered and dried under reduced pressure to obtain the final product.

For the synthesis of 8-arm PEG-pyridyldisulfide, 8-arm PEG-thioacetate was dissolved in dimethylformamide (DMF) and deprotected with 1.05 equivalents of sodium methoxide (Sigma Aldrich, CAS#124-41-4) for 1 h at room temperature under argon in a Schlenk tube. To reduce the deprotected thiols to thiolates, 2 equivalents of Tris(2-carboxyethyl)phosphine hydrochloride (TCEP, Thermo Scientific, CAS#51805-45-9) and 2 equivalents of distilled water were added to the solution. After 2 h at room temperature, 12 equivalents of 2,2'-dithiodipyridine (Aldrithiol-2, Sigma Aldrich, CAS#2127-03-9) was added and the solution was stirred at room temperature for 24 h. The reaction mixture was then dialyzed against 5 L of distilled water in MWCO 3,500 Da dialysis tubing for 48 h, during which the distilled water was changed 4 times. Pyridyldisulfide loading onto the 8-arm PEG was quantified by reduction in 25 mM TCEP in 100 mM HEPES, pH 8.0, and UV-vis spectra were measured at 343 nm to monitor the presence of the pyridine-2-thione leaving group.

For the synthesis of 8-arm PEG-pyridyldisulfide-ALEXAFLUOR647, 8-arm PEG-thioacetate was dissolved in DMF and deprotected with 1.05 equivalents of sodium methoxide (Sigma Aldrich, CAS#124-41-4) for 1 h at room temperature under argon in a Schlenk tube. To reduce the deprotected thiols to thiolates, 2 equivalents of Tris(2-carboxyethyl)phosphine hydrochloride (TCEP, Thermo Scientific, CAS#51805-45-9) and an equal volume of 100 mM HEPES pH 8.0 were added to the solution. After 2 h at room temperature, 0.125 equivalents (equivalent to 1 arm out of 8) of AlexaFluor647-C2-maleimide (Invitrogen) was added to the solution. After 2 h at room temperature, 12 equivalents of 2,2'-dithiodipyridine (Aldrithiol-2, Sigma Aldrich, CAS#2127-03-9) was added and the solution was stirred at room temperature for 24 h. The reaction mixture was then dialyzed against 5 L of distilled water in MWCO 3,500 Da dialysis tubing for 48 h, during which the distilled water was changed 4 times. Pyridyldisulfide loading onto the 8-arm PEG was quantified by reduction in 25 mM TCEP in 100 mM HEPES, pH 8.0, and UV-vis spectra were measured at 343 nm to monitor the presence of the pyridine-2-thione leaving group.

Thiol-containing peptides were conjugated to the 8-arm PEG-pyridyldisulfide by adding stoichiometric quantities of the peptide, dissolved in aqueous 3 M guanidine-HCl (Sigma Aldrich, CAS#50-01-10), to the aqueous solution of 8-arm PEG-pyridyldisulfide at room temperature. Reaction conversion was monitored by measuring UV-vis spectra at 343 nm to quantify the presence of the pyridine-2-thione leaving group. If more than one molecule was to be conjugated to the 8-arm PEG-pyridyldisulfide, the reaction procedure was repeated with the new molecule in the same pot. Once conjugation was completed, the reaction mixture was desalted on a ZEBASPIN desalting column (Thermo Scientific), and the purified product was stored under the appropriate sterile conditions.

The induction of tolerance towards OVA could be demonstrated for the 8-arm PEG-ERY1/MIS-SIINFEKL conjugate (SIINFEKL: SEQ ID NO:3) by administering it either intravenously or extravascularly to mice. This test would also indicate induction of tolerance in humans using human-specific ligands. In such a demonstration, a predetermined number of days following administration, mice would be sacrificed and lymph nodes, spleen, and blood harvested for analysis. Splenocytes and lymph node derived cells are plated and re-stimulated for 3 days ex vivo with OVA and/or SIINFEKL (SEQ ID NO:3) peptide, and their down-regulation of IFNγ, IL-17a, IL-2, and IL-4 expression, and up-regulation of TGF-β1, which are established evidence of tolerance, are measured by ELISA. Intracellular staining of IFNγ, IL-17a, IL-2, and IL-4 is performed using flow cytometry on splenocytes and lymph node derived cells following 6 h of ex vivo re-stimulation with OVA and/or SIINFEKL (SEQ ID NO:3) peptide. Furthermore, flow cytometry is used to characterize the expression profiles of CD4, CD8, and regulatory T-cells from lymph node, spleen, and blood derived cells. Additionally, blood samples are taken from mice at varying time points to measure humoral antibody responses towards the OVA antigen. A variant experiment of the ex vivo re-stimulation is performed to determine if systemic tolerance has been established. Mice are administered with 8-arm PEG-ERY1/MIS-SIINFEKL conjugate (SIINFEKL: SEQ ID NO:3) as described above, OVA is re-administered 9 days later with an adjuvant (lipopolysaccharide, complete Freud's adjuvant, alum, or other), and splenocyte responsiveness to the OVA antigen is assessed by ELISA and/or flow cytometry as described above. The 8-arm PEG-ERY1-SIINFEKL conjugate (SIINFEKL: SEQ ID NO:3) formulation will render splenocytes non-responsive to the second challenge with OVA and adjuvant, which is a method of illustrating effective establishment of systemic tolerance. Following initial administration of the 8-arm PEG-ERY1/MIS-SIINFEKL conjugate formulations (SIINFEKL: SEQ ID NO:3), similar in vivo challenge experiments could be conducted with transgenic cell lines to further demonstrate tolerance, such as adoptive transfer with OT-I T cells, similar to studies described in detail in Example 14. To demonstrate immune tolerance in mouse models of autoimmunity or deimmunization of therapeutic molecules, analogous 8-arm PEG constructs may be made to the relevant antigens as was described here with SIINFEKL (SEQ ID NO:3).

Example 19: Inducing Antigen-Specific Immunological Tolerance Through Non-Covalent Erythrocyte-Binding with Aptamer-Conjugated Antigen Methods may be performed using other non-antibody bioaffinity reagents to measure their ability to induce immunological tolerance through non-covalent erythrocyte binding. Other protein-based affinity moieties, such as designed ankyrin repeat proteins (DARPins) (Steiner, Forrer, et al., 2008), designed armadillo repeat proteins (Parmeggiani, Pellarin, et al., 2008), fibronectin domains (Hackel, Kapila, et al., 2008), and cysteine-knot (knottin) affinity scaffolds (Silverman, Levin, et al., 2009) are screened for those displaying binding affinity to erythrocytes.

Library screening to discover high-affinity DNA/RNA aptamers towards erythrocytes is conducted using the well-established Systematic Evolution of Ligands by Exponential Enrichment (SELEX) method (Archemix, Cambridge, Mass., USA) (Sampson, 2003). Upon discovery of novel DNA/RNA sequences that binds erythrocytes with high affinity, they are chemically synthesized to include an additional chemical reactive group on either their 3' or 5' terminus for conjugation to an antigen and/or polymer micelle/nanoparticle. The chemically synthesized aptamer does, for example, harbor a reactive $NH_2$ group, that is conjugated via EDC/NHS conjugation chemistry with the COOH groups present on either the nanoparticle or antigen or nanoparticle-antigen complex, to create a single bioconjugate comprising of the erythrocyte-binding aptamer and the antigen or antigen-nanoparticle. Various chemical conjugation techniques are attempted by altering orthogonal reactive groups and conjugation schemes on both the aptamer, antigen, and/or antigen-nanoparticle.

In order to demonstrate the induction of tolerance towards OVA, the OVA-aptamer or OVA-nanoparticle-aptamer conjugate is administered either intravenously or extravascularly to mice. At a predetermined number of days following administration, mice are sacrificed and lymph nodes, spleen, and blood are harvested for analysis. Splenocytes and lymph node derived cells are plated and re-stimulated for 3 days ex vivo with OVA and/or SIINFEKL peptide (SEQ ID NO:3), and their down-regulation of IFNγ, IL-17a, IL-2, and IL-4 expression, and up-regulation of TGF-β1, which are established evidence of tolerance, is measured by ELISA. Intracellular staining of IFNγ, IL-17a, IL-2, and IL-4 is performed using flow cytometry on splenocytes and lymph node derived cells following 6 h of ex vivo re-stimulation with OVA and/or SIINFEKL (SEQ ID NO:3) peptide. Furthermore, flow cytometry is used to characterize the expression profiles of CD4, CD8, and regulatory T-cells from lymph node, spleen, and blood derived cells. Additionally, blood samples are taken from mice at varying time points to measure humoral antibody responses towards the OVA antigen. A variant experiment of the ex vivo re-stimulation is performed to determine if systemic tolerance has been established. Mice are administered with OVA-antibody or OVA-antibody-nanoparticle conjugate as described above, OVA is re-administered 9 days later with an adjuvant (lipopolysaccharide, complete Freud's adjuvant, alum, or other), and splenocyte responsiveness to the OVA antigen is assessed by ELISA and/or flow cytometry as described above. The OVA-antibody and/or OVA-antibody-nanoparticle formulations are expected to render splenocytes non-responsive to the second challenge with OVA and adjuvant, thereby illustrating effective establishment of systemic tolerance. Following initial administration with the OVA-aptamer and/or OVA-aptamer-nanoparticle formulations, similar in vivo challenge experiments will be conducted with transgenic cell lines to demonstrate tolerance, such as adoptive transfer with OT-I T cells, similar to studies described in detail in Example 14. To demonstrate immune tolerance in mouse models of autoimmunity or deimmunization of therapeutic molecules, analogous aptamer constructs are made to the relevant antigens as was described here with OVA.

Example 20: Characterizing of Binding to Human Erythrocytes

Figure 18:
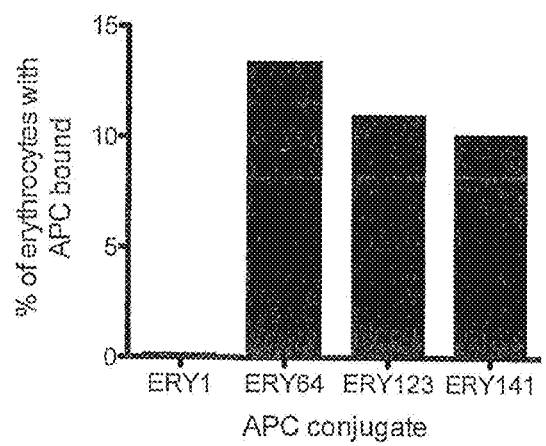
FIG. 18 presents experimental results as a bar graph showing binding of peptidic ligands to human erythrocytes.

To characterize the selected bacterially displayed peptides that bound to human erythrocytes in a non-cell displayed context, the peptides were synthesized chemically and conjugated to the fluorescent protein allophycocyanin (APC). In this manner, the erythrocyte-binding capacity of each peptide was characterized in a soluble context, i.e. as a protein conjugate. As demonstrated in FIG. 18, peptides ERY64, ERY123, and ERY141 bound to human erythrocytes as conjugates of APC APC-Peptide Conjugation Method Peptides were ordered and custom-synthesized via standard fmoc solid-phase peptide synthesis from PolyPeptide Group (Strasbourg, France). 10 equivalents of peptide dissolved in 3 M guanidine-HCl were added to 2 mg/mL maleimide-activated APC (InnovaBiosciences, Cambridge, UK) in PBS. Following a 4 h incubation at 4° C., the reaction was desalted on a 2 mL ZEBA Desalting Column (Thermo Scientific) and stored at 4° C.

Quantification of Erythrocyte Binding by Flow Cytometry Method

Freshly isolated human blood was dissolved 100-fold into PBS supplemented with 20 mg/mL BSA. $5 \times 10^5$ erythrocytes were added to 150 µL of 1 µM APC-peptide conjugate and incubated at 37 C for 45 min. Cells were washed extensively in PBS+20 mg/mL BSA, and analyzed for APC fluorescence on a CyAn ADP Flow cytometer (Beckman Coulter).

Figure 19:
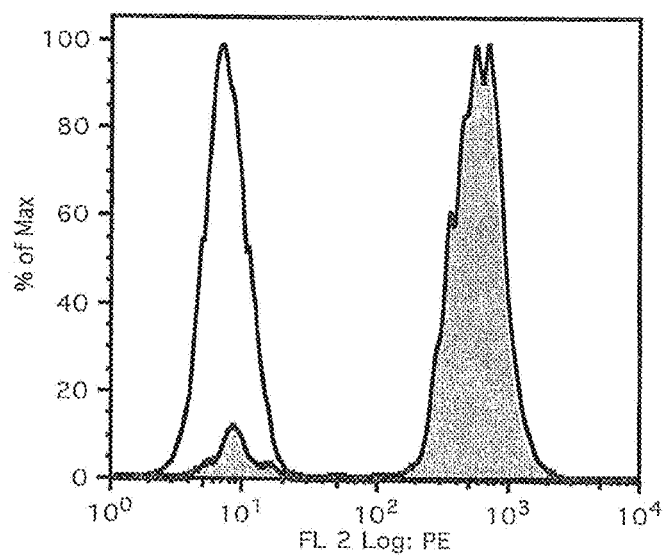
FIG. 19 presents experimental results as a flow cytometry histogram. Mouse erythrocytes were incubated with TER119-SIINFEKL (grey filled histogram) or albumin (empty histogram). Fluorescent signal comes from the anti-6×His-PE antibody used in detection of the scFv.

Example 21: Inducing Antigen-Specific Immunological Tolerance Through Erythrocyte-Binding with Single Chain Antibody-Fused Antigen A recombinant fusion of an scFv to the MHC-I immunodominant domain of OVA, SIINFEKL was created. The resultant scFv (herein termed TER119-SIINFEKL) bound mouse erythrocytes, as demonstrated by flow cytometry in FIG. 19.

Figure 20:
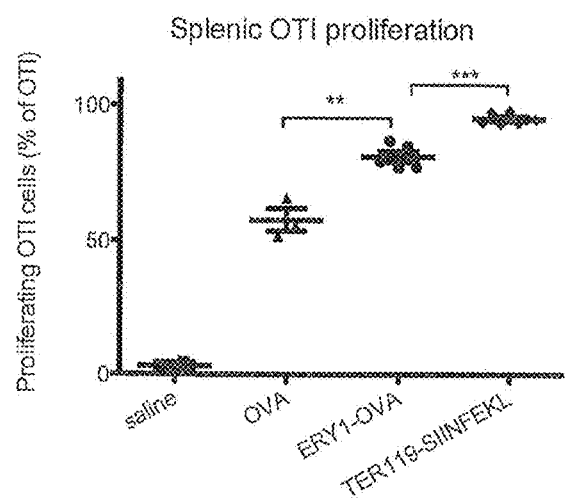
FIG. 20 is a plot of experimental results showing proliferating OT-I CD8 T cells in the spleen following intravenous administration of: saline, OVA, ERY1-OVA, or TER119-SIINFEKL. $P \leq 0.01$, *$P \leq 0.001$

Since ERY1-OVA has already been shown herein to induce this tolerance, it is a useful system to characterize immunological events. It was determined that erythrocyte binding of ERY1-OVA led to efficient cross-presentation of the OVA immunodominant MHC I epitope (SIINFEKL) by antigen presenting cells (APCs) and corresponding cross-priming of reactive T cells. CFSE-labeled OT-I $CD8^+$ T cells ($CD45.2^+$) were adoptively transferred into $CD45.1^+$ mice, and then proliferation of the OT-I $CD8^+$ T cells over 5 days was measured following intravenous administration of 10 µg of OVA, 10 g ERY1-OVA, an equimolar dose of TER119-SIINFEKL, or an equimolar dose of SIINFEKL. OT-I $CD8^+$ T cell proliferation, determined by dilution of the fluor CFSE as measured by flow cytometry, was markedly enhanced in mice administered TER119-SIINFEKL compared to ERY1-OVA or OVA (FIG. 20), demonstrating that erythrocyte-binding increased antigen-specific $CD8^+$ T cell cross-priming compared to the soluble antigen SIINFEKL.

Figure 21:
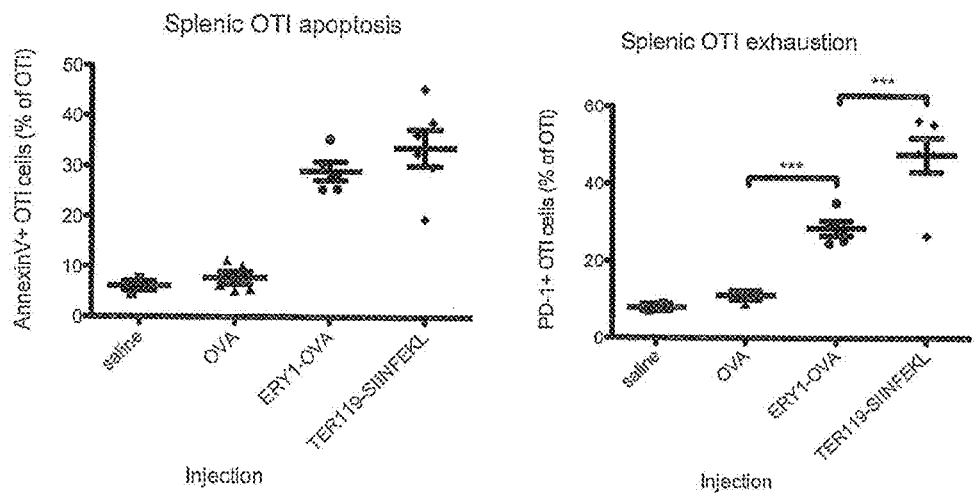
FIG. 21 is a plot of experimental results showing phenotypic characterization of OTI CD8 T cells following adoptive transfer and intravenous administration of: saline, OVA, ERY1-OVA, or TER119-SIINFEKL. Left panel: apoptotic OTI cell induction marked by Annexin-V binding in flow cytometry; Right panel: exhausted OTI cell induction marked by expression of PD-1 in flow cytometry.

To distinguish T cells being expanded into a functional effector phenotype from those being expanded and deleted, the proliferating OT-I $CD8^+$ T cells were analyzed for annexin-V, as a hallmark of apoptosis and thus deletion, as well as the exhaustion marker programmed death-1 (PD-1). TER119-SIINFEKL and ERY1-OVA induced much higher numbers of annexin-$V^+$ and PD-$1^+$ proliferating OT-I $CD8^+$ T cells than OVA (FIG. 21).

Using an established OT-I challenge-to-tolerance model (Liu, Iyoda, et al., 2002), the ability of TER119-SIINFEKL and ERY1-OVA to prevent subsequent immune responses to vaccine-mediated antigen challenge were demonstrated—even with a challenge involving a very strong bacterially-derived adjuvant. To tolerize, 10 µg of either OVA or ERY1-OVA, or an equimolar dose of TER119-SIINFEKL were intravenously administered at 1 and 6 days following adoptive transfer of OT-I $CD8^+$ ($CD45.2^+$) T cells to $CD45.1^+$ mice. After 9 additional days to allow potential deletion of the transferred T cells, the recipient mice were then challenged with OVA adjuvanted with lipopolysaccharide (LPS) by intradermal injection. Characterization of draining lymph node and spleen cells as well as their inflammatory responses 4 d after challenge allowed a determination as to whether or not deletion actually took place.

Intravenous administration of TER119-SIINFEKL or ERY1-OVA resulted in profound reductions in OT-I $CD8^+$ T cell populations in the draining lymph nodes and spleens compared with mice administered unmodified OVA prior to antigen challenge with LPS, demonstrating deletional tolerance. Draining lymph nodes from ERY1-OVA-treated mice contained over 11-fold fewer OT-I $CD8^+$ T cells as compared to OVA-treated mice, and 39-fold fewer than challenge control mice that did not receive intravenous injections of antigen; responses in spleen cells were similar. Draining lymph nodes from TER119-SIINFEKL-treated mice contained over 13-fold fewer OT-I $CD8^+$ T cells as compared to OVA-treated mice, and over 42-fold fewer than challenge control mice that did not receive intravenous injections of antigen; responses in spleen cells were similar. This effective clonal deletion exhibited in mice administered TER119-SIINFEKL or ERY1-OVA supported the earlier observations of enhanced OT-I $CD8^+$ T cell cross-priming (FIG. 20) and furthermore shows that cross-priming occurred in the absence of APC presentation of co-stimulatory molecules to lead to deletional tolerance.

Figure 22:
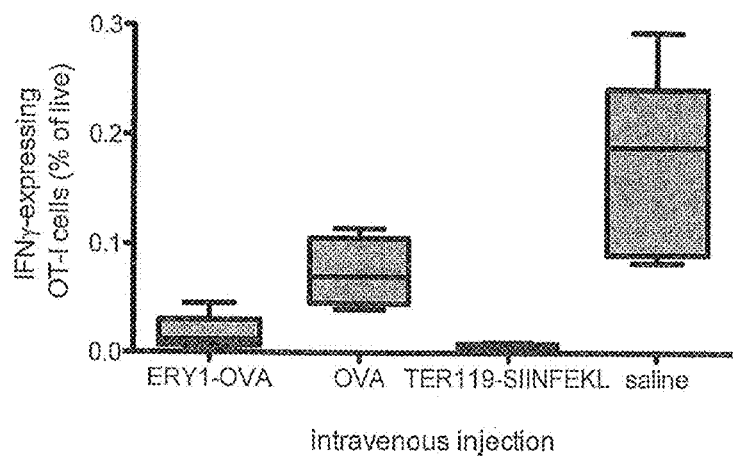
FIG. 22 is a plot of experimental results showing characterization of inflammatory (IFNγ+) OTI T cells in lymph nodes draining the site of challenge from mice tolerized with various injection formulations, as analyzed by flow cytometry.

To further evaluate the immune response following antigen challenge, the inflammatory nature of resident lymph node and spleen cells was characterized by expression of interferon-γ (IFNγ) by OT-I $CD8^+$ T cells (FIG. 22). Following challenge with OVA and LPS, the lymph nodes of mice previously treated with ERY1-OVA harbored 10-fold fewer IFNγ-expressing cells compared to challenge control mice (previously receiving no antigen), and over 4-fold fewer IFNγ-expressing cells compared to mice previously treated with an equivalent dose of OVA. Following challenge with OVA and LPS, the lymph nodes of mice previously treated with TER119-SIINFEKL harbored 33-fold fewer IFNγ-expressing cells compared to challenge control mice (previously receiving no antigen), and over 14-fold fewer IFNγ-expressing cells compared to mice previously treated with an equivalent dose of OVA, demonstrating the importance of erythrocyte binding in tolerogenic protection to challenge; responses in spleen cells were similar.

Animal Methods

Swiss Veterinary authorities previously approved all animal procedures. C57BL/6-Tg(TcraTcrb) 1100Mjb (OT-I) mice (Jackson Labs) were bred at the EPFL Animal Facility, and females were used for splenocyte isolation at 6-12 wk old. 8-12 week old female B6.SJL-Ptprc$^a$Pepc$^b$/Boy (CD45.1) mice (Charles River) were used as recipient hosts for OT-I CD8$^+$ T cell adoptive transfer and tolerance induction studies.

Peptide Design and Synthesis Methods

The (SEQ ID NO: 134)
ERY1 (H$_2$N-WMVLPWLPGTLDGGSGCRG-CONH$_2$) peptide was synthesized using standard solid-phase f-moc chemistry using TGR resin (Nova Biochem) on an automated liquid handler (Chemspeed). The underlined sequence is the ERY1 12-mer sequence that we previously discovered by phage display as a mouse glycophorin-A binder (Kontos and Hubbell, 2010). The GGSG region served as a linker to the cysteine residue used for conjugation; the flanking arginine residue served to lower the pKa and thus increase the reactivity of the cysteine residue (Lutolf, Tirelli, et al., 2001). The peptide was cleaved from the resin for 3 h in 95% tri-fluoroacetic acid, 2.5% ethanedithiol, 2.5% water, and precipitated in ice-cold diethyl ether. Purification was conducted on a preparative HPLC-MS (Waters) using a C18 reverse phase column (PerSpective Biosystems).

ERY1-Antigen Conjugation Methods 10 molar equivalents of succinimidyl-4-(N-maleimidomethyl)cyclohexane-1-carboxylate (SMCC, CAS#64987-85-5, Thermo Scientific) dissolved in dimethylformamide were reacted with 5 mg/mL endotoxin-free (<1 EU/mg) OVA (Hyglos GmbH) in PBS for 1 h at room temperature. Following desalting on a 2 mL ZEBA Desalt spin column (Thermo Scientific), 10 equivalents of ERY1 peptide dissolved in 3 M guanidine-HCl were added and allowed to react for 2 h at room temperature. The conjugate was desalted using 2 mL Zeba Desalt spin columns, 0.2 m sterile filtered, dispensed into working aliquots, and stored at −20 C. Protein concentration was determined via BCA Assay (Thermo Scientific). The scheme results in conjugation of the cysteine side chain on the peptide to lysine side-chains on the antigen.

T Cell Adoptive Transfer Methods

CD8$^+$ T cells from OT-I (CD45.2$^+$) mouse spleens were isolated using a CD8 magnetic bead negative selection kit (Miltenyi Biotec) as per the manufacturer's instructions. Freshly isolated CD8$^+$ OT-I cells were resuspended in PBS and labeled with 1 M carboxyfluorescein succinimidyl ester (CFSE, Invitrogen) for 6 min at room temperature, and the reaction was quenched for 1 min with an equal volume of IMDM with 10% FBS (Gibco). Cells were washed, counted, and resuspended in pure IMDM prior to injection. 3×10$^6$ CFSE-labeled CD8$^+$ OT-I cells were injected intravenously into the tail vein of recipient CD45.1$^+$ mice. For short-term proliferation studies, 10 μg of ERY1-OVA or OVA, or an equimolar dose of TER119-SIINFEKL in 100 μL volume was injected 24 h following adoptive transfer. Splenocytes were harvested 5 d following antigen administration and stained for analysis by flow cytometry.

OT-I Tolerance and Challenge Model Methods

3×10$^5$ CFSE-labeled OT-I CD8$^+$ T cells were injected into CD45.1$^+$ recipient mice as described above. 1 and 6 d following adoptive transfer, mice were intravenously administered 10 μg of ERY1-OVA or OVA, or an equimolar dose of TER119-SIINFEKL in 100 μL saline into the tail vein. 15 d following adoptive transfer, mice were challenged with 5 μg OVA and 25 ng ultra-pure *Escherichia coli* LPS (InvivoGen) in 25 μL intradermally into each rear leg pad (Hock method, total dose of 10 μg OVA and 50 ng LPS). Mice were sacrificed 4 d following challenge, and spleen and draining lymph node cells were isolated for restimulation. For flow cytometry analysis of intracellular cytokines, cells were restimulated in the presence of 1 mg/mL OVA or 1 μg/mL SIINFEKL peptide (Genscript) for 3 h. Brefeldin-A (Sigma, 5 μg/mL) was added and restimulation resumed for an additional 3 h prior to staining and flow cytometry analysis.

Antibodies and Flow Cytometry Methods

The following anti-mouse antibodies were used for flow cytometry: CD1d Pacific Blue, CD3ε PerCP-Cy5.5, CD8αPE-Cy7, CD45.2 Pacific Blue, IFNγ-APC, CD8αAPC-eF780, (all from eBioscience), in addition to fixable live/dead dye (Invitrogen), and annexin-V-Cy5 labeling kit (BioVision). Samples were analyzed on a CyAn ADP flow cytometer (Beckman Coulter). Cells were washed first with PBS, stained for 20 min on ice with live/dead dye, blocked for 20 min on ice with 24G2 hybridoma medium, surface stained for 20 min on ice, fixed in 2% paraformaldehyde for 20 min ice, intracellularly stained in the presence of 0.5% saponin for 45 min on ice, followed by a final wash prior to analysis. For apoptosis staining, annexin-V-Cy5 was added 5 min prior to analysis.

Example 22: Creation of Antigen-Specific Immunological Tolerance Towards Therapeutic Proteins Through Fusion Molecule of Erythrocyte Binding Peptide-and-Conjugated Antigen A mouse erythrocyte-binding variant of asparaginase (ERY1-ASNase) was created by conjugating the mouse erythrocyte-specific peptide ERY1 (Kontos and Hubbell, 2010). To determine the immunogenicity of erythrocyte-bound versus wild-type asparaginase, a study was performed to evaluate to evaluate two regimens, namely exposure to a 2-dose and a 6-dose regimen of the ERY conjugate (ERY1-ASNase) or the native form (ASPARAGINASE MEDAC, Medac GmbH; which was also used as the raw material for the ERY1-ASNase conjugate). In each regimen, 15 μg of ERY1-ASNase or ASNase was administered intravenously every 2 days, and blood was drawn every 7 days.

Figure 23:
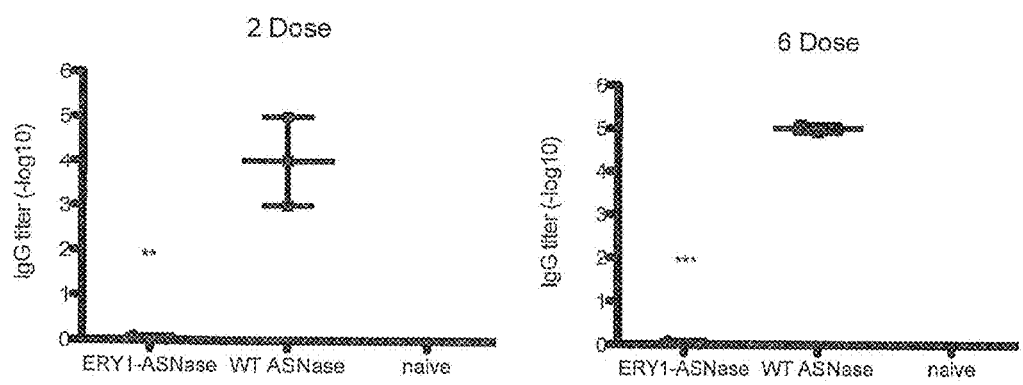
FIG. 23 is a plot of experimental results showing asparaginase (ASNase)-specific serum IgG titers from mice receiving 2 or 6 doses of ERY1-ASNase or wild-type ASNase, 21 days following administration, as determined by ELISA.

Following the exposures at therapeutic doses, antibody titers were measured at various time points, up to 21 days following the final injection. The result is clear in showing vast reduction in immunogenicity through erythrocyte conjugation, with no antibodies observable at all in the 2-dose regimen and the 6-dose regimen series (FIG. 23). By contrast, the wild type, native asparaginase (as currently used clinically, in the product ASPARAGINASE MEDAC), induced vigorous immunity even following the 2 dose regimen.

A prophylaxis study was performed to determine if erythrocyte-binding asparaginase induced bona-fide immune tolerance towards wild-type asparaginase. Mice previously administered with wild-type clinical asparaginase were challenged with an additional dose following the onset of humoral immunity. Antibody levels increased or remained high following re-administration of the protein; this is representative of a dangerous clinical situation of hypersensitivity and shock reactions towards the therapeutic. Mice previously treated with ERY1-conjugated asparaginase failed to induce potent antibody responses even after six challenges with wild-type asparaginase. On average, mice tolerized with erythrocyte-binding asparaginase developed approx. 6000-fold fewer antibodies towards clinical wild-type asparaginase.

ERY1-ASNase Conjugation Method 10 molar equivalents of succinimidyl-4-(N-maleimidomethyl)cyclohexane-1-carboxylate (SMCC, CAS#64987-85-5, Thermo Scientific) dissolved in dimethylformamide were reacted with 5 mg/mL Asparaginase Medac in PBS for 2 h at room temperature. Following desalting on a 2 mL ZEBA Desalt spin column (Thermo Scientific), 2.5 equivalents of ERY1 peptide dissolved in 3 M guanidine-HCl were added and allowed to react for 2 h at room temperature. The conjugate was desalted using 2 mL Zeba Desalt spin columns, 0.2 μm sterile filtered, dispensed into working aliquots, and stored at −20 C. Protein concentration was determined via BCA Assay (Thermo Scientific). The scheme results in conjugation of the cysteine side chain on the peptide to lysine side-chains on the protein.

Flow Cytometry Detection of Binding Method

Freshly isolated human blood was diluted 100-fold into PBS supplemented with 20 mg/mL BSA. Approximately 500,000 erythrocytes were added to 100 nM of asparaginase and incubated at 37 C for 1 h. Following washing, cells were incubated with goat anti-asparaginase (Abnova) for 30 min on ice. Following a second round of washing, cells were incubated with ALEXAFLUOR488-conjugated anti-goat IgG antibody (Invitrogen) for 20 min on ice. After a final wash, cells were analyzed on a flow cytometer to detect for erythrocyte-bound asparaginase.

Asparaginase Administration Method

Desired dosages of ERY1-ASNase or ASNase were prepared in sterile 0.9% saline, and 100 μL of the solution was injected into the tail vein of anesthetized C57BL/6 mice. Blood was drawn at pre-determined time points either by cheek puncture or tail incisions.

Anti-Asparaginase Antibody Detection from Serum Method

Serum from experimental groups was serially diluted into PBS and incubated for 2 h at RT on ASNase-coated ELISA plates. HRP-conjugated anti-mouse IgG (Southern Biotech) was used as the detection antibody.

Example 23: Immune Reversal to Create Tolerance after Immunoreaction

In the clinical case where immunity (exemplified by the presence of anti-drug-antibodies) towards a therapeutic protein or protein of interest has already been induced in the patient, it is desirable to reverse the immune response towards the drug, thus enabling further use of the therapeutic. Again, the clinically available microbial enzyme asparaginase was used in this example to demonstrate the induction of tolerance towards a therapeutic protein in mice with pre-existing immunity towards asparaginase. A mouse erythrocyte-binding variant of asparaginase (ERY1-ASNase) was created by conjugating the mouse erythrocyte-specific peptide ERY1.

A cross-over study was performed to determine if erythrocyte-binding asparaginase could reverse immunity towards clinical asparaginase. Mice were intravenously administered multiple doses of wild-type asparaginase two days apart. 21 days following administration, high levels of anti-asparaginase antibodies were detected in serum. Immunized mice were then therapeutically treated with erythrocyte-binding asparaginase regimens at varying doses. In both dosing regimens, ERY-conjugated asparaginase reduced antibody levels approx. 10-fold, thus reversing pre-existing humoral immunity ERY1-ASNase Conjugation Method 10 molar equivalents of succinimidyl-4-(N-maleimidomethyl)cyclohexane-1-carboxylate (SMCC, CAS#64987-85-5, Thermo Scientific) dissolved in dimethylformamide were reacted with 5 mg/mL ASPARAGINASE MEDAC in PBS for 2 h at room temperature. Following desalting on a 2 mL ZEBA Desalt spin column (Thermo Scientific), 2.5 equivalents of ERY1 peptide dissolved in 3 M guanidine-HCl were added and allowed to react for 2 h at room temperature. The conjugate was desalted using 2 mL ZEBA Desalt spin columns, 0.2 μm sterile filtered, dispensed into working aliquots, and stored at −20 C. Protein concentration was determined via BCA Assay (Thermo Scientific). The scheme results in conjugation of the cysteine side chain on the peptide to lysine side-chains on the protein.

Flow Cytometry Detection of Binding Method

Freshly isolated human blood was diluted 100-fold into PBS supplemented with 20 mg/mL BSA. Approximately 500,000 erythrocytes were added to 100 nM of asparaginase and incubated at 37 C for 1 h. Following washing, cells were incubated with goat anti-asparaginase (Abnova) for 30 min on ice. Following a second round of washing, cells were incubated with ALEXAFLUOR488-conjugated anti-goat IgG antibody (Invitrogen) for 20 min on ice. After a final wash, cells were analyzed on a flow cytometer to detect for erythrocyte-bound asparaginase.

Asparaginase Administration Method

Desired dosages of ERY1-ASNase or ASNase were prepared in sterile 0.9% saline, and 100 μL of the solution was injected into the tail vein of anesthetized C57BL/6 mice. Blood was drawn at pre-determined time points either by cheek puncture or tail incisions.

Anti-Asparaginase Antibody Detection from Serum Method

Serum from experimental groups was serially diluted into PBS and incubated for 2 h at RT on ASNase-coated ELISA plates. HRP-conjugated anti-mouse IgG (Southern Biotech) was used as the detection antibody.

Example 24: Development of Antibodies and Antibody-Fragments that Bind Mouse and/or Human Erythrocytes Several erythrocyte binding antigen constructs have been created. These include those relating to the protein level: TER119-SIINFEKL, TER119-ChrA, and TER119-proinsulin. These also include those relating to the genetic level: TER119-SIINFEKL, TER119-ChrA TER119-proinsulin, TER119-uricase, TER119-InsB9-23, TER119-ISQAVHAAHAEINEAGR (SEQ ID NO:87), TER119-H-2kb, TER119-H-2kd, 10F7-SIINFEKL, 10F7-ChrA, 10F7-proinsulin, and 10F7-uricase.

Methods mRNA from the TER-119 hybridoma clone was obtained as a gift from Prof Shozo Izui at the University of Geneva, Switzerland. Standard reverse transcriptase PCR (RT-PCR) was performed using the SUPERSCRIPT III FIRST STRAND SYNTHESIS SYSTEM (Invitrogen) to create complimentary DNA (cDNA) of the clone. PCR was then conducted using the following set of primers to specifically amplify the DNA sequences of the variable heavy (VH) and variable light (VL) regions of the antibody:

| Primer name | Primer sequence (5' to 3') | SEQ ID NO |
|---|---|---|
| VL-FOR1 | AGC CGG CCA TGG CGG AYA TCC AGC TGA CTC AGC C | SEQ ID NO: 88 |
| VL-FOR2 | AGC CGG CCA TGG CGG AYA TTG TTC TCW CCC AGT C | SEQ ID NO: 89 |
| VL-FOR3 | AGC CGG CCA TGG CGG AYA TTG TGM TMA CTC AGT C | SEQ ID NO: 90 |
| VL-FOR4 | AGC CGG CCA TGG CGG AYA TTG TGY TRA CAC AGT C | SEQ ID NO: 91 |
| VL-FOR5 | AGC CGG CCA TGG CGG AYA TTG TRA TGA CMC AGT C | SEQ ID NO: 92 |
| VL-FOR6 | AGC CGG CCA TGG CGG AYA TTM AGA TRA MCC AGT C | SEQ ID NO: 93 |
| VL-FOR7 | AGC CGG CCA TGG CGG AYA TTC AGA TGA YDC AGT C | SEQ ID NO: 94 |
| VL-FOR8 | AGC CGG CCA TGG CGG AYA TYC AGA TGA CAC AGA C | SEQ ID NO: 95 |
| VL-FOR9 | AGC CGG CCA TGG CGG AYA TTG TTC TCA WCC AGT C | SEQ ID NO: 96 |
| VL-FOR10 | AGC CGG CCA TGG CGG AYA TTG WGC TSA CCC AAT C | SEQ ID NO: 97 |
| VL-FOR11 | AGC CGG CCA TGG CGG AYA TTS TRA TGA CCC ART C | SEQ ID NO: 98 |
| VL-FOR12 | AGC CGG CCA TGG CGG AYR TTK TGA TGA CCC ARA C | SEQ ID NO: 99 |
| VL-FOR13 | AGC CGG CCA TGG CGG AYA TTG TGA TGA CBC AGK C | SEQ ID NO: 100 |
| VL-FOR14 | AGC CGG CCA TGG CGG AYA TTG TGA TAA CYC AGG A | SEQ ID NO: 101 |
| VL-FOR15 | AGC CGG CCA TGG CGG AYA TTG TGA TGA CCC AGW T | SEQ ID NO: 102 |
| VL-FOR16 | AGC CGG CCA TGG CGG AYA TTG TGA TGA CAC AAC C | SEQ ID NO: 103 |
| VL-FOR17 | AGC CGG CCA TGG CGG AYA TTT TGC TGA CTC AGT C | SEQ ID NO: 104 |
| VL-FOR18 | AGC CGG CCA TGG CGG ARG CTG TTG TGA CTC AGG AAT C | SEQ ID NO: 105 |
| VL-REV1 | GAT GGT GCG GCC GCA GTA CGT TTG ATT CCA GCT TG G | SEQ ID NO: 106 |
| VL-REV2 | GAT GGT GCG GCC GCA GTA CGT TTT ATT CCA GCT TG G | SEQ ID NO: 107 |
| VL-REV3 | GAT GGT GCG GCC GCA GTA CGT TTT ATT CCA ACT TT G | SEQ ID NO: 108 |
| VL-REV4 | GAT GGT GCG GCC GCA GTA CGT TTC AGC TCC AGC TTG G | SEQ ID NO: 109 |
| VL-REV5 | GAT GGT GCG GCC GCA GTA CCT AGG ACA GTC AGT TTG G | SEQ ID NO: 110 |
| VL-REV6 | GAT GGT GCG GCC GCA GTA CCT AGG ACA GTG ACC TTG G | SEQ ID NO: 111 |
| VH-FOR1 | GTT ATT GCT AGC GGC TCA GCC GGC AAT GGC GGA KGT RMA GCT TCA GGA GTC | SEQ ID NO: 100 |
| VH-FOR2 | GTT ATT GCT AGC GGC TCA GCC GGC AAT GGC GGA GGT BCA GCT BCA GCA GTC | SEQ ID NO: 112 |
| VH-FOR3 | GTT ATT GCT AGC GGC TCA GCC GGC AAT GGC GCA GGT GCA GCT GAA GSA STC | SEQ ID NO: 113 |
| VH-FOR4 | GTT ATT GCT AGC GGC TCA GCC GGC AAT GGC GGA GGT CCA RCT GCA ACA RTC | SEQ ID NO: 114 |
| VH-FOR5 | GTT ATT GCT AGC GGC TCA GCC GGC AAT GGC GCA GGT YCA GCT BCA GCA RTC | SEQ ID NO: 115 |
| VH-FOR6 | GTT ATT GCT AGC GGC TCA GCC GGC AAT GGC GCA GGT YCA RCT GCA GCA GTC | SEQ ID NO: 116 |
| VH-FOR7 | GTT ATT GCT AGC GGC TCA GCC GGC AAT GGC GCA GGT CCA CGT GAA GCA GTC | SEQ ID NO: 117 |
| VH-FOR8 | GTT ATT GCT AGC GGC TCA GCC GGC AAT GGC GGA GGT GAA SST GGT GGA ATC | SEQ ID NO: 118 |
| VH-FOR9 | GTT ATT GCT AGC GGC TCA GCC GGC AAT GGC GGA VGT GAW GYT GGT GGA GTC | SEQ ID NO: 119 |
| VH-FOR10 | GTT ATT GCT AGC GGC TCA GCC GGC AAT GGC GGA GGT GCA GSK GGT GGA GTC | SEQ ID NO: 120 |
| VH-FOR11 | GTT ATT GCT AGC GGC TCA GCC GGC AAT GGC GGA KGT GCA MCT GGT GGA GTC | SEQ ID NO: 121 |
| VH-FOR12 | GTT ATT GCT AGC GGC TCA GCC GGC AAT GGC GGA GGT GAA GCT GAT GGA RTC | SEQ ID NO: 122 |
| VH-FOR13 | GTT ATT GCT AGC GGC TCA GCC GGC AAT GGC GGA GGT GCA RCT TGT TGA GTC | SEQ ID NO: 123 |
| VH-FOR14 | GTT ATT GCT AGC GGC TCA GCC GGC AAT GGC GGA RGT RAA GCT TCT CGA GTC | SEQ ID NO: 124 |
| VH-FOR15 | GTT ATT GCT AGC GGC TCA GCC GGC AAT GGC GGA AGT GAA RST TGA GGA GTC | SEQ ID NO: 125 |
| VH-FOR16 | GTT ATT GCT AGC GGC TCA GCC GGC AAT GGC GCA GGT TAC TCT RAA AGW GTS TG | SEQ ID NO: 126 |
| VH-FOR17 | GTT ATT GCT AGC GGC TCA GCC GGC AAT GGC GCA GGT CCA ACT VCA GCA RCC | SEQ ID NO: 127 |

-continued

| Primer name | Primer sequence (5' to 3') | SEQ ID NO |
|---|---|---|
| VH-FOR18 | GTT ATT GCT AGC GGC TCA GCC GGC AAT GGC GGA TGT GAA CTT GGA AGT GTC | SEQ ID NO: 128 |
| VH-FOR19 | GTT ATT GCT AGC GGC TCA GCC GGC AAT GGC GGA GGT GAA GGT CAT CGA GTC | SEQ ID NO: 129 |
| VH-REV1 | CCC TTG AAG CTT GCT GAG AAA ACG GTG AGA GTG GT | SEQ ID NO: 130 |
| VH-REV3 | CCC TTG AAG CTT GCT GCA GAG ACA GTG ACC AGA GT | SEQ ID NO: 132 |
| VH-REV4 | CCC TTG AAG CTT GCT GAG GAG ACG GTG ACT GAG GT | SEQ ID NO: 133 |

The amplified VH and VL genes were then digested with restriction endonucleases (NcoI and NotI for VL, NdeI and HindIII for VH), the gene fragments were purified following agarose electrophoresis using a standard kit (Zymo Research, Orange, Calif., USA), and ligated into a cloning plasmid pMAZ360. The cloning plasmid was then sequenced to determine the DNA sequence of the VH and VL genes of TER119.

TER119 and 10F7-antigen DNA constructs were designed and commercially synthesized and obtained from DNA2.0 (Menlo Park, Calif., USA).

Each final completed scFv gene was digested with SfiI and XhoI (NEB, Ipswich, Mass., USA), and ligated into the same sites on the pSecTagA mammalian expression plasmid (Invitrogen, Carlsbad, Calif., USA).

Figure 24:
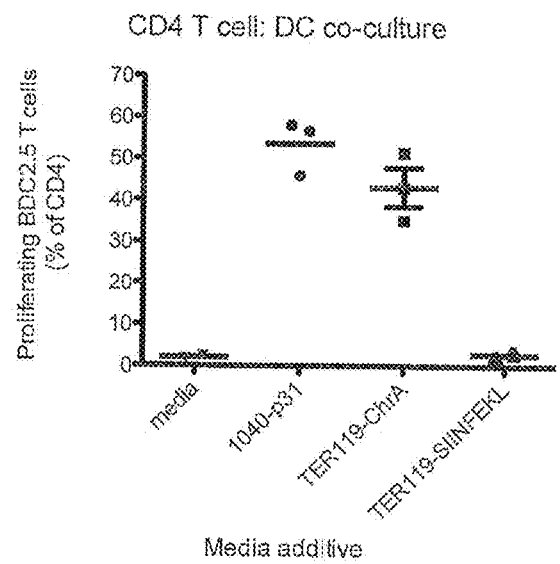
FIG. 24 is a plot of experimental results showing proliferation of CD4 T cells from the transgenic NODBDC2.5 mouse in co-culture with splenic DCs, with various media additives.

Example 25: Induction of Tolerance Towards Diabetogenic Antigens Using Erythrocyte-Binding Diabetes Antigens Chromogranin-A mimotope peptide (termed 1040-p31 or ChrA) was engineered to bind to mouse erythrocytes by recombinantly fusing the peptide to the mouse erythrocyte-specific scFv TER119. The resultant scFv, herein termed TER119-ChrA, tightly bound mouse erythrocytes (data not shown). To study T cell behavior towards the chromogranin-A antigen variants, the NODBDC2.5 transgenic mouse was used, which harbors T cells specific for the recognition of the chromogranin-A antigen. To determine if TER119-ChrA was processed and displayed on major histocompatibility-II (MHC-II) complexes in a manner sufficient for BDC2.5 T cell priming, the antigen was added to a co-culture system with BDC2.5 splenic dendritic cells and CD4 T cells. As demonstrated in FIG. 24, TER119-ChrA was efficiently processed and the correct antigenic domain displayed on MHC-II to prime antigen-specific proliferation of the transgenic BDC2.5 CD4 T cells in vitro, which is a requisite for T cell tolerance in vivo.

Figure 25:
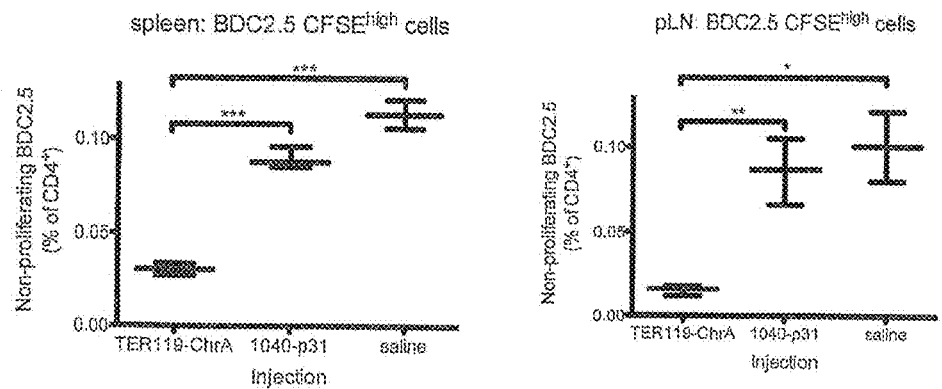
FIG. 25 is a plot of experimental results showing quantification of non-proliferating NODBDC2.5 CD4 T cells following adoptive transfer and intravenous administration of TER119-ChrA, free 1040-p31 peptide, or saline, as determined by flow cytometry.

To determine the consequences of erythrocyte binding of the autoantigen on CD4 proliferation in vivo, a similar proliferation study was conducted using BDC2.5 CD4 T cells labeled with the fluorescent molecule CFSE. Following adoptive transfer of the labeled BDC2.5 CD4 T cells into naïve NOD mice, either 10 μg of TER119-ChrA or an equimolar dose of free soluble 1040-p31 peptide was administered intravenously. As is demonstrated in FIG. 25, mice treated with TER119-ChrA harbored far fewer non-proliferating BDC2.5 CD4 T cells in both the spleen and pancreatic lymph nodes (pLN) compared with mice treated with the soluble 1040-p31 peptide. These data demonstrate that erythrocyte-binding antigen drives potent antigen-specific CD4 T cell signaling and priming in a manner functionally distinct from soluble antigen, similar to the inventors thorough investigations of CD8 T cell deletional tolerance. Such marked reduction in systemic (spleen) and local (pancreatic lymph node) diabetogenic T cells is clear positive indication of a favorable outcome for control of disease onset.

Example 26: Induction of Tolerance Towards Insulin

As already demonstrated herein (for instance, see Example 25), tolerance can be created towards various antigens. This example describes how tolerance to insulin can be created. In order to induce tolerance towards insulin, which is another islet antigen recognized by diabetogenic T cells, insulin is engineered to bind mouse erythrocytes by recombinant fusion to the mouse erythrocyte-specific scFv TER119. The resultant scFv, herein termed TER119-proinsulin, is implemented in the conventional mouse model of spontaneous onset T1D, namely the NOD/ShiLt mouse. The NOD/ShiLt mouse spontaneously undergoes immune cell mediated destruction of insulin-producing pancreatic tissue, thus inducing hyperglycemia and clinical onset of disease. Similarly, human insulin and human erythrocyte binding factors may be used to create tolerance to insulin in humans.

To demonstrate tolerance in this robust spontaneously autoimmune mouse model, TER119-proinsulin is to be administered to young (~3 week old) mice at varying time intervals and doses in order to functionally inactivate and/or delete insulin-reactive T cells. Glucose levels of the treated mice are monitored to assess hyperglycemia and clinical onset of disease. TER119-proinsulin is also used in a therapeutic mode to induce remission of disease. In such a study, TER119-proinsulin is administered to new-onset hyperglycemic mice at varying doses and time intervals, and glucose levels are monitored to assess reduction of hyperglycemia and return to homeostasis, thus demonstrating remission of clinical onset of T1D.

Example 27: Creating Tolerance Towards Cellular Grafts and Transplants by Using Erythrocyte-Binding MHC Molecules A process of creating tolerance of grafts is provided by way of example. Erythrocyte-binding MHC molecules are engineered by chemically conjugating erythrocyte-binding peptides to soluble MHC domains. Alternatively, the MHC molecule may be recombinantly expressed as a fusion with an erythrocyte-specific scFv.

In order to demonstrate tolerance towards MHC molecules by erythrocyte binding, mouse models of cellular grafting, such as tumor grafts, skin grafts, islet transplants, and hematopoietic cell transplants are conducted. In each study, the host mouse is tolerized towards the donor MHC class by administration of erythrocyte-binding MHC prior to or during the graft procedure. Graft acceptance is monitored using methods appropriate for each study; i.e., measurement of tumor growth in tumor grafts, monitoring tissue necrosis or growth in skin transplant, monitoring islet mass and glycemia in islet transplants, and characterizing chimerism in hematopoietic cell transplants.

FURTHER DISCLOSURE

Various embodiments of the invention are described. An embodiment is an isolated peptide comprising at least 5 consecutive amino acid residues of a sequence chosen from the group consisting of SEQ ID NO: 11, SEQ ID NO: 13, SEQ ID NO: 14, SEQ ID NO:15, SEQ ID NO:16, SEQ ID NO:17, SEQ ID NO:1, and conservative substitutions thereof, wherein said sequence specifically binds an erythrocyte. An embodiment is the peptide with one or more residues with a D to L substitution or has a conservative substitution of at least one and no more than two amino acids of the sequences chosen from the group consisting of SEQ ID NO:11, SEQ ID NO:13, SEQ ID NO:14, SEQ ID NO:15, SEQ ID NO:16, SEQ ID NO:17, and SEQ ID NO:1. An embodiment is the peptide with at least 5 consecutive amino acid residues of a sequence chosen from the group consisting of SEQ ID NO:11, SEQ ID NO:13, SEQ ID NO:14, SEQ ID NO:15, SEQ ID NO:16, SEQ ID NO:17, SEQ ID NO:1, and conservative substitutions thereof, wherein said sequence specifically binds an erythrocyte. The peptide may have, e.g., a number of residues between about 10 and about 80. The peptide may further comprise a therapeutic agent, e.g., be chosen from the group consisting of insulin, pramlintide acetate, growth hormone, insulin-like growth factor-1, erythropoietin, type 1 alpha interferon, interferon α2a, interferon α2b, interferon β1a, interferon 3β1b, interferon γ1b, β-glucocerebrosidase, adenosine deaminase, granulocyte colony stimulating factor, granulocyte macrophage colony stimulating factor, interleukin 1, interleukin 2, interleukin 11, factor VIIa, factor VIII, factor IX, exenatide, L-asparaginase, rasburicase, tumor necrosis factor receptor, and enfuvirtide. The peptide may be further comprising a member of the group consisting of an antibody, an antibody fragment, and a single chain antigen binding domain (ScFv). The peptide may be further comprising a tolerogenic antigen, e.g., chosen from the group consisting of proteins deficient by genetic disease, proteins with nonhuman glycosylation, nonhuman proteins, synthetic proteins not naturally found in humans, human food antigens, human transplantation antigens, and human autoimmune antigens. The peptide may have one or more sequences that specifically bind an erythrocyte, the sequences may be repeats of the same sequence or a mix of various sequences that perform said binding.

An embodiment is a method of producing immunotolerance, the method comprising administering a composition comprising a molecular fusion that comprises a tolerogenic antigen and an erythrocyte-binding moiety that specifically binds an erythrocyte in the patient and thereby links the antigen to the erythrocyte, wherein the molecular fusion is administered in an amount effective to produce immunotolerance to a substance that comprises the tolerogenic antigen. An embodiment is the method wherein the molecular fusion consists of at least one erythrocyte-binding moiety directly covalently bonded to the antigen: for instance, a fusion protein comprising the moiety and the antigen. An embodiment is the method wherein the molecular fusion comprises at least one erythrocyte-binding moiety attached to a particle that is attached to or contains the antigen, e.g., wherein the particle is chosen from the group consisting of a microparticle, a nanoparticle, a liposome, a polymersome, and a micelle. An embodiment is the case wherein the tolerogenic antigen comprises a portion of a therapeutic protein, e.g., the protein comprises factor VIII or factor IX. An embodiment is the case wherein the tolerogenic antigen comprises a portion of a nonhuman protein. An embodiment is the case wherein the protein comprises adenosine deaminase, L-asparaginase, rasburicase, antithymocyte globulin, L-arginase, and L-methionase. An embodiment is the method wherein the patient is a human and the tolerogenic antigen comprises a portion of a protein not found in nature. An embodiment is the case wherein the patient is a human and the tolerogenic antigen comprises a glycan of a protein that comprises nonhuman glycosylation. An embodiment is the case wherein the tolerogenic antigen comprises at least a portion of a human transplantation antigen. An embodiment is the case wherein the tolerogenic antigen comprises a portion of a human autoimmune disease protein, e.g., chosen from the group consisting of preproinsulin, proinsulin, insulin, GAD65, GAD67, IA-2, IA-2β, thyroglobulin, thyroid peroxidase, thyrotropin receptor, myelin basic protein, myelin oligodendrocyte glycoprotein, proteolipid protein, collagen II, collagen IV, acetylcholine receptor, matrix metalloprotein 1 and 3, molecular chaperone heat-shock protein 47, fibrillin-1, PDGF receptor α, PDGF receptor β, and nuclear protein SS-A. An embodiment is the case wherein the tolerogenic antigen comprises a portion of a human food, e.g., is chosen from the group consisting of conarachin (Ara h 1), allergen II (Ara h 2), *arachis* agglutinin (Ara h 6), α-lactalbumin (ALA), lactotransferrin, glutein, low molecular weight glutein, α- and γ-gliadin, hordein, secalin, and avenin. An embodiment is the case wherein the erythrocyte-binding moiety is chosen from the group consisting of a peptide ligand, an antibody, an antibody fragment, and a single chain antigen binding domain (ScFv). An embodiment is the case wherein the erythrocyte-binding moiety comprises an antibody, an antibody fragment or an ScFv derived from a hybridoma that produces an antibody against an erythrocyte, with the hybridoma being chosen from the group consisting of BRIC 4, BRIC 5, BRIC 6, BRIC 10, BRIC 14, BRIC 18, BRIC 39, BRIC 66, BRIC 68, BRIC 69, BRIC 87, BRIC 108, BRIC 110, BRIC 111, BRIC 125, BRIC 126, BRIC 128, BRIC 145, BRIC 155, BRIC 157, BRIC 163, BRIC 170, BRIC 198, BRIC 203, BRIC 216, BRIC 220, BRIC 221, BRIC 222, BRIC 229, BRIC 230, BRIC 231, BRIC 235, BRIC 256, BRAC 17, BRAC 18, BGRL 1, BGRL 2, BGRL 11, BGRL 100, BRAD 3, BIRMA D6, BIRMA D10, BIRMA K3, BIRMA K3, 84B; 6A7; COE; or KZ1. An embodiment is the case wherein the erythrocyte-binding moiety specifically binds to a biomolecule chosen from the group consisting of Band 3 (CD233), aquaporin-1, Glut-1, Kidd antigen, RhAg/Rh50 (CD241), Rh (CD240), Rh30CE (CD240CE), Rh30D (CD240D), Kx, glycophorin A, glycophorin B (CD235b), glycophorin C (CD235c), glycophorin D (CD235d), Kell (CD238), Duffy/DARCi (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, and H antigen (CD173). The tolerogenic antigen may comprise a mimotope. An embodiment is the case wherein the scFv comprises some or all of 10F7, e.g., one or more of a light chain of 10F7 and/or a heavy chain of 10F7 and/or a higher affinity variant of a light chain of 10F7 and/or a heavy chain of 10F7. An embodiment is the method wherein the erythrocyte-binding moiety comprises a peptide ligand comprising at least 5 consecutive amino acid residues of a sequence chosen from the group consisting of SEQ ID NO:11, SEQ ID NO:13, SEQ ID NO:14, SEQ ID NO:15, SEQ ID NO:16, SEQ ID NO:17, SEQ ID NO:1, and conservative substitutions thereof, wherein said sequence specifically binds an erythrocyte.

An embodiment is a composition comprising a molecular fusion that comprises a tolerogenic antigen and an erythrocyte-binding moiety that specifically binds an erythrocyte in the patient and thereby links the antigen to the erythrocyte.

An instance is the case wherein the erythrocyte-binding moiety is covalently bonded to the antigen. Another instance is the case wherein the molecular fusion comprises the erythrocyte-binding moiety attached to a particle that is attached to the antigen, e.g., a microparticle, a nanoparticle, a liposome, a polymersome, or a micelle. Examples of a tolerogenic antigen are: a portion of a therapeutic protein, s a portion of a nonhuman protein, a portion (including the whole portion, i.e., all) of a protein not naturally found in a human, a glycan of a protein that comprises nonhuman glycosylation, a portion of a human autoimmune antigen, a portion of a human food. An embodiment is the composition wherein the erythrocyte-binding moiety is chosen from the group consisting of a peptide ligand, an antibody, an antibody fragment, and a single chain antigen binding domain (ScFv), e.g., all or a portion of 10F7. The erythrocyte-binding moiety may comprises a peptide ligand comprising at least 5 consecutive amino acid residues of a sequence chosen from the group consisting of SEQ ID NO: 11, SEQ ID NO: 13, SEQ ID NO:14, SEQ ID NO:15, SEQ ID NO:16, SEQ ID NO:17, SEQ ID NO:1, and conservative substitutions thereof, wherein said sequence specifically binds an erythrocyte. The erythrocyte-binding moiety may be one that comprises a peptide ligand that has a dissociation constant of between about 10 μM and 0.1 nM as determined by equilibrium binding measurements between the peptide and erythrocytes. An embodiment is the case wherein the erythrocyte-binding moiety comprises an antibody, an antibody fragment or an ScFv derived from a hybridoma that produces an antibody against an erythrocyte, with the hybridoma being chosen from the group consisting of BRIC 4, BRIC 5, BRIC 6, BRIC 10, BRIC 14, BRIC 18, BRIC 39, BRIC 66, BRIC 68, BRIC 69, BRIC 87, BRIC 108, BRIC 110, BRIC 111, BRIC 125, BRIC 126, BRIC 128, BRIC 145, BRIC 155, BRIC 157, BRIC 163, BRIC 170, BRIC 198, BRIC 203, BRIC 216, BRIC 220, BRIC 221, BRIC 222, BRIC 229, BRIC 230, BRIC 231, BRIC 235, BRIC 256, BRAC 17, BRAC 18, BGRL 1, BGRL 2, BGRL 11, BGRL 100, BRAD 3, BIRMA D6, BIRMA D10, BIRMA K3, BIRMA K3, 84B; 6A7; COE; or KZ1. An embodiment is the case wherein the erythrocyte-binding moiety specifically binds to a biomolecule chosen from the group consisting of Band 3 (CD233), aquaporin-1, Glut-1, Kidd antigen, RhAg/Rh50 (CD241), Rh (CD240), Rh30CE (CD240CE), Rh30D (CD240D), Kx, glycophorin A, glycophorin B (CD235b), glycophorin C (CD235c), glycophorin D (CD235d), Kell (CD238), Duffy/DARCi (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, and H antigen (CD173). The tolerogenic antigen may comprise a mimotope.

The tolerogenic compositions may be used in treating a pathologic condition, for instance a pathologic condition chosen from the group consisting of transplant rejection, autoimmune disease, food allergy, and immune response against a therapeutic agent.

An embodiment is a pharmaceutically acceptable composition for use in immunoreversal of an immune response against a substance comprising a fusion molecule that comprises an erythrocyte-binding moiety and an antigen of the substance. The composition may have the tolerogenic antigen is chosen from, for example, the group consisting of a protein, a portion of a protein, a human protein or portion thereof, a nonhuman protein or portion thereof, a glycan, a glycan of a protein that comprises nonhuman glycosylation, a human autoimmune antigen, a protein therapeutic for a human or a portion thereof, and a portion of a human food. The composition may have the tolerogenic antigen is chosen from, for example, the group consisting of proteins deficient by genetic disease, proteins with nonhuman glycosylation, nonhuman proteins, synthetic proteins not naturally found in humans, human food antigens, human transplantation antigens, and human autoimmune antigens. The erythrocyte-binding moiety may be provides that specifically binds to a biomolecule chosen from the group consisting of Band 3 (CD233), aquaporin-1, Glut-1, Kidd antigen, RhAg/Rh50 (CD241), Rh (CD240), Rh30CE (CD240CE), Rh30D (CD240D), Kx, glycophorin A, glycophorin B (CD235b), glycophorin C (CD235c), glycophorin D (CD235d), Kell (CD238), Duffy/DARCi (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, and H antigen (CD173). The erythrocyte-binding moiety may be chosen from the group consisting of a peptide ligand, an antibody, an antibody fragment, and a single chain antigen binding domain (ScFv). The erythrocyte-binding moiety may be prepared so that it comprises an antibody, an antibody fragment or an ScFv derived from a hybridoma that produces an antibody against an erythrocyte, with the hybridoma being chosen from the group consisting of BRIC 4, BRIC 5, BRIC 6, BRIC 10, BRIC 14, BRIC 18, BRIC 39, BRIC 66, BRIC 68, BRIC 69, BRIC 87, BRIC 108, BRIC 110, BRIC 111, BRIC 125, BRIC 126, BRIC 128, BRIC 145, BRIC 155, BRIC 157, BRIC 163, BRIC 170, BRIC 198, BRIC 203, BRIC 216, BRIC 220, BRIC 221, BRIC 222, BRIC 229, BRIC 230, BRIC 231, BRIC 235, BRIC 256, BRAC 17, BRAC 18, BGRL 1, BGRL 2, BGRL 11, BGRL 100, BRAD 3, BIRMA D6, BIRMA D10, BIRMA K3, BIRMA K3, 84B; 6A7; COE; or KZ1.

Embodiments include a fusion molecule comprising an erythrocyte-binding moiety and an antigen of asparaginase. As is evident from the multiple disclosures of erythrocyte-binding moieties, there are many options for the same, including: an scFv that binds a human erythrocyte or a peptidic binding ligand chosen from the group consisting of SEQ ID NO:11, SEQ ID NO:12, SEQ ID NO:13, SEQ ID NO:14, SEQ ID NO:15, SEQ ID NO:16, SEQ ID NO:17, and conservative substitutions thereof, wherein said sequence specifically binds an erythrocyte. Such a composition comprising the fusion molecule may be used for inducing tolerance to asparaginase.

Embodiments include a fusion molecule comprising and an erythrocyte-binding moiety and an antigen of chromogranin-A. The antigen may be a mimotope or some or all of a chromogranin-A. As is evident from the multiple disclosures of erythrocyte-binding moieties, there are many options for the same, including: an scFv that binds a human erythrocyte or a peptidic binding ligand chosen from the group consisting of SEQ ID NO:11, SEQ ID NO:12, SEQ ID NO:13, SEQ ID NO:14, SEQ ID NO:15, SEQ ID NO:16, SEQ ID NO:17, and conservative substitutions thereof, wherein said sequence specifically binds an erythrocyte. Such a composition comprising the fusion molecule may be used for inducing tolerance to chromogranin-A and/or for preventing diabetes or reducing progression a diabetes disease.

Another instance is a composition comprising an erythrocyte-binding moiety that specifically binds an erythrocyte joined to an entity chosen from the group consisting of a synthetic polymer, a branched synthetic polymer, and a particle. The particle may be, e.g., a microparticle, a nanoparticle, a liposome, a polymersome, and a micelle. The composition may further comprise a tolerogenic antigen, a therapeutic agent, or a tumor homing ligand.

Embodiments include a method of embolizing a tumor in a patient comprising administering a composition or medicament comprising the composition to a patient that comprises a molecular fusion of an erythrocyte-binding moiety and a tumor-homing ligand, wherein the tumor-homing ligand is an antibody, antibody fragment, a single chain antigen binding domain (ScFv), or peptide ligand that is directed to specifically bind a target chosen from the group consisting of a tumor and tumor vasculature, and wherein the erythrocyte-binding moiety comprises a peptide ligand, an antibody, an antibody fragment, an scFv, or an aptamer that specifically binds erythrocytes. Examples of tumor homing ligands are aminopeptidase-A, aminopeptidase-N, endosialin, cell surface nucleolin, cell surface annexin-1, cell surface p32/gC1q receptor, cell surface plectin-1, fibronectin EDA, fibronectin EDB, interleukin 11 receptor α, tenascin-C, endoglin/CD105, BST-2, galectin-1, VCAM-1, fibrin and tissue factor receptor. The erythrocyte moiety may comprise, e.g., a peptide ligand, an scFv, or an antibody or fragment.

An embodiment is a single chain antigen binding domain (scFv) comprising a peptide ligand that specifically binds an erythrocyte. The peptide may be attached to the scFv or disposed in a linker portion. One or more of the peptide ligands may be included.

All patent applications, patents, and publications mentioned herein are hereby incorporated by reference herein for all purposes; in the case of conflict, the instant specification controls.

REFERENCES

1 Pasut G & Veronese F M (2009) "PEG conjugates in clinical development or use as anticancer agents: an overview." *Adv Drug Deliv Rev* 61(13): 1177-1188.
2 Fishburn C S (2008) "The pharmacology of PEGylation: balancing PD with PK to generate novel therapeutics." *J Pharm Sci* 97(10):4167-4183.
3 Gao W, Liu W, Mackay J A, Zalutsky M R, Toone E J, & Chilkoti A (2009) "In situ growth of a stoichiometric PEG-like conjugate at a protein's N-terminus with significantly improved pharmacokinetics." *Proc Natl Acad Sci USA* 106(36):15231-15236.
4 Huang L, Gough P C, & Defelippis M R (2009) "Characterization of poly(ethylene glycol) and PEGylated products by LC/MS with postcolumn addition of amines." *Anal Chem* 81(2):567-577.
5 Bailon P, Palleroni A, Schaffer C A, Spence C L, Fung W J, Porter J E, Ehrlich G K, Pan W, Xu Z X, Modi M W, Farid A, Berthold W, & Graves M (2001) "Rational design of a potent, long-lasting form of interferon: a 40 kDa branched polyethylene glycol-conjugated interferon alpha-2a for the treatment of hepatitis C." *Bioconiug Chem* 12(2):195-202.
6 Dhalluin C, Ross A, Leuthold L A, Foser S, Gsell B, Miller F, & Senn H (2005) "Structural and biophysical characterization of the 40 kDa PEG-interferon-alpha2a and its individual positional isomers." *Bioconiug Chem* 16(3): 504-517.
7 Dennis M (2002) "Albumin Binding as a General Strategy for Improving the Pharmacokinetics of Proteins." *Journal of Biological Chemistry* 277(38):35035-35043.
8 Walker A, Dunlevy G, Rycroft D, Topley P, Holt L J, Herbert T, Davies M, Cook F, Holmes S, Jespers L, & Herring C (2010) "Anti-serum albumin domain antibodies in the development of highly potent, efficacious and long-acting interferon." *Protein Engineering Design and Selection.*
9 Hall S S, Mitragotri S, & Daugherty P S (2007) "Identification of peptide ligands facilitating nanoparticle attachment to erythrocytes." *Biotechnol Prog* 23(3):749-754.
10 Godsel L M, Wang K, Schodin B A, Leon J S, Miller S D, & Engman D M (2001) "Prevention of autoimmune myocarditis through the induction of antigen-specific peripheral immune tolerance." *Circulation* 103(12):1709-1714.
11 Luo X, Pothoven K L, McCarthy D, DeGutes M, Martin A, Getts D R, Xia G, He J, Zhang X, Kaufman D B, & Miller S D (2008) "ECDI-fixed allogeneic splenocytes induce donor-specific tolerance for long-term survival of islet transplants via two distinct mechanisms." *Proc Natl Acad Sci USA* 105(38): 14527-14532.
12 Fife B T, Guleria I, Gubbels Bupp M, Eagar T N, Tang Q, Bour-Jordan H, Yagita H, Azuma M, Sayegh M H, & Bluestone J A (2006) "Insulin-induced remission in new-onset NOD mice is maintained by the PD-1-PD-L1 pathway." *J Exp Med* 203(12):2737-2747.
13 Miller S D, Turley D M, & Podojil J R (2007) "Antigen-specific tolerance strategies for the prevention and treatment of autoimmune disease." *Nat Rev Immunol* 7(9): 665-677.
14 Maluccio M A, Covey A M, Porat L B, Schubert J, Brody L A, Sofocleous C T, Getrajdman G I, Jarnagin W, Dematteo R, Blumgart L H, Fong Y, & Brown K T (2008) "Transcatheter arterial embolization with only particles for the treatment of unresectable hepatocellular carcinoma." *J Vasc Interv Radiol* 19(6):862-869.
15 Gadaleta C D & Ranieri G (2010) "Trans-arterial chemoembolization as a therapy for liver tumours: New clinical developments and suggestions for combination with angiogenesis inhibitors." *Crit Rev Oncol Hematol.*
16 Huang X, Molema G, King S, Watkins L, Edgington T S, & Thorpe P E (1997) "Tumor infarction in mice by antibody-directed targeting of tissue factor to tumor vasculature." *Science* 275(5299):547-550.
17 Sheridan C (2010) "Fresh from the biologic pipeline-2009." *Nat Biotechnol* 28(4):307-310.
18 Maynard J & Georgiou G (2000) "Antibody engineering." *Annual review of biomedical engineering* 2:339-376.
19 Weisser N E & Hall J C (2009) "Applications of single-chain variable fragment antibodies in therapeutics and diagnostics." *Biotechnol Adv* 27(4):502-520.
20 Moghimi S M & Szebeni J (2003) "Stealth liposomes and long circulating nanoparticles: critical issues in pharmacokinetics, opsonization and protein-binding properties." *Prog Lipid Res* 42(6):463-478.
21 Vogl T J, Naguib N N, Nour-Eldin N E, Rao P, Emami A H, Zangos S, Nabil M, & Abdelkader A (2009) "Review on transarterial chemoembolization in hepatocellular carcinoma: palliative, combined, neoadjuvant, bridging, and symptomatic indications." *Eur J Radiol* 72(3):505-516.
22 Fonsatti E, Nicolay H J, Altomonte M, Covre A, & Maio M (2010) "Targeting cancer vasculature via endoglin/CD105: a novel antibody-based diagnostic and therapeutic strategy in solid tumours." *Cardiovasc Res* 86(1):12-19.
23 Dienst A, Grunow A, Unruh M, Rabausch B, Nor J E, Fries J W, & Gottstein C (2005) "Specific occlusion of 24 Ruoslahti E, Bhatia S N, & Sailor M J (2010) "Targeting of drugs and nanoparticles to tumors." *J Cell Biol* 188 (6):759-768.

25 Thijssen V L, Postel R, Brandwijk R J, Dings R P, Nesmelova I, Satijn S, Verhofstad N, Nakabeppu Y, Baum L G, Bakkers J, Mayo K H, Poirier F, & Griffloen A W (2006) "Galectin-1 is essential in tumor angiogenesis and is a target for antiangiogenesis therapy." *Proc Natl Acad Sci USA* 103(43):15975-15980.

26 Schliemann C, Roesli C, Kamada H, Borgia B, Fugmann T, Klapper W, & Neri D (2010) "In vivo biotinylation of the vasculature in B-cell lymphoma identifies BST-2 as a target for antibody-based therapy." *Blood* 115(3):736-744.

27 Brack S S, Silacci M, Birchler M, & Neri D (2006) "Tumor-targeting properties of novel antibodies specific to the large isoform of tenascin-C." *Clin Cancer Res* 12(10):3200-3208.

28 Rybak J, Roesli C, Kaspar M, Villa A, & Neri D (2007) "The extra-domain A of fibronectin is a vascular marker of solid tumors and metastases." *Cancer Res* 67(22): 10948-10957.

29 Mohandas N & Gallagher P G (2008) "Red cell membrane: past, present, and future." *Blood* 112(10):3939-3948.

30 Rice J J & Daugherty P S (2008) "Directed evolution of a biterminal bacterial display scaffold enhances the display of diverse peptides." *Protein Eng Des Sel* 21(7):435-442.

31 Dane K Y, Chan L A, Rice J J, & Daugherty P S (2006) "Isolation of cell specific peptide ligands using fluorescent bacterial display libraries." *J Immunol Methods* 309 (1-2):120-129.

32 van der Vlies A J, O'Neil C P, Hasegawa U, Hammond N, & Hubbell J A (2010) "Synthesis of pyridyl disulfide-functionalized nanoparticles for conjugating thiol-containing small molecules, peptides, and proteins." *Bioconiug Chem* 21(4):653-662.

33 O'Neil C P, van der Vlies A J, Velluto D, Wandrey C, Demurtas D, Dubochet J, & Hubbell J A (2009) "Extracellular matrix binding mixed micelles for drug delivery applications." *J Control Release* 137(2):146-151.

34 Velluto D, Demurtas D, & Hubbell J A (2008) "PEG-b-PPS diblock copolymer aggregates for hydrophobic drug solubilization and release: cyclosporin A as an example." *Mol Pharm* 5(4):632-642.

35 Reddy S T, Rehor A, Schmoekel H G, Hubbell J A, & Swartz M A (2006) "In vivo targeting of dendritic cells in lymph nodes with poly(propylene sulfide) nanoparticles." *J Control Release* 112(1):26-34.

36 Reddy S T, van der Vlies A J, Simeoni E, Angeli V, Randolph G J, O'Neil C P, Lee L K, Swartz M A, & Hubbell J A (2007) "Exploiting lymphatic transport and complement activation in nanoparticle vaccines." *Nat Biotechnol* 25(10):1159-1164.

37 Kontos S & Hubbell J A (2010) "Improving protein pharmacokinetics by engineering erythrocyte affinity." *Mol. Pharmaceutics* 7(6):2141-2147.

38 Khandelwal S & Saxena R K (2006) "Assessment of survival of aging erythrocyte in circulation and attendant changes in size and CD147 expression by a novel two step biotinylation method." *Exp Gerontol* 41(9):855-861.

39 Ferguson T A, Choi J, & Green D R (2011) "Armed response: how dying cells influence T-cell functions." *Immunol Rev* 241(1):77-88.

40 Yamazaki S, Dudziak D, Heidkamp G F, Fiorese C, Bonito A J, Inaba K, Nussenzweig M C, & Steinman R M (2008) "CD8+CD205+ splenic dendritic cells are specialized to induce Foxp3+ regulatory T cells." *Journal of immunology* (Baltimore, Md.: 1950) 181(10):6923-6933.

41 Holz L E, Warren A, Le Couteur D G, Bowen D G, & Bertolino P (2010) "CD8+ T cell tolerance following antigen recognition on hepatocytes." *Journal of Autoimmunity* 34(1):15-22.

42 Ichikawa S, Mucida D, Tyznik A J, Kronenberg M, & Cheroutre H (2011) "Hepatic stellate cells function as regulatory bystanders." *Journal of immunology* (Baltimore, Md.: 1950) 186(10):5549-5555.

43 Thomson A W & Knolle P A (2010) "Antigen-presenting cell function in the tolerogenic liver environment." *Nat Rev Immunol* 10(11):753-766.

44 Albert M L, Pearce S F, Francisco L M, Sauter B, Roy P, Silverstein R L, & Bhardwaj N (1998) "Immature dendritic cells phagocytose apoptotic cells via alphavbeta5 and CD36, and cross-present antigens to cytotoxic T lymphocytes." *J Exp Med* 188(7):1359-1368.

45 Green D R, Ferguson T, Zitvogel L, & Kroemer G (2009) "Immunogenic and tolerogenic cell death." *Nat Rev Immunol* 9(5):353-363.

46 Bursch L S, Rich B E, & Hogquist K A (2009) "Langerhans cells are not required for the CD8 T cell response to epidermal self-antigens." *J Immunol* 182(8):4657-4664.

47 Liu K, Iyoda T, Saternus M, Kimura Y, Inaba K, & Steinman R M (2002) "Immune tolerance after delivery of dying cells to dendritic cells in situ." *J Exp Med* 196(8): 1091-1097.

48 Darrah P A, Hegde S T, Patel D T, Lindsay R W B, Chen L, Roederer M, & Seder R A (2010) "IL-10 production differentially influences the magnitude, quality, and protective capacity of Th1 responses depending on the vaccine platform." *J Exp Med* 207(7):1421-1433.

49 Lee M S & Kim Y-J (2007) "Signaling pathways downstream of pattern-recognition receptors and their cross talk." *Annu. Rev. Biochem.* 76:447-480.

50 Arnaboldi P M, Roth-Walter F, & Mayer L (2009) "Suppression of Th1 and Th17, but not Th2, responses in a CD8(+) T cell-mediated model of oral tolerance." *Mucosal Immunol* 2(5):427-438.

51 Saint-Lu N, Tourdot S, Razafindratsita A, Mascarell L, Berjont N, Chabre H, Louise A, Van Overtvelt L, & Moingeon P (2009) "Targeting the allergen to oral dendritic cells with mucoadhesive chitosan particles enhances tolerance induction." *Allergy* 64(7):1003-1013.

52 Mueller D L (2010) "Mechanisms maintaining peripheral tolerance." *Nat Immunol* 11(1):21-27.

53 Lutolf M P, Tirelli N, Cerritelli S, Cavalli L, & Hubbell J A (2001) "Systematic modulation of Michael-type reactivity of thiols through the use of charged amino acids." *Bioconiug Chem* 12(6):1051-1056.

54 Steiner D, Forrer P, & Pluckthun A (2008) "Efficient selection of DARPins with sub-nanomolar affinities using SRP phage display." *Journal of Molecular Biology* 382 (5):1211-1227.

55 Parmeggiani F, Pellarin R, Larsen A P, Varadamsetty G, Stumpp M, Zerbe O, Caflisch A, & Plückthun A (2008) "Designed armadillo repeat proteins as general peptide-binding scaffolds: consensus design and computational optimization of the hydrophobic core." *Journal of Molecular Biology* 376(5):1282-1304.

56 Hackel B J, Kapila A, & Wittrup K D (2008) "Picomolar affinity fibronectin domains engineered utilizing loop length diversity, recursive mutagenesis, and loop shuffling." *J Mol Biol* 381(5):1238-1252.
57 Silverman A P, Levin A M, Lahti J L, & Cochran J R (2009) "Engineered cystine-knot peptides that bind alpha (v)beta(3) integrin with antibody-like affinities." *Journal of Molecular Biology* 385(4): 1064-1075.
58 Keefe A D, Pai S, & Ellington A (2010) "Aptamers as therapeutics." *Nat Rev Drug Discov* 9(7):537-550.
59 Rockey W M, Huang L, Kloepping K C, Baumhover N J, Giangrande P H, & Schultz M K (2011) "Synthesis and radiolabeling of chelator-RNA aptamer bioconjugates with copper-64 for targeted molecular imaging." *Bioorg Med Chem* 19(13):4080-4090.
60 Savla R, Taratula O, Garbuzenko O, & Minko T (2011) "Tumor targeted quantum dot-mucin 1 aptamer-doxorubicin conjugate for imaging and treatment of cancer." *J Control Release* 153(1):16-22.
61 Sampson T (2003) "Aptamers and SELEX: the technology." *World Patent Information* (25):123-129.
62 Getts D R, Getts M T, McCarthy D P, Chastain E M L, & Miller S D (2010). "Have we overestimated the benefit of human(ized) antibodies?" *mAbs* 2(6):682-694.

What is claimed is:

1. A composition for immunomodulation to achieve antigen-specific tolerance, the composition comprising: an antigen to which tolerance is desired;

wherein the antigen is selected from the group consisting of high molecular weight glutenin, low molecular weight glutenin, gliadin, hordein, secalin, avenin, and immunogenic fragments thereof;

an erythrocyte-binding moiety, wherein the erythrocyte-binding moiety comprises an antibody fragment that has the ability to non-covalently, specifically bind an exterior erythrocyte surface in situ in blood, wherein the antigen to which tolerance is desired is recombinantly fused or chemically conjugated to the erythrocyte-binding moiety, and wherein, upon administration to a human in which tolerance to the antigen is desired:

the composition binds to CD45 negative cells, but not to CD45 positive cells, and the composition reduces, fails to induce, or prevents inflammatory responses in antigen-specific T cells as compared to when the human is exposed to the antigen alone.

2. The composition of claim 1, wherein the erythrocyte-binding moiety is derived from a 10F7 clone, wherein the antibody fragment is affinity matured, and wherein the composition reduces the number of resident lymph node and spleen cells expressing interferon-gamma (IFNγ), as compared to the number of resident lymph node and spleen cells expressing IFNγ when the human is exposed to the antigen alone.

3. The composition of claim 1, wherein the antibody fragment is directed against glycophorin A.

4. The composition of claim 3, wherein the erythrocyte-binding moiety is derived from a 10F7 clone.

5. The composition of claim 3, wherein the antibody fragment is affinity matured.

6. The composition of claim 1, wherein the erythrocyte-binding moiety is fused via a linker, to the N- or C-terminus of the antigen.

7. The composition of claim 1, wherein the administration of the composition ameliorates celiac disease, and wherein the antigen comprises an immunogenic fragment of gliadin.

8. A composition for immunomodulation to achieve antigen-specific tolerance, the composition comprising:

an antigen recombinantly fused or chemically conjugated with an erythrocyte binding moiety;

said antigen being recognizable by an immune system of a subject, the immune system of the subject being able to respond to the antigen with an unwanted immune response;

wherein the antigen is selected from the group consisting of high molecular weight glutenin, low molecular weight glutenin, gliadin, hordein, secalin, avenin, and immunogenic fragments thereof;

wherein said erythrocyte-binding moiety comprises an antibody fragment directed to glycophorin A;

wherein upon administration of the composition, said erythrocyte-binding moiety non-covalently and specifically binds an erythrocyte in situ in blood and presents said antigen to the immune system of the subject;

wherein the erythrocyte-binding moiety does not specifically bind to other blood components, wherein the other blood components comprises blood proteins, albumin, fibronectin, platelets, and white blood cells; and wherein said composition elicits a tolerogenic response upon administration to said subject.

9. The composition of claim 8, wherein the antigen is a food antigen to which a subject develops an unwanted immune response, wherein the food antigen is associated with celiac disease, and wherein the food antigen is selected from the group consisting gliadin or an immunogenic fragment thereof.

10. The composition of claim 9, wherein the erythrocyte-binding moiety is chemically conjugated to the antigen.

11. The composition of claim 9, wherein the erythrocyte-binding moiety is fused to the antigen via recombinant DNA technology.

12. The composition of claim 9, wherein the erythrocyte-binding moiety is fused, optionally via a linker, to the N- or C-terminus of the antigen.

13. The composition of claim 9, wherein the erythrocyte-binding moiety comprises an antibody fragment, wherein the antibody fragment is derived from a 10F7 clone, and wherein the antibody fragment has undergone affinity maturation.

14. The composition of claim 12, wherein the linker is a peptide, a polymer, an aptamer, a nucleic acid, or a particle.

* * * * *

SEQUENCE LISTING

```
<160> NUMBER OF SEQ ID NOS: 134

<210> SEQ ID NO 1
<211> LENGTH: 12
<212> TYPE: PRT
<213> ORGANISM: Artificial Sequence
<220> FEATURE:
<223> OTHER INFORMATION: erythrocyte-binding peptide

<400> SEQUENCE: 1

Trp Met Val Leu Pro Trp Leu Pro Gly Thr Leu Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Control peptide

<400> SEQUENCE: 2

Pro Leu Leu Thr Val Gly Met Asp Leu Trp Pro Trp
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Epitope

<400> SEQUENCE: 3

Ser Ile Ile Asn Phe Glu Lys Leu
1               5

<210> SEQ ID NO 4
<211> LENGTH: 28
<212> TYPE: PRT
<213> ORGANISM: Artificial Sequence
<220> FEATURE:
<223> OTHER INFORMATION: Erythrocyte Binding Peptide

<400> SEQUENCE: 4

Gly Gln Ser Gly Gln Pro Asn Ser Arg Trp Ile Tyr Met Thr Pro Leu
1               5                   10                  15

Ser Pro Gly Ile Tyr Arg Gly Ser Ser Gly Gly Ser
            20                  25

<210> SEQ ID NO 5
<211> LENGTH: 26
<212> TYPE: PRT
<213> ORGANISM: Artificial Sequence
<220> FEATURE:
```

```
<223> OTHER INFORMATION: Erythrocyte Binding Peptide

<400> SEQUENCE: 5

Gly Gln Ser Gly Gln Ser Trp Ser Arg Ala Ile Leu Pro Leu Phe Lys
1               5                  10                  15

Ile Gln Pro Val Gly Ser Ser Gly Gly Ser
            20                  25

<210> SEQ ID NO 6
<211> LENGTH: 26
<212> TYPE: PRT
<213> ORGANISM: Artificial Sequence
<220> FEATURE:
<223> OTHER INFORMATION: Erythrocyte Binding Peptide

<400> SEQUENCE: 6

Gly Gln Ser Gly Gln Tyr Ile Cys Thr Ser Ala Gly Phe Gly Glu Tyr
1               5                  10                  15

Cys Phe Ile Asp Gly Ser Ser Gly Gly Ser
            20                  25

<210> SEQ ID NO 7
<211> LENGTH: 26
<212> TYPE: PRT
<213> ORGANISM: Artificial Sequence
<220> FEATURE:
<223> OTHER INFORMATION: Erythrocyte Binding Peptide

<400> SEQUENCE: 7

Gly Gln Ser Gly Gln Thr Tyr Phe Cys Thr Pro Thr Leu Leu Gly Gln
1               5                  10                  15

Tyr Cys Ser Val Gly Ser Ser Gly Gly Ser
            20                  25

<210> SEQ ID NO 8
<211> LENGTH: 22
<212> TYPE: PRT
<213> ORGANISM: Artificial Sequence
<220> FEATURE:
<223> OTHER INFORMATION: Erythrocyte Binding Peptide

<400> SEQUENCE: 8

Gly Gln Ser Gly His Trp His Cys Gln Gly Pro Phe Ala Asn Trp Val
1               5                  10                  15

Gly Ser Ser Gly Gly Ser
            20

<210> SEQ ID NO 9
<211> LENGTH: 26
<212> TYPE: PRT
<213> ORGANISM: Artificial Sequence
<220> FEATURE:
<223> OTHER INFORMATION: Erythrocyte Binding Peptide

<400> SEQUENCE: 9

Gly Gln Ser Gly Gln Phe Cys Thr Val Ile Tyr Asn Thr Tyr Thr Cys
1               5                  10                  15

Val Pro Ser Ser Gly Ser Ser Gly Gly Ser
            20                  25

<210> SEQ ID NO 10
<211> LENGTH: 26
<212> TYPE: PRT
<213> ORGANISM: Artificial Sequence
```

```
<220> FEATURE:
<223> OTHER INFORMATION: Erythrocyte Binding Peptide

<400> SEQUENCE: 10

Gly Gln Ser Gly Gln Ser Val Trp Tyr Ser Ser Arg Gly Asn Pro Leu
1               5                   10                  15

Arg Cys Thr Gly Gly Ser Ser Gly Gly Ser
            20                  25

<210> SEQ ID NO 11
<211> LENGTH: 17
<212> TYPE: PRT
<213> ORGANISM: Artificial Sequence
<220> FEATURE:
<223> OTHER INFORMATION: Erythrocyte Binding Peptide

<400> SEQUENCE: 11

Pro Asn Ser Arg Trp Ile Tyr Met Thr Pro Leu Ser Pro Gly Ile Tyr
1               5                   10                  15

Arg

<210> SEQ ID NO 12
<211> LENGTH: 15
<212> TYPE: PRT
<213> ORGANISM: Artificial Sequence
<220> FEATURE:
<223> OTHER INFORMATION: Erythrocyte Binding Peptide

<400> SEQUENCE: 12

Ser Trp Ser Arg Ala Ile Leu Pro Leu Phe Lys Ile Gln Pro Val
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Erythrocyte Binding Peptide

<400> SEQUENCE: 13

Tyr Ile Cys Thr Ser Ala Gly Phe Gly Glu Tyr Cys Phe Ile Asp
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Erythrocyte Binding Peptide

<400> SEQUENCE: 14

Thr Tyr Phe Cys Thr Pro Thr Leu Leu Gly Gln Tyr Cys Ser Val
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Erythrocyte Binding Peptide

<400> SEQUENCE: 15

His Trp His Cys Gln Gly Pro Phe Ala Asn Trp Val
1               5                   10
```

```
<210> SEQ ID NO 16
<211> LENGTH: 15
<212> TYPE: PRT
<213> ORGANISM: Artificial Sequence
<220> FEATURE:
<223> OTHER INFORMATION: Erythrocyte Binding Peptide

<400> SEQUENCE: 16

Phe Cys Thr Val Ile Tyr Asn Thr Tyr Thr Cys Val Pro Ser Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Erythrocyte Binding Peptide

<400> SEQUENCE: 17

Ser Val Trp Tyr Ser Ser Arg Gly Asn Pro Leu Arg Cys Thr Gly
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: peptide linker

<400> SEQUENCE: 18

Gly Gly Gly Gly Ser Gly Gly Gly Ser Gly Gly Gly Gly Ser Gly
1               5                   10                  15

Gly Gly Gly Ser
            20

<210> SEQ ID NO 19
<211> LENGTH: 19
<212> TYPE: PRT
<213> ORGANISM: Artificial Sequence
<220> FEATURE:
<223> OTHER INFORMATION: Erythrocyte binding peptide

<400> SEQUENCE: 19

Trp Met Val Leu Pro Trp Leu Pro Gly Thr Leu Asp Gly Gly Ser Gly
1               5                   10                  15

Cys Arg Gly

<210> SEQ ID NO 20
<211> LENGTH: 19
<212> TYPE: PRT
<213> ORGANISM: Artificial Sequence
<220> FEATURE:
<223> OTHER INFORMATION: control peptide

<400> SEQUENCE: 20

Pro Leu Leu Thr Val Gly Met Asp Leu Trp Pro Trp Gly Gly Ser Gly
1               5                   10                  15

Cys Arg Gly

<210> SEQ ID NO 21
<211> LENGTH: 825
<212> TYPE: DNA
<213> ORGANISM: Artificial Sequence
<220> FEATURE:
<223> OTHER INFORMATION: scFv fragment
```

<400> SEQUENCE: 21

```
atggcaagca tgaccggtgg ccaacaaatg ggtacggaag tgcaactgct ggagtctggc    60
ggtggcctgg ttcagccggg tggcagcttg cgcctgagct gtgcggcgtc tggcttcacc   120
tttagcgtca tgaaaatgag ctgggttcgc caggcaccag gtaaaggcct ggagtgggtg   180
tcggcaatca gcggttccgg tggtagcacc tattacgctg acagcgtgaa aggccgtttt   240
acgatttcgc gtgataacag caagaacacg ctgtacttgc aaatgaatag cctgcgtgca   300
gaggacacgg cagtgtacta ttgtgcgaag agcactcacc tgtacttgtt tgattactgg   360
ggtcaaggca ccctggttac cgttagcagc ggcggtggtg gctccggtgg tggtggtagc   420
ggtggcggtg gttctggtgg tggcggctct gaaattgtcc tgactcagag ccctggcacg   480
ctgagcctga gccgggtga gcgcgcgacg ctgagctgcc gtgcgagcca gtccgttagc   540
aacgcgttcc tggcttggta tcaacagaaa ccgggtcagg cccctcgcct gctgatttac   600
ggtgccagct cccgtgcgac gggcatcccg accgtttttt ccggctccgg tagcggcacc   660
gacttcaccc tgaccatcag ccgcctggag ccggaggatt tcgcggtgta ttactgccag   720
caaatgcgtg ccgtccgcc gaccttcggt cagggtacca aggtcgagat taaggctgcg   780
gccgaacaga aactgatcag cgaagaagat ttgaatggtg ccgcg                   825
```

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22

```
tctaagcttg atggcaagca tgaccggtgg                                     30
```

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23

```
tcgctcgagt catcacgcgg caccattcaa atctt                               35
```

<210> SEQ ID NO 24
<211> LENGTH: 55
<212> TYPE: DNA
<213> ORGANISM: Artificial Sequence
<220> FEATURE:
<223> OTHER INFORMATION: primer

<400> SEQUENCE: 24

```
caacgtacca ggcagccacg gaagcaccat ccagctacca ccaccaccgg agcca         55
```

<210> SEQ ID NO 25
<211> LENGTH: 52
<212> TYPE: DNA
<213> ORGANISM: Artificial Sequence
<220> FEATURE:
<223> OTHER INFORMATION: primer

<400> SEQUENCE: 25

```
gtgcttccgt ggctgcctgg tacgttggat ggtggcggtg gttctggtgg tg            52
```

<210> SEQ ID NO 26
<211> LENGTH: 65
<212> TYPE: DNA
<213> ORGANISM: Artificial Sequence
<220> FEATURE:
<223> OTHER INFORMATION: primer

<400> SEQUENCE: 26
acgtaccagg cagccacgga agcaccatcc aaccaccgga gccgctgcta acgtaaccca    60
gggtg                                                               65

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
attgtcctga ctcagagcc                                                19

<210> SEQ ID NO 28
<211> LENGTH: 34
<212> TYPE: DNA
<213> ORGANISM: Artificial Sequence
<220> FEATURE:
<223> OTHER INFORMATION: PCR primer

<400> SEQUENCE: 28
agccggccat ggcggayatc cagctgactc agcc                               34

<210> SEQ ID NO 29
<211> LENGTH: 34
<212> TYPE: DNA
<213> ORGANISM: Artificial Sequence
<220> FEATURE:
<223> OTHER INFORMATION: PCR primer

<400> SEQUENCE: 29
agccggccat ggcggayatt gttctcwccc agtc                               34

<210> SEQ ID NO 30
<211> LENGTH: 34
<212> TYPE: DNA
<213> ORGANISM: Artificial Sequence
<220> FEATURE:
<223> OTHER INFORMATION: PCR primer

<400> SEQUENCE: 30
agccggccat ggcggayatt gtgmtmactc agtc                               34

<210> SEQ ID NO 31
<211> LENGTH: 34
<212> TYPE: DNA
<213> ORGANISM: Artificial Sequence
<220> FEATURE:
<223> OTHER INFORMATION: PCR primer

<400> SEQUENCE: 31
agccggccat ggcggayatt gtgytracac agtc                               34

<210> SEQ ID NO 32
<211> LENGTH: 34
<212> TYPE: DNA
<213> ORGANISM: Artificial Sequence
<220> FEATURE:

<223> OTHER INFORMATION: PCR primer

<400> SEQUENCE: 32
agccggccat ggcggayatt gtratgacmc agtc    34

<210> SEQ ID NO 33
<211> LENGTH: 34
<212> TYPE: DNA
<213> ORGANISM: Artificial Sequence
<220> FEATURE:
<223> OTHER INFORMATION: PCR primer

<400> SEQUENCE: 33
agccggccat ggcggayatt magatramcc agtc    34

<210> SEQ ID NO 34
<211> LENGTH: 34
<212> TYPE: DNA
<213> ORGANISM: artificial sequence
<220> FEATURE:
<223> OTHER INFORMATION: PCR primer

<400> SEQUENCE: 34
agccggccat ggcggayatt cagatgaydc agtc    34

<210> SEQ ID NO 35
<211> LENGTH: 34
<212> TYPE: DNA
<213> ORGANISM: Artificial Sequence
<220> FEATURE:
<223> OTHER INFORMATION: PCR primer

<400> SEQUENCE: 35
agccggccat ggcggayaty cagatgacac agac    34

<210> SEQ ID NO 36
<211> LENGTH: 34
<212> TYPE: DNA
<213> ORGANISM: Artificial Sequence
<220> FEATURE:
<223> OTHER INFORMATION: PCR primer

<400> SEQUENCE: 36
agccggccat ggcggayatt gttctcawcc agtc    34

<210> SEQ ID NO 37
<211> LENGTH: 34
<212> TYPE: DNA
<213> ORGANISM: Artificial Sequence
<220> FEATURE:
<223> OTHER INFORMATION: PCR primer

<400> SEQUENCE: 37
agccggccat ggcggayatt gwgctsaccc aatc    34

<210> SEQ ID NO 38
<211> LENGTH: 34
<212> TYPE: DNA
<213> ORGANISM: Artificial Sequence
<220> FEATURE:
<223> OTHER INFORMATION: PCR primer

<400> SEQUENCE: 38
agccggccat ggcggayatt stratgaccc artc    34

```
<210> SEQ ID NO 39
<211> LENGTH: 34
<212> TYPE: DNA
<213> ORGANISM: Artificial Sequence
<220> FEATURE:
<223> OTHER INFORMATION: PCR primer

<400> SEQUENCE: 39
agccggccat ggcggayrtt ktgatgaccc arac                              34

<210> SEQ ID NO 40
<211> LENGTH: 34
<212> TYPE: DNA
<213> ORGANISM: Artificial Sequence
<220> FEATURE:
<223> OTHER INFORMATION: PCR primer

<400> SEQUENCE: 40
agccggccat ggcggayatt gtgatgacbc agkc                              34

<210> SEQ ID NO 41
<211> LENGTH: 34
<212> TYPE: DNA
<213> ORGANISM: Artificial Sequence
<220> FEATURE:
<223> OTHER INFORMATION: PCR primer

<400> SEQUENCE: 41
agccggccat ggcggayatt gtgataacyc agga                              34

<210> SEQ ID NO 42
<211> LENGTH: 34
<212> TYPE: DNA
<213> ORGANISM: Artificial Sequence
<220> FEATURE:
<223> OTHER INFORMATION: PCR primer

<400> SEQUENCE: 42
agccggccat ggcggayatt gtgatgaccc agwt                              34

<210> SEQ ID NO 43
<211> LENGTH: 34
<212> TYPE: DNA
<213> ORGANISM: Artificial Sequence
<220> FEATURE:
<223> OTHER INFORMATION: PCR primer

<400> SEQUENCE: 43
agccggccat ggcggayatt gtgatgacac aacc                              34

<210> SEQ ID NO 44
<211> LENGTH: 34
<212> TYPE: DNA
<213> ORGANISM: Artificial Sequence
<220> FEATURE:
<223> OTHER INFORMATION: PCR primer

<400> SEQUENCE: 44
agccggccat ggcggayatt ttgctgactc agtc                              34

<210> SEQ ID NO 45
<211> LENGTH: 37
<212> TYPE: DNA
<213> ORGANISM: Artificial Sequence
<220> FEATURE:
<223> OTHER INFORMATION: PCR primer
```

<400> SEQUENCE: 45
agccggccat ggcggargct gttgtgactc aggaatc                              37

<210> SEQ ID NO 46
<211> LENGTH: 37
<212> TYPE: DNA
<213> ORGANISM: Artificial Sequence
<220> FEATURE:
<223> OTHER INFORMATION: PCR primer

<400> SEQUENCE: 46
gatggtgcgg ccgcagtacg tttgatttcc agcttgg                              37

<210> SEQ ID NO 47
<211> LENGTH: 37
<212> TYPE: DNA
<213> ORGANISM: Artificial Sequence
<220> FEATURE:
<223> OTHER INFORMATION: PCR primer

<400> SEQUENCE: 47
gatggtgcgg ccgcagtacg ttttatttcc agcttgg                              37

<210> SEQ ID NO 48
<211> LENGTH: 37
<212> TYPE: DNA
<213> ORGANISM: Artificial Sequence
<220> FEATURE:
<223> OTHER INFORMATION: PCR primer

<400> SEQUENCE: 48
gatggtgcgg ccgcagtacg ttttatttcc aactttg                              37

<210> SEQ ID NO 49
<211> LENGTH: 37
<212> TYPE: DNA
<213> ORGANISM: Artificial Sequence
<220> FEATURE:
<223> OTHER INFORMATION: PCR primer

<400> SEQUENCE: 49
gatggtgcgg ccgcagtacg tttcagctcc agcttgg                              37

<210> SEQ ID NO 50
<211> LENGTH: 37
<212> TYPE: DNA
<213> ORGANISM: Artificial Sequence
<220> FEATURE:
<223> OTHER INFORMATION: PCR primer

<400> SEQUENCE: 50
gatggtgcgg ccgcagtacc taggacagtc agtttgg                              37

<210> SEQ ID NO 51
<211> LENGTH: 37
<212> TYPE: DNA
<213> ORGANISM: Artificial Sequence
<220> FEATURE:
<223> OTHER INFORMATION: PCR primer

<400> SEQUENCE: 51
gatggtgcgg ccgcagtacc taggacagtg accttgg                              37

<210> SEQ ID NO 52
<211> LENGTH: 51

<212> TYPE: DNA
<213> ORGANISM: Artificial Sequence
<220> FEATURE:
<223> OTHER INFORMATION: PCR primer

<400> SEQUENCE: 52
gttattgcta gcggctcagc cggcaatggc ggakgtrmag cttcaggagt c    51

<210> SEQ ID NO 53
<211> LENGTH: 51
<212> TYPE: DNA
<213> ORGANISM: Artificial Sequence
<220> FEATURE:
<223> OTHER INFORMATION: PCR primer

<400> SEQUENCE: 53
gttattgcta gcggctcagc cggcaatggc ggaggtbcag ctbcagcagt c    51

<210> SEQ ID NO 54
<211> LENGTH: 51
<212> TYPE: DNA
<213> ORGANISM: Artificial Sequence
<220> FEATURE:
<223> OTHER INFORMATION: PCR primer

<400> SEQUENCE: 54
gttattgcta gcggctcagc cggcaatggc gcaggtgcag ctgaagsast c    51

<210> SEQ ID NO 55
<211> LENGTH: 51
<212> TYPE: DNA
<213> ORGANISM: Artificial Sequence
<220> FEATURE:
<223> OTHER INFORMATION: PCR primer

<400> SEQUENCE: 55
gttattgcta gcggctcagc cggcaatggc ggaggtccar ctgcaacart c    51

<210> SEQ ID NO 56
<211> LENGTH: 51
<212> TYPE: DNA
<213> ORGANISM: Artificial Sequence
<220> FEATURE:
<223> OTHER INFORMATION: PCR primer

<400> SEQUENCE: 56
gttattgcta gcggctcagc cggcaatggc gcaggtycag ctbcagcart c    51

<210> SEQ ID NO 57
<211> LENGTH: 51
<212> TYPE: DNA
<213> ORGANISM: Artificial Sequence
<220> FEATURE:
<223> OTHER INFORMATION: PCR primer

<400> SEQUENCE: 57
gttattgcta gcggctcagc cggcaatggc gcaggtycag ctbcagcart c    51

<210> SEQ ID NO 58
<211> LENGTH: 51
<212> TYPE: DNA
<213> ORGANISM: Artificial Sequence
<220> FEATURE:
<223> OTHER INFORMATION: PCR primer

<400> SEQUENCE: 58

```
gttattgcta gcggctcagc cggcaatggc gcaggtycar ctgcagcagt c          51

<210> SEQ ID NO 59
<211> LENGTH: 51
<212> TYPE: DNA
<213> ORGANISM: Artificial Sequence
<220> FEATURE:
<223> OTHER INFORMATION: PCR primer

<400> SEQUENCE: 59
gttattgcta gcggctcagc cggcaatggc gcaggtccac gtgaagcagt c          51

<210> SEQ ID NO 60
<211> LENGTH: 51
<212> TYPE: DNA
<213> ORGANISM: Artificial Sequence
<220> FEATURE:
<223> OTHER INFORMATION: PCR primer

<400> SEQUENCE: 60
gttattgcta gcggctcagc cggcaatggc ggaggtgaas stggtggaat c          51

<210> SEQ ID NO 61
<211> LENGTH: 51
<212> TYPE: DNA
<213> ORGANISM: Artificial Sequence
<220> FEATURE:
<223> OTHER INFORMATION: PCR primer

<400> SEQUENCE: 61
gttattgcta gcggctcagc cggcaatggc ggavgtgawg ytggtggagt c          51

<210> SEQ ID NO 62
<211> LENGTH: 51
<212> TYPE: DNA
<213> ORGANISM: Artificial Sequence
<220> FEATURE:
<223> OTHER INFORMATION: PCR primer

<400> SEQUENCE: 62
gttattgcta gcggctcagc cggcaatggc ggaggtgcag skggtggagt c          51

<210> SEQ ID NO 63
<211> LENGTH: 51
<212> TYPE: DNA
<213> ORGANISM: Artificial Sequence
<220> FEATURE:
<223> OTHER INFORMATION: PCR primer

<400> SEQUENCE: 63
gttattgcta gcggctcagc cggcaatggc ggakgtgcam ctggtggagt c          51

<210> SEQ ID NO 64
<211> LENGTH: 51
<212> TYPE: DNA
<213> ORGANISM: Artificial Sequence
<220> FEATURE:
<223> OTHER INFORMATION: PCR primer

<400> SEQUENCE: 64
gttattgcta gcggctcagc cggcaatggc ggaggtgaag ctgatggart c          51

<210> SEQ ID NO 65
<211> LENGTH: 51
<212> TYPE: DNA
<213> ORGANISM: Artificial Sequence
```

<220> FEATURE:
<223> OTHER INFORMATION: PCR primer

<400> SEQUENCE: 65
gttattgcta gcggctcagc cggcaatggc ggaggtgcar cttgttgagt c        51

<210> SEQ ID NO 66
<211> LENGTH: 51
<212> TYPE: DNA
<213> ORGANISM: Artificial Sequence
<220> FEATURE:
<223> OTHER INFORMATION: PCR primer

<400> SEQUENCE: 66
gttattgcta gcggctcagc cggcaatggc ggargtraag cttctcgagt c        51

<210> SEQ ID NO 67
<211> LENGTH: 51
<212> TYPE: DNA
<213> ORGANISM: Artificial Sequence
<220> FEATURE:
<223> OTHER INFORMATION: PCR primer

<400> SEQUENCE: 67
gttattgcta gcggctcagc cggcaatggc ggaagtgaar sttgaggagt c        51

<210> SEQ ID NO 68
<211> LENGTH: 53
<212> TYPE: DNA
<213> ORGANISM: Artificial Sequence
<220> FEATURE:
<223> OTHER INFORMATION: PCR primer

<400> SEQUENCE: 68
gttattgcta gcggctcagc cggcaatggc gcaggttact ctraaagwgt stg      53

<210> SEQ ID NO 69
<211> LENGTH: 51
<212> TYPE: DNA
<213> ORGANISM: Artificial Sequence
<220> FEATURE:
<223> OTHER INFORMATION: PCR primer

<400> SEQUENCE: 69
gttattgcta gcggctcagc cggcaatggc gcaggtccaa ctvcagcarc c        51

<210> SEQ ID NO 70
<211> LENGTH: 51
<212> TYPE: DNA
<213> ORGANISM: Artificial Sequence
<220> FEATURE:
<223> OTHER INFORMATION: PCR primer

<400> SEQUENCE: 70
gttattgcta gcggctcagc cggcaatggc ggatgtgaac ttggaagtgt c        51

<210> SEQ ID NO 71
<211> LENGTH: 51
<212> TYPE: DNA
<213> ORGANISM: Artificial Sequence
<220> FEATURE:
<223> OTHER INFORMATION: PCR primer

<400> SEQUENCE: 71
gttattgcta gcggctcagc cggcaatggc ggaggtgaag gtcatcgagt c        51

<210> SEQ ID NO 72
<211> LENGTH: 35
<212> TYPE: DNA
<213> ORGANISM: Artificial Sequence
<220> FEATURE:
<223> OTHER INFORMATION: PCR primer

<400> SEQUENCE: 72
cccttgaagc ttgctgagga aacggtgacc gtggt                              35

<210> SEQ ID NO 73
<211> LENGTH: 35
<212> TYPE: DNA
<213> ORGANISM: Artificial Sequence
<220> FEATURE:
<223> OTHER INFORMATION: PCR primer

<400> SEQUENCE: 73
cccttgaagc ttgctgagga gactgtgaga gtggt                              35

<210> SEQ ID NO 74
<211> LENGTH: 35
<212> TYPE: DNA
<213> ORGANISM: Artificial Sequence
<220> FEATURE:
<223> OTHER INFORMATION: PCR primer

<400> SEQUENCE: 74
cccttgaagc ttgctgcaga gacagtgacc agagt                              35

<210> SEQ ID NO 75
<211> LENGTH: 35
<212> TYPE: DNA
<213> ORGANISM: Artificial Sequence
<220> FEATURE:
<223> OTHER INFORMATION: PCR primer

<400> SEQUENCE: 75
cccttgaagc ttgctgagga gacggtgact gaggt                              35

<210> SEQ ID NO 76
<211> LENGTH: 747
<212> TYPE: DNA
<213> ORGANISM: Artificial Sequence
<220> FEATURE:
<223> OTHER INFORMATION: Ter 119 scFv

<400> SEQUENCE: 76
gaggtgaagc tgcaggagtc tggaggaggc ttggtgcaac ctgggggtc tctgaaactc      60 tcctgtgtag cctcaggatt cactttcagg gaccactgga tgaattgggt ccggcaggct     120
cccggaaaga ccatggagtg gattggagat attagacctg atggcagtga cacaaactat     180
gcaccatctg tgaggaatag attcacaatc tccagagaca atgccaggag catcctgtac     240
ctgcagatga gcaatatgag atctgattac acagccactt attactgtgt tagagactca     300
cctacccggg ctgggcttat ggatgcctgg ggtcaaggaa cctcagtcac tgtctcctca     360
gccggtggtg gtggttctgg tggtggtggt tctggcggcg cggctccgg tggtggtgga     420 tccgacattc agatgacgca gtctccttca gtcctgtctg catctgtggg agacagagtc    480
actctcaact gcaaagcaag tcagaatatt aacaagtact taaactggta tcagcaaaag    540
cttggagaag ctcccaaagt cctgatatat aatacaaaca atttgcaaac gggcatccca    600
tcaaggttca gtggcagtgg atctggtaca gatttcacac tcaccatcag tagcctgcag    660

```
cctgaagatt tgccacata tttctgcttt cagcattata cttggcccac gtttggaggt      720
gggaccaagc tggaaatcaa acgtact                                         747

<210> SEQ ID NO 77
<211> LENGTH: 45
<212> TYPE: DNA
<213> ORGANISM: Artificial Sequence
<220> FEATURE:
<223> OTHER INFORMATION: PCR primer

<400> SEQUENCE: 77
actcgcggcc cagccggcca tggcggaggt gaagctgcag gagtc                     45

<210> SEQ ID NO 78
<211> LENGTH: 65
<212> TYPE: DNA
<213> ORGANISM: Artificial Sequence
<220> FEATURE:
<223> OTHER INFORMATION: PCR primer

<400> SEQUENCE: 78
ggagccgccg ccgccagaac caccaccacc agaaccacca ccaccggctg aggagacagt     60
gactg                                                                 65

<210> SEQ ID NO 79
<211> LENGTH: 50
<212> TYPE: DNA
<213> ORGANISM: Artificial Sequence
<220> FEATURE:
<223> OTHER INFORMATION: PCR primer

<400> SEQUENCE: 79
ggcggcggcg gctccggtgg tggtggatcc gacattcaga tgacgcagtc                50

<210> SEQ ID NO 80
<211> LENGTH: 41
<212> TYPE: DNA
<213> ORGANISM: Artificial Sequence
<220> FEATURE:
<223> OTHER INFORMATION: PCR primer

<400> SEQUENCE: 80
gactactagg cccccgaggc cagtacgttt gatttccagc t                         41

<210> SEQ ID NO 81
<211> LENGTH: 793
<212> TYPE: DNA
<213> ORGANISM: Artificial Sequence
<220> FEATURE:
<223> OTHER INFORMATION: 10F7 scFv

<400> SEQUENCE: 81
gttattactc gcggcccagc cggccatggc ggcgcaggtg aaactgcagc agagcggcgc     60
ggaactggtg aaaccgggcg cgagcgtgaa actgagctgc aaagcgagcg gctataccgt    120
taacagctat tttatgcatt ggatgaaaca gcgcccggtg cagggcctgg aatggattgg    180
catgattcgc ccgaacggcg gcaccaccga ttataacgaa aaatttaaaa acaaagcgac    240
cctgaccgtg gataaaagca gcaacaccgc gtatatgcag ctgaacagcc tgaccagcgg    300
cgatagcgcg gtgtattatt gcgcgcgctg ggaaggcagc tattatgcgc tggattattg    360
gggccagggc accaccgtga ccgtgagcag cggcggcggc ggcagcggcg gcggcggcag    420
```

```
cggcggcggc ggcagcgata ttgaactgac ccagagcccg gcgattatga gcgcgaccct      480
gggcgaaaaa gtgaccatga cctgccgcgc gagcagcaac gtgaaatata tgtattggta      540
tcagcagaaa agcggcgcga gcccgaaact gtggatttat taccagcaa acctggcgag       600 cggcgtgccg ggccgcttta gcggcagcgg cagcggcacc agctatagcc tgaccattag      660
cagcgtggaa gcggaagatg cggcgaccta ttattgccag cagtttacca gcagcccgta     720
tacctttggc ggcggcacca aactggaaat aaacgcgcg gcggcggcct cgggggccga      780
gggcggcggt tct                                                         793
```

<210> SEQ ID NO 82
<211> LENGTH: 15
<212> TYPE: PRT
<213> ORGANISM: Artificial Sequence
<220> FEATURE:
<223> OTHER INFORMATION: epitope
<400> SEQUENCE: 82

```
Ser Gly Leu Glu Gln Leu Glu Ser Ile Ile Asn Phe Glu Lys Leu
1               5                   10                  15
```

<210> SEQ ID NO 83
<211> LENGTH: 819
<212> TYPE: DNA
<213> ORGANISM: Artificial Sequence
<220> FEATURE:
<223> OTHER INFORMATION: fusion protein
<400> SEQUENCE: 83

```
gaggtgaagc tgcaggagtc tggaggaggc ttggtgcaac ctggggggtc tctgaaactc       60
tcctgtgtag cctcaggatt cactttcagg gaccactgga tgaattgggt ccggcaggct     120
cccggaaaga ccatggagtg gattgagat attagacctg atggcagtga cacaaactat      180
gcaccatctg tgaggaatag attcacaatc tccagagaca atgccaggag catcctgtac     240
ctgcagatga gcaatatgag atctgattac acagccactt attactgtgt tagagactca     300
cctacccggg ctgggcttat ggatgcctgg ggtcaaggaa cctcagtcac tgtctcctca     360
gccggtggtg gtggttctgg tggtggtggt tctggcggcg cgggctccgg tggtggtgga     420
tccgacattc agatgacgca gtctccttca gtcctgtctg catctgtggg agacagagtc     480
actctcaact gcaaagcaag tcagaatatt aacaagtact aaactggta tcagcaaaag     540 cttggagaag ctcccaaagt cctgatatat aatacaaaca atttgcaaac gggcatccca     600
tcaaggttca gtggcagtgg atctggtaca gatttcacac tcaccatcag tagcctgcag     660
cctgaagatt ttgccacata tttctgcttt cagcattata cttggcccac gtttggaggt     720
gggaccaagc tggaaatcaa acgtactcat catcaccatc atcacggtgg cggttctggc     780
ctggagcagc tggagtctat tattaatttc gaaaaactg                            819
```

<210> SEQ ID NO 84
<211> LENGTH: 10
<212> TYPE: PRT
<213> ORGANISM: Artificial Sequence
<220> FEATURE:
<223> OTHER INFORMATION: antibody portion
<400> SEQUENCE: 84

```
Tyr Val Arg Pro Leu Trp Val Arg Met Glu
1               5                   10
```

<210> SEQ ID NO 85
<211> LENGTH: 804
<212> TYPE: DNA
<213> ORGANISM: Artificial Sequence
<220> FEATURE:
<223> OTHER INFORMATION: fusion protein

<400> SEQUENCE: 85

```
gaggtgaagc tgcaggagtc aggaggaggc ttggtgcaac ctgggggtc tctgaaactc      60
tcctgtgtag cctcaggatt cactttcagg gaccactgga tgaattgggt ccggcaggct    120
cccggaaaga ccatggagtg gattgggat attagacctg atggcagtga cacaaactat    180
gcaccatctg tgaggaatag attcacaatc tccagagaca ataccaggag catcctgtac    240
ctgcagatgg gcaatatgag atctgattac acagccactt attactgtgt tagagactca    300
cctacccggg ctgggcttat ggatgcctgg ggtcaaggaa cctcagtcac tgtctcctca    360
gccggtggtg gtggttctgg tggtggtggt tctggcggcg gcggctccgg tggtggtgga    420
tccgacattc agatgacgca gtctccttca gtcctgtctg catctgtggg agacagagtc    480
actctcaact gcaaagcaag tcagaatatt aacaagtact aaaccggta tcagcaaaag    540
cttggagaag ctcccaaagt cctggtatat aatacaaaca atttgcaaac gggcatccca    600
tcaaggttca gtggcagtgg atctggcaca gatttcacac tcaccatcag tagcctgcag    660
cctgaagatt ttgccacata tttctgcttt cagcattata cttggcccac gtttggaggt    720
gtgaccaagc tggaaatcaa acgtactcat catcaccatc atcacggtgg cggttatgtc    780
agacctctgt gggtcagaat ggaa                                            804
```

<210> SEQ ID NO 86
<211> LENGTH: 1026
<212> TYPE: DNA
<213> ORGANISM: Artificial Sequence
<220> FEATURE:
<223> OTHER INFORMATION: fusion protein

<400> SEQUENCE: 86

```
gaggtgaagc tgcaggagtc aggaggaggc ttggtgcaac ctgggggtc tctgaaactc      60
tcctgtgtag cctcaggatt cactttcagg gaccactgga tgaattgggt ccggcaggct    120
cccggaaaga ccatggagtg gattggagat attagacctg atggcagtga cacaaactat    180
gcaccatctg tgaggaatag attcacaatc tccagagaca atgccaggag catcctgtac    240
ctgcagatga gcaatatgag atctgattac acagccactt attactgtgt tagagactca    300
cctacccggg ctgggcttat ggatgcctgg ggtcaaggaa cctcagtcac tgtctcctca    360
gccggtggtg gtggttctgg tggtggtggt tctggcggcg gcggctccgg tggtggtgga    420
tccgacattc agatgacgca gtctccttca gtcctgtctg catctgtggg agacagagtc    480
actctcaact gcaaagcaag tcagaatatt aacaagtact aaactggta tcagcaaaag    540
cttggagaag ctcccaaagt cctgatatat aatacaaaca atttgcaaac gggcatccca    600
tcaaggttca gtggcagtgg atctggtaca gatttcacac tcaccatcag tagcctgcag    660
cctgaagatt ttgccacata tttctgctct cagcattata cttggcccac gtttgatggt    720
gggaccaagc tggaaatcaa acgtactcat catcaccatc atcacggtgg cggttttgtg    780
aaacagcatc tgtgcggtcc gcatctggtg aagcgctgt atctggtgtg cggcgaacgt    840
ggctttttt tatacccgaa aagccgtcgt gaagtgaag atccgcaggt ggaacagctg    900
gaactgggcg gcagcccggg tgatctgcag accctggccc tggaagtggc gcgtcagaaa    960
```

```
cgtggcattg tggatcagtg ctgcaccagc atttgcagcc tgtatcagct ggaaaactat      1020
tacaac                                                                1026
```

<210> SEQ ID NO 87
<211> LENGTH: 17
<212> TYPE: PRT
<213> ORGANISM: Artificial Sequence
<220> FEATURE:
<223> OTHER INFORMATION: scFv

<400> SEQUENCE: 87

Ile Ser Gln Ala Val His Ala Ala His Ala Glu Ile Asn Glu Ala Gly
1               5                   10                  15

Arg

<210> SEQ ID NO 88
<211> LENGTH: 34
<212> TYPE: DNA
<213> ORGANISM: Artificial Sequence
<220> FEATURE:
<223> OTHER INFORMATION: Primer

<400> SEQUENCE: 88
agccggccat ggcggayatc cagctgactc agcc                                   34

<210> SEQ ID NO 89
<211> LENGTH: 34
<212> TYPE: DNA
<213> ORGANISM: Artificial Sequence
<220> FEATURE:
<223> OTHER INFORMATION: Primer

<400> SEQUENCE: 89
agccggccat ggcggayatt gttctcwccc agtc                                   34

<210> SEQ ID NO 90
<211> LENGTH: 34
<212> TYPE: DNA
<213> ORGANISM: Artificial Sequence
<220> FEATURE:
<223> OTHER INFORMATION: Primer

<400> SEQUENCE: 90
agccggccat ggcggayatt gtgmtmactc agtc                                   34

<210> SEQ ID NO 91
<211> LENGTH: 34
<212> TYPE: DNA
<213> ORGANISM: Artificial Sequence
<220> FEATURE:
<223> OTHER INFORMATION: Primer

<400> SEQUENCE: 91
agccggccat ggcggayatt gtgytracac agtc                                   34

<210> SEQ ID NO 92
<211> LENGTH: 34
<212> TYPE: DNA
<213> ORGANISM: Artificial Sequence
<220> FEATURE:
<223> OTHER INFORMATION: Primer

<400> SEQUENCE: 92
agccggccat ggcggayatt gtratgacmc agtc                                   34

<210> SEQ ID NO 93
<211> LENGTH: 34
<212> TYPE: DNA
<213> ORGANISM: Artificial Sequence
<220> FEATURE:
<223> OTHER INFORMATION: Primer

<400> SEQUENCE: 93
agccggccat ggcggayatt magatramcc agtc                                    34

<210> SEQ ID NO 94
<211> LENGTH: 34
<212> TYPE: DNA
<213> ORGANISM: Artificial Sequence
<220> FEATURE:
<223> OTHER INFORMATION: Primer

<400> SEQUENCE: 94
agccggccat ggcggayatt cagatgaydc agtc                                    34

<210> SEQ ID NO 95
<211> LENGTH: 34
<212> TYPE: DNA
<213> ORGANISM: Artificial Sequence
<220> FEATURE:
<223> OTHER INFORMATION: Primer

<400> SEQUENCE: 95
agccggccat ggcggayaty cagatgacac agac                                    34

<210> SEQ ID NO 96
<211> LENGTH: 34
<212> TYPE: DNA
<213> ORGANISM: Artificial Sequence
<220> FEATURE:
<223> OTHER INFORMATION: Primer

<400> SEQUENCE: 96
agccggccat ggcggayatt gttctcawcc agtc                                    34

<210> SEQ ID NO 97
<211> LENGTH: 34
<212> TYPE: DNA
<213> ORGANISM: Artificial Sequence
<220> FEATURE:
<223> OTHER INFORMATION: Primer

<400> SEQUENCE: 97
agccggccat ggcggayatt gwgctsaccc aatc                                    34

<210> SEQ ID NO 98
<211> LENGTH: 34
<212> TYPE: DNA
<213> ORGANISM: Artificial Sequence
<220> FEATURE:
<223> OTHER INFORMATION: Primer

<400> SEQUENCE: 98
agccggccat ggcggayatt stratgaccc artc                                    34

<210> SEQ ID NO 99
<211> LENGTH: 34
<212> TYPE: DNA
<213> ORGANISM: Artificial Sequence
<220> FEATURE:
<223> OTHER INFORMATION: Primer

```
<400> SEQUENCE: 99
agccggccat ggcggayrtt ktgatgaccc arac                                34

<210> SEQ ID NO 100
<211> LENGTH: 34
<212> TYPE: DNA
<213> ORGANISM: Artificial Sequence
<220> FEATURE:
<223> OTHER INFORMATION: Primer

<400> SEQUENCE: 100
agccggccat ggcggayatt gtgatgacbc agkc                                34

<210> SEQ ID NO 101
<211> LENGTH: 34
<212> TYPE: DNA
<213> ORGANISM: Artificial Sequence
<220> FEATURE:
<223> OTHER INFORMATION: Primer

<400> SEQUENCE: 101
agccggccat ggcggayatt gtgataacyc agga                                34

<210> SEQ ID NO 102
<211> LENGTH: 34
<212> TYPE: DNA
<213> ORGANISM: Artificial Sequence
<220> FEATURE:
<223> OTHER INFORMATION: Primer

<400> SEQUENCE: 102
agccggccat ggcggayatt gtgatgaccc agwt                                34

<210> SEQ ID NO 103
<211> LENGTH: 34
<212> TYPE: DNA
<213> ORGANISM: Artificial Sequence
<220> FEATURE:
<223> OTHER INFORMATION: Primer

<400> SEQUENCE: 103
agccggccat ggcggayatt gtgatgacac aacc                                34

<210> SEQ ID NO 104
<211> LENGTH: 34
<212> TYPE: DNA
<213> ORGANISM: Artificial Sequence
<220> FEATURE:
<223> OTHER INFORMATION: Primer

<400> SEQUENCE: 104
agccggccat ggcggayatt ttgctgactc agtc                                34

<210> SEQ ID NO 105
<211> LENGTH: 37
<212> TYPE: DNA
<213> ORGANISM: Artificial Sequence
<220> FEATURE:
<223> OTHER INFORMATION: Primer

<400> SEQUENCE: 105
agccggccat ggcggargct gttgtgactc aggaatc                             37

<210> SEQ ID NO 106
```

```
<211> LENGTH: 37
<212> TYPE: DNA
<213> ORGANISM: Artificial Sequence
<220> FEATURE:
<223> OTHER INFORMATION: Primer

<400> SEQUENCE: 106
gatggtgcgg ccgcagtacg tttgatttcc agcttgg                              37

<210> SEQ ID NO 107
<211> LENGTH: 37
<212> TYPE: DNA
<213> ORGANISM: Artificial Sequence
<220> FEATURE:
<223> OTHER INFORMATION: Primer

<400> SEQUENCE: 107
gatggtgcgg ccgcagtacg ttttatttcc agcttgg                              37

<210> SEQ ID NO 108
<211> LENGTH: 37
<212> TYPE: DNA
<213> ORGANISM: Artificial Sequence
<220> FEATURE:
<223> OTHER INFORMATION: Primer

<400> SEQUENCE: 108
gatggtgcgg ccgcagtacg ttttatttcc aactttg                              37

<210> SEQ ID NO 109
<211> LENGTH: 37
<212> TYPE: DNA
<213> ORGANISM: Artificial Sequence
<220> FEATURE:
<223> OTHER INFORMATION: Primer

<400> SEQUENCE: 109
gatggtgcgg ccgcagtacg tttcagctcc agcttgg                              37

<210> SEQ ID NO 110
<211> LENGTH: 37
<212> TYPE: DNA
<213> ORGANISM: Artificial Sequence
<220> FEATURE:
<223> OTHER INFORMATION: Primer

<400> SEQUENCE: 110
gatggtgcgg ccgcagtacc taggacagtc agtttgg                              37

<210> SEQ ID NO 111
<211> LENGTH: 37
<212> TYPE: DNA
<213> ORGANISM: Artificial Sequence
<220> FEATURE:
<223> OTHER INFORMATION: Primer

<400> SEQUENCE: 111
gatggtgcgg ccgcagtacc taggacagtg accttgg                              37

<210> SEQ ID NO 112
<211> LENGTH: 51
<212> TYPE: DNA
<213> ORGANISM: Artificial Sequence
<220> FEATURE:
<223> OTHER INFORMATION: Primer

<400> SEQUENCE: 112
```
gttattgcta gcggctcagc cggcaatggc ggaggtbcag ctbcagcagt c         51

<210> SEQ ID NO 113
<211> LENGTH: 51
<212> TYPE: DNA
<213> ORGANISM: Artificial Sequence
<220> FEATURE:
<223> OTHER INFORMATION: Primer

<400> SEQUENCE: 113
gttattgcta gcggctcagc cggcaatggc gcaggtgcag ctgaagsast c         51

<210> SEQ ID NO 114
<211> LENGTH: 51
<212> TYPE: DNA
<213> ORGANISM: Artificial Sequence
<220> FEATURE:
<223> OTHER INFORMATION: Primer

<400> SEQUENCE: 114
gttattgcta gcggctcagc cggcaatggc ggaggtccar ctgcaacart c         51

<210> SEQ ID NO 115
<211> LENGTH: 51
<212> TYPE: DNA
<213> ORGANISM: Artificial Sequence
<220> FEATURE:
<223> OTHER INFORMATION: Primer

<400> SEQUENCE: 115
gttattgcta gcggctcagc cggcaatggc gcaggtycag ctbcagcart c         51

<210> SEQ ID NO 116
<211> LENGTH: 51
<212> TYPE: DNA
<213> ORGANISM: Artificial Sequence
<220> FEATURE:
<223> OTHER INFORMATION: Primer

<400> SEQUENCE: 116
gttattgcta gcggctcagc cggcaatggc gcaggtycar ctgcagcagt c         51

<210> SEQ ID NO 117
<211> LENGTH: 51
<212> TYPE: DNA
<213> ORGANISM: Artificial Sequence
<220> FEATURE:
<223> OTHER INFORMATION: Primer

<400> SEQUENCE: 117
gttattgcta gcggctcagc cggcaatggc gcaggtccac gtgaagcagt c         51

<210> SEQ ID NO 118
<211> LENGTH: 51
<212> TYPE: DNA
<213> ORGANISM: Artificial Sequence
<220> FEATURE:
<223> OTHER INFORMATION: Primer

<400> SEQUENCE: 118
gttattgcta gcggctcagc cggcaatggc ggaggtgaas stggtggaat c         51

<210> SEQ ID NO 119
<211> LENGTH: 51
<212> TYPE: DNA

```
<213> ORGANISM: Artificial Sequence
<220> FEATURE:
<223> OTHER INFORMATION: Primer

<400> SEQUENCE: 119
gttattgcta gcggctcagc cggcaatggc ggavgtgawg ytggtggagt c        51

<210> SEQ ID NO 120
<211> LENGTH: 51
<212> TYPE: DNA
<213> ORGANISM: Artificial Sequence
<220> FEATURE:
<223> OTHER INFORMATION: Primer

<400> SEQUENCE: 120
gttattgcta gcggctcagc cggcaatggc ggaggtgcag skggtggagt c        51

<210> SEQ ID NO 121
<211> LENGTH: 51
<212> TYPE: DNA
<213> ORGANISM: Artificial Sequence
<220> FEATURE:
<223> OTHER INFORMATION: Primer

<400> SEQUENCE: 121
gttattgcta gcggctcagc cggcaatggc ggakgtgcam ctggtggagt c        51

<210> SEQ ID NO 122
<211> LENGTH: 51
<212> TYPE: DNA
<213> ORGANISM: Artificial Sequence
<220> FEATURE:
<223> OTHER INFORMATION: Primer

<400> SEQUENCE: 122
gttattgcta gcggctcagc cggcaatggc ggaggtgaag ctgatggart c        51

<210> SEQ ID NO 123
<211> LENGTH: 51
<212> TYPE: DNA
<213> ORGANISM: Artificial Sequence
<220> FEATURE:
<223> OTHER INFORMATION: Primer

<400> SEQUENCE: 123
gttattgcta gcggctcagc cggcaatggc ggaggtgcar cttgttgagt c        51

<210> SEQ ID NO 124
<211> LENGTH: 51
<212> TYPE: DNA
<213> ORGANISM: Artificial Sequence
<220> FEATURE:
<223> OTHER INFORMATION: Primer

<400> SEQUENCE: 124
gttattgcta gcggctcagc cggcaatggc ggargtraag cttctcgagt c        51

<210> SEQ ID NO 125
<211> LENGTH: 51
<212> TYPE: DNA
<213> ORGANISM: Artificial Sequence
<220> FEATURE:
<223> OTHER INFORMATION: Primer

<400> SEQUENCE: 125
gttattgcta gcggctcagc cggcaatggc ggaagtgaar sttgaggagt c        51
```

```
<210> SEQ ID NO 126
<211> LENGTH: 53
<212> TYPE: DNA
<213> ORGANISM: Artificial Sequence
<220> FEATURE:
<223> OTHER INFORMATION: Primer

<400> SEQUENCE: 126
gttattgcta gcggctcagc cggcaatggc gcaggttact ctraaagwgt stg        53

<210> SEQ ID NO 127
<211> LENGTH: 51
<212> TYPE: DNA
<213> ORGANISM: Artificial Sequence
<220> FEATURE:
<223> OTHER INFORMATION: Primer

<400> SEQUENCE: 127
gttattgcta gcggctcagc cggcaatggc ggatgtgaac ttggaagtgt c          51

<210> SEQ ID NO 128
<211> LENGTH: 51
<212> TYPE: DNA
<213> ORGANISM: Artificial Sequence
<220> FEATURE:
<223> OTHER INFORMATION: Primer

<400> SEQUENCE: 128
gttattgcta gcggctcagc cggcaatggc ggatgtgaac ttggaagtgt c          51

<210> SEQ ID NO 129
<211> LENGTH: 51
<212> TYPE: DNA
<213> ORGANISM: Artificial Sequence
<220> FEATURE:
<223> OTHER INFORMATION: rimer

<400> SEQUENCE: 129
gttattgcta gcggctcagc cggcaatggc ggaggtgaag gtcatcgagt c          51

<210> SEQ ID NO 130
<211> LENGTH: 35
<212> TYPE: DNA
<213> ORGANISM: Artificial Sequence
<220> FEATURE:
<223> OTHER INFORMATION: Primer

<400> SEQUENCE: 130
cccttgaagc ttgctgagga aacggtgacc gtggt                            35

<210> SEQ ID NO 131
<211> LENGTH: 70
<212> TYPE: DNA
<213> ORGANISM: Artificial Sequence
<220> FEATURE:
<223> OTHER INFORMATION: Primer

<400> SEQUENCE: 131
cccttgaccc ttgaagcttg ctgcagagac agtgaccaga gtagcttgct gaggagactg 60
tgagagtggt                                                        70

<210> SEQ ID NO 132
<211> LENGTH: 35
<212> TYPE: DNA
```

-continued

```
<213> ORGANISM: Artificial Sequence
<220> FEATURE:
<223> OTHER INFORMATION: Primer

<400> SEQUENCE: 132
cccttgaagc ttgctgcaga gacagtgacc agagt                              35

<210> SEQ ID NO 133
<211> LENGTH: 35
<212> TYPE: DNA
<213> ORGANISM: Artificial Sequence
<220> FEATURE:
<223> OTHER INFORMATION: Primer

<400> SEQUENCE: 133
cccttgaagc ttgctgagga gacggtgact gaggt                              35

<210> SEQ ID NO 134
<211> LENGTH: 19
<212> TYPE: PRT
<213> ORGANISM: Artificial Sequence
<220> FEATURE:
<223> OTHER INFORMATION: Ligand

<400> SEQUENCE: 134

Trp Met Val Leu Pro Trp Leu Pro Gly Thr Leu Asp Gly Gly Ser Gly
1               5                   10                  15

Cys Arg Gly
```